United States Patent [19]

Bott

[11] Patent Number: 4,781,460

[45] Date of Patent: Nov. 1, 1988

[54] SYSTEM FOR MEASURING THE SIZE DISTRIBUTION OF PARTICLES DISPERSED IN A FLUID

[75] Inventor: Steven E. Bott, Conway, Mass.

[73] Assignee: Coulter Electronics of New England, Inc., Amherst, Mass.

[21] Appl. No.: 68,139

[22] Filed: Jun. 29, 1987

Related U.S. Application Data

[63] Continuation-in-part of Ser. No. 817,048, Jan. 8, 1986, Pat. No. 4,676,641.

[51] Int. Cl.$^4$ .................. G01N 15/02; G01N 21/49
[52] U.S. Cl. ................................ 356/336; 250/564; 250/574; 356/338; 356/340
[58] Field of Search .............. 356/336, 338, 340, 341, 356/343; 250/564, 565, 574

[56] References Cited

U.S. PATENT DOCUMENTS

| | | |
|---|---|---|
| 3,621,220 | 11/1971 | Ford . |
| 4,158,234 | 6/1979 | Grandchamp .................. 356/336 X |
| 4,676,641 | 6/1987 | Bott ................................. 356/336 |

FOREIGN PATENT DOCUMENTS 2453832  10/1975  Fed. Rep. of Germany ...... 356/338

OTHER PUBLICATIONS

Hercher, "Virometer-an Instrument for the Measurement of the Size of Viruses Using an Optical Microscope", Proc. SPIE, vol. 126, pp. 17-22, 1977.
Pinder et al, "A Method of Measuring the Light Scattering of Solutions Containing Dust Particles", J. Phys E-Sci. Instru., vol. 10, No. 4, pp. 400-403.
Product Brochure: "Fast Automatic Measurement of Submicron Particles," Coulter Electronics Inc., 1982.
Product Brochure: "Model N4-Automation & Accuracy Down to 30 Angstroms," Coulter Electronics Inc., 1984.
Product Brochure: "Un Nouvel Instrument Francais," Amtec, date unknown.
Product Brochure: "System 4700" Malvern Instruments Limited, Feb. 1985.
B. E. Dahneke, "Measurement of Suspended Particles by Quasi-Elastic Light Scattering," John Wiley & Sons, New York, 1983.

Primary Examiner—Davis L. Willis
Assistant Examiner—Matthew W. Koren
Attorney, Agent, or Firm—Lahive & Cockfield

[57] ABSTRACT

An apparatus and method which provides a measure of the size distribution of particles dispersed in a fluid based upon an optimum combination of CLS measurements and DLS measurements. The measurement is characterized by relatively high resolution particle sizing. DLS data representative of the autocorrelation function, or power spectrum, of the detected intensity of scattered light for m measurement conditions of a sample, is optimally combined with CLS data representative of the average total detected intensity of scattered light for n measurement conditions, to provide an angle-independent, high resolution size distribution v(r), where $m \geq 1$, $n \geq 0$, $m+n \geq 2$, and at least two of the measurement conditions are different. The size distribution may be expressed in terms of the continuous function v(r) or the histogram v, and may represent distributions weighted by mass, volume, number, surface area, or other measures.

44 Claims, 7 Drawing Sheets

| ORDINATE | ABSCISSA |
|---|---|
| 0.000E-01 | 3.000E+02 X |
| 0.000E-01 | 3.635E+02 X |
| 7.005E+02 | 4.403E+02 |
| 0.000E-01 | 5.335E+02 X |
| 0.000E-01 | 6.463E+02 X |
| 0.000E-01 | 7.830E+02 X |
| 3.496E+01 | 9.487E+02 X |
| 2.252E+00 | 1.149E+03 X |
| 0.000E-01 | 1.392E+03 X |
| 0.000E-01 | 1.687E+03 X |
| 0.000E-01 | 2.044E+03 X |
| 0.000E-01 | 2.476E+03 X |
| 0.000E-01 | 3.000E+03 X |
| 0.000E-01 | 3.636E+03 X |
| 0.000E-01 | 4.403E+03 X |
| 0.000E-01 | 5.335E+03 X |
| 0.000E-01 | 6.463E+03 X |
| 0.000E-01 | 7.830E+03 X |
| 0.000E-01 | 9.487E+03 X |
| 0.000E-01 | 1.149E+04 X |
| 0.000E-01 | 1.392E+04 X |
| 0.000E-01 | 1.687E+04 X |
| 0.000E-01 | 2.044E+04 X |
| 0.000E-01 | 2.476E+04 X |
| 0.000E-01 | 3.000E+04 X |

FIG. 10A
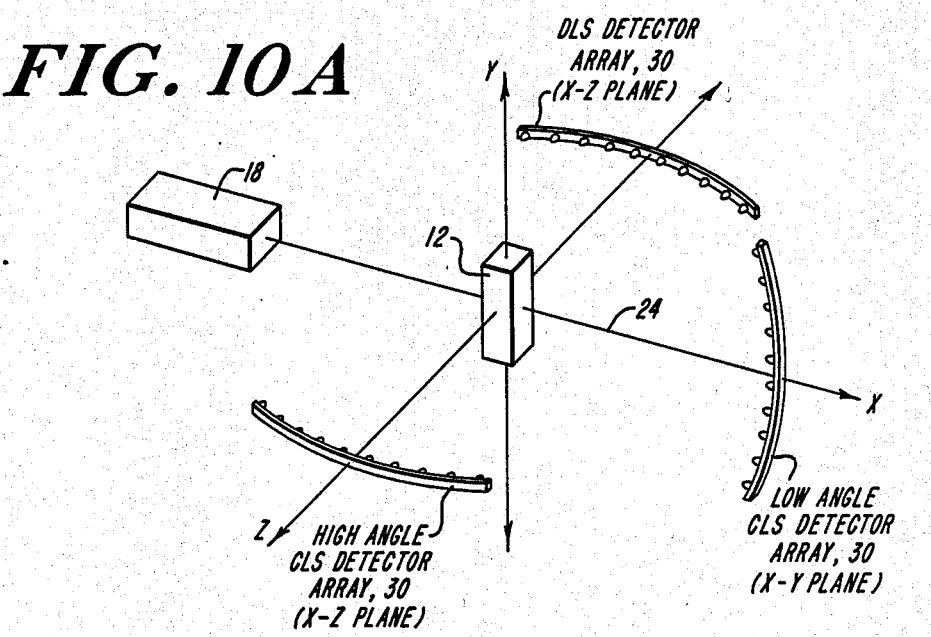
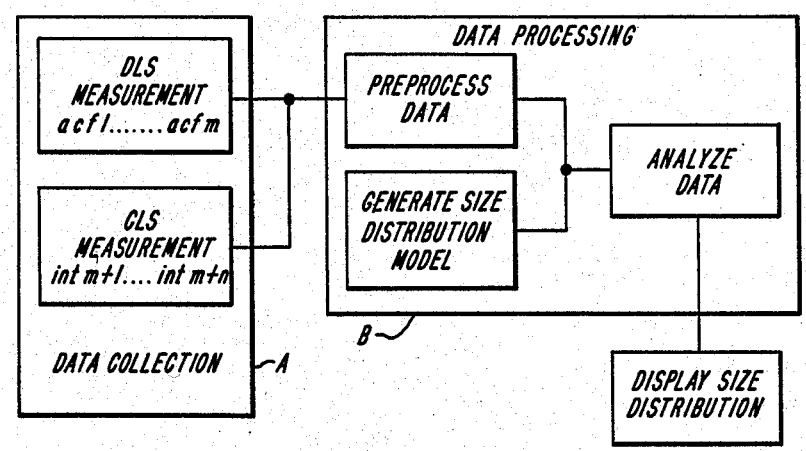
FIG. 10

SYSTEM FOR MEASURING THE SIZE DISTRIBUTION OF PARTICLES DISPERSED IN A FLUID

REFERENCE TO RELATED APPLICATION

The present application is a continuation-in-part of U.S. Ser. No. 817,048, filed 018/86, now U.S. Pat. No. 4,676,641, "System for Measuring the Size Distribution of Particles Dispersed in a Fluid".

FIELD OF THE INVENTION

This invention relates to light scattering instrumentation and more particularly to light scattering systems for measuring the size distribution of particles dispersed in a fluid.

BACKGROUND OF THE DISCLOSURE

There are several prior art techniques for measuring the distribution of the particle size in a sample by using light scattering. Generally, to measure the sizes of individual particles, for example, in a flowing stream of a liquid or gas, the particle-containing sample is illuminated by a constant light source and the intensity of light scattered by the particle is detected. A particle scatters the light by an amount directly related to the particle size; in general, bigger particles scatter more light than smaller particles. The relation between the amount of scattering and particle size may be determined either from theoretical calculations or through calibration process. With knowledge of this relation, for a single particle at a time, the detected scattered light intensity provides a direct measure of the particle size. The distribution of particle sizes in a sample may be determined by individually passing each particle in the sample, or a suitable portion of the sample, through the scattered light detection apparatus and tabulating the sizes of the various particles. In practice, this method is generally restricted to particles greater than 0.5 microns. Moreover, this method is relatively slow since particles must be detected individually. This technique is referred to in the prior art as optical particle counting (OPC).

A second prior art technique of particle sizing by light scattering is referred to as static or "classical" light scattering (CLS). This method is based upon illumination of a sample containing the particles-to-be-sized followed by the measurement of the intensity of scattered light at several predetermined angles. Because of intra-particle destructive interference, the intensity of light scattered from a particle depends on both the size and composition of the particle and the angle at which the measurement is made. This method of particle sizing based on the angular dependence of the scattered intensity can be used to measure the size distribution of a group of particles, as opposed to the first method noted above which is restricted to individual particles.

To implement the CLS measurement method, a sample of particles dispersed in a fluid is illuminated along an input axis, and the intensity of scattered light is measured at several predetermined angles. The scattered light intensity at each angle may be measured simultaneously with a multitude of detectors or consecutively, by moving a single detector around the sample to permit measurement of the intensity at each desired angle.

For large particles, for example, having diameters greater than 1 micron, the scattered light flux is concentrated in the forward direction relative to the input axis. Instruments for sizing large particles are referred to as laser diffraction devices. For sizing of smaller particles, for example, having diameters as low as 0.2 microns, the scattered light flux has significant magnitude both at lower and higher scattering angles relative to the input axis. The angular intensity measurements used on smaller particles are termed total integrated, or average, intensity measurements and may be displayed in a form known as Zimm plots.

A third prior art technique for particle sizing by light scattering is dynamic light scattering (DLS), also known as photon correlation spectroscopy (PCS) or quasi-elastic light scattering (QELS). See B. E. Dahneke, "Measurement of Suspended Particles by Quasi-Elastic Light Scattering," John Wiley & Sons, Inc., New York, 1983. This technique is based on measuring the time-fluctuations of the intensity of light scattered from an illuminated sample containing a group of particles which are diffusing through a fluid, that is, randomly moving due to collisions with solvent molecules and other particles. For example, the particles may be macromolecules dissolved in a liquid, where the macromolecules may be ionized by the loss of a small number of charged atoms.

In accordance with the DLS technique, scattered light intensity is measured as a function of time at a selected angle with respect to an illumination input axis. The light intensity detected at any instant at the detector is dependent on the interference between the light scattered from each illuminated particle in the scattering volume. As the particles randomly diffuse through the solution, the interference of the light scattered from them changes and the intensity at the detector therefore fluctuates. Since smaller particles diffuse faster, the fluctuations resulting from the motion of relatively small particles vary faster then those resulting from the motion of larger particles. Thus, by measuring the time variation of the scattered light fluctuations at the detector, information representative of the distribution of particle sizes is available. More particularly, the autocorrelation function of the measured intensity is related to the distribution of particle sizes in the fluid. Conventional DLS instruments such as the Model N4 photon correlation spectrometer manufactured by Coulter Electronics, Inc., Hialeah, Fla., provide autocorrelation signals for the detected intensity suitable for measuring distributions including particle sizes as low as 0.003 microns. Accordingly, such devices have a size measuring range extending considerably below the above-noted individual particle and CLS methods.

Particle sizing measurements by the known DLS techniques are generally made in the following manner. The particles-to-be-sized are suspended or dissolved in a fluid, forming a sample. The sample is illuminated by a laser beam directed along an input axis. Although a laser is generally used to generate the beam, a non-coherent light source may alternatively be used.

The light scattered from the particles in the sample is detected by a photodetector, such as a photomultiplier, which is positioned at a predetermined angle. The particular angle may be selected by the operator, but usually only one angle is measured at a time. The photodetector produces a signal which varies with time as the scattered light intensity incident on the photodetector varies. This time-varying signal is applied to an autocorrelator analyzer, to compute the autocorrelation function of the photodetector signal. Typically, the autocorrelator computes the value of the autocorrelation function of the detected scattered light at as many as one hundred discrete time points. This autocorrelation function contains the information about the fluctuations in the detected scattered light, from which information about the distribution of particle sizes in the sample can be extracted. Thus, the autocorrelation function (acf) is the raw data of a DLS measurement. While most conventional DLS measurements are performed using this autocorrelation step, it is known that the acf of the intensity signal corresponds to the Fourier Transform of the power spectrum of that signal. Accordingly, a spectrum analyzer may be used in place of the autocorrelator to generate a power spectrum signal including the same information representative of the particle size distribution as is resident in the autocorrelation function. The frequency domain information resident in the power spectrum signal can be used to determine the particle size distribution.

In the prior art, there are several techniques for extracting the particle size distribution from the acf. For use with these techniques, the relationship between the acf and the size distribution can be expressed as:

$$g(t) = K(x(r)) \quad (1)$$

where g(t) is the acf (or a function closely related to the acf), x(r) is the sought distribution of particle sizes (x is a function of r, the particle radius), and K is a function (or operator, linear or non-linear) which relates particle size to the acf. Thus, given the exact form of K, the autocorrelation function resulting from any distribution, x(r), of particle sizes would be known.

Since the acf, g(t), is what is actually measured in practice, the above relation must be inverted to yield the particle size distribution:

$$x(r) = K^{-1}(g(t)) \quad (2)$$

Accordingly, for the measured acf for a sample of particles, the size distribution for those particles can be extracted by applying the operator $K^{-1}$ to the measured acf, g(t). The operator $K^{-1}$ is the generalized inverse of the operator K. In practice however, the acf is "ill-conditioned" so that the inversion process is generally difficult and complex, although there are a number of known techniques for performing the inversion.

An example of the form $K^{-1}$ for one particular commonly used prior art extraction technique is:

$$x = (K^t K + \alpha H)^{-1} K^t g \quad (3)$$

In this example, x is a vector whose components are the proportions of the particles of each size, g is a vector whose components are the values of the acf at different points in time, as computed by the autocorrelator, K is a matrix relating x to g, and H is a matrix which increases the conditioning of the inversion. $K^t$ is the transpose of the matrix K. Alpha ($\alpha$) controls the amount of conditioning imposed on the solution. The inverse operator $K^{-1}$ in this case can be written $K^{-1} = (K^t K + \alpha H)^{-1} K^t$, where alpha ($\alpha$) is a smoothing parameter determined conventionally. The inversion is usually performed along with some non-negativity constraints imposed on the solution; these constraints are formally part of the inverse operator $K^{-1}$. Other known methods for inversion are the histogram method, the singular value decomposition method, the delta function method, and the cubic spline method.

The size distribution, x(r), obtained from this extraction or "inversion" process can be expressed either as a continuous distribution as implied by x(r), where the distribution is defined for particles of any size, or as a discrete size histogram expressed by the vector x, where the distribution of particle sizes is defined at only a set number of particle sizes. The vector x is representative of a group of number $(x(r_1), x(r_2), \ldots, x(r_n))$ giving the relative proportion of scattered light intensity from particles of size $r_1, r_2, \ldots, r_n$, respectively. The size distribution x(r) is referred to as a size histogram x herein below.

The size distribution x(r) and size histogram, x, are "intensity weighted" functions since these are representative of the relative proportion of particles as characterized by the relative amount of scattering intensity from particles of each size. However, these intensity weighted functions are dependent on the angle at which the measurement of scattered light was made. That is, the apparent proportion of particles of each size, as evidenced by the scattered light intensity contribution of particles of different sizes, depends on the angle at which the measurement is made. Thus, size distributions made at different angles cannot be directly compared using the intensity weighted distribution x(r) or histogram x.

Accordingly, if the amount of light scattered per particle, as a function of the scattering angle, is known, either through theoretical calculations or by an empirical method, the intensity weighted size distributions x(r) and histogram x at each angle can be directly compared by first converting those functions to corresponding mass, volume, or number weighted size distributions. For example, the intensity weighted histogram x may be converted in accordance with:

$$v = Cx$$

In this expression, v is the mass, volume or number weighted size histogram and C is the conversion matrix between the intensity weighted histogram, x, and the mass, volume or number weighted histogram, v. Similarly, the size distribution x(r) may be converted into a corresponding mass, volume or number distribution function v(r). Since all of these converted histograms and distribution functions provide the desired angle-independent information about the size distribution particles, they are referred to generally below as v and v(r), respectively.

A volume weighted histogram and distribution function provide a measure of the proportion of the total volume of particles in a sample as a function of particle size. For example, 50% of the volume of a sample of particles might come from particles of size 0.1 micron and the remaining 50% from particles of size 0.3 microns. Similarly, the mass weighted histograms and distributions provide a measure of the mass of particles in a sample as a function of size and the number weighted histograms and distribution of the numbers of particles in a sample as a function of size. For particles of the same density, the mass and volume weighted histograms and functions are the same. Volume, mass and number weighted size histograms and distributions are generally more useful than the corresponding intensity weighted size histograms or distributions since the former relate to quantities which can be directly measured by other means.

All of the prior art light scattering measurement techniques are characterized by low resolution and poor reproducibility, the principal drawbacks of such methods. With respect to DLS sizing measurements, efforts have been made to try to increase the resolution. The general methods used to increase resolution either attempt to improve the signal-to-noise ratio of the measurement by collecting intensity data over a long period or over a large number of short periods and then averaging the results, or by using intensity data collected at several angles.

With the latter method, the data collected at different angles are substantially independent, and therefore data collected at one angle complement those collected at other angles. For example, data collected at lower scattering angles are generally more sensitive to the presence of large particles in the sample while, conversely, data collected at large scattering angles are more sensitive to the presence of smaller particles. A sample containing both large and small particles can therefore be accurately sized by using the data from two or more angles, where relatively lower angle or angles provide information about the larger particles and relatively high angle or angles provide information about the smaller particles. In contrast, measurement at a single low angle would provide relatively little and possibly obscured information about the smaller particles and hence the sizing resolution would be poor.

The prior art method of using several angles to enhance the sizing resolution involves simply making measurements at two or more angles and averaging the volume weighted histograms resulting from the measurements made at the two or more angles. Symbolically, the process of combining information obtained at several scattering angles by averaging results can be expressed by:

$$x_1 = K^{-1}(g_1(t), \theta_1)$$
$$x_2 = K^{-1}(g_2(t), \theta_2)$$
$$\vdots$$
$$x_m = K^{-1}(g_m(t), \theta_m)$$
(4)

where the subscripts 1, 2, ... m refer to measurements made at the scattering angles $\theta_1$ through $\theta_m$. The inclusion of $\theta$ as an argument of the operator $K^{-1}$ indicates that the inversion process, that is, the operator $K^{-1}$, depends on the scattering angles. Each of the m intensity weighted histograms, $x_1, \ldots, x_m$, may be converted to an angle-independent volume weighted histogram, $v_1 \ldots v_m$, and then the m volume weighted histograms may be averaged to produce the "enhanced" resolution result, v:

$$v = (1/m)[v_1 + v_2 + \ldots + v_m]$$

However, this volume weighted distribution, v, is not necessarily the solution which is the best fit to all the data. The size resolution obtainable for a single measurement at a single angle is quite low and the presence of particles of some sizes may not be detected at some angles. Thus, even when the intensity histograms are converted to volume histograms, the histograms obtained at different angles may give very different and apparently contradictory information.

Briefly, the invention disclosed in U.S. patent application Ser. No. 817,048 is an apparatus and method which provides a measure of the size distribution of particles dispersed in a fluid based upon an optimum combination of CLS measurements and DLS measurements, providing a resultant measurement characterized by relatively high resolution particle sizing. More particularly, in accordance with that invention, DLS data representative of the autocorrelation function, or power spectrum, of the detected intensity of scattered light at a plurality of angles about a sample, is optimally combined with CLS data representative of the average total detected intensity at those angles, to provide an angle-independent, high resolution size distribution v(r). The size distribution may be expressed in terms of the continuous function v(r) or the histogram v, and may represent distributions weighted by mass, volume, number, surface area, or other measures.

By way of example, in combining the DLS and CLS data, an angle independent volume weighted histogram may be determined from:

$$v = J^{-1}(g_1(t), g_2(t), \ldots, g_m(t);$$

$$i(\theta_1), \ldots, i(\theta_m), i(\theta_{m+1}), \ldots i(\theta_n))$$

where $g_1(t), \ldots, g_m(t)$ are the determined autocorrelations of the detected light intensities at m scattering angles $\theta_1, \ldots, \theta_m$, and where $i(\theta_1), \ldots, i(\theta_m), i(\theta_{m+1}), \ldots, i(\theta_{m+n})$ are the detected average intensities at the respective m scattering angles; $\theta_1, \ldots, \theta_m$ as well as n additional angles $\theta_{m+1}, \ldots, \theta_{m+n}$, where m is an integer equal to or greater than one and n is an integer equal to or greater than zero. In this form of the invention, the DLS measurements are made at m angles and the CLS measurements are made at m+n angles, including the same angles at which DLS measurements are made. $J^{-1}$ is a single operator which acts simultaneously on all of the autocorrelation functions and average intensity values to provide the "best fit" to all the data. This is in contrast to the m separate $K^{-1}$ operators, one for each angle, set forth in equations (4) above. In various forms of the invention, rather than different angles, acf and intensity measurements may be made at the same angle, but under difficult conditions, for example, temperature, hydrodynamic solution characteristics, or polarization angles, which establish independent intensity characteristics at the sensor.

With the invention, the operator $J^{-1}$ incorporates the information from the CLS measurements as well as the independent information from the DLS measurements, in a manner appropriately normalizing the autocorrelation functions measured at the different scattering conditions. For simplicity, the following descriptions will characterize the various measurements as being made at angles denoted $\theta_i$ although it is only necessary that the measurements be made under conditions which result in independent intensity characteristics.

The resultant distribution, v, based upon the $J^{-1}$ transformation of the autocorrelation functions and the classical scattered intensities, simultaneously in a single procedure, provides an increase in the sizing resolution of the determined particle distributions compared to the prior art techniques which are based upon either the autocorrelation functions of the classical scattering intensities, but not both.

Briefly, according to the invention disclosed in U.S. patent application Ser. No. 817,048, a system is provided for measuring the size distribution $v(r)$ of particles dispersed in a fluid sample, where r is representative of particle size. The system includes means for illuminating the sample with a light beam directed along an input axis. Either a coherent or a non-coherent light source may be used.

A light detector detects the intensity of light from the light beam at m points angularly dispersed from said input axis at a plurality of angles $\theta_1, \ldots, \theta_m$, where m is an integer equal to or greater than one. The detector generates m intensity signals, each of the intensity signals being representative of the detected intensity of the light from the light beam as a function of time at a corresponding one of the m points. In various forms, the invention may be embodied in a homodyne or a heterodyne configuration. In the homodyne form, only scattered light is detected at the m points during the intensity signal measurements, while in the heterodyne form, a portion of the beam is directly incident on the detector at the m points, so that the intensity signal corresponds to a beat signal resulting from both scattered and non-scattered portions of the light beam.

In one form, an autocorrelation processor generates m correlation signals each of the correlation signals being representative of the autocorrelation function of a corresponding one of the intensity signals. Each of the correlation signals equals an associated transformation $J_i$ of the distribution $v(r)$, where $i=1, \ldots, m$. The transformations may be linear or non-linear. Since the autocorrelation functions for the intensity signals are the Fourier Transforms of the power spectra of those signals, the autocorrelation processor is, in one form of the invention, an autocorrelator which directly generates the m correlation signals as m time domain autocorrelation signals $g_i(t)$, where t is time and $i=1, \ldots, m$. In other forms, the autocorrelation processor includes a spectrum analyzer which generates the m correlation signals as m frequency domain power spectrum signals $G_i(f)$, where f is frequency and $i=1, \ldots, m$. Since the power spectrum signal is the Fourier Transform of the autocorrelation signal, the power spectrum signals $G_i(f)$ may be used to provide the same information as the autocorrelation signals $g_i(t)$.

A light detector also detects the time average intensity of scattered light from the light beam at the m points as well as n additional points angularly displaced from the input axis, where n is an integer greater than or equal to zero. The latter detector generates average signals representative of the time average of the intensity of scattered light detected at the respective m+n points.

A size processor, responsive to the correlation signals and the average signals, generates a signal representative of the distribution $v(r)$. The size processor generates a composite correlation signal representative of a weighted direct sum of the m correlation signals. The size processor determines a composite transformation operator $J^{-1}$ which is related to the transformations $J_i$ and the n average signals.

The size processor transforms the composite correlation signal in accordance with the determined composite transformation operator thereby providing a resultant signal which incorporates the size distribution information of both the CLS and DLS data and is representative of the size distribution $v(r)$. In accordance with the invention, either the composite correlation signal or the composite transformation operator is substantially scaled to the average intensities of the scattered light at the respective ones of the m points. This scaling, or normalization, permits the DLS data represented by the composite correlation signal to be optimally combined with the CLS data represented by the average signals.

In one form of the invention, the transformations $J_i$ are linear transformations and the composite transformation operator $J^{-1}$ is the generalized inverse of the operator corresponding to the direct sum of the operators for the associated transformations $J_i$. The inverse transformation operator $J^{-1}$ may correspond to the inverse of the matrix corresponding to the direct sum of the associated transformations $J_i$. Alternatively, the operator $J^{-1}$ may correspond to $$[J^tJ + \alpha H]^{-1} J^t$$

where J is the matrix corresponding to the direct sum of the matrices coresponding to the associated transformations $J_i$, $J^t$ is the transpose of the matrix J, H is a conditioning matrix, and alpha ($\alpha$) is a smoothing parameter. Further, all components of the vector representative of the distribution $v(r)$ may be constrained to be greater than or equal to zero.

In another form, the associated transformations are non-linear, with the size distribution being characterized by $v(r,p)$, where p is a characterization parameter vector having k components. In this form, the composite transformation operator $J^{-1}$ is the p solution algorithm for $$\frac{\partial}{\partial p_l} \sum_{i=1}^{m} \sum_{j=1}^{q} \{J_{ij}[v(r,p)] - g_i(t_j)\}^2 = 0, \, l = 1, \ldots, k$$

where i is an integer $1, \ldots, m$, j is an integer $1, \ldots, q$, l is an integer $1, \ldots, k$, $p_l$ is the $l^{th}$ component of p and where $g_i(t_j)$ is the autocorrelation function of the intensity signal for the $i^{th}$ of said angle at the $j^{th}$ time interval and $J_{ij}$ is an operator related to the associated transformations. The model size distribution $v(r,p)$ may for example be characterized in terms of parameters $\bar{r}$ and $\rho$, the mean particle size of the actual size distribution, and the standard deviation of the actual size distribution, respectively. The solution algorithm for the $p_l$ minimizes the squares of the residuals $J_{ij}[v(r,p)] - g_i(t_j)$ for the various points in time $t_j$ for the various acf's $g_i$. More particularly, $v(r,p)$ may have the form:

$$v(r,p) = \sqrt{\frac{1}{2\pi\sigma^2}} \, e^{-(r-\bar{r})^2/2\sigma^2}$$

where the $J_{ij}$ operator has the form:

$$\int_0^\infty dr \, e^{-\Gamma(r,\theta_i)t_j}$$

where $\Gamma(r,\theta_i)$ has the form:

$$\Gamma(r,\theta_i) = \left[\frac{4\pi n}{\lambda} \sin \frac{1}{2} \theta_i\right]^2 \frac{k_B T}{6\pi\eta r}$$

where n is the refractive index of the sample, $\lambda$ is the wavelength of the light illuminating the sample, $k_B$ is Boltzmann's constant, $\eta$ is the viscosity of the sample and T is absolute temperature.

In another form, the composite correlation signal operator controls the weighted direct sum of the m correlation signals to be unity normalized and the composite transformation operator is substantially scaled to the average intensities of light scattered from the light beam at the respective ones of the m points. In yet another form, the composite correlation signal generator controls the weighted direct sum of the m correlation signals to be substantially scaled to the average intensities of light scattered from the light beam at the respective ones of the m points.

In other forms of that invention, the general method of using information exacted from measurements at two or more scattering angles can be applied to determine size and shape information about particles which are rod-like, ellipsoids or other forms, including "Gaussian coils".

In other forms of that invention, instead of making CLS and DLS measurements at two or more scattering angles, such measurements may be made at one angle under different sets of conditions, for example, different temperatures or hydrodynamic solution characteristics or polarization of the light beam, providing complementary information which is processed to yield enhanced particle characteristic resolution for a wide variety of dynamic systems.

A critical aspect of the invention disclosed in U.S. patent application Ser. No. 817,048 is the recognition that by combining CLS (classical light scattering) data and DLS (dynamic light scattering) data from multiple scattering angles, the resolution and repeatability of particle sizing may be improved over prior art CLS or single angle DLS measurements.

To combine CLS data and DLS data is difficult and the determination of conditions under which the CLS and DLS data can be combined in a single, simultaneous analysis is a complicated process. In particular, one major problem in combining these two types of light scattering measurements is in properly normalizing the DLS data taken at different angles. Briefly, "normalization" refers to adjusting the amplitudes of the autocorrelation functions (acfs) at different angles with respect to the CLS data so that data from all the DLS angles can be analyzed within one comprehensive model.

The normalization of the DLS data to the CLS data is important in view of the following. A CLS measurement at a single angle is the average value of the light scattered from particles of all sizes in the sample being measured, weighted by the intensity of light scattered by particles of each size. The amount of light scattered at a particular angle from a particle of a particular size depends on both the size of the particle and the scattering angle. To make particle size measurements using CLS data alone (that is, average intensity measurements at a multitude of angles), measurements at the selected angles are made and then an analysis procedure is used to find a particle size distribution corresponding to the measured pattern of angular scattering intensity. The selected distribution must be such that the light scattered from every size of particle in the distribution, weighted by the angle dependent intensity of light scattered by particles of each size, must be close, at each angle, to the measured value of the average scattered intensity at that angle.

CLS data is thus a subset of DLS data since the magnitude of the CLS intensity at a particular angle is simply the value of the zero time point of the homodyne DLS autocorrelation function (acf) at that angle. The relation between CLS data and DLS data may be appreciated by considering a plot of the CLS data in a cartesian (X-Y-Z) coordinate system in which the x axis represents scattering angles (e.g. from 0 to 180 degrees), and the y axis represents scattering intensity. In such a coordinate system, a given distribution of particles would be characterized as a curve in the X-Y plane. The height of the curve at any point would be the scattering intensity at the angle corresponding to that point. This curve, or at least a number of points along this curve, correspond to a CLS measurement.

The z axis represents the delay time of an acf of the scattered light intensity. Generally, acf's have the form of decaying exponentials (or sums of decaying exponentials). A number of discrete points along the CLS curve (in the xy plane) correspond to the angles at which DLS measurements may be made. The DLS data for each point (or angle) defines a curve in a plane parallel to the Y-Z plane. These acfs (at one or more angles) are the DLS data. The shape of the acf at each angle in general would be slightly different unless all the particles were the same size. Thus, the matrix of acf data is used in a measurement of the type defined in U.S. patent application Ser. No. 817,048. In the prior art, only the curve in the X-Y plane alone or a single one of the acfs would be analyzed to obtain a (low resolution) particle size distribution. The system of U.S. patent application Ser. No. 817,048 provides particle distribution measurements utilizing the two dimensional "measurement" surface on which all the values of the acfs at all delay times and all scattering angles lie. The intersection of this surface with the X-Y plane is the CLS data curve.

To analyze the matrix of data shown, a model is made describing how the measurement surface, or more precisely, the discrete points on the measurement surface at which actual measurements are made, varies when the parameters (e.g. histogram bin heights) of the particle size distribution vary. Then, when a particular measurement is made, the particle size distribution which leads to a measurement surface closest to the measured measurement surface is the best estimate of the true particle distribution. The best estimate is found by a curve fitting algorithm, such as a non-negative least square (NNLS) algorithm.

The importance of normalization to this process is that in order to accomplish the curve fitting, the measured acfs (which are ordinarily measured without regard to their absolute height) need to be normalized so that their amplitudes, i.e. zero time values, are exactly the amplitudes of the CLS data curve at the angles at which the acfs are measured. If this normalization is not undertaken, the measured measurement surface generally differs from the model measurement surface since in the model measurement surfaces all acfs at time zero must lie on the CLS data curve. Thus, the measured data are normalized to be appropriate to this model.

In order to perform the DLS data normalization, CLS data (i.e. the average intensity of scattered light) must be measured at every DLS angle to obtain the normalization constants. For this reason, U.S. patent application Ser. No. 817,048 defines an analysis in which the DLS data is measured at m angles (m > 0) and the CLS data is measured at those m angles and at n additional angles, i.e. CLS data needs to be measured at all the DLS angles and optionally at some additional angles.

However, it is difficult to accurately obtain the CLS data used for the DLS normalization. More importantly, small errors in the normalization constants lead to serious errors in the extracted particle size distribution. Therefore, it is desireable to find an improved model by which to analyze the data.

Because of the mathematical form of acfs, the amplitude information is mathematically separable from the rest of the information contained in the acf, namely the information contained in its shape. By performing a mathematical transformation in one of several ways, the DLS amplitudes can be removed from the model, thereby allowing the curve fitting to be accomplished without knowledge of the amplitudes of the acfs, i.e. without a normalization in the manner defined in U.S. patent application Ser. No. 817,048.

It is an object of the present invention to provide an improved apparatus and method for measuring the distribution of particle sizes dispersed in a fluid.

Another object is to provide an improved particle size distribution measuring apparatus and method characterized by relatively high resolution.

SUMMARY OF THE INVENTION

Briefly, the present invention is an improved apparatus and method which provides a measure of the size distribution of particles dispersed in a fluid based on an optimum combination of CLS measurements and DLS measurements, without requiring normalization of the DLS acf's to the CLS values at the appropriate angles.

In one form of the invention, the acf's may be determined in the same manner as described in U.S. patent application Ser. No. 817,048. All the shape information in the acf's then is extracted by calculating the moments of the unknown particle size distributions based on the acf's at each DLS angle. Each acf provides a differently weighted estimate of the moments of the particle size distribution. Ways of extracting the moments from an acf are well known and detailed in the scientific literature. The zeroth moment of the particle size distribution is directly related to the amplitude of the acf. The higher order moments and the inverse moments contain the information about the shape of the acf. By determining a sufficient number of moments from an acf, substantially all the shape information in that acf can be utilized.

After extracting the moments, a curve fitting algorithm is used to determine the particle size distribution mostly closely matching the CLS data curve (if this has been measured) and all the extracted moments of all the acfs, except the zeroth moments which contain the amplitude information (i.e. normalization). Thus, with this form of the invention, all the acf information and all the CLS data is used in the analysis except for information concerning the amplitude of the acf's. Since no acf amplitude information is used, no normalization of the acfs to CLS data need be done. Further, CLS data need not be measured at every DLS angle.

In another form of the invention not requiring normalization of the DLS data to CLS data, the amplitude information normally present in an acf is explicitly removed by normalizing the amplitude of each acf to unity. Such a normalization is trivial to perform and, more importantly, obviates the necessity of making CLS measurements at each DLS angle and introducing significant error into the DLS measurements by normalizing them with the CLS measurements. The unity normalized DLS measurements are related by a special transformation ("DLS kernel") to the particle size distribution. The transformation differs from the DLS kernal which relates a particle size distribution to acfs normalized by CLS data (as described in patent application Ser. No. 817,048). The unity normalization in this form of the present invention is, however, such that CLS measurements need not be made at every DLS angle.

In a third form of the present invention not requiring normalization of the DLS data to the CLS data, the data analysis may be performed without using information about the acf amplitudes by allowing the amplitudes to be "floating" parameters in the curve fitting process. Allowing the amplitudes to float means that instead of normalizing the DLS kernel or acfs with the CLS data, the amplitudes of all the acfs are treated as unknown, adjustable parameters in the curve fitting. This process effectively allows the model measurement surface wider latitude in matching the measured acfs, by permitting free adjustment of the acf amplitudes to more closely approach the measured measurement surface. In patent application Ser. No. 817,048, the amplitudes of the acfs were normalized by CLS measurements. In that case, any small error in measuring a CLS data point forces corresponding errors in the entire acf, which for example, may comprise 100 data points which the CLS data point was being used to normalize. In this third form of the present invention, the amplitude of the acf is determined by the acf itself (through the curve fitting process), preventing the situation where a single measurement controls the errors in a large number of other measurements. Again, CLS data need not be measured at every DLS angle and no normalization at all would be performed.

More particularly, the present invention is a system for measuring the size distribution v(r) of particles dispersed in a fluid sample, where r is representative of particle size. The system comprises a light source for illuminating the sample with a light beam directed along an input axis. A detector, or set of detectors, detects the intensity of light scattered from the light beam by the sample for m measurements, each made under an associated one of a set of m measurement conditions, and also for n measurements, each made under an associated one of a set of n measurement conditions, where m is an integer equal to or greater than one, and n is an integer equal or greater than zero, and the sum of m and n is equal to or greater than two, and at least two of the m+n measurement conditions are different.

The detector is adapted to generate m intensity signals, each of the intensity signals being representative of the detected intensity of the scattered light as a function of time under a corresponding one of the measurement conditions of said set of m measurement conditions. The detector also generates n average signals, each of the n average signals being representative of the average intensity of the scattered light detected under a corresponding one of the measurement conditions of the set of n measurement conditions.

An autocorrelator generates m correlation signals. Each of the correlation signals is representative of the autocorrelation function of a corresponding one of the intensity signals and is equal to an associated transformation of the distribution v(r).

A size processor is responsive to the correlation signals and the average signals. The size processor includes a preprocessor responsive to the m correlation signals for generating a composite correlation signal. The size processor also generates a composite scattered light signal from the composite correlation signal and the n average signals. The size processor also determines a composite transformation operator $J^{-1}$ related to the associated transformations and the n average signals. The composite scattered light signal is transformed in accordance with the determined composite transformation operator $J^{-1}$ to generate a size distribution signal representative of the distribution $v(r)$.

In the system, the m+n measurement conditions are controlled whereby the intensity signals are mutually independent and the average signals are mutually independent.

In one form of the invention, the preprocessor is responsive to the m correlation signals for generating m moment signals, where the m moment signals are representative of at least one of the moments of each of the m correlation signals other than the zero$^{th}$ moments of the m correlation signals. The preprocessor further generates a weighted direct sum signal, where the weighted sum signal is representative of the direct sum of the m moment signals and corresponds to the composite correlation signal.

In another form of the invention, the preprocessor is responsive to the m correlation signals for generating m unity normalized correlation signals, where each of the unity normalized correlation signals is representative of the unity normalized form of the corresponding one of the m correlation signals. The preprocessor generates a direct sum signal, which is representative of the direct sum of the unity normalized correlation signals, and corresponds to the composite correlation signal.

In still another form of the invention, the preprocessor generates a direct sum signal, where that sum signal is representative of the direct sum of the m correlation signals and corresponds to the composite correlation signal.

In each of the above forms of the invention, the composite scattered light signal may be the direct sum of the composite correlation signal and the average signals.

In these forms of the invention, the "direct sum" may be defined as set forth in Mostow, G. D., Sampson J. H., *Linear Algebra*, McGraw Hill Book Company, New York 1969, page 165 (particularly, a vector space U is the direct sum of the subspaces $U_1, \ldots, U_r$ if every vector x in U can be expressed in one and only one way as a sum $x = x_1 + \ldots + x_r$, where $x_j$ is in $U_j$ ($j=1, \ldots, r$)). Further, a "composite signal" of a group of signals is defined as any transformation of the elemental signals which preserves all or the bulk of the information contained by the union of the elemental signals. A "direct sum" is a simple form of a composite signal as so defined above. Moreover, the moment signals, however they might be combined, are also a composite signal derived from the original acf's.

A composite transformation operator is defined as a transformation operator comprising the mathematical relationships between a particle size distribution and each datum in a composite signal.

BRIEF DESCRIPTION OF THE DRAWINGS

The foregoing and other objects of this invention, the various features thereof, as well as the invention itself, may be more fully understood from the following description, when read together with the accompanying drawings, in which:

FIG. 10 shows a flow chart illustrating the operation of an embodiment of the present invention;

FIG. 10A shows, in schematic form, an exemplary sensor format for the present invention;

DESCRIPTION OF THE PREFERRED EMBODIMENTS

Figure 1:
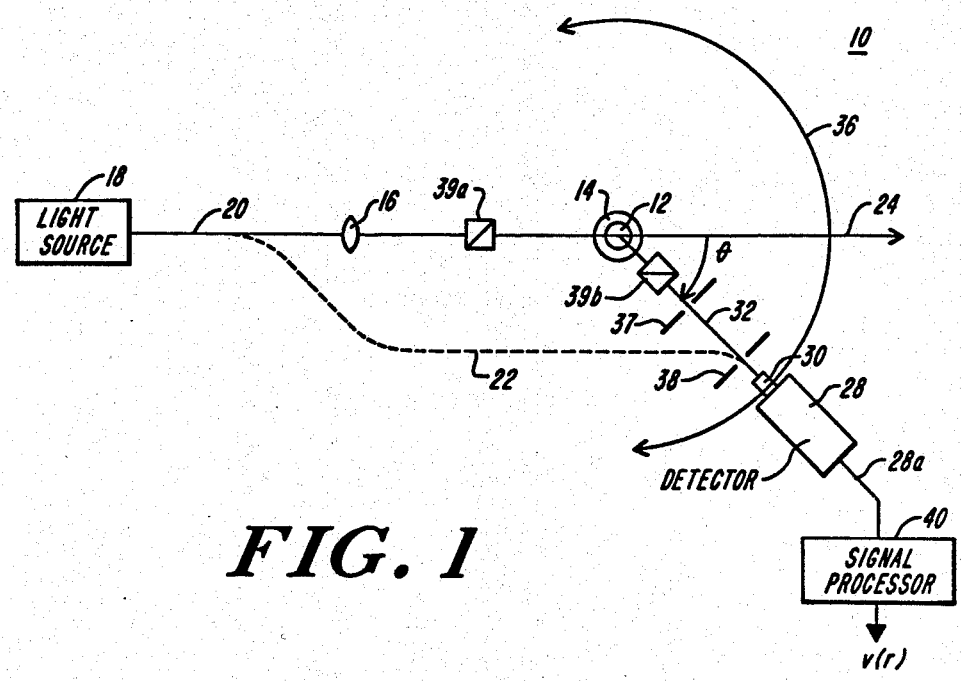
FIG. 1 shows in schematic form, an exemplary system embodying of the present invention.

FIG. 1 shows an exemplary system 10 in accordance with the invention. The system 10 provides an output signal representative of the size distribution of particles $v(r)$ dispersed in a fluid sample 12, where r is representative of particle size. The sample may, for example, include discrete particles or macromolecules suspended in a liquid, or may include ionized macromolecules in a solvent, or may include discrete particles in an aerosol, or any configuration wherein the particles-to-be-sized are dispersed in a fluid, and are subject to Brownian motion in that fluid.

In the embodiment of FIG. 1, the sample 12 is positioned within a bath chamber 14 filled with a temperature-controlled index of refraction matching medium. The system 10 includes a light source 18 which provides a collimated light beam 20 directed along an input axis 24 and focussed by lens 16 onto the sample 12. In the presently described embodiment, the light source 18 is a laser, although in other forms of the invention, a non-coherent light source may be used. The present embodiment is a homodyne configuration in which substantially no non-scattered light is permitted to reach detector 28. In a heterodyne form of the invention, portion of the light beam from source 18 may be coupled directly to the sensor 30, for example, by a fiber optic link indicated by the broken line 22 in FIG. 1.

A light detector 28 includes a sensor 30 having a sensing axis 32 which is positionable at a plurality of points equidistant from and dispersed angularly about the sample 12 along an arc 36. As shown, the input axis 32 is displaced by an angle 0 with respect to axis 24. In various forms of the invention, a detector may be successively positionable along arc 36, or alternatively, a plurality of light detectors might be fixedly positioned at discrete points along the arc 36. The detector 28 provides output signals along lines 28a to a signal processor 40. In the present embodiment, aperture defining devices 37 and 38 are positioned with respect to sensor 30 and the axis 32 in a manner restricting the light detected at sensor 30 to be within a predetermined coherence area.

In addition, the present embodiment includes a pair of polarizers 39a and 39b positioned along the axis 24 before the sample and along the axis 32, respectively. The filters 39a and 39b permit passage only of portions of the light beam and scattered light, respectively, having predetermined polarization. By selectively controlling the polarization angle of these filters, substantially independent intensity signals may be generated for a single angle 0 for each orthogonal polarization angle. For example, in one form, the filter 39a passes right circularly polarized light and the filter 39b may be selectively adapted to pass right circularly polarized light or left circularly polarized light. Alternatively, the filter 39a passes vertically polarized light and the filter 39b may be selectively adapted to pass light characterized by one of two different orthogonal polarizations.

Figure 2:
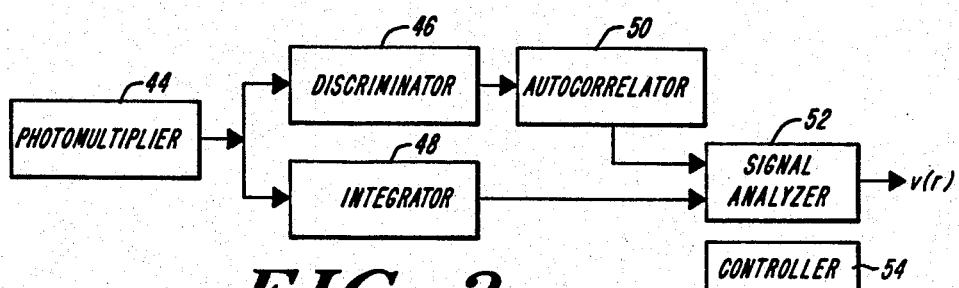
FIG. 2 shows, in block diagram form, an embodiment of the detector and signal processor of the system of FIG. 1.

FIG. 2 shows one form for the detector 28 and the signal processor 40 in which the detector 28 includes a photomultiplier 44 and associated pulse discriminator 46 and an integrator 48. In this form, the signal processor 40 includes an autocorrelator 50, a signal analyzer 52 and a controller 54.

Figure 3:
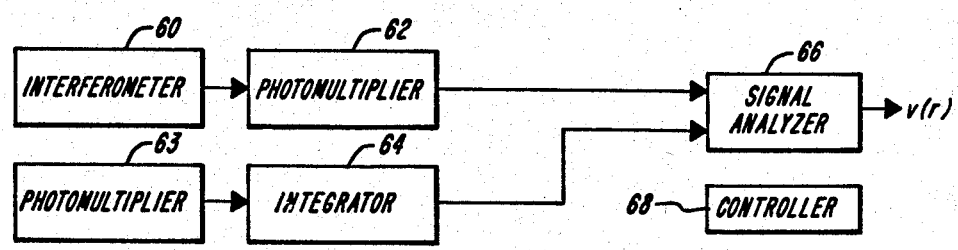
FIG. 3 shows, in block diagram form, another embodiment of the detector and signal processor of the system of FIG. 1.

FIG. 3 shows an alternate form in which the detector 28 includes an interferometer 60 and a photomultiplier 62, which provide a signal representative of the power spectrum of the light intensity at the detector 30, and a photomultiplier 63 and an integretor 64, which provide a signal representative of the time average of the light intensity at detector 30. The signal processor 40 includes a signal analyzer 66 and a controller 68. In FIGS. 2 and 3, the signal analyzers provide the output signal representative of the size distribution v(r).

In operation, briefly, the light source 18 illuminates the sample 12 along the input axis 24 and the sensor 30 of detector 28 detects the intensity of the light scattered by the sample at a plurality of points along arc 36. The intensity measured at the detector 28 is an interference pattern resulting from the in phase contributions of the light scattered from each molecule in the scattering volume of sample 12. In liquid or gaseous samples, the molecules are in motion and the interference pattern at the detector 28 is modulated by the motions of the scattering particles. In the absence of external fields, the motions of the particles are random, and are due just to thermal fluctuations. The fluctuations in scattered electric field at the detector caused by these random motions comprise a stationary random process. The second moment of the process is defined by $$g(t) = \tlim \frac{1}{T} \int_{-T/2}^{T/2} e^*(\tau)e(t + \tau)d \quad (1)$$

where $e(\tau)$ is the electric field of the scattered light at the detector 28 at time $\tau$. $g(t)$ is the autocorrelation function (hereinafter abbreviated "acf") of the process. The acf is a measure of the correlation between the configuration of the scattering molecules at a given time compared to that at any later time, e.g. at very short delay times, the configuration of particles as well as the scattered electric field measured at the detector 28 closely resembles the original configuration; as time passes, that resemblance diminishes. Because the degree of correlation depends on the speed with which and the mechanism by which the configurations change, the acf provides characterization of the dynamics of the particles in the sample. In the configuration of FIG. 2, the acf of the scattered light is determined by a digital correlator 50. Alternatively, in the configuration of FIG. 3, the photomultiplier-discriminator-autocorrelator elements of FIG. 2 are replaced by the interferometer 60 and photomultiplier 62. In the latter configuration, the power spectrum, which is the Fourier Transform of the acf is measured. In both the configuration of FIG. 2 and that of FIG. 3, the information obtained is equivalent and both the acf and power spectrum signals are referred to herein as the DLS data. In practice, the choice between the two forms is determined by the rapidity of fluctuations in the light scattered by the sample 12. Preferably, fluctuations decaying on a time scale slower than 0.01 microseconds are measured by autocorrelation and those faster than 0.01 microseconds are measured by interferometry.

The photomultiplier 44 and integrator 48 of FIG. 2 and the photomultiplier 63 and integrator 64 of FIG. 3 provide signals representative of the average detected intensity at the detector 30. Those signals are referred to herein as the CLS data.

The elements 18, 28, 44, 46, 48 and 50 of the system 10 of FIGS. 1 and 2 may be implemented in part by commercially available devices, such as the Model LSA2+ photon correlation spectrometer and Model 1096 Correlator, manufactured by Langley Ford Instruments, division of Coulter Electronics of New England, Inc., Amherst, Mass. Alternatively, these elements may be implemented by the Coulter Model N4 photon correlation spectrometer, or by the System 4700 spectrometer manufactured by Malvern Instruments, Inc., Framingham, Mass. or Series MM1000 spectrometer manufactured by Amtec, Villeneure-Loubet, France, together with a Coulter Model 1096 correlator.

Figure 4:
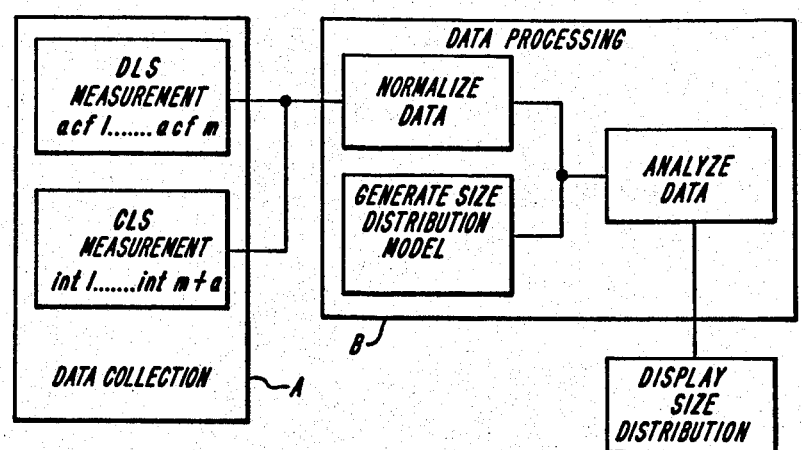
FIG. 4 shows a flow chart illustrating the operation of the system of FIGS. 1 and 2.

FIG. 4 shows a flow chart illustrating the general operation of the system of FIGS. 1 and 2, including a data collection phase, denoted A, and a data processing or analysis phase, denoted B. In accordance with the invention, as shown in FIGS. 1 and 2, the data collection phase A is performed with elements 18 and 28 in two modes. In the first mode, DLS measurements are made an m different angles and the autocorrelator 50 provides m autocorrelation functions, denoted acf 1 . . . acf m in FIG. 4. In the second mode, the CLS measurements are made at the same m angles, where m is an integer greater than or equal to one, and at n additional angles, where n is an integer greater or equal to zero and the integrator 48 provides m+n integrated intensity values, denoted int 1, . . . , int m+n in FIG. 4. These acf and integrated intensity measurements may be made at the same time or sequentially since the resultant data for each measurement is substantially independent. In various forms of the invention, rather than different angles, successive pairs of acf and average intensity measurements can be made at the same angle, but under different conditions, for example, temperature, hydrodynamic solution characteristics, or polarization angles, which establish independent intensity characteristics at the sensor 30. For example, the measurement conditions may be controlled by selectively controlling the polarization of light incident on the sample (the "input light") and the polarization of light scattered from the sample and incident on the detector (the "output light"). The polarization of the input and output light may be controlled to be at the same polarization (e.g. horizontal/horizontal, vertical/vertical, right circular/right circular, or left circular/left circular) or at orthogonal polarizations (e.g. horizontal/vertical, vertical/horizontal, right circular/left circular, left circular/right circular. Also, successive pairs of acf and average intensity measurements can be made at various combinations of angles and these conditions.

Figure 5:
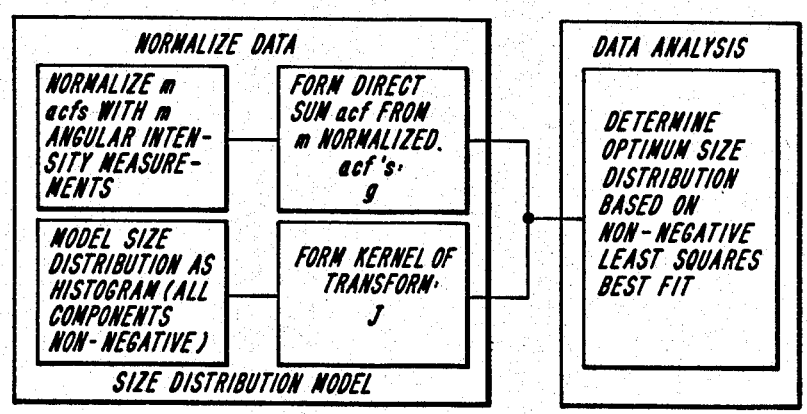
FIGS. 5–7 show detailed flow charts for three implementations of the data processing step of the flow chart of FIG. 4.
Figure 6:
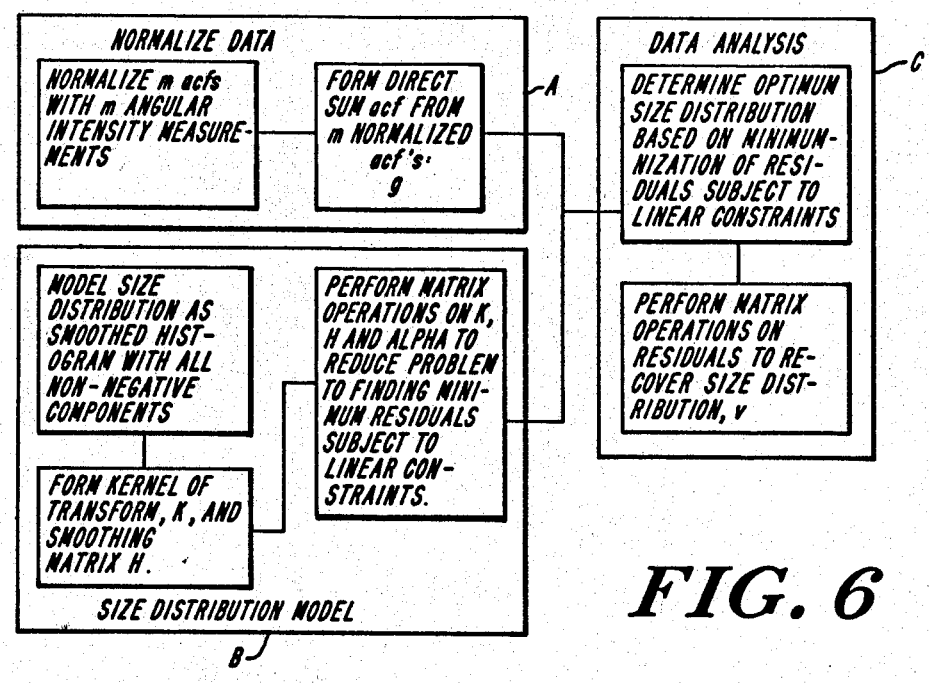
Figure 7:
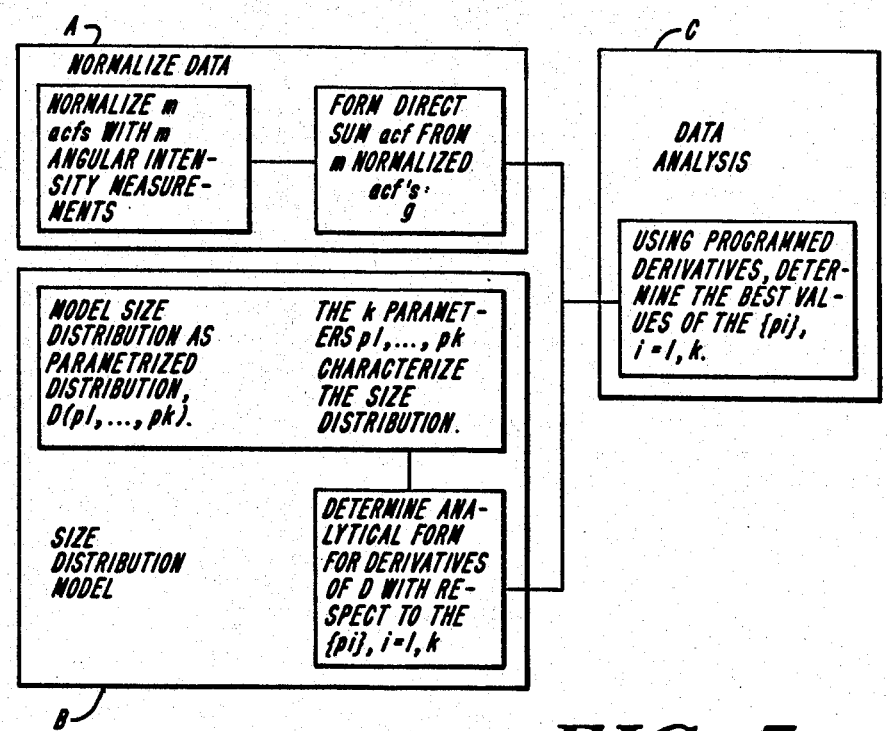

For any of the combinations of angles and conditions at which the CLS and DLS data is measured, FIGS. 5, 6 and 7 illustrate three different signal processing methods which can be implemented by the signal analyzer 52 under the control of controller 54. Each method includes a Normalization Phase, denoted A, and Model Phase, denoted B, and Analysis Phase, denoted C.

In each of the forms of FIGS. 5-7, in the Normalization Phase, the m acf's are first normalized with the angular intensity (CLS) data so that those autocorrelation signals are scaled to the values of the average detected intensities at the m points of detection, forming m normalized acf's. A composite acf is then formed from the direct sum of the m normalized acf's.

In the Model Phase, an analytic, or discrete, model is constructed for use in the Analysis Phase so that the inversion of the equation $$v = J^{-1}(g_1(t), \ldots, g_m(t), i(\theta_1), \ldots, i(\theta_m), i(\theta_{m+1}), \ldots, i(\theta_{m+n}))$$

may be performed. Each of FIGS. 5, 6 and 7 indicates a different exemplary and known form for constructing the model in a conventional manner for ill-conditioned functions.

In FIG. 5, a model size distribution is generated as a histogram having all non-negative components and a kernal J is formed for the transform. To find the size distribution v(r) using this kernel, a programmed digital computer using Non-Negative Least Squares (NNLS) techniques performs a "best fit", see C. Lawson and R. Hanson, "Solving Least Square Problems", Prentice Hall, Inc., Englewood Cliffs, N.J., 1974.

In FIG. 6, a model size distribution is generated as a smoothed histogram with all non-negative components. A kernel J and a smoothing martrix H are formed and a characteristic alpha ($\alpha$) is generated. Then matrix operations are performed on J, H and alpha to reduce the problem to determining the residual vector having the minimum norm subject to linear constraints. To find the size distribution v(r) using J, H and alpha, a programmed digital computer using Least Distance Programming techniques, minimizes the norm of the residuals, $[J_iv]_j - g_i(t_j)$, subject to linear constraints, and matrix operations are then performed to determine v(r); see C. Lawson and R. Hanson, "Solving Least Square Problems", Prentice Hall, Inc., Englewood Cliffs, N.J., 1974.

In FIG. 7, the model size distribution is determined in terms of a parameterized distribution D(p1, p2, ... pk), where the parameters p1, p2 ... pk determine the size distribution. Then an analytical form is determined for derivatives of D with respect to the $\{P_i\}$, i=1, ..., K. A programmed digital computer uses Non-Linear Least Squares fitting techniques to determine the best values of the Pi characterizing v(r) using the program GRADLS; see P. R. Bevington, "Data Reduction and Error Analysis for the Physical Sciences", McGraw Hill Book Co., New York, 1969.

In all of the forms of the invention shown in FIGS. 5-7, the acf's are normalized and then a composite acf is formed. However, in alternate forms of the invention, the acf's may be unity normalized and then used to form the composite acf. Then the kernel J may be normalized and the normalized transformation operator may be used to generate the size distribution. Moreover, the composite acf's in FIGS. 5 and 6 are direct sums of the normalized acf's (and the CLS intensities), where linear transforms are used. In other forms of the inventions, as in FIG. 7, non-linear transforms are used.

Additionally, as described above, the scattered light for the sample is measured alone, forming the basis for a homodyne analysis. Alternatively, the measurement may be made on the scattered light as augmented by non-scattered light from the source, so that a beat signal is in effect produced as the basis for a heterodyne analysis. In those forms, the signals g(t) may be the true autocorrelation of the detected intensity, or may be merely "closely related", for example, where a background level is subtracted out and the square root of the resultant signal is taken. The latter is particularly appropriate for gaussian light in a homodyne configuration.

In the preferred embodiment of FIGS. 1 and 2, the light source 18, detector 28 (including elements 44, 46 and 48) and the autocorrelator 50 are provided by a Langley Ford Model LSA2+ photon correlation spectrometer and a Langley Ford Model 1096 correlator. The signal analyzer 52 and controller 54 are in the form of a Model Universe 137/T digital computer manufactured by Charles River Data Systems, Natick, Mass., having a UNOS operating system with a Fortran 77 Compiler, as produced by Absoft Corporation, Royal Oak, Mich., programmed in accordance with the program set forth in Appendix B. With this configuration, acf and CLS data is collected at two angles, for example, 90° and 30°. As the data is collected, it is automatically stored in the internal memory of the 1096 correlator. After the data at two angles has been collected and stored, the data is transferred to the 137/T computer through a serial (RS-232) port. The 1096 correlator is set to send the data in its 'five channels per line' format. The data, received through the RS-232 port is directly stored to a disk file on the 137/T computer.

The format of the data from the 1096 correlator, as stored in the 137/T computer disk file, is changed into the correct format for the signal processing program, cont2ang.fm, included in Appendix B. This format conversion is accomplished by processing the two data sets (one for each angle) using the 137/T computer programmed in accordance with the program condense.fm shown in Appendix C. Under control of the program, condense.fm, the 137/T computer reads the acf data along with the sample times used in the measurements (also contained in the data sets from the 1096 correlator) and condenses the 256 channels of data for each angle into two sets of 60 channels of data, by combining several channels of the original data into one channel of condensed data. The processed data is written out to a new disk file on the 137/T computer. This process of condensing the data is done only to speed the subsequent data processing, it has no material affect on the sizing results obtained. Under the control of the condense.fm program, the 137/T computer then writes out the 60 acf time points for the first angle, corresponding to the 60 condensed acf points at which the data is measured. The data is written out in the FORTRAN format 5e15.6. Following the acf time points for the first angle are written out the 60 acf time points for the second angle in the same format. This is followed by the 60 condensed acf points for the first angle and then the 60 condensed acf points for the second angle. The acf points are written out in the FORTRAN format 4e17.11.

At this point, a new disk file contains reformatted and condensed data equivalent to the original data collected by the 1096 correlator. This new data file, which contains only time points and acf points for the two angles, if prefixed by a header which informs the signal processing program cont2ang.fm how the data should be handled and gives the program some other information, such as the temperature and viscosities of the sample, the scattering angles, and the like. The contents of the header are described in the first page of the listing in Appendix B and in CONTIN Users Manual, Postfach 10.2209, D-6900 Heidelberg, BRD. For illustrative purposes, a sample header is included in Appendix D. The header is prefixed to the file using the 137/T computer editor, ted.

Figures 8, 9:
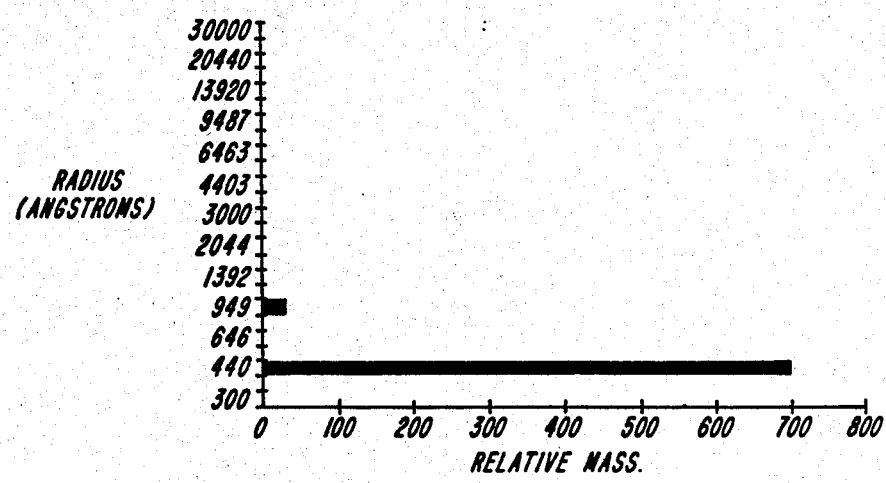
FIGS. 8 and 9 illustrate the mass weighted size distribution determined by an embodiment of the present invention for an exemplary sample of polystyrene latex spheres dispersed in water.

Once the header is prefixed to the data file containing the condensed two angle data, cont2ang.fm is called to process the data and provide the size distribution of the particles contained in the sample. FIGS. 8 and 9 shows the mass weighted size distribution, v(r) generated with this configuration where the sample comprised a mixture of 450 A and 850 A (radius) polystyrene latex spheres (from Seragen Diagnostics) dispersed in water. The measurements were made at scattering angles of 144° (300 second measurement) and 63.2° (900 second measurement) at a temperature of 20 C. FIG. 8 shows a portion of the data output from the cont2ang.fm program for this example, and FIG. 9 shows a graph representative of this data.

The larger sized particles in this sample are less than twice as large as the smaller ones; for light scattering measurements, such relatively closely space peaks are extremely difficult to resolve. The enhanced resolution resulting from combining DLS and CLS data allows clear separation of the two peaks, as shown in FIG. 9.

FIGS. 1–3 also represent embodiments of the invention in which it is not necessary to normalize the DLS data to the CLS data as is required in the embodiments described in conjunction with FIGS. 5–7. In the "non-normalizing" embodiments, the signal analyzer 52 and controller 54 of FIG. 2 and the signal analyzer 66 and controller 68 of FIG. 3 differ from the corresponding elements in the "normalizing" forms of the invention described above. In the preferred form, those elements may also have the form of a Model Universe 137/T digital computer manufactured by Charles River Data Systems, Natick, Mass., programmed as described in more detail below.

FIG. 10 shows a flow chart illustrating the general operation of the system of FIGS. 1 and 2 in one "non-normalizing" form of the invention, including a data collection phase, denoted A, and a data processing or analysis phase, denoted B. In accordance with this non-normalization form of the invention, as shown in FIGS. 1 and 2, the data collection phase A is performed with elements 18 and 28 in two modes. In the first mode, DLS measurements are made an m different measurement conditions, where m is an integer greater than or equal to one, and the autocorrelator 50 provides m autocorrelation functions, denoted acf 1 ... acf m in FIG. 10. In the second mode, the CLS measurements are made at n different measurement conditions, where n is an integer greater than or equal to zero, and m+n is greater than or equal to two, and the integrator 48 provides n integrated intensity values, denoted int m+1, ..., int m+n in FIG. 4. At least two of the m+n measurement conditions are different. These acf and integrated intensity measurements may be made at the same time or sequentially, unless the particle size distribution itself changes substantially with time, since the resultant data for each measurement is substantially independent. Preferably, each of the m measurement conditions differ from each of the n measurement conditions, but there may be CLS and DLS measurements made at the same conditions. In minimum systems, by way of example, for m=1 and n=1, a single DLS measurement and a single CLS measurement at different measurement conditions may be performed, or for m=2 and n=0, two DLS measurements, at different measurement conditions, may be performed. In the latter case, the DLS measurements in effect inherently include some CLS data.

In various forms of the invention, the acf and average intensity measurements are made under different measurement conditions, for example, angles, temperature, hydrodynamic solution characteristics, or polarization angles, i.e. any conditions which establish independent intensity characteristics at the sensor 30. Also, the various acf and average intensity measurements can be made at various combinations of angles and these conditions.

In the embodiment illustrated in FIG. 1, the measurements are made by a single sensor which is controllably positioned to the desired angular positions, as measured with respect to the input axis 24. Polarization controllers in the beam path, and/or sample temperature controllers might also be used to establish independent measurement conditions. However, in the present invention, it is particularly advantageous to utilize separate sensors for CLS measurements and for DLS measurements, since the known criteria for optimal collection optics are diametrically opposed for the respective CLS and DLS measurements. CLS measurements have a highest signal to noise ratio when, at a given angle, scattered light is collected from a relatively large portion of the sample. Conversely, for DLS measurements, high signal to noise ratio is obtained when the collection optics view a relatively small portion of the sample.

It has been found that two separate arcuate photodiode detector arrays (a forward direction array for low, e.g. 6–60 degrees, angle with respect to the beam input axis), and a side direction array for the high, e.g. 60–120 degrees, angle or 90 degrees plus or minus relatively small angles) are well suited for the CLS measurements, and a separate arcuate array (e.g. 45, 90 and 150 degrees) of fiber optic coupled photomultiplier detectors are well suited for the DLS measurements. This configuration is illustrated schematically in FIG. 10A, where, for simplicity, only the light source, sample, CLS sensor arrays, and DLS sensor array are shown. In FIG. 10A, elements corresponding to elements in FIG. 1 are identified with the same reference designations. In the configuration of FIG. 10A, the sample 12 is held in a rectangular cross-section cuvette having opposed pairs of parallel planar lateral sidewalls. The CLS low angle (near zero degrees) sensors and CLS high angle (near 90 degrees) sensors are in arcuate arrays lying in the X-Y plane and the X-Z plane respectively. The DLS photodiode array also lies in the X-Z plane.

Figure 11:
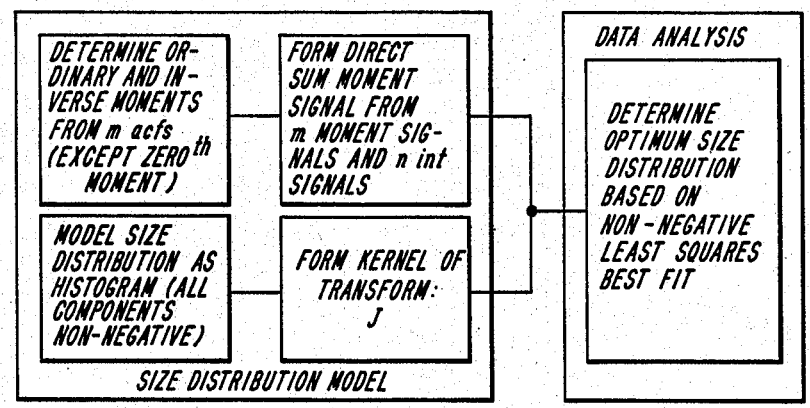
FIGS. 11–13 show detailed flow charts for three implementations of the data processing step of the flow chart of FIG. 10.
Figure 12:
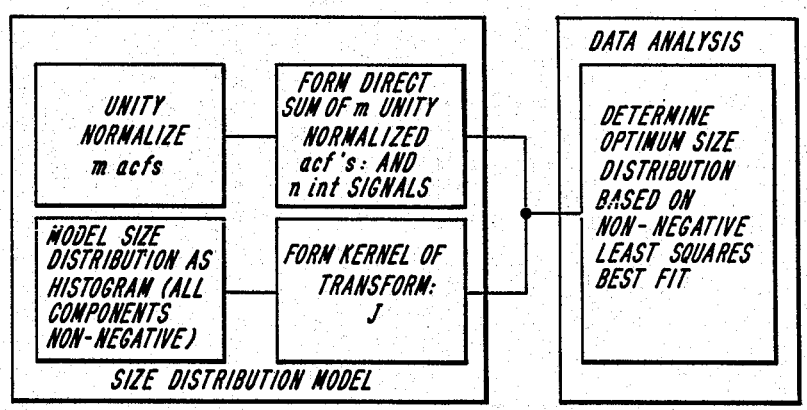
Figure 13:
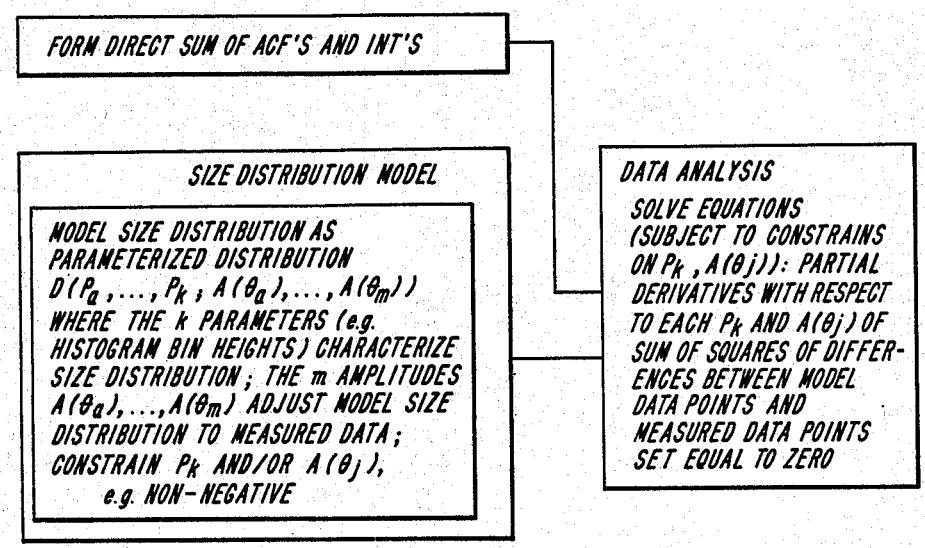

For any of the combinations of angles and/or conditions at which the CLS and DLS data are measured, FIGS. 11, 12 and 13 illustrate three different signal processing methods which can be implemented by the signal analyzer 52 under the control of controller 54. Each method includes a Preprocessing Phase, and Model Phase, and Analysis Phase. In each of FIGS. 11–12, the Analysis Phase is the same non-negative least squares (NNLS) curve fitting process as described in conjunction with FIG. 5, although alternative curve-fitting techniques may be used. In FIG. 13, the Analysis Phase is similar to that shown in FIG. 7.

In the form of FIG. 11, in the Preprocessing Phase, each of the m acf's are first processed to extract their moments (except the zero$^{th}$ moment), and then the resultant m moment signals are combined with the n int signals to form a weighted direct sum. The latter composite scattered light signal is then transferred to the Analysis Phase.

The size distribution Model Phase is substantially the same as that described in connection with FIG. 5, except that the model is constructed for use in the Analysis Phase so that the inversion of the equation $$v = J^{-1}(m_1, \ldots, m_m, i(\theta_{m+1}), \ldots, i(\theta_{m+n}))$$

may be performed, when $m_i$ represents the moments (except the zero$^{th}$ moment) for the $i^{th}$ acf. Alternatively, the forms for constructing the model shown in and described in conjunction with FIGS. 6 and 7 may be used.

In FIG. 11, a model size distribution is generated as a histogram having all non-negative components and a kernel J is formed for the transform. To find the size distribution $v(r)$ using this kernel, a programmed digital computer using Non-Negative Least Squares (NNLS) techniques performs a "best fit."

More particularly, to extract the inverse moments from the acf's, the homodyne scattered light acf, $G(t)$, must first be processed to yield the heterodyne acf, $g(t)$:

$$g(t) = (\sqrt{(G(t) - \text{baseline})})/g(0)$$

where the baseline can be measured conventionally (see, e.g., B. Chu, "Laser Light Scattering", Academic Press, 1976). Then, the natural log of $g(t)$ is curve fitted to a power series in the delay time, t:

$$\ln(g(t)) = K_0/0! + K_1 t/1! + K_2 t^2/2! + \ldots$$

The $\{K_i, i = 0, \ldots, n\}$ are related to the inverse moments of the particle size distribution, $\{k_{-i}, i = 1, \ldots, n\}$, by the equation $k_{-i} = C^i K_i$ where $C = 3\pi\eta/(k_B T q^2)$, $\eta$ is the viscosity of the fluid suspending the particles, $k_B$ is Boltzmann's constant and T is the absolute temperature. q is the magnitude of the scattering vector, defined by $q = 4\pi n \sin(\theta/2)/\lambda$. n is the refractive index of the fluid suspending the particles, $\theta$ is the scattering angle and $\lambda$ is the wavelength of the incident light. The inverse moments are the average values of the inverse central diameters of the particle size distribution, e.g. the 1st inverse moment is the average value of the inverse diameter, $<1/d>$, the 2nd inverse moment is $<<1/d^2> - <1/d>^2>$, . . . . The ordinary moments are $<d>$, $<<d^2> - <d>^2>$, . . . . The process by which this inverse moment extraction is accomplished is described in detail in D. E. Koppel, J. of Che. Phys., vol. 57, p. 4814, 1972.

If a sufficient number of inverse moments are taken, the particle size distribution is completely specified. In the preferred embodiment, the 1st and 2nd order inverse moments are sufficient, taken together with the 1st order moment defined by:

$$k_1 = (1/C) \sum_{i=0}^{A} (g(t_{i+1}) - g(t_i)) \cdot (t_{i+1} - t_i)/2,$$

where A equals the number of time points in the acf. The zero$^{th}$ order moment, which contains the normalization factor, is omitted. Positive subscripts on k are indicative of moments and negative subscripts are indicative of inverse moments.

The particle size distribution is related to the moments extracted from the acfs. As a result, the matrix equation $Kv = g$, relates the product of the kernel matrix, K, by the size distribution vector, v, to the measurement vector, g, where the components of the vector, v, are numbers $\{v_i\}$. These components of v represents the relative amount of particles of size indexed by i, that is, the desired size distribution. The components of the measurement vector, g, are the moments and inverse moments extracted from the acf's and the CLS data. The components of the matrix, K may be defined in the following manner. First, the matrix may be expressed as equation as a group of separate equations:

$$\sum_{i=1}^{B} v_i \cdot c_i(\theta) \cdot d_i^j = k_j(\theta) \quad j = -N, \ldots, +M$$

where B equals the number of bins in the size histogram, N equals the number of inverse moments, M equals the number of ordinary moments, $c_i(\theta)$ is the intensity conversion factor for the $i^{th}$ size bin in the distribution and for the scattering angle, $\theta$, and $d_i$ is the particle diameter for particles in the $i^{th}$ size bin in the distribution. The moments $k_j$ are labelled with the scattering angle, $\theta$, to indicate that the different moments are extracted for each DLS scattering angle used in the analysis. The equation above defines the DLS-related components of the kernel matrix, K, giving:

$$K_{ji}(\theta) = c_i(\theta) \cdot d_i^j.$$

The matrix K is augmented, by direct sum, with the CLS portion of the kernel, in the same manner as set forth in U.S. patent application Ser. No. 817,048.

The matrix equation, $Kv = g$, with components defined as above is then solved with the non-negative least squares (NNLS) curve fitting algorithm, as described in conjunction with FIG. 5.

Appendix E shows a program for processing the acf's using the 1st, 2nd and 3rd inverse moments and the 1st ordinary moment to constrain the curve fitting.

In the form of FIG. 12, the m acf's are unity nomalized (i.e. normalized so that $g(0) = 1$ for each acf) and then a "modified" kernel is used in the form described by the equations:

$$\frac{\sum_{i=1}^{B} v_i c_i^{(k)} e^{-\Gamma_i^{(k)} t_j}}{\sum_{i=1}^{B} v_i c_i^{(k)}} = g(t_j)$$

$$k = 1, \ldots, m$$

$$j = 1, \ldots, \text{number of time points in each } acf(A)$$

where k indexes the scattering angle, i is the size (histogram bin number), j is time (for the acf's), v is the weight distribution and $C^{(k)}$ is the conversion of weight to intensity at the $k^{th}$ angle ($c_i^{(k)}$ corresponds to $c_i(\theta)$, as used above, where $\theta$ is the $k^{th}$ angle). Finally, the curve fit is determined by minimizing the $\{v_i\}$ in the expression $$\sum_{x=1}^{m} \sum_{j=1}^{A} \left( \sum_{i=1}^{B} v_i c_i^{(k)} [e^{-\Gamma^{(k)}t_j} - g(t_j)] \right)^2$$

This process allows the information in the acf to be directly utilized, rather than first extracting the moments, as in the process of FIG. 11. In addition, all information in the acf's is utilized rather than just that in the $n^{th}$ ($n \neq 0$) order moments. The Model Phase and Analysis Phase are substantially the same as those in FIG. 11. Appendix F shows a program for processing the unity normalized acf's at two angles to constrain the curve fitting.

In the form of FIG. 13, generalized curve fitting techniques are applied to the acf's which have not been normalized at all. Generally, $$A(\theta_k) \sum_{i=1}^{B} v_i [c_i^{(k)} e^{-\Gamma^{(k)}t_j}] = g^{(k)}(t_j)$$

$k = 1, \ldots, m$ $j = 1, \ldots,$ number of time points in each $acf(A)$ where $A(\theta_k)$ is the amplitude of the non normalized kth acf. v is obtained by curve fitting the equations $$\frac{\partial}{\partial v_i} \sum_{k=1}^{m} \sum_{j=1}^{A} \left[ A(\theta_k) \sum_{i=1}^{B} v_i c_i^{(k)} e^{\Gamma^{(k)}t_j} - g^{(k)}(t_j) \right]^2 = 0$$

$i = 1, \ldots, B$ $$\frac{\partial}{\partial A(\theta_k)} \sum_{k=1}^{m} \sum_{j=1}^{A} \left[ A(\theta_k) \sum_{i=1}^{B} v_i c_i^{(k)} e^{\Gamma^{(k)}t_j} - g^{(k)}(t_j) \right]^2 = 0$$

$k = 1, \ldots, m$ where $v_i$ is constrained to be non-negative for all of the histogram bins and $A(\theta_k)$ is constrained to be non-negative for all of the DLS measurement angles.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

APPENDIX B

```
C     CONT2ANG.FM
C
C
C     RUSER
C     10        TEMPERATURE (DEG C)
C     11        SAMPLE VISCOSITY (CP)
C     12        SCATTERING ANGLE (DEGREES)
C     13        INCIDENT WAVELENGTH (A)
C     14        REFRACTIVE INDEX OF SAMPLE
C     15        BACKROUND TO SUBTRACT (1ST Q)
C     16        BACKROUND TO SUBTRACT (2ND Q)
C     17        2ND SCATTERING ANGLE (DEGREES)
C     18        RELATIVE AMPLITUDE CORRECTION FOR Q1/Q2
C     20        Q1 (NOT INPUT; USED INTERNALLY)
C     21        Q2 (NOT INPUT; USED INTERNALLY)
C     22        1/ACF(1) (NOT INPUT; USED INTERNALLY)
C     23        1/(ACF(ISTART)*SQRT(RUSER(18)) (NOT INPUT; USED INTERNALLY)
C     24        I1/(I1+I2) ; (I = TOTAL SCATTERED INTENSITY)
C     25        WEIGHTING FACTOR (1/VAR) FOR 1ST ANGLE (LUSER(12,14)=TRUE)
C     26        WEIGHTING FACTOR (1/VAR) FOR 2ND ANGLE (LUSER(12)=TRUE)
C
C     LUSER
C     11        T IF DATA AT TWO Q'S IS TO BE ANALYZED
C     12        T (WITH 13 F) WITH 2ANG DATA, WEIGHTS 2ND ANGLE TO RUSER(26)
C     13        T TO INCLUDE VOLUME (R**3) IN KERNEL
C     14        T (WITH 12 T) WITH 2ANG DATA, WEIGHTS 1ST ANGLE TO RUSER(25)
C     15        T TO INCLUDE FORM FACTOR IN KERNAL WITH SINGLE ANGLE DATA
C     16        T IF SQUARE ROOT OF ACF IS NOT TO BE TAKEN
C     17        T TO EXCLUDE FORM FACTOR IN KERNEL WITH 12 OR 12 AND 14 TRUE
C     18        T IF ACF'S ARE NOT TO BE NORMALIZED (TOTAL INTENSITIES
C               MUST BE ACCURATELY MEASURED AND COMPENSATED IN RUSER(18)).
C     19        T IF MIE INTENSITY CORRECTION IS TO BE USED. (TAKES SPECIAL
C               USERK
C     20        T IF MIE INTENSITY IS TO BE IGNORED IN TWO ANGLE FITS.
C
C     IUSER
C     11        NUMBER OF FIRST DATA POINT OF 2ND Q (USED ONLY IF LUSER(11)=T)
C     12        NUMBER OF DATA POINTS TO USE TO EXTRPOLATE TO ACF(0)
C
      DOUBLE PRECISION PRECIS, RANGE                                    MAIN  5
      DOUBLE PRECISION A, AA, AEQ, AINEQ, PIVOT, REG, RHSNEQ,           MAIN  6
     1 S, SOLBES, SOLUTN, VALPCV, VALPHA, VK1Y1, WORK                   MAIN  7
```

```
      LOGICAL DOMOM, DOUSIN, DOUSNQ, DOUSOU, LAST, NONNEG, ONLY1, PRWT,    MAIN 8
     + PRY, SIMULA, LUSER                                                   MAIN 9
      LOGICAL LBIND                                                         MAIN 0
      DIMENSION T(544), SQRTH(544), Y(544), EXACT(544), YLYFIT(544)         MAIN 1
      DIMENSION G(44), CQUAD(44), VK1Y1(44), S(44,3), VALPHA(44),           MAIN 2
     + VALPCV(44), SOLUTN(44), IISIGN(44), SOLBES(44), SOLPK(44),           MAIN 3
     + AA(44,44)                                                            MAIN 4
      DIMENSION AINEQ(42,44), RHSNEQ(42), LBIND(42)                         MAIN 5
      DIMENSION A(44,44), IWORK(44)                                         MAIN 6
      DIMENSION REG(42,44)                                                  MAIN 7
      DIMENSION AEQ(11,44), PIVOT(11)                                       MAIN 8
      DIMENSION WORK(1976)                                                  MAIN 9
      DIMENSION LSDONE(90,3,2), VDONE(90)                                   MAIN 0
C
C     THE FOLLOWING DIMENSION STATEMENT IS TO ALLOW MIE INTENSITY CORRECTIONS.
C     (LUSER(19) SHOULD BE SET TRUE FOR MIE CORRECTIONS AND THE MIE KERNEL
C     ADDITION TO THE PROGRAM MUST BE IN PLACE.  WHEN OTHER INTENSITY
C     CORRECTIONS ARE EMPLOYED, A DIFFERENT USERK MUST BE INSERTED IN THIS
C     PROGRAM, BUT THE REVISIONS IN THIS ROUTINE NEED NOT BE CHANGED.
      REAL MIEINT(50,2), MIE
C
      CHARACTER IFORMT(70), IFORMW(70), IFORMY(70), LA(6,46), ITITLE(80)
      COMMON /SBLOCK/ PRECIS, RANGE, SRMIN,                                 MAIN 6
     1 ALPST(2), GMNMX(2), PLEVEL(2,2), RSVMNX(2,2), RUSER(100),            MAIN 7
     + EXMAX, SRANGE
                                                                            MAIN 8
      COMMON /IBLOCK/ IGRID, IPLRES, IPRINT, IQUAD, IUNIT, IWT,              MAIN 9
     + LINEPG, MIOERR, MQPITR, NEQ, NERFIT, NG, NINTT, NLINF, NORDER,       MAIN 0
     + ICRIT(2), IPLFIT(2),                                                 MAIN 1
     +           IUSER(50), LSIGN(4,4), MOMNMX(2), NENDZ(2),                MAIN 2
     + NFLAT(4,2), NGL, NGLF1, NIN, NINEQ, NNSGN(2), NOUT, NQPROG(2),       MAIN 3
     + NSGN(4), NY                                                          MAIN 4
      COMMON /CBLOCK/ IFORMT, IFORMW, IFORMY, LA, ITITLE
      COMMON /LBLOCK/ DOMOM, DOUSIN, DOUSNQ, DOUSOU, LAST, NONNEG,          MAIN 5
     1 ONLY1, PRWT, PRY, SIMULA,                                            MAIN 6
     + LUSER(30)                                                            MAIN 7
C
C     THE FOLLOWING LABELLED COMMON WAS ADDED TO AVOID THE NECESSITY OF
C     CONSTANTLY RECOMPUTING THE KERNAL. THE COMMON BLOCK IS ALSO IN
C     GETROW. ASSOCIATED WITH THIS ADDITION IS A SMALL ADDED SECTION IN
C     THIS ROUTINE AND ONE LINE CHANGED IN GETROW.
C     THESE CHANGES ARE MARKED IN THE SOURCE CODE.
C
      COMMON /KERNAL/ USERKK(544,35)
      DATA MY/544/, MA/44/, MG/44/, MREG/42/, MINEQ/42/, MEQ/11/,           MAIN 4
     1 MDONE/90/, MWORK/1976/                                               MAIN 5
      CALL INIT                                                             MAIN 6
  100 CALL INPUT (EXACT,G,MA,MEQ,MG,MINEQ,MREG,MWORK,MY,                    MAIN 0
     + SQRTH,T,Y)
      CALL SETGRD (CQUAD,G,GMNMX,IGRID,IQUAD,MG,NG,NOUT)                    MAIN 4
C
C     THE FOLLOWING SECTION WAS ADDED TO STORE THE KERNAL MATRIX SO THAT
C     IT NEED NOT BE CONSTANTLY RECOMPUTED. THE LABELLED COMMON IN THIS
C     ROUTINE AND IN GETROW STORE THE VALUES, ONE LINE IN GETROW IS
C     CHANGED TO USE THE STORED VALUES.
C
C     THE SECTION HAS BEEN MODIFIED TO ALLOW MIE CORRECTIONS WITHOUT
C     TAKING UNDUE AMOUNTS OF TIME. 10-23-85.
C
      IF(LUSER(19)) THEN
         DO 19 JG=1,NG
            MIEINT(JG,1)=MIE(G(JG),RUSER,12)
            MIEINT(JG,2)=MIE(G(JG),RUSER,17)
            IF(LUSER(13)) THEN
               WGHCOR=G(JG)*G(JG)*G(JG)
               MIEINT(JG,1)=MIEINT(JG,1)/WGHCOR
               MIEINT(JG,2)=MIEINT(JG,2)/WGHCOR
            ENDIF
   19    CONTINUE
         BIGG=0.
         DO 18 JG=1,NG
         DO 18 JJ=1,2
            IF(MIEINT(JG,JJ).GT.BIGG) BIGG=MIEINT(JG,JJ)
   18    CONTINUE
```

```
        DO 17 JG=1,NG
        DO 17 JJ=1,2
            MIEINT(JG,JJ)=MIEINT(JG,JJ)/BIGG
17      CONTINUE
        OPEN(3,FILE='mieang1',STATUS='new')
        OPEN(4,FILE='mieang2',STATUS='new')
        WRITE(3,*) NG
        WRITE(3,511) (G(JG)/5.,MIEINT(JG,1),JG=1,NG)
        WRITE(4,*) NG
        WRITE(4,511) (G(JG)/5.,MIEINT(JG,2),JG=1,NG)
511     FORMAT(E10.3,1x,E10.3)
        CLOSE(3)
        CLOSE(4)
        DO 20 JT=1,NY
        DO 20 JG=1,NG
            IF(.NOT.LUSER(20)) THEN
                IF(JT.LT.IUSER(11))USERKK(JT,JG)=USERK(JT,T,JG,G)*
     +                          MIEINT(JG,1)
                IF(JT.GE.IUSER(11))USERKK(JT,JG)=USERK(JT,T,JG,G)*
     +                          MIEINT(JG,2)
            ELSE
                IF(JT.LT.IUSER(11))USERKK(JT,JG)=USERK(JT,T,JG,G)
                IF(JT.GE.IUSER(11))USERKK(JT,JG)=USERK(JT,T,JG,G)
            ENDIF
            IF(JT.LT.IUSER(11) .AND. .NOT.LUSER(18))
     +                          USERKK(JT,JG)=USERKK(JT,JG)*RUSER(22)
            IF(JT.GE.IUSER(11) .AND. .NOT.LUSER(18))
     +                          USERKK(JT,JG)=USERKK(JT,JG)*RUSER(23)
20      CONTINUE
        ELSE
        DO 21 JT=1,NY
        DO 21 JG=1,NG
            USERKK(JT,JG)=USERK(JT,T,JG,G)
21      CONTINUE
        ENDIF
C
C   END OF ADDED LINES
C
        IF (SIMULA)   CALL USERSI (EXACT,MY,T,Y)                        MAIN 8
        IF (SIMULA)   CALL WRITYT (EXACT,G,IPRINT,IWT,MG,NOUT,NY, PRY,  MAIN 2
     +SIMULA,SQRTW,T,Y)                                                 MAIN 3
        IF (.NOT.ONLY1)   CALL USERSX (EXACT,G,MG)                      MAIN 7
        MINEQ=0                                                         MAIN 8
        NGL=NG+NLINF                                                    MAIN 9
        NGLP1=NGL+1                                                     MAIN 0
        IF (DOUSNQ)   CALL USERNQ (AINEQ,MG,MINEQ)                      MAIN 4
        IF (NONNEG)   CALL SETNNG (AINEQ,MINEQ,NG,NGLP1,NINEQ)          MAIN 8
        IF (IWT.EQ.1 .OR. IWT.EQ.4) GO TO 200                           MAIN 9
        CALL ANALYZ (1,                                                 MAIN 5
     + A,AA,AEQ,AINEQ,CQUAD,EXACT,G,IISIGN,IWORK,LBIND,LSDONE,MA,       MAIN 6
     + MDONE,MEQ,MG,MINEQ,MREG,MWORK,MY,PIVOT,REG,RHSNEQ,S,SOLBES,      MAIN 7
     + SOLPK,SOLUTN,SQRTW,T,VALPCV,VALPHA,VDONE,VK1Y1,WORK,             MAIN 8
     4 Y,YLYFIT)                                                        MAIN 9
        CALL SETWT (                                                    MAIN 3
     1 CQUAD,G,IUNIT,IWT,MWORK,MY,NERFIT,NG,NGL,NLINF,NOUT,NY,PRWT,     MAIN 4
     2 SOLBES,SQRTW,SRANGE,T,WORK,Y,YLYFIT)                             MAIN 5
200     CALL ANALYZ (2,                                                 MAIN 9
     1 A,AA,AEQ,AINEQ,CQUAD,EXACT,G,IISIGN,IWORK,LBIND,LSDONE,MA,       MAIN 0
     2 MDONE,MEQ,MG,MINEQ,MREG,MWORK,MY,PIVOT,REG,RHSNEQ,S,SOLBES,      MAIN 1
     3 SOLPK,SOLUTN,SQRTW,T,VALPCV,VALPHA,VDONE,VK1Y1,WORK,             MAIN 2
     4 Y,YLYFIT)                                                        MAIN 3
        IF (.NOT.LAST)   GO TO 100                                      MAIN 4
        STOP                                                            MAIN 5
        END                                                             MAIN 6
        BLOCK DATA                                                      BLCKD3
        DOUBLE PRECISION PRECIS, RANGE                                  BLCKD4
        CHARACTER IFORMT(70), IFORMW(70), IFORMY(70),LA(6,46),ITITLE(80)
        LOGICAL DOMOM, DOUSIN, DOUSNQ, DOUSOU, LAST, NONNEG, ONLY1, PRWT, BLCKD5
     1 PRY, SIMULA, LUSER                                               BLCKD6
        COMMON /SBLOCK/ PRECIS, RANGE, SRMIN,                           BLCKD7
     1 ALPST(2), GMNMX(2), PLEVEL(2,2), RSVMNX(2,2), RUSER(100),        BLCKD8
     2 EXMAX, SRANGE                                                    BLCKD9
        COMMON /IBLOCK/ IGRID, IPLRES, IPRINT, IQUAD, IUNIT, IWT,       BLCKD0
```

```
      1 LINEPG, MIOERR, MQPITR, NEQ, NERFIT, NG, NINTT, NLINF, NORDER,    BLCKD1
      2 ICRIT(2), IPLFIT(2),                                                BLDKD2
      3              IUSER(50), LSIGN(4,4), MOMNMX(2), NENDZ(2),            BLCKD3
      4 NFLAT(4,2), NGL, NGLP1, NIN, NINEQ, NNSGN(2), NOUT, NQPROG(2),     BLCKD4
      5 NSGN(4), NY                                                         BLCKD5
        COMMON /CBLOCK/ IFORMT, IFORMW, IFORMY, LA,ITITLE
        COMMON /LBLOCK/ DOMOM, DOUSIN, DOUSNQ, DOUSOU, LAST, NONNEG,      BLCKD6
      1 ONLY1, PRWT, PRY, SIMULA,                                          BLCKD7
      2 LUSER(30)                                                          BLCKD8
        DATA RANGE/1.D250/, SRANGE/1.E35/, NIN/5/, NOUT/9/                 BLCKD4
        DATA ALPST/2*0./, GMNMX/1., 100./, PLEVEL/4*.5/,                   BLCKD5
      1 RSVMNX/2*1., 1.E3, 1.E-3/, RUSER/100*0./, SRMIN/.01/               BLCKD6
        DATA ICRIT/2*1/,                                                   BLCKD7
      1 IFORMT/'(','5','E','1','5','.','6',')',62*' '/,                    BLCKD8
      2 IFORMW/'(','5','E','1','5','.','6',')',62*' '/,                    BLCKD9
      3 IFORMY/'(','5','E','1','5','.','6',')',62*' '/,                    BLCKD0
      4 IGRID/2/, IPLFIT/2*2/, IPLRES/2/, IPRINT/3/, IQUAD/3/, IUNIT/-1/, BLCKD1
      5 IUSER/50*0/, IWT/1/, LINEPG/60/,                                   BLCKD2
      6 LSIGN/16*0/, MIOERR/5/, MOMNMX/-1, 3/, MQPITR/35/,                 BLCKD3
      7 NENDZ/1, 1/, NEQ/0/, NERFIT/10/, NFLAT/8*0/, NG/35/,               BLCKD4
      8 NINTT/1/, NLINF/0/, NNSGN/2*0/, NORDER/2/, NQPROG/19, 0/,          BLCKD5
      9 NSGN/4*0/                                                          BLCKD6
        DATA DOMOM/.TRUE./, DOUSIN/.FALSE./, DOUSNQ/.TRUE./,              BLCKD7
      1 DOUSOU/.FALSE./, LAST/.TRUE./,                                     BLCKD8
      2 LUSER/30*.FALSE./, NONNEG/.TRUE./, ONLY1/.TRUE./,                  BLCKD9
      3 PRWT/.TRUE./, PRY/.TRUE./,                                         BLCKD0
      4 SIMULA/.FALSE./                                                    BLCKD1
        END                                                                BLCKD4
        SUBROUTINE ANALYZ (ISTAGE,                                         ANLYZ3
      1 A,AA,AEQ,AINEQ,CQUAD,EXACT,G,IISIGN,IWORK,LBIND,LSDONE,MA,         ANLYZ4
      2 MDONE,MEQ,MG,MINEQ,MREG,MWORK,MY,PIVOT,REG,RHSNEQ,S,SOLBES,        ANLYZ5
      3 SOLPK,SOLUTN,SQRTW,T,VALPCV,VALPHA,VDONE,VK1Y1,WORK,               ANLYZ6
      4 Y,YLYFIT)                                                          ANLYZ7
        DOUBLE PRECISION PRECIS, RANGE                                     ANLYZ8
        DOUBLE PRECISION A, AA, ABS, AEQ, AINEQ, ALPBES, ALPHA,            ANLYZ9
      1 ALPOLD, ONE, PIVOT, RALPFL, REG, RHSNEQ,                           ANLYZ0
      2 S, SOLBES, SOLUTN, VALPCV, VALPHA, VK1Y1, WORK, ZERO               ANLYZ1
        DOUBLE PRECISION SOL1(44),ACDIFF(544),SOLDIF(44),DDUM,KERROW(44)
        LOGICAL FSTSOL
        LOGICAL DOMOM, DOUSIN, DOUSNQ, DOUSOU, LAST, NONNEG, ONLY1, PRWT, ANLYZ2
      1 PRY, SIMULA, LUSER                                                 ANLYZ3
        LOGICAL LDUM, LBIND, FLAT, PPLTPR, HEADNG, NEWPAG                  ANLYZ4
        CHARACTER IFORMT(70), IFORMW(70), IFORMY(70),LA(6,46), ITITLE(80)
        DIMENSION A(MA,MG), T(MY), Y(MY), SQRTW(MY), G(MG), CQUAD(MG),    ANLYZ5
      1 REG(MREG,MG), AEQ(MEQ,MG), PIVOT(MEQ), VK1Y1(MG), S(MG,3),         ANLYZ6
      2 AINEQ(MINEQ,MG), VALPHA(MG), VALPCV(MG), RHSNEQ(MINEQ),            ANLYZ7
      3 WORK(MWORK), IWORK(MA), EXACT(MG), SOLUTN(MG), LBIND(MINEQ),       ANLYZ8
      4 IISIGN(MG), SOLBES(MG), LSDONE(MDONE,3,2), VDONE(MDONE),           ANLYZ9
      5 SOLPK(MG), YLYFIT(MY), AA(MG,MG)                                   ANLYZ0
        DIMENSION PREJ(2), LLSIGN(5), SAVBES(7)
        CHARACTER IHOLER(6)
        COMMON /SBLOCK/ PRECIS, RANGE, SRMIN,                              ANLYZ2
      1 ALPST(2), GMNMX(2), PLEVEL(2,2), RSVMNX(2,2), RUSER(100),          ANLYZ3
      2 EXMAX, SRANGE                                                      ANLYZ4
        COMMON /IBLOCK/ IGRID, IPLRES, IPRINT, IQUAD, IUNIT, IWT,          ANLYZ5
      1 LINEPG, MIOERR, MQPITR, NEQ, NERFIT, NG, NINTT, NLINF, NORDER,    ANLYZ6
      2 ICRIT(2), IPLFIT(2),
      3              IUSER(50), LSIGN(4,4), MOMNMX(2), NENDZ(2),            ANLYZ8
      4 NFLAT(4,2), NGL, NGLP1, NIN, NINEQ, NNSGN(2), NOUT, NQPROG(2),    ANLYZ9
      5 NSGN(4), NY                                                        ANLYZ0
        COMMON /CBLOCK/ IFORMT, IFORMW, IFORMY,LA, ITITLE
        COMMON /LBLOCK/ DOMOM, DOUSIN, DOUSNQ, DOUSOU, LAST, NONNEG,      ANLYZ1
      1 ONLY1, PRWT, PRY, SIMULA,                                          ANLYZ2
      2 LUSER(30)                                                          ANLYZ3
        DATA IHOLER/'A','N','A','L','Y','Z'/, RALPHA/1./                   ANLYZ4
        ABS(ALPHA)=DABS(ALPHA)                                             ANLYZ5
        SINGLE(ONE)=SNGL(ONE)                                              ANLYZ6
        ZERO=0.D0                                                          ANLYZ9
        ONE=1.D0                                                           ANLYZ1
        CALL SEQACC (                                                      ANLYZ6
```

```
      1 A,CQUAD,G,ISTAGE,IUNIT,IWT,MA,MG,NG,NGL,NGLP1,NLINF,NY,           ANLYZ7
      2 RANGE,SQRTW,T,Y)                                                  ANLYZ8
        NGLY=MINO(NGL,NY)                                                 ANLYZ9
        NGLE=NGL-NEQ                                                      ANLYZ0
        CALL SETREG (MG,MREG,NENDZ,NG,NGL,NGLE,NGLP1,NORDER,              ANLYZ4
      1 NOUT,NREG,PRECIS,REG)                                             ANLYZ5
        IF (NEQ .GT. 0) CALL USEREQ (AEQ,CQUAD,MEQ,MG)                    ANLYZ9
        CALL ELIMEQ (AEQ,MEQ,MG,PIVOT,NEQ,NGL,A,MA,REG,MREG,NREG,NGLP1,   ANLYZ3
      1 NGLY,VK1Y1,RANGE)                                                 ANLYZ4
        IF (NORDER.EQ.0 .AND. NEQ.EQ.0) GO TO 300                         ANLYZ5
        CALL SVDRS2 (REG(1,NEQ+1),MREG,NREG,NGLE,REG(1,NGLP1),MREG,       ANLYZ9
      1 1,S,IERROR,RANGE)                                                 ANLYZ0
        IF (IERROR .NE. 1) CALL ERRMES (1,.TRUE.,IHOLER,NOUT)             ANLYZ1
        CALL DIAREG (A,AEQ,MA,MEQ,MG,MREG,NEQ,NGL,NGLE,NGLY,NOUT,PIVOT,   ANLYZ2
      1 RANGE,REG,S)                                                      ANLYZ3
  300 CALL SVDRS2 (A,MA,NGLY,NGLE,A(1,NGLP1),MA,1,S,IERROR,RANGE)         ANLYZ8
        IF (IERROR .NE. 1) CALL ERRMES (2,.TRUE.,IHOLER,NOUT)             ANLYZ9
        CALL DIAGA (A,MA,MG,MREG,NEQ,NGL,NGLE,NGLP1,NGLY,REG,S)           ANLYZ0
        DO 320 J=1,NGLE                                                   ANLYZ1
        YLYFIT(J)=S(J,1)                                                  ANLYZ2
  320 CONTINUE                                                            ANLYZ3
 5320 FORMAT (//30X,'SINGULAR VALUES'//(1P10E13.3))                       ANLYZ4
        WRITE (NOUT,5320) (YLYFIT(J),J=1,NGLE)                            ANLYZ5
        IF (NINEQ .GT. 0) CALL SETGA1 (NINEQ, A,AINEQ,MA,MG,MINEQ,MREG,   ANLYZ9
      1NGL,NGLE,REG)                                                      ANLYZ0
        IF (MAXO(NQPROG(1),NQPROG(2)).LE.0 .AND. ALPST(ISTAGE).LE.0.)     ANLYZ1
      1 CALL ERRMES (3,.TRUE.,IHOLER,NOUT)                                ANLYZ2
        BTEST=SRANGE                                                      ANLYZ3
        ALPBES=ZERO                                                       ANLYZ4
        VARZ=SRANGE                                                       ANLYZ5
        LDUM=.TRUE.                                                       ANLYZ9
        DO 410 ICOL=1,2                                                   ANLYZ0
          IF (ALPST(ISTAGE).LE.0. .OR. ICOL.EQ.1) GO TO 412               ANLYZ1
          K=1                                                             ANLYZ2
          ALPHA=ALPST(ISTAGE)                                             ANLYZ3
          BTEST=SRANGE                                                    ANLYZ4
          GO TO 425                                                       ANLYZ5
  412   IF (NQPROG(ICOL)-1) 410,420,415                                   ANLYZ6
  415   RTOT=RSVMNX(2,ICOL)/(RSVMNX(1,ICOL)*PRECIS)                       ANLYZ7
          IF (RTOT .LE. 1.) CALL ERRMES (4,.TRUE.,IHOLER,NOUT)            ANLYZ8
          RALPHA=RTOT**(1./FLOAT(NQPROG(ICOL)-1))                         ANLYZ9
  420   ALPHA=RSVMNX(1,ICOL)*PRECIS*S(1,1)                                ANLYZ0
          K=NQPROG(ICOL)                                                  ANLYZ1
          FSTSOL=.TRUE.
  425   DO 430 J=1,K                                                      ANLYZ2
          CALL SETVAL (ALPHA,LDUM,NINEQ,                                  ANLYZ3
      1 A,AINEQ,MA,MG,MINEQ,MREG,NGL,NGLE,REG,RHSNEQ,S,VALPCV,VALPHA,     ANLYZ4
      2 VK1Y1)                                                            ANLYZ5
          NEWPAG=IABS(IPRINT).GE.3 .OR. (ISTAGE.EQ.2 .AND.                ANLYZ6
      1   IPRINT.GT.0) .OR. LDUM                                          ANLYZ7
          PPLTPR=IABS(IPRINT).GE.2 .OR. ISTAGE.EQ.2                       ANLYZ8
          HEADNG=PPLTPR .OR. LDUM                                         ANLYZ9
          CALL LDPETC (.TRUE.,NINEQ,.TRUE.,ICRIT(ISTAGE),DOMOM,PPLTPR,    ANLYZ0
      1   .TRUE.,ALPHA,HEADNG,NEWPAG,ALPBES,VAR,                          ANLYZ1
      2   A,AA,AINEQ,BTEST,CQUAD,DEGFRE,DEGFRZ,EXACT,G,IERROR,            ANLYZ2
      3   ISTAGE,IWORK,LBIND,MA,MG,MINEQ,MREG,MWORK,MY,                   ANLYZ3
      4   NGLE,NGLY,PREJ,REG,RHSNEQ,S,SAVBES,SOLBES,                      ANLYZ4
      5   SOLUTN,SQRTW,T,VALPCV,VALPHA,VARREG,VARZ,WORK,Y,YLYFIT)         ANLYZ5
          IF (IERROR.NE.1) GO TO 980
          IF(.NOT.FSTSOL) GO TO 910
          DO 900 KK=1,NG
  900   SOL1(KK)=SOLUTN(KK)
          FSTSOL=.FALSE.
  910   CONTINUE
          DO 920 KK=1,NG
  920   SOLDIF(KK)=SOLUTN(KK)-SOL1(KK)
C         WRITE(NOUT,950) (SOL1(KK),SOLUTN(KK),SOLDIF(KK),KK=1,NG)
C 950   FORMAT('1ST ',E12.6,' CURRENT ',E12.6,' DIFF ',E12.6)
          DO 915 KK=1,NY
          CALL GETROW (KK,KERROW,.FALSE.,0,1,IUNIT,                       GEYLY5
      1   SQRTW,NY,NGL,IWT,NG,CQUAD,G,T,NLINF,Y)                          GEYLY6
          DDDUM=0D0
```

```
            DO 916 KL=1,NG
916     DDDUM=DDDUM+SOLDIF(KL)*KERROW(KL)
        ACDIFF(KK)=DDDUM
915     CONTINUE
        DDDUM=0D0
        DO 930 KK=1,NY
930     DDDUM=DDDUM+ACDIFF(KK)*ACDIFF(KK)
        WRITE(NOUT,940)NG,NY,DDDUM
940     FORMAT(1X,'NG=',I5,' NY=',I5,
     1  '&&&&&&&&&&&&&&&&SUM OF SQUARES OF DIFFERENCE SOLUTION=',E15.8)
980     CONTINUE
        IF (IERROR.EQ.1 .AND. PPLTPR) CALL RUNRES (3,SOLUTN,.FALSE.,     ANLYZ6
     1  SINGLE(ALPHA/S(1,1)), CQUAD,G,IPLFIT,IPLRES,ISTAGE,ITITLE,IUNIT, ANLYZ7
     2IWT,LINEPG,MWORK,NG, NGL,NLINF,NOUT,NY,SQRTW,SRANGE,T,WORK,Y,      ANLYZ8
     3YLYFIT)                                                            ANLYZ9
        ALPHA=ALPHA*RALPHA                                               ANLYZ0
        LDUM=.FALSE.                                                     ANLYZ1
430     CONTINUE                                                         ANLYZ2
410 CONTINUE                                                             ANLYZ3
    IF (BTEST .GE. SRANGE) CALL ERRMES (5,.TRUE.,IHOLER,NOUT)            ANLYZ4
    CALL RUNRES (2,SOLBES,.TRUE.,SINGLE(ALPBES/S(1,1)),                  ANLYZ5
   1 CQUAD,G,IPLFIT,IPLRES,ISTAGE,ITITLE,IUNIT,IWT,LINEPG,MWORK,NG,      ANLYZ6
   2 NGL,NLINF,NOUT,NY,SQRTW,SRANGE,T,WORK,Y,YLYFIT)                     ANLYZ7
    IF (NNSGN(ISTAGE) .LE. 0)  GO TO 700                                 ANLYZ8
    NGM1=NG-1                                                            ANLYZ4
    NNINEQ=NINEQ-1                                                       ANLYZ5
    IF (NONNEG)  GO TO 510                                               ANLYZ6
    NNINEQ=NINEQ+NGM1                                                    ANLYZ7
    IF (NNINEQ .LE. MINEQ)  GO TO 510                                    ANLYZ8
    CALL ERRMES (6,.FALSE.,IHOLER,NOUT)                                  ANLYZ9
    GO TO 790                                                            ANLYZ0
510 IROW=NNINEQ-NGM1                                                     ANLYZ1
    DO 520 J=1,NGM1                                                      ANLYZ2
      IROW=IROW+1                                                        ANLYZ3
      DO 525 ICOL=1,NGLP1                                                ANLYZ4
        AINEQ(IROW,ICOL)=ZERO                                            ANLYZ5
525   CONTINUE                                                           ANLYZ6
      AINEQ(IROW,J)=ONE                                                  ANLYZ7
      AINEQ(IROW,J+1)=-ONE                                               ANLYZ8
      IISIGN(J)=1                                                        ANLYZ9
520 CONTINUE                                                             ANLYZ0
    CALL SETGA1 (NNINEQ,                                                 ANLYZ1
   1 A,AINEQ,MA,MG,MINEQ,MREG,NGL,NGLE,REG)                              ANLYZ2
    NNSGNI=MIN0(NNSGN(ISTAGE),4)                                         ANLYZ3
    ALPOLD=ZERO                                                          ANLYZ4
    IF (ISTAGE .EQ. 1) BTEST=SRANGE                                      ANLYZ5
    DO 600 INSGN=1,NNSGNI                                                ANLYZ0
      NSGNI=NSGN(INSGN)                                                  ANLYZ1
      LNINEQ=NNINEQ                                                      ANLYZ2
      IF (NONNEG)  LNINEQ=LNINEQ+(NSGNI-(1+LSIGN(1,INSGN))/2)/2+1        ANLYZ3
      IF (LNINEQ .LE. MINEQ)  GO TO 610                                  ANLYZ4
      CALL ERRMES (7,.FALSE.,IHOLER,NOUT)                                ANLYZ5
      GO TO 790                                                          ANLYZ6
610   NNQUSR=NINEQ                                                       ANLYZ7
      IF (NONNEG)  NNQUSR=NNQUSR-NG                                      ANLYZ8
      RALPFL=ONE                                                         ANLYZ9
      IF (MAX0(NOPROG(1),NOPROG(2)) .GT. 1)  RALPFL=RALPHA               ANLYZ0
      ALPHA=ALPBES/RALPFL                                                ANLYZ1
      MFLAT=MAX0(1,NFLAT(INSGN,ISTAGE))                                  ANLYZ2
      IF (RALPFL .LE. ONE)  MFLAT=1                                      ANLYZ3
      DO 620 JFLAT=1,MFLAT                                               ANLYZ8
        ALPHA=ALPHA*RALPFL                                               ANLYZ9
        IF (ABS(ALPOLD/ALPHA-ONE) .LE. 1.E3*PRECIS)  GO TO 630           ANLYZ0
        ALPOLD=ALPHA                                                     ANLYZ1
        LDUM=INSGN.EQ.1 .AND. JFLAT.EQ.1                                 ANLYZ2
        CALL SETVAL (ALPHA,LDUM,NNINEQ,                                  ANLYZ3
   1  A,AINEQ,MA,MG,MINEQ,MREG,NGL,NGLE,REG,RHSNEQ,S,VALPCV,VALPHA,      ANLYZ4
   2  VK1Y1)                                                             ANLYZ5
630     J=INSGN                                                          ANLYZ6
        CALL SETSGN (J,NSGNI,LSIGN,NOUT,LLSIGN,NG,SOLBES,SRANGE)         ANLYZ7
        CALL ANPEAK (LNINEQ,                                             ANLYZ1
```

```
      1     A,AA,AINEQ,ALPHA,BTEST,CQUAD,DEGFRZ,EXACT,FLAT,G,IISIGN,        ANLYZ2
      2     ISTAGE,IWORK,LBIND,LLSIGN,LSDONE,MA,MDONE,MG,MINEQ,              ANLYZ3
      3     MREG,MWORK,MY,NGLE,NGLY,NNINEQ,NNQUSR,                           ANLYZ4
      4     NSGNI,REG,RHSNEQ,S,SAVBES,SOLBES,SOLPK,                          ANLYZ5
      5     SOLUTN,SQRTW,T,VALPCV,VALPHA,VARZ,VDONE,WORK,Y,YLYFIT)            ANLYZ6
            IF (.NOT.FLAT)  GO TO 650                                          ANLYZ7
  620 CONTINUE                                                                 ANLYZ8
  650 DO 660 J=1,NGL                                                           ANLYZ2
         SOLUTN(J)=SOLPK(J)                                                    ANLYZ3
  660 CONTINUE                                                                 ANLYZ4
      CALL RUNRES (1,SOLUTN,.FALSE.,SINGLE(ALPHA/S(1,1)),                     ANLYZ5
     1 CQUAD,G,IPLFIT,IPLRES,ISTAGE,ITITLE,IUNIT,IWT,LINEPG,MWORK,NG,         ANLYZ6
     2 NGL,NLINF,NOUT,NY,SQRTW,SRANGE,T,WORK,Y,YLYFIT)                        ANLYZ7
  600 CONTINUE                                                                 ANLYZ8
      IF (ISTAGE.EQ.2 .OR. .NOT.NONNEG)  GO TO 700                             ANLYZ9
      NINEQ=NINEQ-NG                                                           ANLYZ3
      CALL SETNNG (AINEQ,MINEQ,NG,NGLP1,NINEQ)                                 ANLYZ4
  700 IF (ISTAGE .EQ. 1)  GO TO 800                                            ANLYZ5
 5700 FORMAT ('1CONTIN - VERSION 1 (NOV 1980)',3X,80A1,4X,                    ANLYZ9
     1 'CHOSEN SOLUTION'//5X,'ALPHA',4X,                                      ANLYZ0
     2 'ALPHA/S(1)',5X,'OBJ. FCTN.',7X,'VARIANCE',6X,'STD. DEV.',4X,          ANLYZ1
     3 'DEG FREEDOM',4X,'PROB1 TO REJECT    PROB2 TO REJECT'/                ANLYZ2
     4 1X,1PE9.2,E14.2,2E15.5,E15.3,0PF15.3,2F19.3)                           ANLYZ3
      RTOT=ALPBES                                                              ANLYZ4
      WRITE (NOUT,5700) ITITLE,RTOT,SAVBES                                    ANLYZ5
      DO 710 J=1,NGL                                                           ANLYZ0
         YLYFIT(J)=SOLBES(J)                                                   ANLYZ1
  710 CONTINUE                                                                 ANLYZ2
      CALL PLPRIN (G,YLYFIT,EXACT,NG,ONLY1,NOUT,SRANGE,NLINF,NG,NGL)          ANLYZ3
      IF (DOUSOU)  CALL USEROU (G,YLYFIT,EXACT,MG)                             ANLYZ4
      IF (DOMOM)  CALL MOMENT (G,YLYFIT,CQUAD,NG,MOMNMX(1),MOMNMX(2),         ANLYZ5
     1 NOUT)                                                                   ANLYZ6
  790 IF (ISTAGE .NE. 2)  STOP                                                 ANLYZ7
  800 RETURN                                                                   ANLYZ8
      END                                                                      ANLYZ9
      SUBROUTINE ANPEAK (LNINEQ,                                              ANEAK2
     1     A,AA,AINEQ,ALPHA,BTEST,CQUAD,DEGFRZ,EXACT,FLAT,G,IISIGN,           ANEAK3
     2     ISTAGE,IWORK,LBIND,LLSIGN,LSDONE,MA,MDONE,MG,MINEQ,                ANEAK4
     3     MREG,MWORK,MY,NGLE,NGLY,NNINEQ,NNQUSR,                             ANEAK5
     4     NSGNI,REG,RHSNEQ,S,SAVBES,SOLBES,SOLPK,                            ANEAK6
     5     SOLUTN,SQRTW,T,VALPCV,VALPHA,VARZ,VDONE,WORK,Y,YLYFIT)             ANEAK7
      DOUBLE PRECISION PRECIS, RANGE                                          ANEAK8
      DOUBLE PRECISION A, AA, AINEQ, ALPHA, DUB, REG, RHSNEQ, S,              ANEAK9
     1 SOLBES, SOLUTN, VALPCV, VALPHA, WORK                                   ANEAK0
      LOGICAL DOMOM, DOUSIN, DOUSNQ, DOUSOU, LAST, NONNEG, ONLY1, PRWT,       ANEAK1
     1 PRY, SIMULA, LUSER                                                     ANEAK2
      LOGICAL DONE, FLAT, LDUM, LBIND, FFLAT                                  ANEAK3
      CHARACTER IFORMT(70), IFORMW(70), IFORMY(70),LA(6,46), ITITLE(80),
     + IHOLER(6), ISTAR(4)
      DIMENSION S(MG,3), LLSIGN(5), LSDONE(MDONE,3,2), VDONE(MDONE),          ANEAK4
     1 A(MA,MG), REG(MREG,MG), RHSNEQ(MINEQ), VALPHA(MG), IISIGN(MG),         ANEAK5
     2 AINEQ(MINEQ,MG), WORK(MWORK), IWORK(MA), VALPCV(MG),                   ANEAK6
     3 G(MG), EXACT(MG), CQUAD(MG), SOLUTN(MG),                               ANEAK7
     4 LBIND(MINEQ), SOLPK(MG), AA(MG,MG), SOLBES(MG),                        ANEAK8
     5 SQRTW(MY), T(MY), Y(MY), YLYFIT(MY), SAVBES(7)                         ANEAK9
      DIMENSION  JSTAGE(4), INC(4), PREJ(2),                                  ANEAK0
     1 VARTRY(4), LLSTRY(5,4)                                                 ANEAK1
      COMMON /SBLOCK/ PRECIS, RANGE, SRMIN,                                   ANEAK2
     1 ALPST(2), GMNMX(2), FLEVEL(2,2), RSVMNX(2,2), RUSER(100),              ANEAK3
     2 EXMAX, SRANGE                                                          ANEAK4
      COMMON /IBLOCK/ IGRID, IPLRES, IPRINT, IQUAD, IUNIT, IWT,               ANEAK5
     1 LINEPG, MIOERR, MQPITR, NEQ, NERFIT, NG, NERTT,-NLINF, NORDER,         ANEAK6
     2 ICRIT(2), IPLFIT(2),
     3 IUSER(50), LSIGN(4,4), MOMNMX(2), NENDZ(2),                            ANEAK8
     4 NFLAT(4,2), NGL, NGLP1, NIN, NINEQ, NNSGN(2), NOUT, NQPROG(2),         ANEAK9
     5 NSGN(4), NY                                                            ANEAK0
      COMMON /CBLOCK/ IFORMT, IFORMW, IFORMY,LA, ITITLE
      COMMON /LBLOCK/ DOMOM, DOUSIN, DOUSNQ, DOUSOU, LAST, NONNEG,            ANEAK1
     1 ONLY1, PRWT, PRY, SIMULA,                                              ANEAK2
     2 LUSER(30)                                                              ANEAK3
      DATA IHOLER/'A','N','P','E','A','K'/,                                   ANEAK4
```

```
      1 ISTAR/' ','x','X','F'/                                      ANEAK5
        NSGNM1=NSGNI-1                                               ANEAK6
        DONE=.FALSE.                                                 ANEAK7
        FLAT=.FALSE.                                                 ANEAK8
        NDONE=0                                                      ANEAK9
        NQPITR=0                                                     ANEAK0
        ITER=0                                                       ANEAK1
        VARRBS=SRANGE                                                ANEAK2
        DUB=0.                                                       ANEAK3
        DO 110 J=1,NSGNI                                             ANEAK4
          JSTAGE(J)=0                                                ANEAK5
          INC(J)=1                                                   ANEAK6
  110   CONTINUE                                                     ANEAK7
 5200   FORMAT (' ',I15,'-EXTREMA-CONSTRAINED ANALYSIS'/             ANEAK8
      1 'OALPHA =',1PE9.2,5X,'ALPHA/S(1) =',E9.2/                    ANEAK9
      2 'OITER.       OBJ. FCTN.          VARIANCE',7X,              ANEAK0
      3 'STD. DEV.   DEG FREEDOM   PROB1 REJ   PROB2 REJ',10X,       ANEAK1
      4 'EXTREMA INDICES')                                           ANEAK2
        DUM=ALPHA/S(1,1)                                             ANEAK3
        DDUM=ALPHA                                                   ANEAK4
        WRITE (NOUT,5200) NSGNM1,DDUM,DUM                            ANEAK5
  200   ITER=ITER+1                                                  ANEAK9
        IF (NDONE .LE. 0)  GO TO 230                                 ANEAK0
        DO 210 K=1,NDONE                                             ANEAK5
          DO 220 J=1,NSGNM1                                          ANEAK6
            L=IABS(LLSIGN(J+1))                                      ANEAK7
            LL=LSDONE(K,J,1)                                         ANEAK8
            IF ((LL.LE.0 .AND. L.NE.-LL)                             ANEAK9
      1     .OR.     (LL.GT.0 .AND. L.LT.LL))  GO TO 210             ANEAK0
            LL=LSDONE(K,J,2)                                         ANEAK1
            IF ((LL.LE.0 .AND. L.NE.-LL)  .OR.   (LL.GT.0 .AND. L.GT.LL))ANEAK2
      1     GO TO 210                                                ANEAK3
  220     CONTINUE                                                   ANEAK4
          LSTAR=3                                                    ANEAK5
          VARREG=VDONE(K)                                            ANEAK6
          GO TO 320                                                  ANEAK7
  210   CONTINUE                                                     ANEAK8
  230   CALL UPDSGN (NSGNI,LLSIGN,                                   ANEAK3
      1 A,AINEQ,IISIGN,MA,MG,MINEQ,MREG,NGLE,NGLP1,NNINEQ,           ANEAK4
      2 NNQUSR,NONNEG,NOUT,REG,RHSNEQ,S,VALPHA)                      ANEAK5
        NQPITR=NQPITR+1                                              ANEAK6
        IF (NQPITR .LE. MQPITR)  GO TO 235                           ANEAK7
        CALL ERRMES (1,.FALSE.,IHOLER,NOUT)                          ANEAK8
        GO TO 790                                                    ANEAK9
  235   LDUM=ISTAGE .EQ. 1                                           ANEAK0
        CALL LDPETC (.FALSE.,LNINEQ,LDUM,ICRIT(ISTAGE),.FALSE.,.FALSE., ANEAK4
      1 .FALSE.,ALPHA,.FALSE.,.FALSE.,DUB,VAR,                       ANEAK5
      2 A,AA,AINEQ,BTEST,CQUAD,DEGFRE,DEGFRZ,EXACT,G,IERROR,         ANEAK6
      3 ISTAGE,IWORK,LBIND,MA,MG,MINEQ,MREG,MWORK,MY,                ANEAK7
      4 NGLE,NGLY,PREJ,REG,RHSNEQ,S,SAVBES,SOLBES,                   ANEAK8
      5 SOLUTN,SQRTW,T,VALPCV,VALPHA,VARREG,VARZ,WORK,Y,YLYFIT)      ANEAK9
        IF (IERROR .EQ. 1)  GO TO 240                                ANEAK0
        LSTAR=4                                                      ANEAK1
        VARREG=SRANGE                                                ANEAK2
        GO TO 320                                                    ANEAK3
  240   NDONE=NDONE+1                                                ANEAK4
        IF (NDONE .LE. MDONE)  GO TO 250                             ANEAK5
        CALL ERRMES (2,.FALSE.,IHOLER,NOUT)                          ANEAK6
        GO TO 790                                                    ANEAK7
  250   CALL UPDDON (                                                ANEAK3
      1 NSGNM1,LLSIGN,LSDONE,MDONE,NDONE,NNQUSR,LBIND,MINEQ,         ANEAK4
      2 NG,VARREG,VDONE)                                             ANEAK5
        LSTAR=1                                                      ANEAK6
        IF (VARREG .GE. VARRBS)  GO TO 320                           ANEAK7
        LSTAR=2                                                      ANEAK1
        VARRBS=VARREG                                                ANEAK2
        DO 310 J=1,NGL                                               ANEAK3
          SOLPK(J)=SOLUTN(J)                                         ANEAK4
  310   CONTINUE                                                     ANEAK5
        FLAT=FFLAT (NSGNI,NONNEG,NG,SOLUTN,SRMIN,NNQUSR,LBIND,       ANEAK6
      1 MINEQ,LLSIGN)                                                ANEAK7
 5320   FORMAT (1X,A1,I4,1PE16.6,E16.5,E16.3,0PF14.3,2F12.3,8X,5I5)  ANEAK1
  320   DUM=SRANGE                                                   ANEAK2
```

```
      DDUM=FLOAT(NY)-DEGFRE                                              ANEAK3
      IF (LSTAR.LE.2 .AND. DDUM.GT.0.)  DUM=SQRT(VAR/DDUM)               ANEAK4
      IF (LSTAR .LE. 2)  WRITE (NOUT,5320) ISTAR(LSTAR),ITER,VARREG,VAR, ANEAK5
     1 DUM,DEGFRE,PREJ,(LLSIGN(J),J=1,NSGNI)                             ANEAK6
 5322 FORMAT (1X,A1,I4,1PE16.6,78X,5I5)                                  ANEAK7
      IF (LSTAR .GE. 3)  WRITE (NOUT,5322) ISTAR(LSTAR),ITER,VARREG,     ANEAK8
     1 (LLSIGN(J),J=1,NSGNI)                                             ANEAK9
      CALL UPDLLS (NSGNI,JSTAGE,NOUT,VARTRY,VARREG,LLSTRY,LLSIGN,        ANEAK3
     1 INC,DONE)                                                         ANEAK4
      IF (.NOT.DONE)  GO TO 200                                          ANEAK8
      CALL PLPRIN (G,SOLPK,EXACT,NG,ONLY1,NOUT,SRANGE,NLINF,NG,NGL)      ANEAK9
      IF (DOUSOU)  CALL USEROU (G,SOLPK,EXACT,MG)                        ANEAK0
      IF (DOMOM)  CALL MOMENT (G,SOLPK,CQUAD,NG,MOMNMX(1), MOMNMX(2),    ANEAK1
     1NOUT)                                                              ANEAK2
      GO TO 795                                                          ANEAK3
  790 FLAT=.FALSE.                                                       ANEAK4
  795 LLSTRY(1,1)=1                                                      ANEAK9
      LLSTRY(2,1)=NG                                                     ANEAK0
      CALL UPDSGN (1,LLSTRY,                                             ANEAK1
     1 A,AINEQ,IISIGN,MA,MG,MINEQ,MREG,NGLE,NGLP1,NNINEQ,                ANEAK2
     2 NNQUSR,NONNEG,NOUT,REG,RHSNEQ,S,VALPHA)                           ANEAK3
      RETURN                                                             ANEAK4
      END                                                                ANEAK5
      FUNCTION BETAIN (X,A,B,NOUT)                                       BEAIN1
      LOGICAL SWAP                                                       BEAIN2
      CHARACTER IHOLER(6)                                                BEAIN3
      DATA IHOLER/'B','E','T','A','I','N'/, TOL/1.E-5/                   BEAIN4
      IF (X.LT.0. .OR. X.GT.1. .OR. AMIN1(A,B).LE.0. .OR. AMAX1(A,B)     BEAIN5
     1.GE.2.E+4)  CALL ERRMES (1,.TRUE.,IHOLER,NOUT)                     BEAIN6
      BETAIN=X                                                           BEAIN7
      IF (X.LE.0. .OR. X.GE.1.)  RETURN                                  BEAIN8
      SWAP=X .GT. .5                                                     BEAIN9
      IF (SWAP)  GO TO 150                                               BEAIN0
      XX=X                                                               BEAIN1
      AA=A                                                               BEAIN2
      BB=B                                                               BEAIN3
      GO TO 200                                                          BEAIN4
  150 XX=1.-X                                                            BEAIN9
      AA=B                                                               BEAIN0
      BB=A                                                               BEAIN1
  200 CX=1.-XX                                                           BEAIN2
      R=XX/CX                                                            BEAIN3
      IMAX=MAX0(0,INT((R*BB-AA-1.)/(R+1.)))                              BEAIN7
      RI=FLOAT(IMAX)                                                     BEAIN8
      SUM=0.                                                             BEAIN9
      TERMAX=(AA+RI)*ALOG(XX)+(BB-RI-1.)*ALOG(CX)+GAMLN(AA+BB)-          BEAIN0
     1 GAMLN(AA+RI+1.)-GAMLN(BB-RI)                                      BEAIN1
      IF (TERMAX .LT. -50.)  GO TO 700                                   BEAIN2
      TERMAX=EXP(TERMAX)                                                 BEAIN3
      TERM=TERMAX                                                        BEAIN4
      SUM=TERM                                                           BEAIN5
      I1=IMAX+1                                                          BEAIN9
      DO 250 I=I1,20000                                                  BEAIN0
        RI=FLOAT(I)                                                      BEAIN1
        TERM=TERM*R*(BB-RI)/(AA+RI)                                      BEAIN2
        SUM=SUM+TERM                                                     BEAIN3
        IF (ABS(TERM) .LE. TOL*SUM)  GO TO 300                           BEAIN4
  250 CONTINUE                                                           BEAIN5
      CALL ERRMES (2,.TRUE.,IHOLER,NOUT)                                 BEAIN6
  300 IF (IMAX .EQ. 0)  GO TO 700                                        BEAIN7
      TERM=TERMAX                                                        BEAIN1
      RI=FLOAT(IMAX)                                                     BEAIN2
      DO 320 I=1,IMAX                                                    BEAIN3
        TERM=TERM*(AA+RI)/(R*(BB-RI))                                    BEAIN4
        SUM=SUM+TERM                                                     BEAIN5
        IF (ABS(TERM) .LE. TOL*SUM)  GO TO 700                           BEAIN6
        RI=RI-1.                                                         BEAIN7
  320 CONTINUE                                                           BEAIN8
  700 BETAIN=SUM                                                         BEAIN9
      IF (SWAP)  BETAIN=1.-BETAIN                                        BEAIN0
      RETURN                                                             BEAIN1
      END                                                                BEAIN2
```

```
      SUBROUTINE CQTRAP (G,CQUAD,NG)                               CQRAP4
      DIMENSION G(NG), CQUAD(NG)                                   CQRAP5
      JJ=NG-1                                                      CQRAP6
      DELOLD=0.                                                    CQRAP7
      DO 110 J=1,JJ                                                CQRAP8
        DEL=.5*(G(J+1)-G(J))                                       CQRAP9
        CQUAD(J)=DEL+DELOLD                                        CQRAP0
        DELOLD=DEL                                                 CQRAP1
  110 CONTINUE                                                     CQRAP2
      CQUAD(NG)=DELOLD                                             CQRAP3
      RETURN                                                       CQRAP4
      END                                                          CQRAP5
      SUBROUTINE CVNEQ (ALPHA,IERROR,NNNNEQ,SOLUTN,                CVNEQ1
     1 A,AA,AINEQ,DEGFRE,LBIND,MA,MG,MINEQ,MREG,MWORK,NGL,NGLE,    CVNEQ2
     2 NGLP1,NGLY,NOUT,RANGE,REG,S,VALPCV,WORK)                    CVNEQ3
      DOUBLE PRECISION A, AA, ABS, AINEQ, ALPHA, DUB, RANGE, REG, S, CVNEQ4
     1 SOLUTN, VALPCV, WORK, ZERO                                  CVNEQ5
      LOGICAL LBIND                                                CVNEQ6
      DIMENSION AA(MG,MG), WORK(MWORK), A(MA,MG), S(MG,3), SOLUTN(MG), CVNEQ7
     1 AINEQ(MINEQ,MG), VALPCV(MG), REG(MREG,MG), LBIND(MINEQ)     CVNEQ8
      CHARACTER IHOLER(6)                                          CVNEQ9
      DATA IHOLER/'C','V','N','E','Q',' '/                         CVNEQ0
      ABS(DUB)=DABS(DUB)                                           CVNEQ1
      ZERO=0.D0                                                    CVNEQ3
      DEGFRE=0.                                                    CVNEQ4
      IERROR=1                                                     CVNEQ5
      NGLEP1=NGLE+1                                                CVNEQ6
      IY=NGLEP1*(NNNNEQ+2)                                         CVNEQ7
      IW=-NNNNEQ                                                   CVNEQ8
      NBIND=0                                                      CVNEQ9
      IF (NNNNEQ .EQ. 0) GO TO 180                                 CVNEQ0
      DO 150 IROW=1,NNNNEQ                                         CVNEQ1
        IY=IY+1                                                    CVNEQ2
        LBIND(IROW)=WORK(IY) .GT. ZERO                             CVNEQ3
        IF (.NOT.LBIND(IROW)) GO TO 150                            CVNEQ4
        L=0                                                        CVNEQ9
        DO 152 ICOL=1,NGL                                          CVNEQ0
          IF (ABS(AINEQ(IROW,ICOL)) .LE. ZERO) GO TO 152           CVNEQ1
          IF (L .NE. 0) GO TO 154                                  CVNEQ2
          L=ICOL                                                   CVNEQ3
  152   CONTINUE                                                   CVNEQ4
        SOLUTN(L)=AINEQ(IROW,NGLP1)/AINEQ(IROW,L)                  CVNEQ5
  154   NBIND=NBIND+1                                              CVNEQ1
        IW=IW+1                                                    CVNEQ2
        IIW=IW+NNNNEQ                                              CVNEQ3
        DO 160 ICOL=1,NGLE                                         CVNEQ4
          WORK(IIW)=A(IROW,ICOL)/S(ICOL,2)                         CVNEQ5
          IIW=IIW+NNNNEQ                                           CVNEQ6
  160   CONTINUE                                                   CVNEQ7
        DUB=AINEQ(IROW,NGLP1)                                      CVNEQ8
        DO 170 J=1,NGL                                             CVNEQ9
          DUB=DUB-AINEQ(IROW,J)*VALPCV(J)                          CVNEQ0
  170   CONTINUE                                                   CVNEQ1
        WORK(IIW)=DUB                                              CVNEQ2
  150 CONTINUE                                                     CVNEQ3
      IF (NBIND .LT. NGLE) GO TO 180                               CVNEQ4
      CALL ERRMES (1,.FALSE.,IHOLER,NOUT)                          CVNEQ5
 5180 FORMAT (1X,2I4)                                              CVNEQ6
      WRITE (NOUT,5180) NBIND,NGLE                                 CVNEQ7
      STOP                                                         CVNEQ8
  180 DO 190 J=1,NGLY                                              CVNEQ9
        DO 195 K=1,NGLE                                            CVNEQ0
          AA(J,K)=ZERO                                             CVNEQ1
  195   CONTINUE                                                   CVNEQ2
        AA(J,J)=S(J,1)                                             CVNEQ3
        AA(J,NGLEP1)=A(J,NGLP1)-S(J,1)*REG(J,NGLP1)                CVNEQ4
  190 CONTINUE                                                     CVNEQ5
      IF (NBIND .EQ. 0) GO TO 200                                  CVNEQ6
      IW=NGLP1*NNNNEQ+1                                            CVNEQ7
      IIW=IW+NGL                                                   CVNEQ8
      CALL ELIMEQ (WORK,NNNNEQ,MG,WORK(IW),NBIND,NGLE,AA,MG,AA,MG, CVNEQ9
```

```
     1 0,NGLEP1,NGLY,WORK(IIW),RANGE)                                CVNEQ0
       J=NBIND+1                                                     CVNEQ1
       CALL SVDRS2 (AA(1,J),MG,NGLY,NGLE-NBIND,AA(1,NGLEP1),          CVNEQ2
     1 MG,0,WORK,IERROR,RANGE)                                       CVNEQ3
       IF (IERROR .EQ. 1)  GO TO 250                                  CVNEQ4
       CALL ERRMES (2,.FALSE.,IHOLER,NOUT)                            CVNEQ5
       RETURN                                                         CVNEQ6
 200   DO 210 J=1,NGLE                                                CVNEQ7
         WORK(J)=S(J,1)                                               CVNEQ8
 210   CONTINUE                                                       CVNEQ9
 250   DUM=ALPHA**2                                                   CVNEQ0
       K=MIN0(NGLY,NGLE-NBIND)                                        CVNEQ1
       DO 260 J=1,K                                                   CVNEQ2
         DDUM=WORK(J)**2                                              CVNEQ3
         DEGFRE=DEGFRE+DDUM/(DUM+DDUM)                                CVNEQ4
 260   CONTINUE                                                       CVNEQ5
       RETURN                                                         CVNEQ6
       END                                                            CVNEQ7
       SUBROUTINE DIAGA (A,MA,MG,MREG,NEQ,NGL,NGLE,NGLP1,NGLY,REG,S)  DIAGA8
       DOUBLE PRECISION A, DUM, REG, S, ZERO                          DIAGA9
       DIMENSION A(MA,MG), REG(MREG,MG), S(MG,3)                      DIAGA0
       ZERO=0.D0                                                      DIAGA2
       IF (NGLY .GE. NGLE)  GO TO 150                                 DIAGA3
       K=NGLY+1                                                       DIAGA4
       DO 140 J=K,NGLE                                                DIAGA5
         S(J,1)=ZERO                                                  DIAGA6
         A(J,NGLP1)=ZERO                                              DIAGA7
 140   CONTINUE                                                       DIAGA8
 150   DO 160 IROW=1,NGL                                              DIAGA9
         DO 170 ICOL=1,NGLE                                           DIAGA0
           IICOL=NEQ                                                  DIAGA1
           DUM=ZERO                                                   DIAGA2
           DO 180 J=1,NGLE                                            DIAGA3
             IICOL=IICOL+1                                            DIAGA4
             DUM=DUM+REG(IROW,IICOL)*A(J,ICOL)                        DIAGA5
 180       CONTINUE                                                   DIAGA6
           S(ICOL,2)=DUM                                              DIAGA7
 170     CONTINUE                                                     DIAGA8
         DO 190 ICOL=1,NGLE                                           DIAGA9
           REG(IROW,ICOL)=S(ICOL,2)                                   DIAGA0
 190     CONTINUE                                                     DIAGA1
 160   CONTINUE                                                       DIAGA2
       DO 210 IROW=1,NGLE                                             DIAGA3
         DUM=ZERO                                                     DIAGA4
         DO 220 ICOL=1,NGLE                                           DIAGA5
           DUM=DUM+A(ICOL,IROW)*REG(ICOL,NGLP1)                       DIAGA6
 220     CONTINUE                                                     DIAGA7
         S(IROW,2)=DUM                                                DIAGA8
 210   CONTINUE                                                       DIAGA9
       DO 250 IROW=1,NGLE                                             DIAGA0
         REG(IROW,NGLP1)=S(IROW,2)                                    DIAGA1
 250   CONTINUE                                                       DIAGA2
       IF (NGLE .GE. NGLY)  GO TO 800                                 DIAGA3
       J=NGLE+1                                                       DIAGA4
       DO 260 IROW=J,NGLY                                             DIAGA5
         S(IROW,1)=ZERO                                               DIAGA6
         REG(IROW,NGLP1)=ZERO                                         DIAGA7
 260   CONTINUE                                                       DIAGA8
 800   RETURN                                                         DIAGA9
       END                                                            DIAGA0
       SUBROUTINE DIAREG (A,AEQ,MA,MEQ,MG,MREG,NEQ,NGL,NGLE,NGLY,     DIREG9
     1 NOUT,PIVOT,RANGE,REG,S)                                        DIREG0
       DOUBLE PRECISION A, AEQ, DUM, ONE, PIVOT, RANGE, REG, S, ZERO  DIREG1
       DIMENSION S(MG,3), REG(MREG,MG), A(MA,MG), PIVOT(MEQ),         DIREG2
     1 AEQ(MEQ,MG)                                                    DIREG3
       CHARACTER IHOLER(6)
       DATA IHOLER/'D','I','A','R','E','G'/                           DIREG4
       ZERO=0.D0                                                      DIREG6
       ONE=1.D0                                                       DIREG8
       ICOL=NEQ                                                       DIREG9
       DO 120 J=1,NGLE                                                DIREG0
         ICOL=ICOL+1                                                  DIREG1
```

```
         IF (S(J,1) .GT. ZERO) GO TO 125                          DIREG2
         CALL ERRMES (1,.FALSE.,IHOLER,NOUT)                      DIREG3
         K=J-1                                                    DIREG4
5125     FORMAT (1X,I3)                                           DIREG5
         WRITE (NOUT,5125) K                                      DIREG6
         STOP                                                     DIREG7
125      DUM=ONE/S(J,1)                                           DIREG8
         IROW=NGL+1                                               DIREG9
         DO 130 I=1,NGLE                                          DIREG4
            IROW=IROW-1                                           DIREG5
            IIROW=IROW-NEQ                                        DIREG6
            REG(IROW,ICOL)=REG(IIROW,ICOL)*DUM                    DIREG7
130      CONTINUE                                                 DIREG8
         IF (NEQ .EQ. 0) GO TO 120                                DIREG9
         DO 135 I=1,NEQ                                           DIREG0
            REG(I,ICOL)=ZERO                                      DIREG0
135      CONTINUE                                                 DIREG1
120   CONTINUE                                                    DIREG2
      DO 150 IROW=1,NGLY                                          DIREG3
         ICOL=NEQ                                                 DIREG7
         DO 155 J=1,NGLE                                          DIREG8
            ICOL=ICOL+1                                           DIREG9
            DUM=ZERO                                              DIREG0
            L=NEQ                                                 DIREG1
            DO 160 K=1,NGLE                                       DIREG2
               L=L+1                                              DIREG3
               DUM=DUM+A(IROW,L)*REG(L,ICOL)                      DIREG4
160         CONTINUE                                              DIREG5
            S(J,1)=DUM                                            DIREG6
155      CONTINUE                                                 DIREG7
         DO 165 J=1,NGLE                                          DIREG8
            A(IROW,J)=S(J,1)                                      DIREG9
165      CONTINUE                                                 DIREG1
150   CONTINUE                                                    DIREG2
      IF (NEQ .EQ. 0) GO TO 800                                   DIREG3
      I=NEQ                                                       DIREG8
      DO 210 J=1,NEQ                                              DIREG9
         CALL H12 (2,I,I+1,NGL,AEQ(I,1),MEQ,PIVOT(I),REG(1,NEQ+1),DIREG0
     1   1,MREG,NGLE,RANGE)                                       DIREG1
         I=I-1                                                    DIREG2
210   CONTINUE                                                    DIREG3
800   RETURN                                                      DIREG4
      END                                                         DIREG5
      DOUBLE PRECISION FUNCTION DIFF(X,Y)                         DIFF 6
      DOUBLE PRECISION X, Y                                       DIFF 7
      DIFF=X-Y                                                    DIFF 8
      RETURN                                                      DIFF 9
      END                                                         DIFF 0
      SUBROUTINE ELIMEQ (AEQ,MEQ,MG,PIVOT,NEQ,NGL,A,MA,REG,MREG,  ELMEQ7
     1 NREG,NGLP1,NGLY,VK1Y1,RANGE)                               ELMEQ8
      DOUBLE PRECISION A, AEQ, DUM, PIVOT, RANGE, REG, VK1Y1, ZERO ELMEQ9
      DIMENSION AEQ(MEQ,MG), PIVOT(1), A(MA,MG), REG(MREG,MG),    ELMEQ0
     1 VK1Y1(1)                                                   ELMEQ1
      ZERO=0.D0                                                   ELMEQ3
      DO 120 J=1,NGL                                              ELMEQ4
         VK1Y1(J)=ZERO                                            ELMEQ5
120   CONTINUE                                                    ELMEQ6
      IF (NEQ .EQ. 0) RETURN                                      ELMEQ7
      DO 150 I=1,NEQ                                              ELMEQ8
         II=I                                                     ELMEQ9
         IAEQ=MINO(I+1,NEQ)                                       ELMEQ0
         CALL H12 (1,II,I+1,NGL,AEQ(I,1),MEQ,PIVOT(I),AEQ(IAEQ,1),ELMEQ1
     1   MEQ,1,NEQ-I,RANGE)                                       ELMEQ2
         CALL H12 (2,II,I+1,NGL,AEQ(I,1),MEQ,PIVOT(I),A(1,1),     ELMEQ3
     1   MA,1,NGLY,RANGE)                                         ELMEQ4
         IF (NREG .GT. 0) CALL H12 (2,II,I+1,NGL,AEQ(I,1),MEQ, PIVOT(I)ELMEQ5
     1,REG(1,1),MREG,1,NREG,RANGE)                                ELMEQ6
150   CONTINUE                                                    ELMEQ7
      VK1Y1(1)=AEQ(1,NGLP1)/AEQ(1,1)                              ELMEQ8
      IF (NEQ .EQ. 1) GO TO 200                                   ELMEQ9
      DO 170 I=2,NEQ                                              ELMEQ0
```

```
          DUM=ZERO                                                      ELMEQ1
          K=I-1                                                         ELMEQ2
          DO 180 J=1,K                                                  ELMEQ3
            DUM=DUM+AEQ(I,J)*VK1Y1(J)                                   ELMEQ4
180       CONTINUE                                                      ELMEQ5
          VK1Y1(I)=(AEQ(I,NGLP1)-DUM)/AEQ(I,I)                          ELMEQ6
170    CONTINUE                                                         ELMEQ7
200    CALL LH1405 (A(1,NGLP1),NGLY,NEQ,A,MA,VK1Y1)                     ELMEQ8
       IF (NREG .GT. 0)  CALL LH1405 (REG(1,NGLP1),NREG,NEQ,REG,MREG,   ELMEQ9
      1 VK1Y1)                                                          ELMEQ0
       I=NEQ                                                            ELMEQ1
       DO 230 J=1,NEQ                                                   ELMEQ2
          CALL H12 (2,I,I+1,NGL,AEQ(I,1),MEQ,PIVOT(I),VK1Y1,1,MG,1,RANGE) ELMEQ3
          I=I-1                                                         ELMEQ4
230    CONTINUE                                                         ELMEQ5
       RETURN                                                           ELMEQ6
       END                                                              ELMEQ7
       SUBROUTINE ERRMES (N,ABORT,IHOLER,IWRITE)                        ERMES3
       LOGICAL ABORT                                                    ERMES4
       CHARACTER IHOLER(6)                                              ERMES5
5000   FORMAT ('0ERROR ',6A1,I2,'.  (CHECK USERS GUIDE.)  ',            ERMES6
      1 46('xx'))                                                       ERMES7
       WRITE (IWRITE,5000) IHOLER,N                                     ERMES8
       IF (ABORT)  STOP                                                 ERMES9
       RETURN                                                           ERMES0
       END                                                              ERMES1
       LOGICAL FUNCTION FFLAT (NSGNI,NONNEG,NG,SOLUTN,SRMIN,NNQUSR,     FFLAT7
      1 LBIND,MINEQ,LLSIGN)                                             FFLAT8
       DOUBLE PRECISION ABS, AMAX1, SMIN, SOLUTN, ZERO                  FFLAT9
       LOGICAL NONNEG, LBIND                                            FFLAT0
       DIMENSION SOLUTN(NG), LBIND(MINEQ), LLSIGN(NSGNI)                FFLAT1
       AMAX1(SMIN,ZERO)=DMAX1(SMIN,ZERO)                                FFLAT2
       ABS(SMIN)=DABS(SMIN)                                             FFLAT3
       ZERO=0.D0                                                        FFLAT5
       SMIN=ZERO                                                        FFLAT6
       IF (.NOT.NONNEG)  GO TO 120                                      FFLAT7
       DO 110 J=1,NG                                                    FFLAT8
          SMIN=AMAX1(SMIN,SOLUTN(J))                                    FFLAT9
110    CONTINUE                                                         FFLAT0
       SMIN=SMIN*SRMIN                                                  FFLAT1
120    FFLAT=.FALSE.                                                    FFLAT2
       K=NNQUSR                                                         FFLAT3
       NGM1=NG-1                                                        FFLAT4
       DO 130 J=1,NGM1                                                  FFLAT5
          K=K+1                                                         FFLAT6
          IF (LBIND(K) .AND. ABS(SOLUTN(J)) .GE. SMIN)  GO TO 140       FFLAT7
          FFLAT=.FALSE.                                                 FFLAT8
          GO TO 130                                                     FFLAT9
140       IF (FFLAT)  GO TO 800                                         FFLAT0
          FFLAT=.TRUE.                                                  FFLAT1
          IF (NSGNI .LT. 2)  GO TO 140                                  FFLAT2
          DO 145 L=2,NSGNI                                              FFLAT3
             LL=IABS(LLSIGN(L))                                         FFLAT4
             IF (J.EQ.LL .OR. J.EQ.LL+1)  GO TO 130                     FFLAT5
145       CONTINUE                                                      FFLAT6
          GO TO 140                                                     FFLAT7
130    CONTINUE                                                         FFLAT8
       FFLAT=.FALSE.                                                    FFLAT9
800    RETURN                                                           FFLAT0
       END                                                              FFLAT1
       FUNCTION FISHNI (F,DF1,DF2,NOUT)                                 FIHNI9
       CHARACTER IHOLER(6)                                              FIHNI0
       DATA IHOLER/'F','I','S','H','N','I'/                             FIHNI1
       IF (AMIN1(DF1,DF2) .GT. 0.)  GO TO 150                           FIHNI2
       CALL ERRMES (1,.FALSE.,IHOLER,NOUT)                              FIHNI3
       FISHNI=1.                                                        FIHNI4
       RETURN                                                           FIHNI5
150    HDF1=.5*DF1                                                      FIHNI6
       HDF2=.5*DF2                                                      FIHNI7
       DUM=DF1*F                                                        FIHNI8
       FISHNI=BETAIN(DUM/(DF2+DUM),HDF1,HDF2,NOUT)                      FIHNI9
       RETURN                                                           FIHNI0
       END                                                              FIHNI1
```

```
      FUNCTION GAMLN (XARG)                                        GAMLN4
      X=XARG                                                       GAMLN5
      P=1.                                                         GAMLN6
      GAMLN=0.                                                     GAMLN7
  110 IF (X .GE. 7.)  GO TO 150                                    GAMLN8
      P=P*X                                                        GAMLN9
      X=X+1.                                                       GAMLNO
      GO TO 110                                                    GAMLN1
  150 IF (XARG .LT. 7.)  GAMLN=-ALOG(P)                            GAMLN2
      Z=1./X**2                                                    GAMLN3
      GAMLN=GAMLN+(X-.5)*ALOG(X)-X+.9189385-(((Z/1680.-             GAMLN4
     1 7.936508E-4)*Z+2.777778E-3)*Z-8.333333E-2)/X                GAMLN5
      RETURN                                                       GAMLN6
      END                                                          GAMLN7
      FUNCTION GETPRU (SOL,                                        GEPRU3
     1 CQUAD,G,IUNIT,IWT,MWORK,NG,NGL,NLINF,NY,SQRTW,T,WORK,       GEPRU4
     2 Y,YLYFIT)                                                   GEPRU5
      DOUBLE PRECISION SOL, WORK                                   GEPRU6
      DIMENSION WORK(MWORK), SQRTW(NY), CQUAD(NG), G(NG), T(NY),   GEPRU7
     1 Y(NY), YLYFIT(NY), SOL(NGL)                                 GEPRU8
      CALL GETYLY (SOL,                                            GEPRU9
     1 CQUAD,G,IUNIT,IWT,MWORK,NG,NGL,NLINF,NY,SQRTW,T,WORK,Y,YLYFIT) GEPRUO
      YLYOLD=-YLYFIT(1)                                            GEPRU1
      NRUN=0                                                       GEPRU2
      DDUM=0.                                                      GEPRU3
      DO 110 IROW=1,NY                                             GEPRU4
        DUM=YLYFIT(IROW)                                           GEPRU5
        DDUM=DDUM+SIGN(1.,DUM)                                     GEPRU6
        IF (DUM*YLYOLD .LT. 0.)  NRUN=NRUN+1                       GEPRU7
        YLYOLD=DUM                                                 GEPRU8
  110 CONTINUE                                                     GEPRU9
      RN1=.5*(FLOAT(NY)+DDUM)                                      GEPRUO
      RN2=RN1-DDUM                                                 GEPRU1
      DUM=2.*RN1*RN2                                               GEPRU2
      RMU=DUM/(RN1+RN2)+1.                                         GEPRU3
      SIG=SQRT(DUM*(DUM-RN1-RN2)/(RN1+RN2-1.))/(RN1+RN2)           GEPRU4
      GETPRU=-1.                                                   GEPRU5
      IF (AMIN1(RN1,RN2) .GT. 9.5)  GETPRU=PGAUSS((FLOAT(NRUN)-RMU+.5)/ GEPRU6
     1 SIG)                                                        GEPRU7
      RETURN                                                       GEPRU8
      END                                                          GEPRU9
      SUBROUTINE GETROW (IROW,A,INIT,ISTAGE,INC,IUNIT,             GEROW5
     1 SQRTW,NY,NGL,IWT,NG,CQUAD,G,T,NLINF,Y)                      GEROW6
      DOUBLE PRECISION A                                           GEROW7
      LOGICAL INIT                                                 GEROW8
      DIMENSION SQRTW(NY), A(1), CQUAD(NG), G(NG), T(NY), Y(NY)    GEROW9
C
C     THE FOLLOWING LABELLED COMMON HAS ADDED TO STORE THE VALUES OF
C     THE KERNAL TO AVOID CONSTANT RECOMPUTING. ASSOCIATED COMMON IS
C     IN MAIN.
C
      COMMON /KERNAL/ USERKK(544,35)
      SWT=SQRTW(IROW)                                              GEROWO
      JJ=1+INC*NGL                                                 GEROW1
      IF (IUNIT.LT.0 .OR. INIT)  GO TO 200                         GEROW2
      READ (IUNIT) (A(J),J=1,JJ,INC)                               GEROW6
      GO TO 300                                                    GEROW7
  200 K=1                                                          GEROW1
      DO 210 J=1,NG                                                GEROW2
        JJJ=J                                                      GEROW3
C
C        A(K)=CQUAD(J)*SWT*USERK(IROW,T,JJJ,G)                     GEROW4
C     THE PRECEDING LINE HAS BEEN REPLACED BY THE FOLLOWING LINE SO THAT
C     THE KERNAL IS STORED IN MEMORY RATHER THAN CONSTANTLY RECOMPUTED.
C     ASSOCIATED WITH THIS CHANGE IS AN ADDITIONAL LABELLED COMMON
C     'KERNAL' IN THIS SUBROUTINE, IN MAIN, AND A SMALL ADDED SECTION
C     IN MAIN.
C
        A(K)=CQUAD(J)*SWT*USERKK(IROW,JJJ)
        K=K+INC                                                    GEROW5
  210 CONTINUE                                                     GEROW6
```

```
      IF (NLINF .LE. 0)  GO TO 230                           GEROW7
      DO 220 J=1,NLINF                                       GEROW8
        JJJ=J                                                GEROW9
        A(K)=SWT*USERLF(IROW,JJJ,T,NY)                       GEROW0
        K=K+INC                                              GEROW1
  220 CONTINUE                                               GEROW2
  230 A(K)=Y(IROW)*SWT                                       GEROW3
      IF (IUNIT .LT. 0)  GO TO 800                           GEROW4
      WRITE (IUNIT) (A(J),J=1,JJ,INC)                        GEROW5
  300 IF (IROW .EQ. NY)  REWIND IUNIT                        GEROW6
  800 RETURN                                                 GEROW7
      END                                                    GEROW8
      SUBROUTINE GETYLY (SOL,                                GEYLY8
     1 CQUAD,G,IUNIT,IWT,MWORK,NG,NGL,NLINF,NY,SQRTW,T,WORK,Y,YLYFIT)  GEYLY9
      DOUBLE PRECISION DUM, SOL, WORK                        GEYLY0
      DIMENSION WORK(MWORK), SQRTW(NY), CQUAD(NG), G(NG), T(NY),  GEYLY1
     1 Y(NY), YLYFIT(NY), SOL(NGL)                           GEYLY2
      DO 110 IROW=1,NY                                       GEYLY3
        IIROW=IROW                                           GEYLY4
        CALL GETROW (IIROW,WORK,.FALSE.,0,1,IUNIT,           GEYLY5
     1  SQRTW,NY,NGL,IWT,NG,CQUAD,G,T,NLINF,Y)               GEYLY6
        DUM=WORK(NGL+1)                                      GEYLY7
        DO 120 ICOL=1,NGL                                    GEYLY8
          DUM=DUM-WORK(ICOL)*SOL(ICOL)                       GEYLY9
  120   CONTINUE                                             GEYLY0
        YLYFIT(IROW)=DUM                                     GEYLY1
  110 CONTINUE                                               GEYLY2
      RETURN                                                 GEYLY3
      END                                                    GEYLY4
      SUBROUTINE G1 (A,B,COS,SIN,SIG)                        G1   3
      DOUBLE PRECISION A, ABS, B, COS, ONE, SIG, SIGN, SIN, SQRT,  G1   5
     1 XR, YR, ZERO                                          G1   6
      ABS(A)=DABS(A)                                         G1   7
      SQRT(A)=DSQRT(A)                                       G1   8
      SIGN(A,B)=DSIGN(A,B)                                   G1   9
      ZERO=0.D0                                              G1   1
      ONE=1.D0                                               G1   3
      IF (ABS(A).LE.ABS(B))  GO TO 10                        G1   4
      XR=B/A                                                 G1   5
      YR=SQRT(ONE+XR**2)                                     G1   6
      COS=SIGN(ONE/YR,A)                                     G1   7
      SIN=COS*XR                                             G1   8
      SIG=ABS(A)*YR                                          G1   9
      RETURN                                                 G1   0
   10 IF (B)  20,30,20                                       G1   1
   20 XR=A/B                                                 G1   2
      YR=SQRT(ONE+XR**2)                                     G1   3
      SIN=SIGN(ONE/YR,B)                                     G1   4
      COS=SIN*XR                                             G1   5
      SIG=ABS(B)*YR                                          G1   6
      RETURN                                                 G1   7
   30 SIG=ZERO                                               G1   8
      COS=ZERO                                               G1   9
      SIN=ONE                                                G1   0
      RETURN                                                 G1   1
      END                                                    G1   2
      SUBROUTINE G2   (COS,SIN,X,Y)                          G2   3
      DOUBLE PRECISION COS, SIN, X, XR, Y                    G2   7
      XR=COS*X+SIN*Y                                         G2   8
      Y=-SIN*X+COS*Y                                         G2   9
      X=XR                                                   G2   0
      RETURN                                                 G2   1
      END                                                    G2   2
      SUBROUTINE H12 (MODE,LPIVOT,L1,M,U,IUE,UP,C,ICE,ICV,NCV,RANGE)  H12  5
      DIMENSION U(IUE,1), C(1)                               H12  6
      DOUBLE PRECISION SM,B                                  H12  7
      DOUBLE PRECISION ABS, AMAX1, C, CL, CLINV, DOUBLE, ONE, RANGE,  H12  8
     1 RANGIN, SIGN, SM1, SQRT, U, UP                        H12  9
      ABS(SM)=DABS(SM)                                       H12  0
      AMAX1(SM,ONE)=DMAX1(SM,ONE)                            H12  1
      DOUBLE(SM)=SM                                          H12  3
      SQRT(SM)=DSQRT(SM)                                     H12  4
```

```
      SIGN(SM,ONE)=DSIGN(SM,ONE)                              H12  5
      ONE=1.D0                                                H12  7
      IF (0.GE.LPIVOT.OR.LPIVOT.GE.L1.OR.L1.GT.M)  RETURN     H12  9
      RANGIN=ONE/RANGE                                        H12  0
      CL=ABS(U(1,LPIVOT))                                     H12  1
      IF (MODE.EQ.2)  GO TO 60                                H12  2
          DO 10 J=L1,M                                        H12  4
   10     CL=AMAX1(ABS(U(1,J)),CL)                            H12  5
      IF (CL .LE. RANGIN)  GO TO 130                          H12  6
      CLINV=ONE/CL                                            H12  7
      SM=(DOUBLE(U(1,LPIVOT))*CLINV)**2                       H12  8
          DO 30 J=L1,M                                        H12  9
   30     SM=SM+(DOUBLE(U(1,J))*CLINV)**2                     H12  0
      SM1=SM                                                  H12  2
      CL=-SIGN(CL*SQRT(SM1),U(1,LPIVOT))                      H12  3
      UP=U(1,LPIVOT)-CL                                       H12  4
      U(1,LPIVOT)=CL                                          H12  5
      GO TO 70                                                H12  6
   60 IF (CL .LE. RANGIN)  GO TO 130                          H12  9
   70 IF (NCV.LE.0)  RETURN                                   H12  0
      B=DOUBLE(UP)*U(1,LPIVOT)                                H12  1
      IF (B .GE. -RANGIN)  GO TO 130                          H12  4
      B=ONE/B                                                 H12  5
      I2=1-ICV+ICE*(LPIVOT-1)                                 H12  6
      INCR=ICE*(L1-LPIVOT)                                    H12  7
          DO 120 J=1,NCV                                      H12  8
          I2=I2+ICV                                           H12  9
          I3=I2+INCR                                          H12  0
          I4=I3                                               H12  1
          SM=C(I2)*DOUBLE(UP)                                 H12  2
              DO 90 I=L1,M                                    H12  3
              SM=SM+C(I3)*DOUBLE(U(1,I))                      H12  4
   90         I3=I3+ICE                                       H12  5
          IF (SM)  100,120,100                                H12  6
  100     SM=SM*B                                             H12  7
          C(I2)=C(I2)+SM*DOUBLE(UP)                           H12  8
              DO 110 I=L1,M                                   H12  9
              C(I4)=C(I4)+SM*DOUBLE(U(1,I))                   H12  0
  110         I4=I4+ICE                                       H12  1
  120     CONTINUE                                            H12  2
  130 RETURN                                                  H12  3
      END                                                     H12  4
      SUBROUTINE INIT                                         INIT 6
      DOUBLE PRECISION PRECIS, RANGE                          INIT 7
      DOUBLE PRECISION ONE, ZERO, PREMIN, DIFF,               INIT 8
     1 SMALL, SIZE, PTRY, DELTRY, AMAX1                       INIT 9
      LOGICAL DOMOM, DOUSIN, DOUSNQ, DOUSOU, LAST, NONNEG, ONLY1, PRWT,  INIT 0
     1 PRY, SIMULA, LUSER                                     INIT 1
      LOGICAL DONE1                                           INIT 2
      CHARACTER IHOLER(6), IFORMT(70), IFORMW(70), IFORMY(70),
     + LA(6,46), ITITLE(80)
      COMMON /SBLOCK/ PRECIS, RANGE, SRMIN,                   INIT 4
     1 ALPST(2), GMNMX(2), PLEVEL(2,2), RSVMNX(2,2), RUSER(100),  INIT 5
     2 EXMAX, SRANGE                                          INIT 6
      COMMON /IBLOCK/ IGRID, IPLRES, IPRINT, IQUAD, IUNIT, IWT,  INIT 7
     1 LINEPG, MIOERR, MQPITR, NEQ, NERFIT, NG, NINTT, NLINF, NORDER,  INIT 8
     2 ICRIT(2), IPLFIT(2),
     3  IUSER(50), LSIGN(4,4), MOMNMX(2), NENDZ(2),           INIT 0
     4 NFLAT(4,2), NGL, NGLP1, NIN, NINEQ, NNSGN(2), NOUT, NQPROG(2),  INIT 1
     5 NSGN(4), NY                                            INIT 2
      COMMON /CBLOCK/ IFORMT, IFORMW, IFORMY, LA,ITITLE
      COMMON /LBLOCK/ DOMOM, DOUSIN, DOUSNQ, DOUSOU, LAST, NONNEG,  INIT 3
     1 ONLY1, PRWT, PRY, SIMULA,                              INIT 4
     2 LUSER(30)                                              INIT 5
      DATA IHOLER/'I','N','I','T',' ',' '/                    INIT 6
      AMAX1(PTRY,PRECIS)=DMAX1(PTRY,PRECIS)                   INIT 7
      ONE=1.D0                                                INIT 9
      ZERO=0.D0                                               INIT 1
      PREMIN=1.D-8                                            INIT 3
      FACT=RANGE**(-.025)                                     INIT 4
      SMALL=ONE/RANGE                                         INIT 5
      DONE1=.FALSE.                                           INIT 6
```

```
      SIZE=RANGE                                                    INIT 7
      DO 110 J=1,80                                                 INIT 8
        PTRY=PREMIN                                                 INIT 9
        DO 120 K=1,150                                              INIT 0
          PTRY=.5*PTRY                                              INIT 1
          DELTRY=PTRY*SIZE                                          INIT 2
          IF (DELTRY .LT. SMALL)  GO TO 140                         INIT 3
          IF (DIFF(SIZE+DELTRY,SIZE) .LE. ZERO)  GO TO 130          INIT 4
  120   CONTINUE                                                    INIT 5
  130   IF (DONE1)  PRECIS=AMAX1(PTRY,PRECIS)                       INIT 6
        IF (.NOT.DONE1)  PRECIS=PTRY                                INIT 7
        DONE1=.TRUE.                                                INIT 8
        SIZE=FACT*SIZE                                              INIT 9
  110 CONTINUE                                                      INIT 0
  140 PRECIS=20.*PRECIS                                             INIT 1
      IF (PRECIS .GT. PREMIN)  CALL ERRMES (1,.TRUE.,IHOLER,NOUT)   INIT 2
      MIDERR=MAX0(2,MIDERR)                                         INIT 3
      EXMAX=ALOG(SRANGE)                                            INIT 4
      RETURN                                                        INIT 5
      END                                                           INIT 6
      SUBROUTINE INPUT (EXACT,G,MA,MEQ,MG,MINEQ,MREG,MWORK,MY,SQRTW,T,Y)INPUT8
      DOUBLE PRECISION PRECIS, RANGE                                INPUT9
      LOGICAL DOMOM, DOUSIN, DOUSNQ, DOUSOU, LAST, NONNEG, ONLY1, PRWT, INPUT0
     1 PRY, SIMULA, LUSER                                           INPUT1
      LOGICAL LERR                                                  INPUT2
      DIMENSION SQRTW(MY), T(MY), Y(MY), EXACT(MY), G(MG)           INPUT3
      CHARACTER LIN(6)
      CHARACTER IHOLER(6), LA(6,46), LA1(6,14),LA2(6,11),IFORMY(70),
     + LA3(6,14), LA4(6,7), ITITLE(80), IFORMT(70), IFORMW(70)
      COMMON /CBLOCK/ IFORMT, IFORMW, IFORMY, LA,ITITLE
      COMMON /SBLOCK/ PRECIS, RANGE, SRMIN,                         INPUT6
     1 ALPST(2), GMNMX(2), PLEVEL(2,2), RSVMNX(2,2), RUSER(100),    INPUT7
     2 EXMAX, SRANGE                                                INPUT8
      COMMON /IBLOCK/ IGRID, IPLRES, IPRINT, IQUAD, IUNIT, IWT,     INPUT9
     1 LINEPG, MIDERR, MOPTIR, NEQ, NERFIT, NG, NINTT, NLINF, NORDER, INPUT0
     2 ICRIT(2), IPLFIT(2),
     3  IUSER(50), LSIGN(4,4), MOMNMX(2), NENDZ(2),                 INPUT2
     4 NFLAT(4,2), NGL, NGLP1, NIN, NINEQ, NNSGN(2), NOUT, NQPROG(2), INPUT3
     5 NSGN(4), NY                                                  INPUT4
      COMMON /LBLOCK/ DOMOM, DOUSIN, DOUSNQ, DOUSOU, LAST, NONNEG,  INPUT5
     1 ONLY1, PRWT, PRY, SIMULA,                                    INPUT6
     2 LUSER(30)                                                    INPUT7
      EQUIVALENCE (LA(1,1),LA1(1,1)), (LA(1,15),LA2(1,1)),          INPUT2
     1 (LA(1,26),LA3(1,1)), (LA(1,40),LA4(1,1))                     INPUT3
      DATA MLA/46/, IHOLER/'I','N','P','U','T',' '/                 INPUT4
      DATA LA1/                                                     INPUT5
     1 'S','R','M','I','N',' ',' ','A','L','P','S','T',' ',' ',     INPUT6
     2 'G','M','N','M','X',' ','P','L','E','V','E','L',             INPUT7
     3 'R','S','V','M','N','X','R','U','S','E','R',' ',             INPUT8
     4 'I','G','R','I','D',' ','I','P','L','R','E','S',             INPUT9
     5 'I','P','R','I','N','T','I','Q','U','A','D',' ',             INPUT0
     6 'I','U','N','I','T',' ',' ','I','W','T',3X' ',                  IU
     7 'L','I','N','E','P','G','M','I','O','E','R','R'/                IU
      DATA LA2/                                                     INPUT3
     1 'M','Q','P','I','T','R',                                     INPUT4
     2 'N','E','Q',3X' ','N','E','R','F','I','T',                   INPU4
     3 'N','G',' ',' ',' ',' ','N','I','N','T','T',' ',             INPUT6
     4 'N','L','I','N','F',' ','N','O','R','D','E','R',             INPUT7
     5 'I','C','R','I','T',' ',                                     INPUT8
     6 'I','F','O','R','M','T','I','F','O','R','M','W',             INPUT9
     7 'I','F','O','R','M','Y'/                                     INPUT0
      DATA LA3/                                                     INPUT1
     1 'I','P','L','F','I','T','I','U','S','E','R',' ',             INPUT2
     2 'L','S','I','G','N',' ','M','O','M','N','M','X',             INPUT3
     3 'N','E','N','D','Z',' ','N','F','L','A','T',' ',             INPUT4
     4 'N','N','S','G','N',' ','N','Q','P','R','O','G',             INPUT5
     5 'N','S','G','N',' ',' ','D','O','M','O','M',' ',             INPUT6
     6 'D','O','U','S','I','N','D','O','U','S','N','Q',             INPUT7
     7 'D','O','U','S','O','U','L','A','S','T',' ',' '/             INPUT8
```

```
      DATA LA4/                                                      INPUT9
     1 'N','O','N','N','E','G','O','N','L','Y','1',' ',              INPUT0
     2 'P','R','W','T',' ',' ','P','R','Y',' ',' ',' ',              INPUT1
     3 'S','I','M','U','L','A','L','U','S','E','R',' ',              INPUT2
     4 'E','N','D',' ',' ',' '/                                      INPUT3
5001 FORMAT (' ')                                                    INPUT4
5100 FORMAT (80A1)                                                   INPUT5
     READ (NIN,5100) ITITLE                                          INPUT6
5101 FORMAT ('1CONTIN - VERSION 1 (NOV 1980)',10X,80A1               INPUT7
     1 //40X,'INPUT DATA FOR CHANGES TO COMMON VARIABLES'/)          INPUT8
     WRITE (NOUT,5101) ITITLE                                        INPUT9
     NIOERR=0                                                        INPUT0
5200 FORMAT (1X,6A1,I8,E15.6)                                        INPUT1
 200 READ (NIN,5200) LIN,IIN,RIN                                     INPUT2
     WRITE (NOUT,5001)                                               INPUT3
     WRITE (NOUT,5200) LIN,IIN,RIN                                   INPUT4
     DO 210 J=1,MLA                                                  INPUT5
       DO 220 K=1,6                                                  INPUT6
         IF (LIN(K) .NE. LA(K,J))  GO TO 210                         INPUT7
 220   CONTINUE                                                      INPUT8
       IF (J .EQ. MLA)  GO TO 300                                    INPUT9
       JJ=J                                                          INPUT0
       CALL STORIN (JJ,NIOERR,LIN,IIN,RIN)                           INPUT1
       GO TO 200                                                     INPUT2
 210 CONTINUE                                                        INPUT3
     CALL ERRMES (1,.FALSE.,IHOLER,NOUT)                             INPUT4
     WRITE (NOUT,5001)                                               INPUT5
     NIOERR=NIOERR+1                                                 INPUT6
     IF (NIOERR .GE. MIOERR)  STOP                                   INPUT7
     GO TO 200                                                       INPUT8
 300 CALL READYT (MY,NIOERR,SQRTW,T,Y)                                INPUT9
     CALL WRITIN (EXACT,G,MG,MY,SQRTW,T,Y)
     LERR=.FALSE.                                                    INPUT4
     DO 410 K=1,2                                                    INPUT5
       DO 420 J=1,2                                                  INPUT6
         IF (K.EQ.2 .OR. (IWT.NE.1 .AND. IWT.NE.4))  LERR=           INPUT7
     1LERR .OR.      PLEVEL(J,K).LT.0. .OR. PLEVEL(J,K)              INPUT8
     2.GT.1. .OR. ICRIT(K).LT.1       .OR. ICRIT(K).GT.2             INPUT9
         IF (NQPROG(K) .GT. 0)  LERR=LERR .OR. RSVMNX(J,K).LE.0.     INPUT0
 420   CONTINUE                                                      INPUT1
 410 CONTINUE                                                        INPUT2
     LERR=LERR .OR. MINO(IGRID,IQUAD,IWT,NG-1,NG+NLINF-NEQ).LT.1 .OR. INPUT3
    1 MINO(NLINF,NEQ).LT.0 .OR.                                      INPUT4
    2 MAXO(IGRID-3,IQUAD-3,IWT-5,NEQ-MEQ,NG+NLINF+2-MINO(MG,MA),     INPUT5
    3 NG+NLINF+1-MREG,NORDER-5,                                      INPUT6
    4 MAXO(MG,NY)-MY,MAXO((MINEQ+2)*(MG+1)-4,MG+NLINF+1)-MWORK) .GT. 0 INPUT7
     IF (.NOT.LERR)  GO TO 500                                       INPUT8
     CALL ERRMES (2,.FALSE.,IHOLER,NOUT)                             INPUT9
5420 FORMAT (' MY =',I5,5X,'MA =',I3,5X,'MG =',I3,5X,'MREG =',I3,5X, INPUT0
    1 'MINEQ =',I3,5X,'MEQ =',I3,5X,'MWORK =',I5)                    INPUT1
     WRITE (NOUT,5420) MY,MA,MG,MREG,MINEQ,MEQ,MWORK                 INPUT2
     STOP                                                            INPUT3
 500 IF (NIOERR .NE. 0)  STOP                                        INPUT4
     RETURN                                                          INPUT5
     END                                                             INPUT6
     SUBROUTINE LDP (G,MDG,M,N,H,X,XNORM,W,INDEX,MODE,RANGE)         LDP  2
     DOUBLE PRECISION DIFF, FAC, G, H, ONE, RANGE, RNORM,            LDP  7
    1 SQRT, W, X, XNORM, ZERO                                        LDP  8
     INTEGER INDEX(M)                                                LDP  9
     DIMENSION G(MDG,N), H(M), X(1), W(1)                            LDP  0
     SQRT(FAC)=DSQRT(FAC)                                            LDP  1
     ZERO=0.D0                                                       LDP  3
     ONE=1.D0                                                        LDP  5
     IF (N.LE.0)  GO TO 120                                          LDP  6
       DO 10 J=1,N                                                   LDP  7
  10     X(J)=ZERO                                                   LDP  8
     XNORM=ZERO                                                      LDP  9
     IF (M.LE.0)  GO TO 110                                          LDP  0
     IW=0                                                            LDP  2
       DO 30 J=1,M                                                   LDP  3
         DO 20 I=1,N                                                 LDP  4
           IW=IW+1                                                   LDP  5
```

```
20       W(IW)=G(J,I)                                              LDP  6
         IW=IW+1                                                   LDP  7
30       W(IW)=H(J)                                                LDP  8
   IF=IW+1                                                         LDP  9
         DO 40 I=1,N                                               LDP  1
         IW=IW+1                                                   LDP  2
40       W(IW)=ZERO                                                LDP  3
   W(IW+1)=ONE                                                     LDP  4
   NP1=N+1                                                         LDP  6
   IZ=IW+2                                                         LDP  7
   IY=IZ+NP1                                                       LDP  8
   IWDUAL=IY+M                                                     LDP  9
   CALL NNLS (W,NP1,NP1,M,W(IF),W(IY),RNORM,W(IWDUAL),W(IZ),INDEX, LDP  1
  1           MODE,RANGE)                                          LDP  2
   IF (MODE.NE.1) RETURN                                           LDP  4
   IF (RNORM) 130,130,50                                           LDP  5
50 FAC=ONE                                                         LDP  6
   IW=IY-1                                                         LDP  7
         DO 60 I=1,M                                               LDP  8
         IW=IW+1                                                   LDP  9
60       FAC=FAC-H(I)*W(IW)                                        LDP  1
   IF (DIFF(ONE+FAC,ONE)) 130,130,70                               LDP  3
70 FAC=ONE/FAC                                                     LDP  4
         DO 90 J=1,N                                               LDP  5
         IW=IY-1                                                   LDP  6
            DO 80 I=1,M                                            LDP  7
            IW=IW+1                                                LDP  8
80          X(J)=X(J)+G(I,J)*W(IW)                                 LDP  0
90       X(J)=X(J)*FAC                                             LDP  1
         DO 100 J=1,N                                              LDP  2
100      XNORM=XNORM+X(J)**2                                       LDP  3
   XNORM=SQRT(XNORM)                                               LDP  4
110 MODE=1                                                         LDP  6
    RETURN                                                         LDP  7
120 MODE=2                                                         LDP  9
    RETURN                                                         LDP  0
130 MODE=4                                                         LDP  2
    RETURN                                                         LDP  3
    END                                                            LDP  4
    SUBROUTINE LDPETC (FINDVZ,NNNNEQ,SSEARC,IICRIT,DDOMOM,PPLTPR,  LDETC2
   1 PRLDP,ALPHA,HEADNG,NEWPAG,ALPBES,VAR,                         LDETC3
   2 A,AA,AINEQ,BTEST,CQUAD,DEGFRE,DEGFRZ,EXACT,G,IERROR,          LDETC4
   3 ISTAGE,IWORK,LBIND,MA,MG,MINEQ,MREG,MWORK,MY,                 LDETC5
   4 NGLE,NGLY,PREJ,REG,RHSNEQ,S,SAVBES,SOLBES,                    LDETC6
   5 SOLUTN,SQRTW,T,VALPCV,VALPHA,VARREG,VARZ,WORK,Y,YLYFIT)       LDETC7
    DOUBLE PRECISION PRECIS, RANGE                                 LDETC8
    DOUBLE PRECISION A, AA, AINEQ, ALPBES, ALPHA, DUB, REG,        LDETC9
   1 RHSNEQ, S, SOLBES, SOLUTN, VALPCV, VALPHA, WORK, ZERO         LDETC0
    LOGICAL DOMOM, DOUSIN, DOUSNQ, DOUSOU, LAST, NONNEG, ONLY1, PRWT, LDETC1
   1 PRY, SIMULA, LUSER                                            LDETC2
    LOGICAL FINDVZ, SSEARC, PPLTPR, LBIND, PRLDP, DDOMOM,          LDETC3
   1 NEWPAG, HEADNG                                                LDETC4
    DIMENSION SOLUTN(MG), VALPHA(MG), S(MG,3), A(MA,MG),           LDETC5
   1 AINEQ(MINEQ,MG), RHSNEQ(MINEQ), WORK(MWORK), IWORK(MA),       LDETC6
   2 REG(MREG,MG), VALPCV(MG), G(MG), EXACT(MG),                   LDETC7
   3 CQUAD(MG), SOLBES(MG), PREJ(2), SAVBES(7),                    LDETC8
   4 LBIND(MINEQ), AA(MG,MG), SQRTW(MY), T(MY), Y(MY), YLYFIT(MY)  LDETC9
    CHARACTER IHOLER(6), ISTAR(2), IFORMT(70), IFORMW(70),
   + IFORMY(70), LA(6,46), ITITLE(80)
    COMMON /CBKOCK/ IFORMT,IFORMW,IFORMY,LA,ITITLE
    COMMON /SELOCK/ PRECIS, RANGE, SRMIN,                          LDETC1
   1 ALPST(2), GMNMX(2), PLEVEL(2,2), RSVMNX(2,2), RUSER(100),     LDETC2
   2 EXMAX, SRANGE                                                 LDETC3
    COMMON /IBLOCK/ IGRID, IPLRES, IPRINT, IQUAD, IUNIT, IWT,      LDETC4
   1 LINEPG, MIOERR, MQPITR, NEQ, NERFIT, NG, NINTT, NLINF, NORDER, LDETC5
   2 ICRIT(2), IPLFIT(2),                                          LDETC6
   3 IUSER(50), LSIGN(4,4), MOMNMX(2), NENDZ(2),                   LDETC7
   4 NFLAT(4,2), NGL, NGLP1, NIN, NINEQ, NNSGN(2), NOUT, NQPROG(2), LDETC8
   5 NSGN(4), NY                                                   LDETC9
    COMMON /LBLOCK/ DOMOM, DOUSIN, DOUSNQ, DOUSOU, LAST, NONNEG,   LDETC0
```

```
    1 ONLY1, PRWT, PRY, SIMULA,                                        LDETC1
    2 LUSER(30)                                                        LDETC2
      DATA IHOLER/'L','D','P','E','T','C'/,ISTAR/' ','*'/              LDETC3
      ZERO=0.DO                                                        LDETC5
      DEGFRE=0.                                                        LDETC6
      LSTAR=1                                                          LDETC7
      VAR=SRANGE                                                       LDETC8
      VARREG=SRANGE                                                    LDETC9
      DO 105 J=1,NGL                                                   LDETC0
         SOLUTN(J)=VALPHA(J)                                           LDETC1
         S(J,3)=ZERO                                                   LDETC2
  105 CONTINUE                                                         LDETC3
      IF (NNNNEQ .EQ. 0)  GO TO 240                                    LDETC4
      CALL LDP (A,MA,NNNNEQ,NGLE,RHSNEQ,S(1,3),DUB,WORK,IWORK,IERROR,  LDETC9
    1 RANGE)                                                           LDETC0
      GO TO (240,210,220,230),IERROR                                   LDETC1
  210 CALL ERRMES (1,.TRUE.,IHOLER,NOUT)                               LDETC2
  220 DDUM=ALPHA/S(1,1)                                                LDETC3
 5220 FORMAT ('0MAX. ITERATIONS IN NNLS FOR ALPHA/S(1) =',1PE9.2)      LDETC4
      WRITE (NOUT,5220) DDUM                                           LDETC5
      RETURN                                                           LDETC6
  230 CALL ERRMES (2,.TRUE.,IHOLER,NOUT)                               LDETC7
  240 VARREG=0.                                                        LDETC8
      DO 250 ICOL=1,NGLE                                               LDETC9
         DUB=S(ICOL,2)*S(ICOL,3)                                       LDETC3
         VARREG=VARREG+(DUB+S(ICOL,2)**2*S(ICOL,1)*(A(ICOL,NGLP1)-    LDETC7
    1    S(ICOL,1)*REG(ICOL,NGLP1)))**2                                LDETC8
         DO 255 IROW=1,NGL                                             LDETC9
            SOLUTN(IROW)=SOLUTN(IROW)+REG(IROW,ICOL)*DUB               LDETC0
  255    CONTINUE                                                      LDETC1
  250 CONTINUE                                                         LDETC2
      CALL CVNEQ (ALPHA,IERROR,NNNNEQ,SOLUTN,                          LDETC3
    1 A,AA,AINEQ,DEGFRE,LBIND,MA,MG,MINEQ,MREG,MWORK,NGL,NGLE,         LDETC4
    2 NGLP1,NGLY,NOUT,RANGE,REG,S,VALPCV,WORK)                         LDETC5
      CALL GETYLY (SOLUTN,                                             LDETC9
    1 CQUAD,G,IUNIT,IWT,MWORK,NG,NGL,NLINF,NY,SQRTH,T,WORK,Y,YLYFIT)   LDETC0
      VAR=0.                                                           LDETC1
      DO 310 J=1,NY                                                    LDETC2
         VAR=VAR+YLYFIT(J)**2                                          LDETC3
  310 CONTINUE                                                         LDETC4
      VARREG=VARREG*ALPHA**2+VAR                                       LDETC5
      IF (VARZ.LT.VAR .OR. .NOT.FINDVZ .OR. IERROR.NE.1) GO TO 320     LDETC6
      LSTAR=2                                                          LDETC7
      BTEST=SRANGE                                                     LDETC8
      ALPBES=ZERO                                                      LDETC9
      DEGFRZ=DEGFRE                                                    LDETC0
      VARZ=VAR                                                         LDETC1
  320 PREJ(1)=-1.                                                      LDETC2
      PREJ(2)=-1.                                                      LDETC3
      IF (VARZ.GE.SRANGE .OR. IERROR.NE.1)  GO TO 325                  LDETC4
      DDUM=AMAX1(0.,VAR/VARZ-1.)                                       LDETC5
      DDDUM=AMAX1(0.,FLOAT(NY)-DEGFRZ)                                 LDETC6
      PREJ(1)=FISHNI(DDUM*DDDUM/DEGFRZ,DEGFRZ,DDDUM,NOUT)              LDETC7
      PREJ(2)=1.                                                       LDETC8
      IF (DEGFRZ-DEGFRE .GT. .1) PREJ(2)=FISHNI(DDUM*DDDUM/ (DEGFRZ-  LDETC9
    1 DEGFRE),DEGFRZ-DEGFRE,DDDUM,NOUT)                                LDETC0
 5999 FORMAT (' ')                                                     LDETC1
  325 IF (NEWPAG) WRITE (NOUT,5999)                                    LDETC2
      IF (.NOT.HEADNG) GO TO 326                                       LDETC3
 5300 FORMAT (/10X,80A1,10X,'PRELIMINARY UNWEIGHTED ANALYSIS')         LDETC4
      IF (ISTAGE .EQ. 1) WRITE (NOUT,5300) ITITLE                     LDETC5
 5302 FORMAT (/10X,80A1)                                               LDETC6
      IF (ISTAGE .EQ. 2) WRITE (NOUT,5302) ITITLE                     LDETC7
 5310 FORMAT (/6X,'ALPHA',4X,'ALPHA/S(1)',5X,                          LDETC8
    1 'OBJ. FCTN.',7X,'VARIANCE',6X,'STD. DEV.',4X,'DEG FREEDOM',4X,  LDETC9
    2 'PROB1 TO REJECT',4X,'PROB2 TO REJECT')                          LDETC0
      WRITE (NOUT,5310)                                                LDETC1
 5320 FORMAT (1X,A1,1PE9.2,E14.2,2E15.5,E15.3,0PF15.3,2F19.3)          LDETC2
  326 DDUM=ALPHA/S(1,1)                                                LDETC3
      DDDUM=ALPHA                                                      LDETC4
      STDDEV=SRANGE                                                    LDETC5
      IF (FLOAT(NY) .GT. DEGFRE) STDDEV=SQRT(VAR/(FLOAT(NY)-DEGFRE))  LDETC6
      IF (PRLDP) WRITE (NOUT,5320) ISTAR(LSTAR),DDDUM,DDUM,VARREG,VAR, LDETC7
```

```
      1 STDDEV,DEGFRE,PREJ                                       LDETC8
        IF (.NOT.PPLTPR) GO TO 328                               LDETC9
        DO 327 J=1,NGL                                           LDETC4
          YLYFIT(J)=SOLUTN(J)                                    LDETC5
    327 CONTINUE                                                 LDETC6
        CALL PLPRIN (G,YLYFIT,EXACT,NG,ONLY1,NOUT,SRANGE,        LDETC7
      1 NLINF,NG,NGL)                                            LDETC8
        IF (DOUSOU) CALL USEROU (G,YLYFIT,EXACT,NG)              LDETC9
        IF (DDOMOM) CALL MOMENT (G,YLYFIT,CQUAD,NG, MOMNMX(1),MOMNMX(2), LDETC0
      1NOUT)                                                     LDETC1
    328 IF (.NOT.SSEARC .OR. VARZ.GE.SRANGE) GO TO 800           LDETC2
        TEST=PREJ(IICRIT)-PLEVEL(IICRIT,ISTAGE)                  LDETC3
        IF (ALPHA .LT. ALPBES) TEST=ABS(TEST)                    LDETC0
        IF (TEST .GE. BTEST) GO TO 800                           LDETC1
        SAVBES(1)=ALPHA/S(1,1)                                   LDETC2
        SAVBES(2)=VARREG                                         LDETC3
        SAVBES(3)=VAR                                            LDETC4
        SAVBES(4)=STDDEV                                         LDETC5
        SAVBES(5)=DEGFRE                                         LDETC6
        SAVBES(6)=PREJ(1)                                        LDETC7
        SAVBES(7)=PREJ(2)                                        LDETC8
        BTEST=ABS(TEST)                                          LDETC9
        ALPBES=ALPHA                                             LDETC0
        DO 330 J=1,NGL                                           LDETC1
          SOLBES(J)=SOLUTN(J)                                    LDETC2
    330 CONTINUE                                                 LDETC3
    800 RETURN                                                   LDETC4
        END                                                      LDETC5
        SUBROUTINE LH1405 (F,M2,M1,E,ME,X)                       LH4053
        DOUBLE PRECISION DUM, E, F, X                            LH4054
        DIMENSION F(1), E(ME,M1), X(M1)                          LH4055
        DO 110 I=1,M2                                            LH4056
          DUM=F(I)                                               LH4057
          DO 120 J=1,M1                                          LH4058
            DUM=DUM-E(I,J)*X(J)                                  LH4059
    120   CONTINUE                                               LH4050
          F(I)=DUM                                               LH4051
    110 CONTINUE                                                 LH4052
        RETURN                                                   LH4053
        END                                                      LH4054
        SUBROUTINE MOMENT (X,Y,CQUAD,N,IDEGMN,IDEGMX,NOUT)       MOENT4
        DIMENSION X(N), Y(N), CQUAD(N)                           MOENT5
        DIMENSION AMOM(4,5), PKEND(4)                            MOENT6
        DATA RMIN/1.E-3/                                         MOENT7
        NM=MIN0(5,IDEGMX-IDEGMN+1)                               MOENT8
        IF (NM .LT. 1) RETURN                                    MOENT9
   5110 FORMAT (/9X,'TOTAL CURVE',8X,3(19X,'PEAK',I2,9X)/        MOENT0
      1 ' J',3X,'MOMENT(J)',3X,'M(J)/M(J-1)',                    MOENT1
      2 3(11X,'MOMENT(J)',3X,'M(J)/M(J-1)'))                     MOENT2
        WRITE (NOUT,5110) (J,J=1,3)                              MOENT3
        THRESH=ABS(Y(1))                                         MOENT4
        DO 110 J=2,N                                             MOENT5
          THRESH=AMAX1(THRESH,ABS(Y(J)))                         MOENT6
    110 CONTINUE                                                 MOENT7
        THRESH=RMIN*THRESH                                       MOENT8
        IPEAK=2                                                  MOENT9
        DO 120 JPEAK=1,4                                         MOENT0
          DO 120 JDEG=1,NM                                       MOENT1
            AMOM(JPEAK,JDEG)=0.                                  MOENT2
    120 CONTINUE                                                 MOENT3
        DLAST=Y(2)-Y(1)                                          MOENT4
        DO 150 J=1,N                                             MOENT5
          PKEND(IPEAK)=X(J)                                      MOENT6
          IF (J.EQ.1 .OR. J.EQ.N) GO TO 160                      MOENT7
          DNEXT=Y(J+1)-Y(J)                                      MOENT8
          IF (DLAST.LT.-THRESH .AND. DNEXT.GT.THRESH)IPEAK=MIN0(IPEAK+1,4)MOENT9
          IF (ABS(DNEXT) .GT. THRESH) DLAST=DNEXT                MOENT0
    160   IF (IDEGMN.LT.0 .AND. ABS(X(J)).LE.0.) RETURN          MOENT1
          TERM=Y(J)*CQUAD(J)                                     MOENT2
          IF(IDEGMN .NE. 0) TERM=TERM*X(J)**IDEGMN               MOENT3
          DO 170 JDEG=1,NM                                       MOENT4
```

```
          AMOM(IPEAK,JDEG)=AMOM(IPEAK,JDEG)+TERM                    MOENT5
          IF (JDEG .LT. NM) TERM=TERM*X(J)                           MOENT6
170     CONTINUE                                                    MOENT7
150   CONTINUE                                                      MOENT8
      DO 180 JDEG=1,NM                                              MOENT9
        DO 180 JPEAK=2,IPEAK                                        MOENT0
          AMOM(1,JDEG)=AMOM(1,JDEG)+AMOM(JPEAK,JDEG)                MOENT1
180   CONTINUE                                                      MOENT2
5180  FORMAT (1X,I2,1PE12.4,3E34.4)                                 MOENT3
      WRITE (NOUT,5180) IDEGMN,(AMOM(J,1),J=1,IPEAK)                MOENT4
      IF (NM .EQ. 1) GO TO 300                                      MOENT5
      J=IDEGMN                                                      MOENT6
      DO 210 JDEG=2,NM                                              MOENT7
        J=J+1                                                       MOENT8
        DO 220 JPEAK=1,IPEAK                                        MOENT9
          IF (ABS(AMOM(JPEAK,JDEG-1)) .GT. 0.) AMOM(JPEAK,JDEG-1)=  MOENT0
     1      AMOM(JPEAK,JDEG)/AMOM(JPEAK,JDEG-1)                     MOENT1
220     CONTINUE                                                    MOENT2
5220    FORMAT (1X,I2,1PE12.4,E14.4,3(E20.4,E14.4))                 MOENT3
        WRITE (NOUT,5220) J,(AMOM(JPEAK,JDEG),AMOM(JPEAK,JDEG-1),   MOENT4
     1    JPEAK=1,IPEAK)                                            MOENT5
210   CONTINUE                                                      MOENT6
5230  FORMAT (' CURRENT PEAK ENDS AND NEXT PEAK BEGINS AT',         MOENT7
     1  1PE11.3,10X,2(16X,E11.3,7X))                                MOENT8
300   IF (IPEAK .GT. 2) WRITE (NOUT,5230)(PKEND(J),J=2,IPEAK)       MOENT9
      RETURN                                                        MOENT0
      END                                                           MOENT1
      SUBROUTINE NNLS (A,MDA,M,N,B,X,RNORM,W,ZZ,INDEX,MODE,RANGE)   NNLS 2
      DOUBLE PRECISION A, ABS, ALPHA, ASAVE, B, CC, DIFF, DUMMY,    NNLS 3
     1 FACTOR, RANGE, RNORM, SM, SQRT, SS, T, TWO, UNORM, UP, W,    NNLS 4
     2 WMAX, X, ZERO, ZTEST, ZZ                                     NNLS 5
      DIMENSION A(MDA,N), B(1), X(1), W(1), ZZ(1)                   NNLS 6
      INTEGER INDEX(N)                                              NNLS 7
      ABS(T)=DABS(T)                                                NNLS 8
      SQRT(T)=DSQRT(T)                                              NNLS 9
      ZERO=0.D0                                                     NNLS 1
      TWO=2.D0                                                      NNLS 3
      FACTOR=1.D-4                                                  NNLS 5
      MODE=1                                                        NNLS 7
      IF (M.GT.0.AND.N.GT.0) GO TO 10                               NNLS 8
      MODE=2                                                        NNLS 9
      RETURN                                                        NNLS 0
10    ITER=0                                                        NNLS 1
      ITMAX=3*N                                                     NNLS 2
          DO 20 I=1,N                                               NNLS 6
          X(I)=ZERO                                                 NNLS 7
20        INDEX(I)=I                                                NNLS 8
      IZ2=N                                                         NNLS 0
      IZ1=1                                                         NNLS 1
      NSETP=0                                                       NNLS 2
      NPP1=1                                                        NNLS 3
30    CONTINUE                                                      NNLS 5
      IF (IZ1.GT.IZ2.OR.NSETP.GE.M) GO TO 350                       NNLS 9
          DO 50 IZ=IZ1,IZ2                                          NNLS 3
          J=INDEX(IZ)                                               NNLS 4
          SM=ZERO                                                   NNLS 5
              DO 40 L=NPP1,M                                        NNLS 6
40            SM=SM+A(L,J)*B(L)                                     NNLS 7
50        W(J)=SM                                                   NNLS 8
60    WMAX=ZERO                                                     NNLS 0
          DO 70 IZ=IZ1,IZ2                                          NNLS 1
          J=INDEX(IZ)                                               NNLS 2
          IF (W(J).LE.WMAX) GO TO 70                                NNLS 3
          WMAX=W(J)                                                 NNLS 4
          IZMAX=IZ                                                  NNLS 5
70        CONTINUE                                                  NNLS 6
      IF (WMAX) 350,350,80                                          NNLS 1
80    IZ=IZMAX                                                      NNLS 2
      J=INDEX(IZ)                                                   NNLS 3
      ASAVE=A(NPP1,J)                                               NNLS 9
      CALL H12 (1,NPP1,NPP1+1,M,A(1,J),1,UP,DUMMY,1,1,0,RANGE)      NNLS 0
      UNORM=ZERO                                                    NNLS 1
```

```
      IF (NSETP.EQ.0)   GO TO 100                                  NNLS 2
          DO 90 L=1,NSETP                                          NNLS 3
 90       UNORM=UNORM+A(L,J)**2                                    NNLS 4
      UNORM=SQRT(UNORM)                                            NNLS 5
100   IF (DIFF(UNORM+ABS(A(NPP1,J))*FACTOR,UNORM))    130,130,110  NNLS 6
110       DO 120 L=1,M                                             NNLS 1
120       ZZ(L)=B(L)                                               NNLS 2
      CALL H12 (2,NPP1,NPP1+1,M,A(1,J),1,UP,ZZ,1,1,1,RANGE)        NNLS 3
      ZTEST=ZZ(NPP1)/A(NPP1,J)                                     NNLS 4
      IF (ZTEST)   130,130,140                                     NNLS 0
130   A(NPP1,J)=ASAVE                                              NNLS 4
      W(J)=ZERO                                                    NNLS 5
      GO TO 60                                                     NNLS 6
140       DO 150 L=1,M                                             NNLS 3
150       B(L)=ZZ(L)                                               NNLS 4
      INDEX(IZ)=INDEX(IZ1)                                         NNLS 6
      INDEX(IZ1)=J                                                 NNLS 7
      IZ1=IZ1+1                                                    NNLS 8
      NSETP=NPP1                                                   NNLS 9
      NPP1=NPP1+1                                                  NNLS 0
      IF (IZ1.GT.IZ2)   GO TO 170                                  NNLS 2
          DO 160 JZ=IZ1,IZ2                                        NNLS 3
          JJ=INDEX(JZ)                                             NNLS 4
160       CALL H12 (2,NSETP,NPP1,M,A(1,J),1,UF,A(1,JJ),1,MDA,1,RANGE)  NNLS 5
170   CONTINUE                                                     NNLS 6
      IF (NSETP.EQ.M)   GO TO 190                                  NNLS 8
          DO 180 L=NPP1,M                                          NNLS 9
180       A(L,J)=ZERO                                              NNLS 0
190   CONTINUE                                                     NNLS 1
      W(J)=ZERO                                                    NNLS 3
      ASSIGN 200 TO NEXT                                           NNLS 6
      GO TO 400                                                    NNLS 7
200   CONTINUE                                                     NNLS 8
210   ITER=ITER+1                                                  NNLS 4
      IF (ITER.LE.ITMAX)   GO TO 220                               NNLS 5
      MODE=3                                                       NNLS 6
      GO TO 350                                                    NNLS 7
220   CONTINUE                                                     NNLS 8
      ALPHA=TWO                                                    NNLS 3
          DO 240 IP=1,NSETP                                        NNLS 4
          L=INDEX(IP)                                              NNLS 5
          IF (ZZ(IP))   230,230,240                                NNLS 6
230       T=-X(L)/(ZZ(IP)-X(L))                                    NNLS 8
          IF (ALPHA.LE.T)   GO TO 240                              NNLS 9
          ALPHA=T                                                  NNLS 0
          JJ=IP                                                    NNLS 1
240       CONTINUE                                                 NNLS 2
      IF (ALPHA.EQ.TWO)   GO TO 330                                NNLS 7
          DO 250 IP=1,NSETP                                        NNLS 2
          L=INDEX(IP)                                              NNLS 3
250       X(L)=X(L)+ALPHA*(ZZ(IP)-X(L))                            NNLS 4
      I=INDEX(JJ)                                                  NNLS 9
260   X(I)=ZERO                                                    NNLS 0
      IF (JJ.EQ.NSETP)   GO TO 290                                 NNLS 2
      JJ=JJ+1                                                      NNLS 3
          DO 280 J=JJ,NSETP                                        NNLS 4
          II=INDEX(J)                                              NNLS 5
          INDEX(J-1)=II                                            NNLS 6
          CALL G1 (A(J-1,II),A(J,II),CC,SS,A(J-1,II))              NNLS 7
          A(J,II)=ZERO                                             NNLS 8
              DO 270 L=1,N                                         NNLS 9
              IF (L.NE.II)   CALL G2 (CC,SS,A(J-1,L),A(J,L))       NNLS 0
270           CONTINUE                                             NNLS 1
280       CALL G2 (CC,SS,B(J-1),B(J))                              NNLS 2
290   NPP1=NSETP                                                   NNLS 3
      NSETP=NSETP-1                                                NNLS 4
      IZ1=IZ1-1                                                    NNLS 5
      INDEX(IZ1)=I                                                 NNLS 6
          DO 300 JJ=1,NSETP                                        NNLS 4
          I=INDEX(JJ)                                              NNLS 5
          IF (X(I))   260,260,300                                  NNLS 6
```

```
300     CONTINUE                                                        NNLS 7
        DO 310 I=1,M                                                    NNLS 1
310     ZZ(I)=B(I)                                                      NNLS 2
    ASSIGN 320 TO NEXT                                                  NNLS 3
    GO TO 400                                                           NNLS 4
320 CONTINUE                                                            NNLS 5
    GO TO 210                                                           NNLS 6
330     DO 340 IP=1,NSETP                                               NNLS 9
        I=INDEX(IP)                                                     NNLS 0
340     X(I)=ZZ(IP)                                                     NNLS 1
    GO TO 30                                                            NNLS 3
350 SM=ZERO                                                             NNLS 0
    IF (NPP1.GT.M)  GO TO 370                                           NNLS 1
        DO 360 I=NPP1,M                                                 NNLS 2
360     SM=SM+B(I)**2                                                   NNLS 3
    GO TO 390                                                           NNLS 4
370     DO 380 J=1,N                                                    NNLS 5
380     W(J)=ZERO                                                       NNLS 6
390 RNORM=SQRT(SM)                                                      NNLS 7
    RETURN                                                              NNLS 8
400     DO 430 L=1,NSETP                                                NNLS 3
        IP=NSETP+1-L                                                    NNLS 4
        IF (L.EQ.1)  GO TO 420                                          NNLS 5
            DO 410 II=1,IP                                              NNLS 6
410         ZZ(II)=ZZ(II)-A(II,JJ)*ZZ(IP+1)                             NNLS 7
420     JJ=INDEX(IP)                                                    NNLS 8
430     ZZ(IP)=ZZ(IP)/A(IP,JJ)                                          NNLS 9
    GO TO NEXT, (200,320)                                               NNLS 0
    END                                                                 NNLS 1
    FUNCTION PGAUSS (X)                                                 PGUSS6
    AX=ABS(X)                                                           PGUSS7
    PGAUSS=1.+AX*(.196854+AX*(.115194+AX*(3.44E-4+AX*.019527)))         PGUSS8
    PGAUSS=1./PGAUSS**2                                                 PGUSS9
    PGAUSS=.5*PGAUSS**2                                                 PGUSS0
    IF (X .GT. 0.)  PGAUSS=1.-PGAUSS                                    PGUSS1
    RETURN                                                              PGUSS2
    END                                                                 PGUSS3
    SUBROUTINE PLPRIN (X,Y1,Y2,N,ONLY1,NOUT,SRANGE,NLINF,NG,MY1)        PLRIN6
    LOGICAL ONLY1                                                       PLRIN7
    DIMENSION X(N), Y1(MY1), Y2(N)                                      PLRIN8
    CHARACTER ICHAR(4), IH(108)
    DATA ICHAR/' ','X','O','*'/                                         PLRIN9
C
C   PRINT OUT DATA AND FIT TO FILE 'datafit' TO USE FOR PLOTTING
C
    IF (.NOT. ONLY1) THEN
        IJK=N/2
        IANG=IJK
        IF(IJK.GT.256) THEN
            IANG=IJK
            IJK=256
        ENDIF
        OPEN(4,FILE='data',STATUS='NEW')
        OPEN(3,FILE='fit',STATUS='NEW')
        WRITE(4,*) IJK
        WRITE(3,*) IJK
        WRITE(4,500) (X(J),Y2(J),J=1,IJK)
        WRITE(3,500) (X(J),Y1(J),J=1,IJK)
500     FORMAT(E10.3,1X,E10.3)
        CLOSE(4)
        CLOSE(3)
        OPEN(4,FILE='data1',STATUS='NEW')
        OPEN(3,FILE='fit1',STATUS='NEW')
        WRITE(4,*) IJK
        WRITE(3,*) IJK
        WRITE(4,500) (X(J),Y2(J),J=IANG+1,IANG+IJK)
        WRITE(3,500) (X(J),Y1(J),J=IANG+1,IANG+IJK)
        CLOSE(4)
        CLOSE(3)
    ENDIF
    YMIN=SRANGE                                                         PLRIN0
    YMAX=-SRANGE
```

```
      DO 120 J=1,N                                              PLRIN1
        YMIN=AMIN1(YMIN,Y1(J))                                  PLRIN2
        YMAX=AMAX1(YMAX,Y1(J))                                  PLRIN3
        IF (ONLY1)  GO TO 120                                   PLRIN4
        YMIN=AMIN1(YMIN,Y2(J))                                  PLRIN5
        YMAX=AMAX1(YMAX,Y2(J))                                  PLRIN6
  120 CONTINUE                                                  PLRIN7
      DUM=YMAX-YMIN                                             PLRIN8
      IF (DUM .LE. 0.)  DUM=1.                                  PLRIN9
      R=107.99/DUM                                              PLRIN0
      WRITE (NOUT,5120)                                         PLRIN1
 5120 FORMAT (/4X,'ORDINATE',3X,'ABSCISSA')                     PLRIN2
      L2=1                                                      PLRIN3
      DO 150 J=1,N                                              PLRIN4
        DO 155 L1=1,108                                         PLRIN5
          IH(L1)=ICHAR(1)                                       PLRIN6
  155   CONTINUE                                                PLRIN7
        L1=INT((Y1(J)-YMIN)*R)+1                                PLRIN8
        IH(L1)=ICHAR(2)                                         PLRIN9
        IF (ONLY1)  GO TO 160                                   PLRIN0
        L2=INT((Y2(J)-YMIN)*R)+1                                PLRIN1
        IH(L2)=ICHAR(3)                                         PLRIN2
        IF (L1 .EQ. L2)  IH(L2)=ICHAR(4)                        PLRIN3
  160   WRITE (NOUT,5160) Y1(J),X(J),IH                         PLRIN4
 5160   FORMAT (1X,1P2E11.3,108A1)                              PLRIN5
  150 CONTINUE                                                  PLRIN6
      IF (NLINF .LE. 0)  GO TO 800                              PLRIN7
      L2=NC+1                                                   PLRIN8
 5200 FORMAT ('0LINEAR COEFFICIENTS =',1P8E13.4/(22X,8E13.4))   PLRIN9
      WRITE (NOUT,5200) (Y1(J),J=L2,MY1)                        PLRIN0
  800 RETURN                                                    PLRIN1
      END                                                       PLRIN2
                                                                PLRIN3
      SUBROUTINE PLRES (YLYFIT,NMAX,N,PRUNS,RALPS1,NOUT,LINEPG,ITITLE) PLRES6
      DIMENSION YLYFIT(NMAX), LCHARJ(20),LABEL(6), BOUND(21)    PLRES7
      CHARACTER IHOLER(6), JCHAR(8), LINE1(20), LINE(131)
     + , ITITLE(80)
      DATA JCHAR/'*','-','U','L',' ','O','-','+'/,              PLRES9
     1 IHOLER/'P','L','R','E','S',' '/, MPAGE/30/               PLRES0
      IF (LINEPG .GE. 17)  GO TO 100                            PLRES1
      CALL ERRMES (1,.FALSE.,IHOLER,NOUT)                       PLRES2
      RETURN                                                    PLRES3
  100 MPLOT=(LINEPG-3)/16                                       PLRES4
      MLINE=MIN0(20,(LINEPG-3)/MPLOT-3)                         PLRES5
      RMIN=YLYFIT(1)                                            PLRES6
      RMAX=YLYFIT(1)                                            PLRES7
      DO 110 J=2,N                                              PLRES8
      RMIN=AMIN1(RMIN,YLYFIT(J))                                PLRES9
  110 RMAX=AMAX1(RMAX,YLYFIT(J))                                PLRES0
 5200 FORMAT (' ',9X,80A1//                                     PLRES1
     1 ' PLOT OF WEIGHTED RESIDUALS (FOR ALPHA/S(1) =',         PLRES2
     2 1PE9.2,') MAX = U =',E8.1,5X,'MIN = L =',E8.1,9X,        PLRES3
     3 'RANDOM RUNS PROB. =',0PF7.4)                            PLRES4
      WRITE (NOUT,5200) ITITLE,RALPS1,RMAX,RMIN,PRUNS           PLRES5
      DELTA=(RMAX-RMIN)/FLOAT(MLINE-1)                          PLRES6
      BOUND(1)=RMAX+.5*DELTA                                    PLRES7
      K=MLINE+1                                                 PLRES8
      DO 120 J=2,K                                              PLRES9
      BOUND(J)=BOUND(J-1)-DELTA                                 PLRES0
  120 IF (BOUND(J)*BOUND(J-1) .LT. 0.)  JAXIS=J-1               PLRES1
      LABEL(1)=-110                                             PLRES2
      DO 130 J=2,6                                              PLRES3
  130 LABEL(J)=LABEL(J-1)+20                                    PLRES4
      K=MLINE-1                                                 PLRES5
      DO 140 J=2,K                                              PLRES6
      LINE1(J)=JCHAR(5)                                         PLRES7
  140 LCHARJ(J)=5                                               PLRES8
      LINE1(1)=JCHAR(3)                                         PLRES9
      LINE1(JAXIS)=JCHAR(6)                                     PLRES0
      LINE1(MLINE)=JCHAR(4)                                     PLRES1
      LCHARJ(1)=7                                               PLRES2
      LCHARJ(JAXIS)=2                                           PLRES3
      LCHARJ(MLINE)=7                                           PLRES4
```

```
      NPOINT=0                                                        PLRES5
      DO 200 NPAGE=1,MPAGE                                            PLRES6
      IF (NPAGE .GT. 1) WRITE( NOUT,5999)                             PLRES7
5999  FORMAT ('1')                                                    PLRES8
      DO 210 NPLOT=1,MPLOT                                            PLRES9
5001  FORMAT (' ')                                                    PLRES0
      WRITE (NOUT,5001)                                               PLRES1
      NST=NPOINT+1                                                    PLRES2
      NEND=NPOINT+130                                                 PLRES3
      NPOINT=NEND                                                     PLRES4
      NLIM=MIN0(NEND,N)                                               PLRES5
      DO 220 NLINE=1,MLINE                                            PLRES6
      LCHAR=LCHARJ(NLINE)                                             PLRES7
      LINE(1)=LINE1(NLINE)                                            PLRES8
      BMAX=BOUND(NLINE)                                               PLRES9
      BMIN=BOUND(NLINE+1)                                             PLRES0
      K=1                                                             PLRES1
      DO 230 J=NST,NLIM                                               PLRES2
      K=K+1                                                           PLRES3
      LINE(K)=JCHAR(LCHAR)                                            PLRES4
      IF (YLYFIT(J).LT.BMAX .AND. YLYFIT(J).GE.BMIN) LINE(K)=JCHAR(1) PLRES5
230   CONTINUE                                                        PLRES6
      K=NLIM-NST+2                                                    PLRES7
      IF (NLINE.NE.1 .AND. NLINE.NE.MLINE) GO TO 235                  PLRES8
      DO 232 J=11,K,10                                                PLRES9
232   IF (LINE(J) .NE. JCHAR(1)) LINE(J)=JCHAR(8)                     PLRES0
5230  FORMAT (1X,A1,130A1)                                            PLRES1
235   WRITE ( NOUT,5230) (LINE(J),J=1,K)                              PLRES2
220   CONTINUE                                                        PLRES3
      DO 240 J=1,6                                                    PLRES4
240   LABEL(J)=LABEL(J)+130                                           PLRES5
5240  FORMAT (3X,6(16X,I4)/)                                          PLRES6
      WRITE ( NOUT,5240) LABEL                                        PLRES7
      IF (NLIM .EQ. N) RETURN                                         PLRES8
210   CONTINUE                                                        PLRES9
200   CONTINUE                                                        PLRES0
      CALL ERRMES (2,.FALSE.,IHOLER,NOUT)                             PLRES1
      RETURN                                                          PLRES2
      END                                                             PLRES3
      SUBROUTINE QRBD (IPASS,Q,E,NN,V,MDV,NRV,C,MDC,NCC,RANGE)        QRBD 7
      DOUBLE PRECISION ABS, AMAX1, C, CS, DIFF, DNORM, E, F,          QRBD 8
     1 G, H,                                                          QRBD 9
     2 ONE, Q, RANGE, SN, SQRT, SQRTRG, T, TWO, V, X, Y, Z, ZERO      QRBD 0
      LOGICAL WNTV ,HAVERS,FAIL                                       QRBD 1
      DIMENSION Q(NN),E(NN),V(MDV,1),C(MDC,1)                         QRBD 2
      AMAX1(ZERO,ONE)=DMAX1(ZERO,ONE)                                 QRBD 3
      ABS(ONE)=DABS(ONE)                                              QRBD 4
      SQRT(ONE)=DSQRT(ONE)                                            QRBD 5
      ZERO=0.D0                                                       QRBD 7
      ONE=1.D0                                                        QRBD 9
      TWO=2.D0                                                        QRBD 1
      SQRTRG=SQRT(RANGE)                                              QRBD 2
      N=NN                                                            QRBD 4
      IPASS=1                                                         QRBD 5
      IF (N.LE.0) RETURN                                              QRBD 6
      N10=10*N                                                        QRBD 7
      WNTV=NRV.GT.0                                                   QRBD 8
      HAVERS=NCC.GT.0                                                 QRBD 9
      FAIL=.FALSE.                                                    QRBD 0
      NQRS=0                                                          QRBD 1
      E(1)=ZERO                                                       QRBD 2
      DNORM=ZERO                                                      QRBD 3
         DO 10 J=1,N                                                  QRBD 4
10       DNORM=AMAX1(ABS(Q(J))+ABS(E(J)),DNORM)                       QRBD 5
         DO 200 KK=1,N                                                QRBD 6
         K=N+1-KK                                                     QRBD 7
20          IF(K.EQ.1) GO TO 50                                       QRBD 1
            IF(DIFF(DNORM+Q(K),DNORM)) 50,25,50                       QRBD 2
25          CS=ZERO                                                   QRBD 7
            SN=-ONE                                                   QRBD 8
               DO 40 II=2,K                                           QRBD 9
               I=K+1-II                                               QRBD 0
```

```
                F=-SN*E(I+1)                                 QRBD 1
                E(I+1)=CS*E(I+1)                             QRBD 2
                CALL G1 (Q(I),F,CS,SN,Q(I))                  QRBD 3
                IF (.NOT.WNTV) GO TO 40                      QRBD 6
                    DO 30 J=1,NRV                            QRBD 7
30                      CALL G2 (CS,SN,V(J,I),V(J,K))        QRBD 8
40              CONTINUE                                     QRBD 1
50          DO 60 LL=1,K                                     QRBD 6
                L=K+1-LL                                     QRBD 7
                IF(DIFF(DNORM+E(L),DNORM)) 55,100,55         QRBD 8
55              IF(DIFF(DNORM+Q(L-1),DNORM)) 60,70,60        QRBD 9
60          CONTINUE                                         QRBD 0
            GO TO 100                                        QRBD 3
70          CS=ZERO                                          QRBD 6
            SN=-ONE                                          QRBD 7
                DO 90 I=L,K                                  QRBD 8
                F=-SN*E(I)                                   QRBD 9
                E(I)=CS*E(I)                                 QRBD 0
                IF(DIFF(DNORM+F,DNORM)) 75,100,75            QRBD 1
75              CALL G1 (Q(I),F,CS,SN,Q(I))                  QRBD 2
                IF (.NOT.HAVERS) GO TO 90                    QRBD 3
                    DO 80 J=1,NCC                            QRBD 4
80                      CALL G2 (CS,SN,C(I,J),C(L-1,J))      QRBD 5
90              CONTINUE                                     QRBD 6
100         Z=Q(K)                                           QRBD 9
            IF (L.EQ.K) GO TO 170                            QRBD 0
            X=Q(L)                                           QRBD 3
            Y=Q(K-1)                                         QRBD 4
            G=E(K-1)                                         QRBD 5
            H=E(K)                                           QRBD 6
            F=((Y-Z)*(Y+Z)+(G-H)*(G+H))/(TWO*H*Y)            QRBD 7
            G=ABS(F)                                         QRBD 1
            IF (G .LT. SQRTRG) G=SQRT(ONE+G**2)              QRBD 2
            IF (F.LT.ZERO) GO TO 110                         QRBD 3
            T=F+G                                            QRBD 4
            GO TO 120                                        QRBD 5
110         T=F-G                                            QRBD 6
120         F=((X-Z)*(X+Z)+H*(Y/T-H))/X                      QRBD 7
            CS=ONE                                           QRBD 0
            SN=ONE                                           QRBD 1
            LP1=L+1                                          QRBD 2
                DO 160 I=LP1,K                               QRBD 3
                G=E(I)                                       QRBD 4
                Y=Q(I)                                       QRBD 5
                H=SN*G                                       QRBD 6
                G=CS*G                                       QRBD 7
                CALL G1 (F,H,CS,SN,E(I-1))                   QRBD 8
                F=X*CS+G*SN                                  QRBD 9
                G=-X*SN+G*CS                                 QRBD 0
                H=Y*SN                                       QRBD 1
                Y=Y*CS                                       QRBD 2
                IF (.NOT.WNTV) GO TO 140                     QRBD 3
                    DO 130 J=1,NRV                           QRBD 6
130                     CALL G2 (CS,SN,V(J,I-1),V(J,I))      QRBD 7
140             CALL G1 (F,H,CS,SN,Q(I-1))                   QRBD 8
                F=CS*G+SN*Y                                  QRBD 9
                X=-SN*G+CS*Y                                 QRBD 0
                IF (.NOT.HAVERS) GO TO 160                   QRBD 1
                    DO 150 J=1,NCC                           QRBD 2
150                     CALL G2 (CS,SN,C(I-1,J),C(I,J))      QRBD 3
160             CONTINUE                                     QRBD 7
            E(L)=ZERO                                        QRBD 8
            E(K)=F                                           QRBD 9
            Q(K)=X                                           QRBD 0
            NQRS=NQRS+1                                      QRBD 1
            IF (NQRS.LE.N10) GO TO 20                        QRBD 2
            FAIL=.TRUE.                                      QRBD 5
170         IF (Z.GE.ZERO) GO TO 190                         QRBD 8
            Q(K)=-Z                                          QRBD 9
            IF (.NOT.WNTV) GO TO 190                         QRBD 0
                DO 180 J=1,NRV                               QRBD 1
```

```
180          V(J,K)=-V(J,K)                              QRBD 2
190       CONTINUE                                       QRBD 3
200       CONTINUE                                       QRBD 6
      IF (N.EQ.1) RETURN                                 QRBD 7
          DO 210 I=2,N                                   QRBD 8
          IF (Q(I).GT.Q(I-1)) GO TO 220                  QRBD 9
210       CONTINUE                                       QRBD 0
      IF (FAIL) IPASS=2                                  QRBD 1
      RETURN                                             QRBD 2
220       DO 270 I=2,N                                   QRBD 5

T=Q(I-1)                                       QRBD 6
          K=I-1                                          QRBD 7
          DO 230 J=I,N                                   QRBD 8
          IF (T.GE.Q(J)) GO TO 230                       QRBD 9
          T=Q(J)                                         QRBD 0
          K=J                                            QRBD 1
230       CONTINUE                                       QRBD 2
      IF (K.EQ.I-1) GO TO 270                            QRBD 3
      Q(K)=Q(I-1)                                        QRBD 4
      Q(I-1)=T                                           QRBD 5
      IF (.NOT.HAVERS) GO TO 250                         QRBD 6
          DO 240 J=1,NCC                                 QRBD 7
          T=C(I-1,J)                                     QRBD 8
          C(I-1,J)=C(K,J)                                QRBD 9
240       C(K,J)=T                                       QRBD 0
250   IF (.NOT.WNTV) GO TO 270                           QRBD 1
          DO 260 J=1,NRV                                 QRBD 2
          T=V(J,I-1)                                     QRBD 3
          V(J,I-1)=V(J,K)                                QRBD 4
260       V(J,K)=T                                       QRBD 5
270       CONTINUE                                       QRBD 6
      IF (FAIL) IPASS=2                                  QRBD 9
      RETURN                                             QRBD 0
      END                                                QRBD 1
      FUNCTION RANDOM(DIX)                               RADOM9
      DOUBLE PRECISION A,P,DIX,B15,B16,XHI,XALO,LEFTLO,FHI,K   RADOM5
      DATA A/16807.D0/,B15/32768.D0/,B16/65536.D0/,P/2147483647.D0/   RADOM8
      XHI = DIX / B16                                    RADOM1
      XHI = XHI - DMOD(XHI,1.D0)                         RADOM2
      XALO=(DIX-XHI*B16)*A                               RADOM4
      LEFTLO = XALO/B16                                  RADOM6
      LEFTLO = LEFTLO - DMOD(LEFTLO,1.D0)                RADOM7
      FHI = XHI*A + LEFTLO                               RADOM9
      K = FHI/B15                                        RADOM1
      K = K - DMOD(K,1.D0)                               RADOM2
      DIX = (((XALO-LEFTLO*B16) - P) + (FHI-K*B15)*B16) + K   RADOM5
      IF (DIX .LT. 0.D0) DIX = DIX + P                   RADOM7
      RANDOM=DIX*4.656612875D-10                         RADOM9
      RETURN                                             RADOM0
      END                                                RADOM1
      SUBROUTINE READYT (MY,NIOERR,SQRTW,T,Y)            REDYT9
      DOUBLE PRECISION PRECIS, RANGE                     REDYT0
      LOGICAL DOMOM, DOUSIN, DOUSNQ, DOUSOU, LAST, NONNEG, ONLY1, PRWT,   REDYT1
     1 PRY, SIMULA, LUSER                                REDYT2
      DIMENSION SQRTW(MY), T(MY), Y(MY)                  REDYT3
      CHARACTER IHOLER(6), LAA(6,2), LIN(6),IFORMT(70), IFORMW(70)
     + , IFORMY(70), LA(6,46), ITITLE(80)
      COMMON /CBLOCK/ IFORMT, IFORMW, IFORMY, LA, ITITLE
      COMMON /SBLOCK/ PRECIS, RANGE, SRMIN,              REDYT5
     1 ALPST(2), GMNMX(2), PLEVEL(2,2), RSVMNX(2,2), RUSER(100),   REDYT6
     2 EXMAX, SRANGE                                     REDYT7
      COMMON /IBLOCK/ IGRID, IPLRES, IPRINT, IQUAD, IUNIT, IWT,   REDYT8
     1 LINEPG, MIOERR, MQPITR, NEQ, NERFIT, NG, NINTT, NLINF, NORDER,   REDYT9
     2 ICRIT(2), IPLFIT(2),                              REDYT0
     3 IUSER(50), LSIGN(4,4), MOMNMX(2), NENDZ(2),       REDYT1
     4 NFLAT(4,2), NGL, NGLP1, NIN, NINEQ, NNSGN(2), NOUT, NQPROG(2),   REDYT2
     5 NSGN(4), NY                                       REDYT3
      COMMON /LBLOCK/ DOMOM, DOUSIN, DOUSNQ, DOUSOU, LAST, NONNEG,   REDYT4
     1 ONLY1, PRWT, PRY, SIMULA,                         REDYT5
     2 LUSER(30)                                         REDYT6
      DATA IHOLER/'R','E','A','D','Y','T'/, LAA/         REDYT7
```

```
      1 'N','S','T','E','N','D','N','Y',' ',' ',' ',' '/               REDYT8
        IF (NINTT .LE. 0)  GO TO 200                                    REDYT9
        NY=0                                                            REDYT3
        DO 110 J=1,NINTT                                                REDYT4
 5110   FORMAT (1X,6A1,I8,2E15.7)                                       REDYT5
        READ (NIN,5110) LIN,NT,TSTART,TEND                              REDYT6
        WRITE (NOUT,5110) LIN,NT,TSTART,TEND                            REDYT7
        DO 120 K=1,6                                                    REDYT8
           IF (LIN(K) .NE. LAA(K,1))  GO TO 130                         REDYT9
  120   CONTINUE                                                        REDYT0
        GO TO 140                                                       REDYT1
  130   CALL ERRMES (1,.FALSE.,IHOLER,NOUT)                             REDYT2
        GO TO 190                                                       REDYT3
  140   IF (NT.GE.2 .AND. NT+NY.LE.MY)  GO TO 150                       REDYT4
        CALL ERRMES (2,.FALSE.,IHOLER,NOUT)                             REDYT5
        GO TO 190                                                       REDYT6
  150   DUM=(TEND-TSTART)/FLOAT(NT-1)                                   REDYT7
        NY=NY+1                                                         REDYT8
        T(NY)=TSTART                                                    REDYT9
        DO 160 K=2,NT                                                   REDYT0
        NY=NY+1                                                         REDYT1
  160   T(NY)=T(NY-1)+DUM                                               REDYT2
        GO TO 110                                                       REDYT3
  190   NIOERR=NIOERR+1                                                 REDYT4
        IF (NIOERR .GE. MIOERR)  STOP                                   REDYT5
  110   CONTINUE                                                        REDYT6
        GO TO 300                                                       REDYT7
  200   READ (NIN,5110) LIN,NY                                          REDYT1
        WRITE (NOUT,5110) LIN,NY                                        REDYT2
        DO 210 K=1,6                                                    REDYT3
           IF (LIN(K) .NE. LAA(K,2))  GO TO 220                         REDYT4
  210   CONTINUE                                                        REDYT5
        GO TO 230                                                       REDYT6
  220   CALL ERRMES (3,.FALSE.,IHOLER,NOUT)                             REDYT7
        GO TO 235                                                       REDYT8
  230   IF (NY .LE. MY)  GO TO 240                                      REDYT9
        CALL ERRMES (4,.FALSE.,IHOLER,NOUT)                             REDYT0
  235   NIOERR=NIOERR+1                                                 REDYT1
        RETURN                                                          REDYT2
  240   READ (NIN,6007) (T(J),J=1,NY)                                   REDYT3
  300   IF(.NOT.SIMULA) READ (NIN,6008) (Y(J),J=1,NY)                   REDYT7
 6007   FORMAT(5E15.6)
 6008   FORMAT(4E17.11)
        IF (IWT .EQ. 4)  GO TO 420                                      REDYT8
        DO 410 J=1,NY                                                   REDYT2
        SQRTW(J)=1.                                                     REDYT3
  410   CONTINUE                                                        REDYT4
  420   IF (IWT .EQ. 4)  READ (NIN,6007) (SQRTW(J),J=1,NY)              REDYT8
        IF (DOUSIN)  CALL USERIN (T,Y,SQRTW,MY)                         REDYT2
        DO 430 J=1,NY                                                   REDYT3
        IF (SQRTW(J) .GE. 0.)  GO TO 440                                REDYT4
        CALL ERRMES (5,.FALSE.,IHOLER,NOUT)                             REDYT5
 5440   FORMAT (1X,1P10E13.5)                                           REDYT6
        WRITE (NOUT,5440) (SQRTW(K),K=1,NY)                             REDYT7
        NIOERR=NIOERR+1                                                 REDYT8
        GO TO 800                                                       REDYT9
  440   SQRTW(J)=SQRT(SQRTW(J))                                         REDYT0
  430   CONTINUE                                                        REDYT1
  800   RETURN                                                          REDYT2
        END                                                             REDYT3
        SUBROUTINE RGAUSS (X1,X2,TWOPI,DIX)                             RGUSS4
        DOUBLE PRECISION DIX                                            RGUSS5
        X1=SQRT(-2.*ALOG(RANDOM(DIX)))                                  RGUSS6
        DUM=TWOPI*RANDOM(DIX)                                           RGUSS7
        X2=X1*SIN(DUM)                                                  RGUSS8
        X1=X1*COS(DUM)                                                  RGUSS9
        RETURN                                                          RGUSS0
        END                                                             RGUSS1
```

```
      SUBROUTINE RUNRES (ILEVEL,SOL,NEWPAG,RALPS1,                    RURES3
     1 CQUAD,G,IPLFIT,IPLRES,ISTAGE,ITITLE,IUNIT,IWT,LINEPG,MWORK,NG,  RURES4
     2 NGL,NLINF,NOUT,NY,SQRTW,SRANGE,T,WORK,Y,YLYFIT)                 RURES5
      DOUBLE PRECISION  SOL, WORK                                     RURES6
      LOGICAL NEWPAG                                                   RURES7
      CHARACTER ITITLE(80)
      DIMENSION SOL(NGL), WORK(MWORK), SQRTW(NY), CQUAD(NG), G(NG),    RURES8
     1 T(NY), Y(NY), YLYFIT(NY),  IPLFIT(2)                            RURES9
      PRUNS=GETPRU (SOL,                                               RURES0
     1 CQUAD,G,IUNIT,IWT,MWORK,NG,NGL,NLINF,NY,SQRTW,T,WORK,           RURES1
     2 Y,YLYFIT)                                                       RURES2
      IF (ILEVEL.LE.IPLRES)  GO TO 150                                 RURES3
 5100 FORMAT ('1',9X,80A1)                                             RURES4
      IF (NEWPAG) .WRITE (NOUT,5100) ITITLE                            RURES5
 5110 FORMAT ('O(FOR ALPHA/S(1) =',1PE9.2,                             RURES6
     1 ') PROB. THAT A RANDOMLY CHOSEN ORDER OF SIGNS WOULD HAVE',     RURES7
     2 ' NO MORE RUNS THAN THE RESIDUALS =',0PF7.4)                    RURES8
      WRITE (NOUT,5110) RALPS1,PRUNS                                   RURES9
      GO TO 200                                                        RURES0
  150 CALL PLRES (YLYFIT,NY,NY,PRUNS,RALPS1,NOUT,LINEPG,ITITLE)
  200 IF (ILEVEL .GT. IPLFIT(ISTAGE)) GO TO 800
      DO 210 J=1,NY
      YLYFIT(J)=Y(J)-YLYFIT(J)/SQRTW(J)
  210 CONTINUE
 5210 FORMAT (//'OPLOT OF DATA (O) AND FIT TO DATA (X).',
     1 '   ORDINATES LISTED ARE FIT VALUES.')
      WRITE (NOUT,5210)                                                RURES1
      CALL PLPRIN (T,YLYFIT,Y,NY,.FALSE.,NOUT,SRANGE,0,0,NY)           RURES2
      DO 220 J=1,NY                                                    RURES6
         YLYFIT(J)=(Y(J)-YLYFIT(J))*SQRTW(J)                           RURES7
  220 CONTINUE                                                         RURES8
  800 RETURN                                                           RURES9
      END                                                              RURES0
      SUBROUTINE SEQACC (                                              SEACC3
     1 A,CQUAD,G,ISTAGE,IUNIT,IWT,MA,MG,NG,NGL,NGLP1,NLINF,NY,         SEACC4
     2 RANGE,SQRTW,T,Y)                                                SEACC5
      DOUBLE PRECISION A, RANGE, RHO, ZERO                             SEACC6
      DIMENSION A(MA,MG), T(NY), Y(NY), SQRTW(NY), G(NG), CQUAD(NG)    SEACC7
      ZERO=0.D0                                                        SEACC9
      L=0                                                              SEACC0
      NGL=NG+NLINF                                                     SEACC1
      NGLP1=NGL+1                                                      SEACC2
      DO 200 IT=1,NY                                                   SEACC3
         IP=L+1                                                        SEACC4
         IIT=IT                                                        SEACC5
         CALL GETROW (IIT,A(IP,1),.TRUE.,ISTAGE,MA,IUNIT,              SEACC6
     1   SQRTW,NY,NGL,IWT,NG,CQUAD,G,T,NLINF,Y)                        SEACC7
         IF (L.LE.0 .OR. NY.LE.NGL)  GO TO 230                         SEACC8
         J=MIN0(NGLP1,L)                                               SEACC9
         DO 220 I=1,J                                                  SEACC0
            II=I                                                       SEACC1
            CALL H12 (1,II,IP,IP,A(1,I),1,RHO,A(1,I+1),1,MA,NGLP1-I,RANGE)SEACC2
  220    CONTINUE                                                      SEACC3
  230    L=MIN0(NGLP1,IP)                                              SEACC4
  200 CONTINUE                                                         SEACC5
      IF (NY .LE. NGL)  GO TO 350                                      SEACC6
      DO 300 J=2,NGL                                                   SEACC7
         L=J-1                                                         SEACC8
         DO 310 K=1,L                                                  SEACC9
            A(J,K)=ZERO                                                SEACC0
  310    CONTINUE                                                      SEACC1
  300 CONTINUE                                                         SEACC2
      GO TO 800                                                        SEACC3
  350 L=NY+1                                                           SEACC4
      DO 360 J=L,NGL                                                   SEACC5
         DO 370 K=1,NGLP1                                              SEACC6
            A(J,K)=ZERO                                                SEACC7
  370    CONTINUE                                                      SEACC8
  360 CONTINUE                                                         SEACC9
```

```
      READ (NIN,5100) (G(J),J=1,NG)                                USRGR3
 5100 FORMAT (5E15.6)                                              USRGR4
      CALL CQTRAP (G,CQUAD,NG)                                     USRGR8
      RETURN                                                       USRGR9
      END                                                          USRGR0
      SUBROUTINE USERIN (T,Y,SQRTW,MY)                             USRIN3
      DOUBLE PRECISION PRECIS, RANGE                               USRIN4
      LOGICAL DOMOM, DOUSIN, DOUSNQ, DOUSOU, LAST, NONNEG, ONLY1, PRWT, USRIN5
     1 PRY, SIMULA, LUSER                                          USRIN6
      DIMENSION T(MY), Y(MY), SQRTW(MY)                            USRIN7
      COMMON /SBLOCK/ PRECIS, RANGE, SRMIN,                        USRIN8
     1 ALPST(2), GMNMX(2), PLEVEL(2,2), RSVMNX(2,2), RUSER(100),   USRIN9
     2 EXMAX, SRANGE                                               USRIN0
      COMMON /IBLOCK/ IGRID, IPLRES, IPRINT, IQUAD, IUNIT, IWT,    USRIN1
     1 LINEPG, MIOERR, MQPITR, NEQ, NERFIT, NG, NINTT, NLINF, NORDER, USRIN2
     2 ICRIT(2), IPLFIT(2),
     3   IUSER(50), LSIGN(4,4), MOMNMX(2), NENDZ(2),               USRIN4
     4 NFLAT(4,2), NGL, NGLP1, NIN, NINEQ, NNSGN(2), NOUT, NQPROG(2), USRIN5
     5 NSGN(4), NY                                                 USRIN6
      COMMON /LBLOCK/ DOMOM, DOUSIN, DOUSNQ, DOUSOU, LAST, NONNEG, USRIN7
     1 ONLY1, PRWT, PRY, SIMULA,                                   USRIN8
     2 LUSER(30)                                                   USRIN9
C
      HFANG=RUSER(12)*8.7266464E-3
      QK=4.E0*3.1415927*SIN(HFANG)*RUSER(14)/RUSER(13)
      RUSER(20)=QK
      DC=1.380622E10*(RUSER(10)+2.7316E2)/(6.E0*3.1415927*RUSER(11))
      Q2DC=QK*QK*DC
C
C  SOME OF THESE ADDED LINES ARE TO IMPLEMENT FINDING SIMULTANEOUS
C  SOLUTIONS OF DATA COLLECTED AT DIFFERENT ANGLES
C
      IEND=NY
      IF(.NOT.LUSER(11)) GO TO 1
      HFANG2=RUSER(17)*8.7266464E-3
      QK2=QK*SIN(HFANG2)/SIN(HFANG)
      RUSER(21)=QK2
      Q2DC2=QK2*QK2*DC
      IEND=IUSER(11)-1
      ISTART=IUSER(11)
C
    1 DO 2 J=1,IEND
    2 Y(J)=Y(J)-RUSER(15)
      IF(.NOT.LUSER(11)) GO TO 6
      DO 3 J=ISTART,NY
    3 Y(J)=Y(J)-RUSER(16)
C
C  ADDED SECTION TO EXTRAPOLATE TO ACF(0) TO GET TRUE AMPLITUDE.
C  EXTRAPOLATION IS BASED ON THE FIRST 4 DATA POINTS.
C
    6 NEXTR=IUSER(12)
      CALL EXTRP(T,Y,1,NEXTR,YNORM)
      YNORM=SQRT(1./YNORM)
      RUSER(22)=YNORM
      IF(.NOT.LUSER(11)) GO TO 4
      CALL EXTRP(T,Y,ISTART,NEXTR,YNORM2)
      YNORM2=SQRT(1./YNORM2)
      RUSER(23)=YNORM2/SQRT(RUSER(18))
C
    4 IF(LUSER(16)) GO TO 5
      DO 110 J=1,NY
      Y(J)=SIGN(SQRT(ABS(Y(J))),Y(J))
  110 CONTINUE
C
    5 DO 10 K=1,IEND
   10 T(K)=T(K)*Q2DC
  800 RETURN
      END                                                          SEACC0
      SUBROUTINE SETGA1 (NNINEQ,                                   SEACC1
     1 A,AINEQ,MA,MG,MINEQ,MREG,NGL,NGLE,REG)                      SEGA14
      DOUBLE PRECISION A, AINEQ, DUM, REG, ZERO                    SEGA15
      DIMENSION AINEQ(MINEQ,MG), REG(MREG,MG), A(MA,MG)            SEGA16
                                                                   SEGA17
```

```
      ZERO=0.DO                                                SEGA19
      DO 120 IROW=1,NNINEQ                                     SEGA10
        DO 130 ICOL=1,NGLE                                     SEGA11
          DUM=ZERO                                             SEGA12
          DO 140 J=1,NGL                                       SEGA13
            DUM=DUM+AINEQ(IROW,J)*REG(J,ICOL)                  SEGA14
140       CONTINUE                                             SEGA15
          A(IROW,ICOL)=DUM                                     SEGA16
130     CONTINUE                                               SEGA17
120   CONTINUE                                                 SEGA18
      RETURN                                                   SEGA19
      END                                                      SEGA10
      SUBROUTINE SETGRD (CQUAD,G,GMNMX,IGRID,IQUAD,MG,NG,NOUT) SEGRD2
      DIMENSION G(MG), CQUAD(MG), GMNMX(2)                     SEGRD3
      CHARACTER IHOLER(6)                                      SEGRD4
      DATA IHOLER/'S','E','T','G','R','D'/                     SEGRD5
      IF (IGRID .NE. 3)  GO TO 200                             SEGRD6
      CALL USERGR (G,CQUAD,MG)                                 SEGRD0
      GO TO 300                                                SEGRD1
200   IF (IGRID.EQ.2 .AND. AMIN1(GMNMX(1),GMNMX(2)).LE.0.)     SEGRD2
     1 CALL ERRMES (1,,FALSE.,IHOLER,NOUT)                     SEGRD3
      G(1)=GMNMX(1)                                            SEGRD7
      DELTA=(USERTR(GMNMX(2),1)-USERTR(GMNMX(1),1))/FLOAT(NG-1) SEGRD8
      DO 210 J=2,NG                                            SEGRD9
        DUM=USERTR(G(J-1),1)+DELTA                             SEGRD0
        G(J)=USERTR(DUM,2)                                     SEGRD1
210   CONTINUE                                                 SEGRD2
300   IF (NG .LE. 2)  GO TO 350                                SEGRD6
      DELOLD=G(2)-G(1)                                         SEGRD7
      DO 310 J=3,NG                                            SEGRD8
        DEL=G(J)-G(J-1)                                        SEGRD9
        IF (DEL*DELOLD .GT. 0.)  GO TO 315                     SEGRD0
        CALL ERRMES (2,,FALSE.,IHOLER,NOUT)                    SEGRD1
5310    FORMAT (1X,1P10E13.3)                                  SEGRD2
        WRITE (NOUT,5310) (G(K),K=1,NG)                        SEGRD3
        STOP                                                   SEGRD4
315     DELOLD=DEL                                             SEGRD5
310   CONTINUE                                                 SEGRD6
350   IF (IGRID .EQ. 3)  GO TO 800                             SEGRD7
      IF (IQUAD .NE. 1)  GO TO 420                             SEGRD1
      DO 410 J=1,NG                                            SEGRD5
        CQUAD(J)=1.                                            SEGRD6
410   CONTINUE                                                 SEGRD7
      GO TO 800                                                SEGRD8
420   IF (IQUAD .NE. 2)  GO TO 450                             SEGRD9
      CALL CQTRAP (G,CQUAD,NG)                                 SEGRD3
      GO TO 500                                                SEGRD4
450   IF (IQUAD .NE. 3)  CALL ERRMES (3,,TRUE.,IHOLER,NOUT)    SEGRD5
      CQUAD(1)=DELTA/3.                                        SEGRD0
      CQ2=2.*CQUAD(1)                                          SEGRD1
      CQ4=CQ2+CQ2                                              SEGRD2
      JJ=NG-1                                                  SEGRD3
      DO 460 J=2,JJ,2                                          SEGRD4
        CQUAD(J)=CQ4                                           SEGRD5
        CQUAD(J+1)=CQ2                                         SEGRD6
460   CONTINUE                                                 SEGRD7
      IF (MOD(NG,2) .EQ. 0)  GO TO 470                         SEGRD8
      CQUAD(NG)=CQUAD(1)                                       SEGRD9
      GO TO 500                                                SEGRD0
470   CQUAD(NG)=1.5*CQUAD(1)                                   SEGRD1
      CQUAD(NG-1)=CQUAD(1)+CQUAD(NG)                           SEGRD2
500   IF (IGRID .NE. 2)  GO TO 800                             SEGRD3
      DO 510 J=1,NG                                            SEGRD7
        CQUAD(J)=CQUAD(J)/USERTR(G(J),3)                       SEGRD8
510   CONTINUE                                                 SEGRD9
800   RETURN                                                   SEGRD0
      END                                                      SEGRD1
      SUBROUTINE SETNNG (AINEQ,MINEQ,NG,NGLP1,NINEQ)           SENNG5
      DOUBLE PRECISION AINEQ, ONE, ZERO                        SENNG6
      DIMENSION AINEQ(MINEQ,NGLP1)                             SENNG7
      ZERO=0.DO                                                SENNG9
      ONE=1.DO                                                 SENNG1
      DO 210 J=1,NG                                            SENNG2
```

```
      NINEQ=NINEQ+1                                              SENNG3
      DO 220 K=1,NGLP1                                           SENNG4
        AINEQ(NINEQ,K)=ZERO                                      SENNG5
220   CONTINUE                                                   SENNG6
      AINEQ(NINEQ,J)=ONE                                         SENNG7
210 CONTINUE                                                     SENNG8
   RETURN                                                        SENNG9
   END                                                           SENNG0
   SUBROUTINE SETREG (MG,MREG,NENDZ,NG,NGL,NGLE,NGLP1,NORDER,    SEREG5
  1 NOUT,NREG,PRECIS,REG)                                        SEREG6
   DOUBLE PRECISION ABS, AMAX1, PRECIS, REG, RMAX, RMIN, SQRT,   SEREG7
  1 ONE, ZERO                                                    SEREG8
   DIMENSION REG(MREG,MG), NENDZ(2)                              SEREG9
   DIMENSION DC(6,6)                                             SEREG0
   CHARACTER IHOLER(6)
   DATA DC/1., 5*0.,    -1., 1., 4*0.,   1., -2., 1., 3*0.,      SEREG1
  1 -1., 3., -3., 1., 2*0.,   1., -4., 6., -4., 1., 0.,          SEREG2
  2 -1., 5., -10., 10., -5., 1./,                                SEREG3
  3 IHOLER/'S','E','T','R','E','G'/                              SEREG4
   ABS(RMIN)=DABS(RMIN)                                          SEREG5
   AMAX1(RMIN,RMAX)=DMAX1(RMIN,RMAX)                             SEREG6
   SQRT(RMIN)=DSQRT(RMIN)                                        SEREG7
   ZERO=0.D0                                                     SEREG9
   ONE=1.D0                                                      SEREG1
   IF (NORDER .GE. 0) GO TO 200                                  SEREG2
   CALL USERRG (REG,MREG,MG,NREG)                                SEREG6
   IF (NREG .LE. 0) CALL ERRMES (1,.TRUE.,IHOLER,NOUT)           SEREG7
   GO TO 300                                                     SEREG8
200 IF (NORDER .GT. 5) CALL ERRMES (2,.TRUE.,IHOLER,NOUT)        SEREG9
   IF (MIN0(NENDZ(1),NENDZ(2)).GE.0 .AND.   NENDZ(1)+NENDZ(2)    SEREG0
  1.LE.NORDER) GO TO 205                                         SEREG1
   CALL ERRMES (3,.FALSE.,IHOLER,NOUT)                           SEREG2
   NENDZ(1)=MAX0(0,MIN0(NENDZ(1),NORDER))                        SEREG3
   NENDZ(2)=MAX0(0,MIN0(NORDER-NENDZ(1),NENDZ(2)))               SEREG4
205 NREG=NG+NENDZ(1)+NENDZ(2)-NORDER                             SEREG5
   IF (MAX0(NREG,NGLE) .GE. MREG) CALL ERRMES (4,.TRUE.,IHOLER,NOUT)SEREG6
   NORDP1=NORDER+1                                               SEREG7
   DO 210 J=1,NREG                                               SEREG8
     DO 220 K=1,NGLP1                                            SEREG9
       REG(J,K)=ZERO                                             SEREG0
220    CONTINUE                                                  SEREG1
     L=J-NENDZ(1)-1                                              SEREG2
     DO 230 K=1,NORDP1                                           SEREG3
       L=L+1                                                     SEREG4
       IF (L.GE.1 .AND. L.LE.NG)  REG(J,L)=DC(K,NORDP1)          SEREG5
230    CONTINUE                                                  SEREG6
210 CONTINUE                                                     SEREG7
300 RMAX=ZERO                                                    SEREG2
   DO 310 J=1,NREG                                               SEREG3
     DO 315 K=1,NGL                                              SEREG4
       RMAX=AMAX1(RMAX,ABS(REG(J,K)))                            SEREG5
315    CONTINUE                                                  SEREG6
310 CONTINUE                                                     SEREG7
   RMIN=RMAX*AMAX1(1.E-4*ONE,SQRT(1.E-1*PRECIS))                 SEREG8
   DO 320 ICOL=1,NGL                                             SEREG2
     DO 330 IROW=1,NREG                                          SEREG3
       IF (ABS(REG(IROW,ICOL)) .GT. ZERO)  GO TO 320             SEREG4
330    CONTINUE                                                  SEREG5
     NREG=NREG+1                                                 SEREG6
     IF (NREG .GE. MREG) CALL ERRMES (5,.TRUE.,IHOLER,NOUT)      SEREG7
     DO 335 J=1,NGLP1                                            SEREG8
       REG(NREG,J)=ZERO                                          SEREG9
335    CONTINUE                                                  SEREG0
     REG(NREG,ICOL)=RMIN                                         SEREG1
320 CONTINUE                                                     SEREG2
   IF (NREG .GE. NGLE) GO TO 800                                 SEREG3
   K=NGLE-NREG                                                   SEREG8
   DO 350 J=1,NGL                                                SEREG9
     DO 360 IROW=1,NREG                                          SEREG0
       IF (ABS(REG(IROW,J)) .LT. RMIN)  GO TO 360                SEREG1
       DO 370 ICOL=1,NGL                                         SEREG2
         IF (ICOL.NE.J .AND. ABS(REG(IROW,J)).GE.RMIN) GO TO 360 SEREG3
```

```
370     CONTINUE
        GO TO 350
360     CONTINUE
        K=K-1
        IROW=NGLE-K
        DO 380 ICOL=1,NGLP1
          REG(IROW,ICOL)=ZERO
380     CONTINUE
        REG(IROW,J)=RMIN
        IF (K) 390,390,350
350   CONTINUE
      CALL ERRMES (6,.TRUE.,IHOLER,NOUT)
390   NREG=NGLE
800   RETURN
      END
      SUBROUTINE SETSGN (INSGN,NSGNI,LSIGN,NOUT,LLSIGN,NG,SOLBES,
     1 SRANGE)
      DOUBLE PRECISION SOLBES
      DIMENSION LSIGN(4,INSGN), LLSIGN(5), SOLBES(NG)
      CHARACTER IHOLER(6)
      DATA IHOLER/'S','E','T','S','G','N'/
      IF (NSGNI.LT.1 .OR. NSGNI.GT.4 .OR. IABS(LSIGN(1,INSGN)).NE.1)
     1 CALL ERRMES (1,.TRUE.,IHOLER,NOUT)
      LLSIGN(1)=LSIGN(1,INSGN)
      LLSIGN(NSGNI+1)=NG
      IF (NSGNI .EQ. 1) GO TO 800
      DO 110 ISGN=2,NSGNI
        LLSIGN(ISGN)=LSIGN(ISGN,INSGN)
        IF (IABS(LLSIGN(ISGN)) .GT. IABS(LLSIGN(ISGN-1))
     1 .AND. IABS(LLSIGN(ISGN)) .LT. NG  .AND. LLSIGN(ISGN)*
     2 LLSIGN(ISGN-1) .LT. 0) GO TO 110
        IF (ISGN.NE.2 .OR. NSGNI.NE.2) CALL ERRMES(2,.TRUE.,IHOLER,
     1 NOUT)
        F=FLOAT(LLSIGN(1))
        PK=SRANGE
        DO 120 J=1,NG
          DUM=F*SOLBES(J)
          IF (DUM .GE. PK) GO TO 120
          PK=DUM
          LLSIGN(2)=-ISIGN(J,LLSIGN(1))
120     CONTINUE
110   CONTINUE
800   RETURN
      END
      SUBROUTINE SETVAL (ALPHA,INIT,NNINEQ,
     1 A,AINEQ,MA,MG,MINEQ,MREG,NGL,NGLE,REG,RHSNEQ,S,VALPCV,VALPHA,
     2 VK1Y1)
      DOUBLE PRECISION A, AINEQ, ALPHA, ALPHA2, DDUM, DUM, FACT,
     1 ONE, REG, RHSNEQ, S, SQRT, VALPCV, VALPHA, VK1Y1
      LOGICAL INIT
      DIMENSION S(MG,3), VK1Y1(MG), REG(MREG,MG), A(MA,MG),
     1 VALPHA(MG), VALPCV(MG), AINEQ(MINEQ,MG), RHSNEQ(MINEQ)
      SQRT(DUM)=DSQRT(DUM)
      ONE=1.D0
      IF (.NOT.INIT) GO TO 108
      DO 105 J=1,NGLE
        S(J,2)=ONE
105   CONTINUE
108   ALPHA2=ALPHA**2
      DO 110 J=1,NGL
        VALPCV(J)=VK1Y1(J)
        VALPHA(J)=VK1Y1(J)
110   CONTINUE
      NGLP1=NGL+1
      DO 120 J=1,NGLE
        DDUM=ONE/(S(J,1)**2+ALPHA2)
        DUM=(ALPHA2*REG(J,NGLP1)+S(J,1)*A(J,NGLP1))*DDUM
        DDUM=SQRT(DDUM)
        FACT=DDUM/S(J,2)
        S(J,2)=DDUM
        DO 125 K=1,NGL
          VALPHA(K)=VALPHA(K)+DUM*REG(K,J)
```

```
125   CONTINUE
      IF (NNINEQ .LE. 0)  GO TO 120
      DUM=REG(J,NGLP1)
      DO 130 K=1,NGL
         VALPCV(K)=VALPCV(K)+DUM*REG(K,J)
130   CONTINUE
      DO 140 K=1,NNINEQ
         A(K,J)=FACT*A(K,J)
140   CONTINUE
120 CONTINUE
      IF (NNINEQ .LE. 0)  GO TO 800
      DO 150 K=1,NNINEQ
         DUM=AINEQ(K,NGLP1)
         DO 160 J=1,NGL
            DUM=DUM-AINEQ(K,J)*VALPHA(J)
160      CONTINUE
         RHSNEQ(K)=DUM
150 CONTINUE
800 RETURN
    END
    SUBROUTINE SETWT (
   1 CQUAD,G,IUNIT,IWT,MWORK,MY,NERFIT,NG,NGL,NLINF,NOUT,NY,PRWT,
   2 SOLBES,SQRTW,SRANGE,T,WORK,Y,YLYFIT)
      DOUBLE PRECISION SOLBES, WORK
      LOGICAL PRWT
      DIMENSION SOLBES(NGL), WORK(MWORK), SQRTW(MY), CQUAD(NG),
   1 G(NG), T(MY), Y(MY), YLYFIT(MY)
      CHARACTER IHOLER(6)
      DATA IHOLER/'S','E','T','W','T',' '/
      CALL GETYLY (SOLBES,
   1 CQUAD,G,IUNIT,IWT,MWORK,NG,NGL,NLINF,NY,SQRTW,T,WORK,Y,YLYFIT)
      ERRFIT=0.
      IF (NERFIT.LE.0)  GO TO 200
      ABSMIN=SRANGE
      DO 110 J=1,NY
         DUM=ABS(Y(J)-YLYFIT(J))
         IF (DUM .GE. ABSMIN)  GO TO 110
         ABSMIN=DUM
         L=J
110   CONTINUE
      JMAX=MIN0(NY,L+NERFIT/2)
      JMIN=MAX0(1,JMAX-NERFIT+1)
      DUM=0.
      DO 120 J=JMIN,JMAX
         DUM=DUM+YLYFIT(J)**2
120   CONTINUE
      ERRFIT=SQRT(DUM/FLOAT(JMAX-JMIN+1))
200   IF (IWT .NE. 5)  GO TO 250
      CALL USERWT (Y,YLYFIT,MY,ERRFIT,SQRTW)
      GO TO 700
250   IF (IWT.NE.2 .AND. IWT.NE.3)  CALL ERRMES (1,.TRUE.,IHOLER,NOUT)
      DO 260 J=1,NY
         DUM=AMAX1(ABS(Y(J)-YLYFIT(J)),ERRFIT)
         IF (DUM .LE. 0.)  CALL ERRMES (2,.TRUE.,IHOLER,NOUT)
         SQRTW(J)=1./DUM
         IF (IWT .EQ. 2)  SQRTW(J)=SQRT(SQRTW(J))
260   CONTINUE
5260 FORMAT (//' ERRFIT =',1PE9.2//20X,
   1 'SQUARE ROOTS OF LEAST SQUARES WEIGHTS'//
   2 (1X,1P10E13.4))
700   IF (PRWT)  WRITE (NOUT,5260) ERRFIT,(SQRTW(J),J=1,NY)
      RETURN
      END
      SUBROUTINE STORIN (JL,NIOERR,LIN,IIN,RIN)
      DOUBLE PRECISION PRECIS, RANGE
      LOGICAL DOMOM, DOUSIN, DOUSNQ, DOUSOU, LAST, NONNEG, ONLY1, PRWT,
   1 PRY, SIMULA, LUSER
      LOGICAL LEQUIV(10)
      CHARACTER IFORMT(70),IFORMW(70),IFORMY(70),LA(6,46),ITITLE(80)
      DIMENSION LIN(6), IEQUIV(15)
      COMMON /SBLOCK/ PRECIS, RANGE, SRMIN,
   1 ALPST(2), GMNMX(2), PLEVEL(2,2), RSVMNX(2,2), RUSER(100),
```

```
     2 EXMAX, SRANGE                                                STRIN2
       COMMON /CBLOCK/ IFORMT,IFORMW,IFORMY, LA,ITITLE
       COMMON /IBLOCK/ IGRID, IPLRES, IPRINT, IQUAD, IUNIT, IWT,    STRIN3
     1 LINEPG, MIOERR, MQPITR, NEQ, NERFIT, NG, NINTT, NLINF, NORDER, STRIN4
     2 ICRIT(2), IPLFIT(2),                                          STRIN5
     3  IUSER(50), LSIGN(4,4), MOMNMX(2), NENDZ(2),                  STRIN6
     4 NFLAT(4,2), NGL, NGLP1, NIN, NINEQ, NNSGN(2), NOUT, NQPROG(2), STRIN7
     5 NSGN(4), NY                                                   STRIN8
       COMMON /LBLOCK/ DOMOM, DOUSIN, DOUSNQ, DOUSOU, LAST, NONNEG,  STRIN9
     1 ONLY1, PRWT, PRY, SIMULA,                                    STRIN0
     2 LUSER(30)                                                    STRIN1
       EQUIVALENCE (IGRID,IEQUIV(1)), (DOMOM,LEQUIV(1))             STRIN2
       IFINT(RIN)=INT(RIN*1.001)                                    STRIN3
       IF (JL .GT. 1)  GO TO 200                                    STRIN4
       SRMIN=RIN                                                    STRIN5
       RETURN                                                       STRIN6
   200 IF (JL .GT. 6)  GO TO 300                                    STRIN7
       JLL=JL-1                                                     STRIN8
       GO TO (202,203,204,205,206),JLL                              STRIN9
   202 IF (IIN.LT.1 .OR. IIN.GT.2)  GO TO 805                       STRIN0
       ALPST(IIN)=RIN                                               STRIN1
       RETURN                                                       STRIN2
   203 IF (IIN.LT.1 .OR. IIN.GT.2)  GO TO 805                       STRIN3
       GMNMX(IIN)=RIN                                               STRIN4
       RETURN                                                       STRIN5
  5204 FORMAT (4F5.2)                                               STRIN6
   204 READ (NIN,5204) PLEVEL                                       STRIN7
       WRITE (NOUT,5204) PLEVEL                                     STRIN8
       RETURN                                                       STRIN9
  5205 FORMAT (4E10.3)                                              STRIN0
   205 READ (NIN,5205) RSVMNX                                       STRIN1
       WRITE (NOUT,5205) RSVMNX                                     STRIN2
       RETURN                                                       STRIN3
   206 IF (IIN.LT.1 .OR. IIN.GT.100)  GO TO 805                     STRIN8
       RUSER(IIN)=RIN                                               STRIN9
       RETURN                                                       STRIN0
   300 IF (JL .GT. 21)  GO TO 400                                   STRIN1
       IEQUIV(JL-6)=IIN                                             STRIN2
       RETURN                                                       STRIN3
   400 IF (JL .GT. 34)  GO TO 500                                   STRIN4
       JLL=JL-21                                                    STRIN5
       GO TO (422,423,424,425,426,427,428,429,430,431,432,433,434),JLL STRIN6
   422 IF (IIN.LT.1 .OR. IIN.GT.2)  GO TO 805                       STRIN7
       ICRIT(IIN)=IFINT(RIN)                                        STRIN8
       RETURN                                                       STRIN9
  5423 FORMAT (1X,70A1)                                             STRIN0
   423 READ (NIN,5423) IFORMT                                       STRIN1
       WRITE (NOUT,5423) IFORMT                                     STRIN2
       RETURN                                                       STRIN3
   424 READ (NIN,5423) IFORMW                                       STRIN4
       WRITE (NOUT,5423) IFORMW                                     STRIN5
       RETURN                                                       STRIN6
   425 READ (NIN,5423) IFORMY                                       STRIN7
       WRITE (NOUT,5423) IFORMY                                     STRIN8
       RETURN                                                       STRIN9
   426 IF (IIN.LT.1 .OR. IIN.GT.2)  GO TO 805                       STRIN0
       IPLFIT(IIN)=IFINT(RIN)                                       STRIN1
       RETURN                                                       STRIN2
   427 IF (IIN.LT.1 .OR. IIN.GT.50)  GO TO 805                      STRIN7
       IUSER(IIN)=IFINT(RIN)                                        STRIN8
       RETURN                                                       STRIN9
  5428 FORMAT (16I5)                                                STRIN0
   428 READ (NIN,5428) LSIGN                                        STRIN1
       WRITE (NOUT,5428) LSIGN                                      STRIN2
       RETURN                                                       STRIN3
   429 IF (IIN.LT.1 .OR. IIN.GT.2)  GO TO 805                       STRIN4
       MOMNMX(IIN)=IFINT(RIN)                                       STRIN5
       RETURN                                                       STRIN6
   430 IF (IIN.LT.1 .OR. IIN.GT.2)  GO TO 805                       STRIN7
       NENDZ(IIN)=IFINT(RIN)                                        STRIN8
       RETURN                                                       STRIN9
```

```
    431 READ (NIN,5428) NFLAT                                       STRIN0
        WRITE (NOUT,5428) NFLAT                                     STRIN1
        RETURN                                                      STRIN2
    432 IF (IIN.LT.1 .OR. IIN.GT.2)  GO TO 805                      STRIN3
        NNSGN(IIN)=IFINT(RIN)                                       STRIN4
        RETURN                                                      STRIN5
    433 IF (IIN.LT.1 .OR. IIN.GT.2)  GO TO 805                      STRIN6
        NQPROG(IIN)=IFINT(RIN)                                      STRIN7
        RETURN                                                      STRIN8
    434 IF (IIN.LT.1 .OR. IIN.GT.4)  GO TO 805                      STRIN9
        NSGN(IIN)=IFINT(RIN)                                        STRIN0
        RETURN                                                      STRIN1
    500 IF (JL .GT. 44)  GO TO 645                                  STRIN2
        LEQUIV(JL-34)=.NOT.LEQUIV(JL-34)                            STRIN3
        RETURN                                                      STRIN4
    645 IF (IIN.LT.1 .OR. IIN.GT.30)  GO TO 805                     STRIN9
        LUSER(IIN)=.NOT.LUSER(IIN)                                  STRIN0
        RETURN                                                      STRIN1
    805 WRITE (NOUT,5805) IIN,LIN                                   STRIN2
   5805 FORMAT (' SUBSCRIPT =',I3,' OF ',6A1,' IS OUT OF RANGE. .', STRIN3
       1 44('xx'))                                                  STRIN4
        NIOERR=NIOERR+1                                             STRIN5
        IF (NIOERR .GE. MIOERR)  STOP                               STRIN6
        RETURN                                                      STRIN7
        END                                                         STRIN8
        SUBROUTINE SVDRS2 (A,MDA,MM,NN,B,MDB,NB,S,IERROR,RANGE)     SVRS27
        DOUBLE PRECISION A, B, ONE, RANGE, S, T, ZERO               SVRS28
        DIMENSION A(MDA,1),B(MDB,1),S(NN,3)                         SVRS29
        ZERO=0.D0                                                   SVRS21
        ONE=1.D0                                                    SVRS23
        N=NN
        IERROR=6                                                    SVRS29
        IF (N.LE.0.OR.MM.LE.0)  RETURN                              SVRS20
        IERROR=1                                                    SVRS21
        J=N                                                         SVRS22
     10 CONTINUE                                                    SVRS23
           DO 20 I=1,MM                                             SVRS24
           IF (A(I,J))  50,20,50                                    SVRS25
     20    CONTINUE                                                 SVRS26
        IF (J.EQ.N)  GO TO 40                                       SVRS27
           DO 30 I=1,MM                                             SVRS21
     30    A(I,J)=A(I,N)                                            SVRS22
     40 CONTINUE                                                    SVRS23
        A(1,N)=J                                                    SVRS24
        N=N-1                                                       SVRS25
     50 CONTINUE                                                    SVRS26
        J=J-1                                                       SVRS27
        IF (J.GE.1)  GO TO 10                                       SVRS28
        NS=0                                                        SVRS29
        IF (N.EQ.0)  GO TO 240                                      SVRS22
        I=1                                                         SVRS23
        M=MM                                                        SVRS26
     60 IF (I.GT.N.OR.I.GE.M)  GO TO 150                            SVRS27
        IF (A(I,I))  90,70,90                                       SVRS28
     70    DO 80 J=1,N                                              SVRS29
           IF (A(I,J))  90,80,90                                    SVRS20
     80    CONTINUE                                                 SVRS21
        GO TO 100                                                   SVRS22
     90 I=I+1                                                       SVRS23
        GO TO 60                                                    SVRS24
    100 IF(NB.LE.0)  GO TO 115                                      SVRS25
           DO 110 J=1,NB                                            SVRS28
           T=B(I,J)                                                 SVRS29
           B(I,J)=B(M,J)                                            SVRS20
    110    B(M,J)=T                                                 SVRS21
    115    DO 120 J=1,N                                             SVRS22
    120    A(I,J)=A(M,J)                                            SVRS23
        IF (M.GT.N)  GO TO 140                                      SVRS24
           DO 130 J=1,N                                             SVRS25
    130    A(M,J)=ZERO                                              SVRS26
    140 CONTINUE                                                    SVRS27
        M=M-1                                                       SVRS28
        GO TO 60                                                    SVRS20
                                                                    SVRS21
```

```
150 CONTINUE                                                              SVRS23
    L=MINO(M,N)                                                           SVRS29
       DO 170 J=1,L                                                       SVRS23
       IF (J.GE.M) GO TO 160                                              SVRS24
       JJ=J                                                               SVRS25
       CALL H12 (1,JJ,J+1,M,A(1,J),1,T,A(1,J+1),1,MDA,N-J,RANGE)          SVRS26
       CALL H12 (2,JJ,J+1,M,A(1,J),1,T,B,1,MDB,NB,RANGE)                  SVRS27
160    IF (J.GE.N-1) GO TO 170                                            SVRS28
       CALL H12 (1,J+1,J+2,N,A(J,1),MDA,S(J,3),A(J+1,1),MDA,1,M-J,        SVRS29
    1  RANGE)                                                             SVRS20
170    CONTINUE                                                           SVRS21
    IF (N.EQ.1) GO TO 190                                                 SVRS25
       DO 180 J=2,N                                                       SVRS26
       S(J,1)=A(J,J)                                                      SVRS27
180    S(J,2)=A(J-1,J)                                                    SVRS28
190 S(1,1)=A(1,1)                                                         SVRS29
    NS=N                                                                  SVRS21
    IF (M.GE.N) GO TO 200                                                 SVRS22
    NS=M+1                                                                SVRS23
    S(NS,1)=ZERO                                                          SVRS24
    S(NS,2)=A(M,M+1)                                                      SVRS25
200 CONTINUE                                                              SVRS26
       DO 230 K=1,N                                                       SVRS21
       I=N+1-K                                                            SVRS22
       IF(I.GT.MINO(M,N-2)) GO TO 210                                     SVRS23
       CALL H12 (2,I+1,I+2,N,A(I,1),MDA,S(I,3),A(1,I+1),1,MDA,N-I,        SVRS24
    1  RANGE)                                                             SVRS25
210    DO 220 J=1,N                                                       SVRS26
220    A(I,J)=ZERO                                                        SVRS27
230    A(I,I)=ONE                                                         SVRS28
    CALL QRBD (IPASS,S(1,1),S(1,2),NS,A,MDA,N,B,MDB,NB,RANGE)             SVRS22
    GO TO (240,310), IPASS                                                SVRS24
240 CONTINUE                                                              SVRS25
    IF (NS.GE.N) GO TO 260                                                SVRS26
    NSP1=NS+1                                                             SVRS27
       DO 250 J=NSP1,N                                                    SVRS28
250    S(J,1)=ZERO                                                        SVRS29
260 CONTINUE                                                              SVRS20
    IF (N.EQ.NN) RETURN                                                   SVRS21
    NP1=N+1                                                               SVRS22
       DO 280 J=NP1,NN                                                    SVRS25
       S(J,1)=A(1,J)                                                      SVRS26
       DO 270 I=1,N                                                       SVRS27
270    A(I,J)=ZERO                                                        SVRS28
280    CONTINUE                                                           SVRS29
       DO 300 K=NP1,NN                                                    SVRS21
       I=S(K,1)                                                           SVRS22
       S(K,1)=ZERO                                                        SVRS23
       DO 290 J=1,NN                                                      SVRS24
       A(K,J)=A(I,J)                                                      SVRS25
290    A(I,J)=ZERO                                                        SVRS26
       A(I,K)=ONE                                                         SVRS27
300    CONTINUE                                                           SVRS28
    RETURN                                                                SVRS20
310 IERROR=5                                                              SVRS21
    RETURN                                                                SVRS22
    END                                                                   SVRS23
    SUBROUTINE UPDDON (                                                   UPDON0
    1 NSGNM1,LLSIGN,LSDONE,MDONE,NDONE,NNQUSR,LBIND,MINEQ,                UPDON1
    2 NG,VARI,VDONE)                                                      UPDON2
    LOGICAL LBIND, STORE                                                  UPDON3
    DIMENSION LLSIGN(5), LSDONE(MDONE,3,2), LBIND(MINEQ),                 UPDON4
    1 VDONE(MDONE)                                                        UPDON5
    STORE=NSGNM1 .GE. 1                                                   UPDON6
    IF (.NOT.STORE) GO TO 700                                             UPDON7
    VDONE(NDONE)=VARI                                                     UPDON8
    DO 110 J=1,NSGNM1                                                     UPDON9
      L=IABS(LLSIGN(J+1))                                                 UPDON0
      KK=L-IABS(LLSIGN(J))-1                                              UPDON1
      LL=L+NNQUSR+1                                                       UPDON2
      IF (KK .EQ. 0) GO TO 130                                            UPDON3
      DO 120 K=1,KK                                                       UPDON4
```

```
         LL=LL-1
         IF (.NOT.LBIND(LL))  GO TO 130                         UPDON6
  120  CONTINUE                                                 UPDON7
         LL=LL-1                                                UPDON8
  130  LSDONE(NDONE,J,1)=MINO(LL-NNQUSR+1,L)                    UPDON9
         KK=IABS(LLSIGN(J+2))-L-1                               UPDON0
         LL=NNQUSR-1+L                                          UPDON1
         IF (KK .EQ. 0)  GO TO 150                              UPDON2
         DO 140 K=1,KK                                          UPDON3
            LL=LL+1                                             UPDON4
            IF (.NOT.LBIND(LL))  GO TO 150                      UPDON5
  140    CONTINUE                                               UPDON6
         LL=LL+1                                                UPDON7
  150  LSDONE(NDONE,J,2)=MAXO(LL-NNQUSR-1,L)                    UPDON8
         IF (LSDONE(NDONE,J,1) .EQ. L)  LSDONE(NDONE,J,1)=-L    UPDON9
         IF (LSDONE(NDONE,J,2) .EQ. L)  LSDONE(NDONE,J,2)=-L    UPDON0
  110  CONTINUE                                                 UPDON1
       IF (NDONE .LE. 1)  GO TO 700                             UPDON5
       KK=NDONE-1                                               UPDON6
       DO 210 K=1,KK                                            UPDON7
         DO 220 J=1,NSGNM1                                      UPDON8
            IF (IABS(LSDONE(NDONE,J,1)) .NE. IABS(LSDONE(K,J,1))UPDON9
     1    .OR.   IABS(LSDONE(NDONE,J,2)) .NE. IABS(LSDONE(K,J,2)))UPDON0
     2    GO TO 210                                             UPDON1
  220    CONTINUE                                               UPDON2
         VARI=VDONE(K)                                          UPDON3
         STORE=.FALSE.                                          UPDON4
         GO TO 700                                              UPDON5
  210  CONTINUE                                                 UPDON6
  700  IF (.NOT.STORE)  NDONE=NDONE-1                           UPDON7
       RETURN                                                   UPDON8
       END                                                      UPDON9
       SUBROUTINE UPDLLS (NSGNI,JSTAGE,NOUT,VARTRY,VARI,LLSTRY, UPLLS2
     1 LLSIGN,INC,DONE)                                         UPLLS3
       LOGICAL DONE                                             UPLLS4
       DIMENSION JSTAGE(NSGNI), VARTRY(NSGNI), LLSTRY(5,NSGNI), UPLLS5
     1 LLSIGN(5), INC(NSGNI)                                    UPLLS6
       CHARACTER IHOLER(6)                                      UPLLS7
       DATA IHOLER/'U','P','D','L','L','S'/                     UPLLS8
       IF (NSGNI .LE. 1)  GO TO 790                             UPLLS9
       NSGNP1=NSGNI+1                                           UPLLS0
       DONE=.FALSE.                                             UPLLS1
       L=NSGNP1                                                 UPLLS2
       DO 200 JLL=2,NSGNI                                       UPLLS3
         L=L-1                                                  UPLLS7
         JSTAGE(L)=JSTAGE(L)+1                                  UPLLS5
         IF (JSTAGE(L) .LT. 1)  CALL ERRMES (1,.TRUE.,IHOLER,NOUT)UPLLS6
         IF (JSTAGE(L)-2)  300,400,500                          UPLLS7
  300    IF (L .LT. NSGNI)  GO TO 330                           UPLLS8
         VARTRY(L)=VARI                                         UPLLS3
         DO 310 J=1,NSGNP1                                      UPLLS4
            LLSTRY(J,L)=IABS(LLSIGN(J))                         UPLLS5
  310    CONTINUE                                               UPLLS6
         GO TO 350                                              UPLLS7
  330    VARTRY(L)=VARTRY(L+1)                                  UPLLS2
         DO 340 J=1,NSGNP1                                      UPLLS3
            LLSTRY(J,L)=LLSTRY(J,L+1)                           UPLLS4
  340    CONTINUE                                               UPLLS5
  350    DO 360 LL=2,NSGNI                                      UPLLS0
            LLSIGN(LL)=ISIGN(LLSTRY(LL,L),LLSIGN(LL))           UPLLS1
  360    CONTINUE                                               UPLLS2
         LL=LLSTRY(L,L)+INC(L)                                  UPLLS3
         LLSIGN(L)=ISIGN(LL,LLSIGN(L))                          UPLLS4
         IF (LL.GT.LLSTRY(L-1,L) .AND. LL.LT.LLSTRY(L+1,L))  GO TO 800 UPLLS8
         IF (LL.LE.LLSTRY(L-1,L) .OR. L.GE.NSGNI)  GO TO 370    UPLLS2
         LLSIGN(L+1)=ISIGN(LLSTRY(L+1,L)+1,LLSIGN(L+1))         UPLLS6
         IF (IABS(LLSIGN(L+1)) .LT. LLSTRY(L+2,L))  GO TO 800   UPLLS7
         IF (L+1 .GE. NSGNI)  GO TO 370                         UPLLS2
         LLSIGN(L+2)=ISIGN(LLSTRY(L+2,L)+1,LLSIGN(L+2))         UPLLS6
         IF (IABS(LLSIGN(L+2)) .LT. LLSTRY(L+3,L))  GO TO 800   UPLLS7
  370    IF (JSTAGE(L) .GT. 1)  GO TO 510                       UPLLS2
         JSTAGE(L)=2                                            UPLLS3
         GO TO 420                                              UPLLS4
```

```
400    IF (VARI-VARTRY(L)) 300,410,420                          UPLLS1
410    JSTAGE(L)=1                                              UPLLS6
       GO TO 300                                                UPLLS7
420    INC(L)=-1                                                UPLLS2
       GO TO 350                                                UPLLS3
500    IF (VARI .LE. VARTRY(L))  GO TO 300                      UPLLS0
510    DO 520 LL=L,NSGNI                                        UPLLS5
          JSTAGE(LL)=0                                          UPLLS6
          INC(LL)=1                                             UPLLS7
520    CONTINUE                                                 UPLLS8
       VARI=VARTRY(L)                                           UPLLS9
200 CONTINUE                                                    UPLLS0
790 DONE=.TRUE.                                                 UPLLS4
800 RETURN                                                      UPLLS5
    END                                                         UPLLS6
    SUBROUTINE UPDSGN (NNSGNI,LLLSGN,                           UPSGN8
   1 A,AINEQ,IISIGN,MA,MG,MINEQ,MREG,NGLE,NGLP1,NNINEQ,         UPSGN9
   2 NNQUSR,NONNEG,NOUT,REG,RHSNEQ,S,VALPHA)                    UPSGN0
    DOUBLE PRECISION A, AINEQ, ONE, REG, RHSNEQ, S, VALPHA, ZERO UPSGN1
    LOGICAL NONNEG                                              UPSGN2
    DIMENSION LLLSGN(5), A(MA,MG), REG(MREG,MG), S(MG,3),       UPSGN3
   1 RHSNEQ(MINEQ), VALPHA(MG), IISIGN(MG), AINEQ(MINEQ,MG)     UPSGN4
    CHARACTER IHOLER(6)                                         UPSGN5
    DATA IHOLER/'U','P','D','S','G','N'/                        UPSGN6
    ZERO=0.D0                                                   UPSGN8
    ONE=1.D0                                                    UPSGN0
    IROW=NNQUSR                                                 UPSGN1
    IIROW=NNINEQ                                                UPSGN2
    NNSGNP=NNSGNI+1                                             UPSGN3
    DO 110 JS=1,NNSGNP                                          UPSGN4
       LS=LLLSGN(JS)                                            UPSGN5
       ICMIN=IABS(LS)                                           UPSGN6
       IF (JS .LE. NNSGNI)  GO TO 114                           UPSGN7
       IF (NONNEG .AND. LLLSGN(NNSGNI).GT.0)  GO TO 116         UPSGN8
       GO TO 110                                                UPSGN9
114    ICMAX=IABS(LLLSGN(JS+1))-1                               UPSGN0
       IF (ICMIN .GT. ICMAX)  CALL ERRMES (1,.TRUE.,IHOLER,NOUT) UPSGN1
       IF (.NOT.NONNEG .OR. LS.GT.0)  GO TO 130                 UPSGN2
116    IIROW=IIROW+1                                            UPSGN6
       IF (IIROW .GT. MINEQ)  CALL ERRMES (2,.TRUE.,IHOLER,NOUT) UPSGN7
       DO 120 IICOL=1,NGLE                                      UPSGN8
          A(IIROW,IICOL)=REG(ICMIN,IICOL)*S(IICOL,2)            UPSGN9
120    CONTINUE                                                 UPSGN0
       RHSNEQ(IIROW)=-VALPHA(ICMIN)                             UPSGN1
       DO 125 IICOL=1,NGLP1                                     UPSGN2
          AINEQ(IIROW,IICOL)=ZERO                               UPSGN3
125    CONTINUE                                                 UPSGN4
       AINEQ(IIROW,ICMIN)=ONE                                   UPSGN5
       IF (JS .GT. NNSGNI)  GO TO 110                           UPSGN6
130    DO 140 ICOL=ICMIN,ICMAX                                  UPSGN0
          IROW=IROW+1                                           UPSGN1
          IF (IROW .GT. NNINEQ)  CALL ERRMES (3,.TRUE.,IHOLER,NOUT) UPSGN2
          IF (IISIGN(ICOL)*LS .GT. 0)  GO TO 140                UPSGN3
          IISIGN(ICOL)=-IISIGN(ICOL)                            UPSGN4
          DO 145 IICOL=1,NGLE                                   UPSGN5
             A(IROW,IICOL)=-A(IROW,IICOL)                       UPSGN6
145       CONTINUE                                              UPSGN7
          RHSNEQ(IROW)=-RHSNEQ(IROW)                            UPSGN8
140    CONTINUE                                                 UPSGN9
110 CONTINUE                                                    UPSGN0
    RETURN                                                      UPSGN1
    END                                                         UPSGN2
    SUBROUTINE USEREQ (AEQ,CQUAD,MEQ,MG)                        USREQ4
    DOUBLE PRECISION PRECIS, RANGE                              USREQ5
    DOUBLE PRECISION AEQ                                        USREQ6
    LOGICAL DOMOM, DOUSIN, DOUSNQ, DOUSOU, LAST, NONNEG, ONLY1, PRWT, USREQ7
   1 PRY, SIMULA, LUSER                                         USREQ8
    DIMENSION AEQ(MEQ,MG), CQUAD(MG)                            USREQ9
    COMMON /SBLOCK/ PRECIS, RANGE, SRMIN,                       USREQ0
   1 ALPST(2), GMNMX(2), PLEVEL(2,2), RSVMNX(2,2), RUSER(100),  USREQ1
   2 EXMAX, SRANGE                                              USREQ2
    COMMON /IBLOCK/ IGRID, IPLRES, IPRINT, IQUAD, IUNIT, IWT,   USREQ3
```

```
      1 LINEPG, MIDERR, MQPITR, NEQ, NERFIT, NG, NINTT, NLINF, NORDER,    USREQ4
      2 ICRIT(2), IPLFIT(2),
      3  IUSER(50), LSIGN(4,4), MOMNMX(2), NENDZ(2),                      USREQ6
      4 NFLAT(4,2), NGL, NGLP1, NIN, NINEQ, NNSGN(2), NOUT, NQPROG(2),    USREQ7
      5 NSGN(4), NY
       COMMON /LBLOCK/ DOMOM, DOUSIN, DOUSNQ, DOUSOU, LAST, NONNEG,       USREQ8
      1 ONLY1, PRWT, PRY, SIMULA,                                         USREQ9
      2 LUSER(30)                                                         USREQ0
       ZERO=0.D0                                                          USREQ1
       ONE=1.D0                                                           USREQ3
       IF (NEQ.GE.1 .AND. NEQ.LE.3) GO TO 105                             USREQ5
 5105 FORMAT (/' NEQ =',I3,' IS NOT 1, 2 OR 3 IN USEREQ.')                USREQ0
       WRITE (NOUT,5105) NEQ                                              USREQ1
       STOP                                                               USREQ2
  105 L=MIN0(NEQ,2)                                                       USREQ3
       DO 110 J=1,L                                                       USREQ4
         DO 120 K=1,NGL                                                   USREQ5
           AEQ(J,K)=ZERO                                                  USREQ6
  120    CONTINUE                                                         USREQ7
         AEQ(J,NGLP1)=RUSER(J)                                            USREQ8
  110 CONTINUE                                                            USREQ9
       AEQ(1,NG)=ONE                                                      USREQ0
       IF (NEQ .GT. 1)  AEQ(2,1)=ONE                                      USREQ1
       IF (NEQ .NE. 3)  GO TO 800                                         USREQ2
       DO 130 K=1,NGL                                                     USREQ3
         AEQ(3,K)=ZERO                                                    USREQ4
         IF (K .LE. NG)  AEQ(3,K)=CQUAD(K)                                USREQ5
  130 CONTINUE                                                            USREQ6
       AEQ(3,NGLP1)=RUSER(6)                                              USREQ7
  800 RETURN                                                              USREQ8
       END                                                                USREQ9
       FUNCTION USEREX (IROW,T,MY)                                        USREQ0
       DOUBLE PRECISION PRECIS, RANGE                                     USREX3
       LOGICAL DOMOM, DOUSIN, DOUSNQ, DOUSOU, LAST, NONNEG, ONLY1, PRWT,  USREX4
      1 PRY, SIMULA, LUSER                                                USREX5
       DIMENSION T(MY)                                                    USREX6
       COMMON /SBLOCK/ PRECIS, RANGE, SRMIN,                              USREX7
      1 ALPST(2), GMNMX(2), PLEVEL(2,2), RSVMNX(2,2), RUSER(100),         USREX8
      2 EXMAX, SRANGE                                                     USREX9
       COMMON /IBLOCK/ IGRID, IPLRES, IPRINT, IQUAD, IUNIT, IWT,          USREX0
      1 LINEPG, MIDERR, MQPITR, NEQ, NERFIT, NG, NINTT, NLINF, NORDER,    USREX1
      2 ICRIT(2), IPLFIT(2),                                              USREX2
      3  IUSER(50), LSIGN(4,4), MOMNMX(2), NENDZ(2),
      4 NFLAT(4,2), NGL, NGLP1, NIN, NINEQ, NNSGN(2), NOUT, NQPROG(2),    USREX4
      5 NSGN(4), NY                                                       USREX5
       COMMON /LBLOCK/ DOMOM, DOUSIN, DOUSNQ, DOUSOU, LAST, NONNEG,       USREX6
      1 ONLY1, PRWT, PRY, SIMULA,                                         USREX7
      2 LUSER(30)                                                         USREX8
       EX=RUSER(5)*T(IROW)                                                USREX9
       USEREX=RUSER(9)                                                    USREX6
       IF (EX .LT. EXMAX)  USEREX=USEREX+RUSER(4)*EXP(-EX)                USREX7
       RETURN                                                             USREX8
       END                                                                USREX9
       SUBROUTINE USERGR (G,CQUAD,MG)                                     USREX0
       DOUBLE PRECISION PRECIS, RANGE                                     USRGR2
       LOGICAL DOMOM, DOUSIN, DOUSNQ, DOUSOU, LAST, NONNEG, ONLY1, PRWT,  USRGR3
      1 PRY, SIMULA, LUSER                                                USRGR4
       DIMENSION G(MG), CQUAD(MG)                                        USRGR5
       COMMON /SBLOCK/ PRECIS, RANGE, SRMIN,                              USRGR6
      1 ALPST(2), GMNMX(2), PLEVEL(2,2), RSVMNX(2,2), RUSER(100),         USRGR7
      2 EXMAX, SRANGE                                                     USRGR8
       COMMON /IBLOCK/ IGRID, IPLRES, IPRINT, IQUAD, IUNIT, IWT,          USRGR9
      1 LINEPG, MIDERR, MQPITR, NEQ, NERFIT, NG, NINTT, NLINF, NORDER,    USRGR0
      2 ICRIT(2), IPLFIT(2),                                              USRGR1
      3  IUSER(50), LSIGN(4,4), MOMNMX(2), NENDZ(2),
      4 NFLAT(4,2), NGL, NGLP1, NIN, NINEQ, NNSGN(2), NOUT, NQPROG(2),    USRGR3
      5 NSGN(4), NY                                                       USRGR4
       COMMON /LBLOCK/ DOMOM, DOUSIN, DOUSNQ, DOUSOU, LAST, NONNEG,       USRGR5
      1 ONLY1, PRWT, PRY, SIMULA,                                         USRGR6
      2 LUSER(30)                                                         USRGR7
                                                                          USRGR8
```

```
      return
      end
c
c  Subroutine bhmie calculates amplitude scattering matrix
c  elements and efficiencies for extinction, total scattering
c  and backscattering for a given size parameter and
c  relative refractie index.
c
      subroutine bhmie(theta,x,refrel,nang,s1,s2,qext,qsca,qback)
      parameter (maxang=1)
      dimension amu(10),theta(10),pi(10),tau(10),pi0(10),pi1(10)
      complex d(300),y,refrel,xi,xi0,xi1,an,bn,s1(maxang),s2(maxang)
      double precision psi0,psi1,psi,dn,dx
      dx=x
      y=x*refrel
c
c  Series terminated after nstop terms.
c
      xstop=x+4.*x**.3333+2.0
      nstop=xstop
      ymod=cabs(y)
      nmx=amax1(xstop,ymod)+15
      dang=1.570796327/float(nang-1)
      do 555 j=1,nang
  555 amu(j)=cos(theta(j))
c
c  Logarithmic derivative d(j) calculated by downward
c  recurrence beginning with initial alue 0.0 + ix0.0
c  at j=nmx
c
      d(nmx)=cmplx(0.0,0.0)
      nn=nmx-1
      do 120 n=1,nn
      rn=nmx-n+1
  120 d(nmx-n)=(rn/y)-(1./(d(nmx-n+1)+rn/y))
      do 666 j=1,nang
      pi0(j)=0.0
  666 pi1(j)=1.0
      nn=2*nang-1
      do 777 j=1,nn
      s1(j)=cmplx(0.0,0.0)
  777 s2(j)=cmplx(0.0,0.0)
c
c  Ricatti-Bessel functions with real arguement x
c  calculated by upward recurrence.
c
      psi0=dcos(dx)
      psi1=dsin(dx)
      chi0=-sin(x)
      chi1=cos(x)
      apsi0=psi0
      apsi1=psi1
      xi0=cmplx(apsi0,-chi0)
      xi1=cmplx(apsi1,-chi1)
      qsca=0.0
      n=1
  200 dn=n
      rn=n
      fn=(2.*rn+1.)/(rn*(rn+1.))
      psi=(2.*dn-1.)*psi1/dx-psi0
      apsi=psi
      chi=(2.*rn-1.)*chi1/x-chi0
      xi=cmplx(apsi,-chi)
      an=(d(n)/refrel+rn/x)*apsi-apsi1
      an=an/((d(n)/refrel+rn/x)*xi-xi1)
      bn=(refrel*d(n)+rn/x)*apsi-apsi1
```

1 LINEPG, MIDERR, MOPITR, NEQ, NERFIT, NG, NINTT, NLINF, NORDER,    USERK1
      2 ICRIT(2), IPLFIT(2),
      3  IUSER(50), LSIGN(4,4), MOMNMX(2), NENDZ(2),
      4 NFLAT(4,2), NGL, NGLP1, NIN, NINEQ, NNSGN(2), NOUT, NQPROG(2),    USERK3
      5 NSGN(4), NY                                                       USERK4
         COMMON /LBLOCK/ DOMOM, DOUSIN, DOUSNQ, DOUSOU, LAST, NONNEG,      USERK5
                                                                          USERK6

```
    1 ONLY1, PRHT, PRY, SIMULA,                                    USERK7
    2 LUSER(30)                                                    USERK8
      DATA IHOLER/'U','S','E','R','K',' '/                         USERK9
      IF (JT.GT.NY .OR. JG.GT.NG .OR. MIN0(JT,JG).LE.0) CALL ERRMES (1,USERK0
   1.TRUE.,IHOLER,NOUT)                                            USERK1
      EX=T(JT)/G(JG)                                               USERK5
      R=G(JG)*1E-3
      USERK=0.                                                     USERK6
      IF (EX .GT. EXMAX) RETURN
      WGHT=1.
      IF (LUSER(15)) GO TO 4
      IF(.NOT.LUSER(11)) GO TO 5
    4 WGHT=1.
      IF(JT.LT.IUSER(11)) WGHT=WGHT*RUSER(22)
      IF(JT.GE.IUSER(11)) WGHT=WGHT*RUSER(23)
    5 USERK=WGHT*EXP(-EX)
      RETURN                                                       USERK8
      END                                                          USERK9
c   mie.fs
c
c   Userk.mie calculates the size parameter (x) and relative
c   refractive index (refrel) for a given sphere refractive
c   index, medium refractive index, radius, and free space
c   wavelength.  It then calls bhmie, the subroutine that computes
c   the amplitude scattering matrix and efficiencies.
c
      real function mie(radius,ruser,iangle)
      parameter (maxang=1)
      real theta(10), ruser(100)
      complex refrel,s1(maxang),s2(maxang)
c
c   refmed = (real) refractive index of surrounding medium.
c
      refmed=ruser(14)
c
c   refractive index of sphere = refre + i*refim.  For now, assume PSL.
c
      refre=1.6
      refim=0.0
      refrel=cmplx(refre,refim)/refmed
c
c   Radius (rad) and wavelength (wavel) same units.  Get various quantities
c   ready to call bhmie.
c
      wavel=ruser(13)
      x=2.*3.14159265*radius*refmed/wavel
      nang=1
      convrt=1.7453293e-2
      theta(1)=ruser(iangle)*convrt
      call bhmie(theta,x,refrel,nang,s1,s2,qext,qsca,qback)
c
c   s1 and s2 are used to calculate the (perpendicular) mie intensities.
c
      do 10 j=1,nang
         s11=0.5*cabs(s2(j))*cabs(s2(j))
         s11=s11+0.5*cabs(s1(j))*cabs(s1(j))
         s12=0.5*cabs(s2(j))*cabs(s2(j))
         s12=s12-0.5*cabs(s1(j))*cabs(s1(j))
         mie=s11-s12
   10 continue
      DO 15 K=1,IEND
   15 Y(K)=Y(K)*YNORM
      IF(.NOT.LUSER(11)) GO TO 800

DO 11 K=ISTART,NY
   11 T(K)=T(K)*Q2DC2
      DO 16 K=ISTART,NY
   16 Y(K)=Y(K)*YNORM2
c
```

```
C     THE FOLLOWING LINES ARE NOT VERY USEFUL. THEY WERE ADDED TO ALLOW
C     WEIGHTING OUT OF ONE OF THE TWO SETS OF DATA IN SIMULTANEOUS TWO
C     ANGLE FITS. THEY SHOULD BE REPLACED BY A WEIGHTING SCHEME TO
C     CORRECTLY WEIGHT THE DATA FROM THE TWO ANGLE BY THE TOTAL SCATTERED
C     INTENSITY.
C
      IF(.NOT.LUSER(12)) GO TO 800
      DO 23 J=1,IEND
   23 SQRTW(J)=1.
      DO 25 J=ISTART,NY
   25 SQRTW(J)=RUSER(25)
      IF(.NOT.LUSER(14)) GO TO 800
      DO 27 J=1,IEND
   27 SQRTW(J)=RUSER(26)
      DO 28 J=ISTART,NY
   28 SQRTW(J)=1.
  800 CONTINUE                                                          USRIN7
      RETURN
      END                                                               USRIN8
      SUBROUTINE EXTRP(T,Y,IFIRST,NEXTR,COEFF1)
      REAL T(1), Y(1)
      DOUBLE PRECISION AEXTR(2,2), AEX(2,2), B1, B2, DENOM
      AEXTR(1,2)=0.
      AEXTR(2,2)=0.
      B1=0.
      B2=0.
      DO 100 J=IFIRST,IFIRST+NEXTR-1
         AEXTR(1,2)=AEXTR(1,2)+T(J)
         AEXTR(2,2)=AEXTR(2,2)+T(J)*T(J)
         B1=B1+Y(J)
         B2=B2+Y(J)*T(J)
  100 CONTINUE
      AEXTR(1,1)=NEXTR
      AEXTR(2,1)=AEXTR(1,2)
      DO 110 I=1,2
      DO 110 J=1,2
         AEX(I,J)=AEXTR(I,J)
  110 CONTINUE
      DENOM=AEX(1,1)*AEX(2,2)-AEX(1,2)*AEX(2,1)
      AEX(1,1)=B1
      AEX(2,1)=B2
      AEX(1,2)=AEXTR(1,2)
      AEX(2,2)=AEXTR(2,2)
      COEFF1=(AEX(1,1)*AEX(2,2)-AEX(1,2)*AEX(2,1))/DENOM
      RETURN
      END
      FUNCTION USERK (JT,T,JG,G)                                        USERK1
      REAL MIE
      DOUBLE PRECISION PRECIS, RANGE                                    USERK2
      LOGICAL DOMOM, DOUSIN, DOUSNQ, DOUSOU, LAST, NONNEG, ONLY1, PRWT, USERK3
     1 PRY, SIMULA, LUSER                                               USERK4
      DIMENSION T(JT), G(JG)                                            USERK5
      CHARACTER IHOLER(6)
      COMMON /SBLOCK/ PRECIS, RANGE, SRMIN,                             USERK7
     1 ALPST(2), GMNMX(2), PLEVEL(2,2), RSVMNX(2,2), RUSER(100),        USERK8
     2 EXMAX, SRANGE                                                    USERK9
      COMMON /IBLOCK/ IGRID, IPLRES, IPRINT, IQUAD, IUNIT, IWT,         USERK0
      bn=bn/((refrel*d(n)+rn/x)*xi-xi1)
      qsca=qsca+(2.*rn+1.)*(cabs(an)*cabs(an)+cabs(bn)*cabs(bn))
      do 789 j=1,nang
      jj=2*nang-j
      pi(j)=pi1(j)
      tau(j)=rn*amu(j)*pi(j)-(rn+1.)*pi0(j)
      p=(-1.)**(n-1)
      s1(j)=s1(j)+fn*(an*pi(j)+bn*tau(j))
      t=(-1.)**n
      s2(j)=s2(j)+fn*(an*tau(j)+bn*pi(j))
      if(j.eq.jj) go to 789
      s1(jj)=s1(jj)+fn*(an*pi(j)*p+bn*tau(j)*t)
      s2(jj)=s2(jj)+fn*(an*tau(j)*t+bn*pi(j)*p)
```

```
789 continue
    psi0=psi1
    psi1=psi
    apsi1=psi1
    chi0=chi1
    chi1=chi
    xi1=cmplx(apsi1,-chi1)
    n=n+1
    rn=n
    do 999 j=1,nang
    pi1(j)=((2.*rn-1.)/(rn-1.))*amu(j)*pi(j)
    pi1(j)=pi1(j)-rn*pi0(j)/(rn-1.)
999 pi0(j)=pi(j)
    if(n-1-nstop) 200,300,300
300 qsca=(2./(x*x))*qsca
    qext=(4./(x*x))*real(s1(1))
    qback=(4./(x*x))*cabs(s1(2*nang-1))*cabs(s1(2*nang-1))
    return
    end
    SUBROUTINE USERNQ (AINEQ,MG,MINEQ)                              USRNQ8
    DOUBLE PRECISION PRECIS, RANGE                                  USRNQ9
    DOUBLE PRECISION AINEQ, ONE, ZERO                               USRNQ0
    LOGICAL DOMOM, DOUSIN, DOUSNQ, DOUSOU, LAST, NONNEG, ONLY1, PRWT, USRNQ1
   1 PRY, SIMULA, LUSER                                             USRNQ2
    DIMENSION AINEQ(MINEQ,MG)                                       USRNQ3
    COMMON /SBLOCK/ PRECIS, RANGE, SRMIN,                           USRNQ4
   1 ALPST(2), GMNMX(2), PLEVEL(2,2), RSVMNX(2,2), RUSER(100),      USRNQ5
   2 EXMAX, SRANGE                                                  USRNQ6
    COMMON /IBLOCK/ IGRID, IPLRES, IPRINT, IQUAD, IUNIT, IWT,       USRNQ7
   1 LINEPG, MIOERR, MOPITR, NEQ, NERFIT, NG, NINTT, NLINF, NORDER, USRNQ8
   2 ICRIT(2), IPLFIT(2),
   3 IUSER(50), LSIGN(4,4), MOMNMX(2), NENDZ(2),                    USRNQ0
   4 NFLAT(4,2), NGL, NGLP1, NIN, NINEQ, NNSGN(2), NOUT, NQPROG(2), USRNQ1
   5 NSGN(4), NY                                                    USRNQ2
    COMMON /LBLOCK/ DOMOM, DOUSIN, DOUSNQ, DOUSOU, LAST, NONNEG,    USRNQ3
   1 ONLY1, PRWT, PRY, SIMULA,                                      USRNQ4
   2 LUSER(30)                                                      USRNQ5
    ZERO=0.D0                                                       USRNQ7
    ONE=1.D0                                                        USRNQ9
    IF (NLINF .LE. 0) RETURN                                        USRNQ4
    NINEQ=NLINF                                                     USRNQ5
    DO 110 J=1,NINEQ                                                USRNQ6
      DO 120 K=1,NGLP1                                              USRNQ7
        AINEQ(J,K)=ZERO                                             USRNQ8
120   CONTINUE                                                      USRNQ9
      K=NG+J                                                        USRNQ0
      AINEQ(J,K)=ONE                                                USRNQ1
110 CONTINUE                                                        USRNQ2
    RETURN                                                          USRNQ3
    END                                                             USRNQ4
    SUBROUTINE USEROU (G,SOL,EXACT,MG)                              USROU1
    DOUBLE PRECISION PRECIS, RANGE                                  USROU2
    LOGICAL DOMOM, DOUSIN, DOUSNQ, DOUSOU, LAST, NONNEG, ONLY1, PRWT, USROU3
   1 PRY, SIMULA, LUSER                                             USROU4
    DIMENSION G(MG), SOL(MG), EXACT(MG)                             USROU5
    DIMENSION FCAP(4,16), F(4)                                      USROU3
    COMMON /SBLOCK/ PRECIS, RANGE, SRMIN,                           USROU4
   1 ALPST(2), GMNMX(2), PLEVEL(2,2), RSVMNX(2,2), RUSER(100),      USROU5
   2 EXMAX, SRANGE                                                  USROU6
    COMMON /IBLOCK/ IGRID, IPLRES, IPRINT, IQUAD, IUNIT, IWT,       USROU7
   1 LINEPG, MIOERR, MOPITR, NEQ, NERFIT, NG, NINTT, NLINF, NORDER, USROU8
   2 ICRIT(2), IPLFIT(2),
   3 IUSER(50), LSIGN(4,4), MOMNMX(2), NENDZ(2),                    USROU0
   4 NFLAT(4,2), NGL, NGLP1, NIN, NINEQ, NNSGN(2), NOUT, NQPROG(2), USROU1
   5 NSGN(4), NY                                                    USROU2
    COMMON /LBLOCK/ DOMOM, DOUSIN, DOUSNQ, DOUSOU, LAST, NONNEG,    USROU3
   1 ONLY1, PRWT, PRY, SIMULA,                                      USROU4
   2 LUSER(30)                                                      USROU5
    DATA NSPECT/16/, NCLASS/4/, FCAP/                               USROU6
   1   .79,.00,.05,.16 ,  .41,.16,.23,.20 ,  .23,.40,.13,.24 ,      USROU7
   2   .28,.14,.17,.41 ,  .45,.24,.06,.25 ,  .09,.34,.34,.23 ,      USROU8
   3   .02,.51,.09,.38 ,  .39,.00,.24,.37 ,  .07,.52,.26,.15 ,      USROU9
```

```
     4     .24,.15,.18,.43 ,    .51,.24,.12,.13 ,    .62,.05,.17,.16 ,         USROU0
     5     .37,.15,.26,.22 ,                         .28,.33,.03,.36 ,         USROU1
     6                          .54,.12,.19,.15 ,    .26,.44,.13,.17 /         USROU2
      SUMF=0.                                                                  USROU3
      DO 110 J=1,NCLASS                                                        USROU4
        F(J)=0.                                                                USROU5
        DO 120 K=1,NSPECT                                                      USROU6
          F(J)=F(J)+SOL(K)*FCAP(J,K)                                           USROU7
  120   CONTINUE                                                               USROU8
        SUMF=SUMF+F(J)                                                         USROU9
  110 CONTINUE                                                                 USROU0
      DO 140 J=1,NCLASS                                                        USROU1
        F(J)=F(J)/SUMF                                                         USROU2
  140 CONTINUE                                                                 USROU3
      SUMF=SUMF/RUSER(14)                                                      USROU4
 5140 FORMAT (/8X,'HELIX',3X,'BETA-SHEET',4X,'BETA-TURN',4X,                   USROU9
     1 'REMAINDER',6X,'SCALE FACTOR'/4F13.2,F18.3)                             USROU0
      WRITE (NOUT,5140) F,SUMF                                                 USROU1
      RETURN                                                                   USROU2
      END                                                                      USROU3
      SUBROUTINE USERRG (REG,MREG,MG,NREG)                                     USRRG2
      DOUBLE PRECISION PRECIS, RANGE                                           USRRG3
      DOUBLE PRECISION REG                                                     USRRG4
      LOGICAL DOMOM, DOUSIN, DOUSNQ, DOUSOU, LAST, NONNEG, ONLY1, PRWT,        USRRG5
     1 PRY, SIMULA, LUSER                                                      USRRG6
      DIMENSION REG(MREG,MG)                                                   USRRG7
      COMMON /SBLOCK/ PRECIS, RANGE, SRMIN,                                    USRRG8
     1 ALPST(2), GMNMX(2), PLEVEL(2,2), RSVMNX(2,2), RUSER(100),               USRRG9
     2 EXMAX, SRANGE                                                           USRRG0
      COMMON /IBLOCK/ IGRID, IPLRES, IPRINT, IQUAD, IUNIT, IWT,                USRRG1
     1 LINEPG, MIOERR, MQPITR, NEQ, NERFIT, NG, NINTT, NLINF, NORDER,          USRRG2
     2 ICRIT(2), IPLFIT(2),
     3 IUSER(50), LSIGN(4,4), MOMNMX(2), NENDZ(2),                             USRRG4
     4 NFLAT(4,2), NGL, NGLP1, NIN, NINEQ, NNSGN(2), NOUT, NQPROG(2),          USRRG5
     5 NSGN(4), NY                                                             USRRG6
      COMMON /LBLOCK/ DOMOM, DOUSIN, DOUSNQ, DOUSOU, LAST, NONNEG,             USRRG7
     1 ONLY1, PRWT, PRY, SIMULA,                                               USRRG8
     2 LUSER(30)                                                               USRRG9
      NREG=NG                                                                  USRRG4
      DO 110 J=1,NREG                                                          USRRG5
        DO 120 K=1,NGL                                                         USRRG6
          REG(J,K)=0.                                                          USRRG7
  120   CONTINUE                                                               USRRG8
        REG(J,J)=1.                                                            USRRG9
  110 CONTINUE                                                                 USRRG0
      J=IUSER(1)                                                               USRRG1
      K=J+NG-1                                                                 USRRG2
      IF (LUSER(1)) GO TO 200                                                  USRRG3
 5200 FORMAT (5E15.6)                                                          USRRG4
      READ (NIN,5200) (RUSER(L),L=J,K)                                         USRRG5
      WRITE (NOUT,5200) (RUSER(L),L=J,K)                                       USRRG6
      LUSER(1)=.TRUE.                                                          USRRG7
  200 IROW=0                                                                   USRRG8
      DO 210 L=J,K                                                             USRRG9
        IROW=IROW+1                                                            USRRG0
        REG(IROW,NGLP1)=RUSER(L)                                               USRRG1
  210 CONTINUE                                                                 USRRG2
      RETURN                                                                   USRRG3
      END                                                                      USRRG4
      SUBROUTINE USERSI (EXACT,MY,T,Y)                                         USRSI1
      DOUBLE PRECISION PRECIS, RANGE                                           USRSI2
      DOUBLE PRECISION DUB                                                     USRSI3
      LOGICAL DOMOM, DOUSIN, DOUSNQ, DOUSOU, LAST, NONNEG, ONLY1, PRWT,        USRSI4
     1 PRY, SIMULA, LUSER                                                      USRSI5
      CHARACTER IFORMT(70), IFORMW(70), IFORMY(70),LA(6,46), ITITLE(80)
      DIMENSION T(MY), EXACT(MY), Y(MY)                                        USRSI6
      DIMENSION RN(2)                                                          USRSI7
      COMMON /CBLOCK/ IFORMT, IFORMW, IFORMY,LA, ITITLE
      COMMON /SBLOCK/ PRECIS, RANGE, SRMIN,                                    USRSI8
     1 ALPST(2), GMNMX(2), PLEVEL(2,2), RSVMNX(2,2), RUSER(100),               USRSI9
     2 EXMAX, SRANGE                                                           USRSI0
      COMMON /IBLOCK/ IGRID, IPLRES, IPRINT, IQUAD, IUNIT, IWT,                USRSI1
```

```
      1 LINEPG, MIOERR, MQPITR, NEQ, NERFIT, NG, NINTT, NLINF, NORDER,      USRSI2
      2 ICRIT(2), IPLFIT(2),
      3  IUSER(50), LSIGN(4,4), MOMNMX(2), NENDZ(2),                        USRSI4
      4 NFLAT(4,2), NGL, NGLP1, NIN, NINEQ, NNSGN(2), NOUT, NQPROG(2),      USRSI5
      5 NSGN(4), NY                                                         USRSI6
        COMMON /LBLOCK/ DOMOM, DOUSIN, DOUSNQ, DOUSOU, LAST, NONNEG,        USRSI7
      1 ONLY1, PRWT, PRY, SIMULA,                                           USRSI8
      2 LUSER(30)                                                           USRSI9
        TWOPI=6.2831853072D0                                                USRSI0
        DUB=DBLE(FLOAT(IUSER(3)))                                           USRSI1
        L=NY                                                                USRSI2
        DO 150 J=1,L                                                        USRSI3
          JJ=J                                                              USRSI4
          EXACT(J)=1.+USEREX(JJ,T,NY)**2                                    USRSI0
          K=2-MOD(J,2)                                                      USRSI5
          IF (K .EQ. 1)  CALL RGAUSS (RN(1),RN(2),TWOPI,DUB)                USRSI6
          Y(J)=EXACT(J)+RUSER(3)*RN(K)*SQRT(EXACT(J))                       USRSI5
          EXACT(J)=SIGN(SQRT(ABS(EXACT(J)-1.)),EXACT(J)-1.)                 USRSI4
          Y(J)=SIGN(SQRT(ABS(Y(J)-1.)),Y(J)-1.)                             USRSI5
  150   CONTINUE                                                            USRSI6
        RETURN                                                              USRSI7
        END                                                                 USRSI8
        SUBROUTINE USERSX (EXACT,G,MG)                                      USRSX6
        DOUBLE PRECISION PRECIS, RANGE                                      USRSX7
        LOGICAL DOMOM, DOUSIN, DOUSNQ, DOUSOU, LAST, NONNEG, ONLY1, PRWT,   USRSX8
      1 PRY, SIMULA, LUSER                                                  USRSX9
        DIMENSION EXACT(MG), G(MG)                                          USRSX0
        COMMON /SBLOCK/ PRECIS, RANGE, SRMIN,                               USRSX1
      1 ALPST(2), GMNMX(2), PLEVEL(2,2), RSVMNX(2,2), RUSER(100),           USRSX2
      2 EXMAX, SRANGE                                                       USRSX3
        COMMON /IBLOCK/ IGRID, IPLRES, IPRINT, IQUAD, IUNIT, IWT,           USRSX4
      1 LINEPG, MIOERR, MQPITR, NEQ, NERFIT, NG, NINTT, NLINF, NORDER,      USRSX5
      2 ICRIT(2), IPLFIT(2),
      3 IUSER(50), LSIGN(4,4), MOMNMX(2), NENDZ(2),
      4 NFLAT(4,2), NGL, NGLP1, NIN, NINEQ, NNSGN(2), NOUT, NQPROG(2),      USRSX8
      5 NSGN(4), NY                                                         USRSX9
        COMMON /LBLOCK/ DOMOM, DOUSIN, DOUSNQ, DOUSOU, LAST, NONNEG,        USRSX0
      1 ONLY1, PRWT, PRY, SIMULA,                                           USRSX1
      2 LUSER(30)                                                           USRSX2
        IF (RUSER(8).GE.1. .AND. RUSER(8).LE.20.)  GO TO 120                USRSX7
 5120   FORMAT (/' RUSER(8) =',E12.4,' IS OUT OF RANGE IN USERSX.')         USRSX8
        WRITE (NOUT,5120) RUSER(8)                                          USRSX9
        STOP                                                                USRSX0
  120   EXMIN=-ALOG(SRANGE)                                                 USRSX1
        FACTL=GAMLN(RUSER(8)+1.)                                            USRSX2
        DO 150 J=1,NG                                                       USRSX3
          EXACT(J)=0.                                                       USRSX4
          IF (G(J)) 160,150,180                                             USRSX5
  160     WRITE (NOUT,5160)                                                 USRSX6
 5160     FORMAT (/' NEGATIVE G IN USEREX.')                                USRSX7
          STOP                                                              USRSX8
  180     EX=RUSER(8)*ALOG(G(J))-G(J)-FACTL                                 USRSX9
          IF (EX .GE. EXMIN)  EXACT(J)=EXP(EX)                              USRSX0
  150   CONTINUE                                                            USRSX1
        RETURN                                                              USRSX2
        END                                                                 USRSX3
        FUNCTION USERTR (X,IFUNCT)                                          USRTR8
        DOUBLE PRECISION PRECIS, RANGE                                      USRTR9
        LOGICAL DOMOM, DOUSIN, DOUSNQ, DOUSOU, LAST, NONNEG, ONLY1, PRWT,   USRTR0
      1 PRY, SIMULA, LUSER                                                  USRTR1
        COMMON /SBLOCK/ PRECIS, RANGE, SRMIN,                               USRTR2
      1 ALPST(2), GMNMX(2), PLEVEL(2,2), RSVMNX(2,2), RUSER(100),           USRTR3
      2 EXMAX, SRANGE                                                       USRTR4
        COMMON /IBLOCK/ IGRID, IPLRES, IPRINT, IQUAD, IUNIT, IWT,           USRTR5
      1 LINEPG, MIOERR, MQPITR, NEQ, NERFIT, NG, NINTT, NLINF, NORDER,      USRTR6
      2 ICRIT(2), IPLFIT(2),
      3 IUSER(50), LSIGN(4,4), MOMNMX(2), NENDZ(2),
      4 NFLAT(4,2), NGL, NGLP1, NIN, NINEQ, NNSGN(2), NOUT, NQPROG(2),      USRTR9
      5 NSGN(4), NY                                                         USRTR0
        COMMON /LBLOCK/ DOMOM, DOUSIN, DOUSNQ, DOUSOU, LAST, NONNEG,        USRTR1
      1 ONLY1, PRWT, PRY, SIMULA,                                           USRTR2
      2 LUSER(30)                                                           USRTR3
```

```
      CHARACTER IHOLER(6)
      DATA IHOLER/'U','S','E','R','T','R'/                              USRTR4
      IF (IFUNCT.LT.1 .OR. IFUNCT.GT.3) CALL ERRMES (1,.TRUE., IHOLER,  USRTR5
     1NOUT)                                                             USRTR6
      IF (IGRID .NE. 1) GO TO 200                                       USRTR7
      USERTR=1.                                                         USRTR8
      IF (IFUNCT .NE. 3) USERTR=X                                       USRTR3
      RETURN                                                            USRTR4
  200 IF (IGRID .NE. 2) CALL ERRMES (2,.TRUE.,IHOLER,NOUT)              USRTR5
      GO TO (210,220,230),IFUNCT                                        USRTR6
  210 USERTR=ALOG(X)                                                    USRTR7
      RETURN                                                            USRTR1
  220 USERTR=EXP(X)                                                     USRTR2
      RETURN                                                            USRTR6
  230 USERTR=1./X                                                       USRTR7
      RETURN                                                            USRTR1
      END                                                               USRTR2
      SUBROUTINE USERWT (Y,YLYFIT,MY,ERRFIT,SQRTW)                      USRTR3
      DOUBLE PRECISION PRECIS, RANGE                                    USRWT1
      LOGICAL DOMOM, DOUSIN, DOUSNQ, DOUSOU, LAST, NONNEG, ONLY1, PRWT, USRWT2
     1 PRY, SIMULA, LUSER                                               USRWT3
      DIMENSION Y(MY), YLYFIT(MY), SQRTW(MY)                            USRWT4
      COMMON /SBLOCK/ PRECIS, RANGE, SRMIN,                             USRWT5
     1 ALPST(2), GMNMX(2), PLEVEL(2,2), RSVMNX(2,2), RUSER(100),        USRWT6
     2 EXMAX, SRANGE                                                    USRWT7
      COMMON /IBLOCK/ IGRID, IPLRES, IPRINT, IQUAD, IUNIT, IWT,         USRWT8
     1 LINEPG, MIOERR, MQPITR, NEQ, NERFIT, NG, NINTT, NLINF, NORDER,   USRWT9
     2 ICRIT(2), IPLFIT(2),                                             USRWT0
     3 IUSER(50), LSIGN(4,4), MOMNMX(2), NENDZ(2),
     4 NFLAT(4,2), NGL, NGLP1, NIN, NINEQ, NNSGN(2), NOUT, NQPROG(2),   USRWT3
     5 NSGN(4), NY                                                      USRWT4
      COMMON /LBLOCK/ DOMOM, DOUSIN, DOUSNQ, DOUSOU, LAST, NONNEG,      USRWT5
     1 ONLY1, PRWT, PRY, SIMULA,                                        USRWT6
     2 LUSER(30)                                                        USRWT7
      DO 110 J=1,NY                                                     USRWT2
      DUM=AMAX1(ABS(Y(J)-YLYFIT(J)),ERRFIT)                             USRWT3
      SQRTW(J)=2.*DUM/SQRT(DUM*DUM+1.)                                  USRWT4
  110 CONTINUE                                                          USRWT5
      RETURN                                                            USRWT6
      END                                                               USRWT7
      SUBROUTINE WRITIN (EXACT,G,MG,MY,SQRTW,T,Y)
      DOUBLE PRECISION PRECIS, RANGE                                    WRTIN9
      LOGICAL DOMOM, DOUSIN, DOUSNQ, DOUSOU, LAST, NONNEG, ONLY1, PRWT, WRTIN0
     1 PRY, SIMULA, LUSER                                               WRTIN1
      LOGICAL LEQUIV(10)                                                WRTIN2
      DIMENSION EXACT(MY), SQRTW(MY), T(MY), Y(MY)
      DIMENSION IEQUIV(15), G(MG)                                       WRTIN4
      CHARACTER IFORMT(70), IFORMW(70), IFORMY(70), LA(6,46),ITITLE(80)
      COMMON /CBLOCK/ IFORMT, IFORMW, IFORMY, LA, ITITLE
      COMMON /SBLOCK/ PRECIS, RANGE, SRMIN,                             WRTIN5
     1 ALPST(2), GMNMX(2), PLEVEL(2,2), RSVMNX(2,2), RUSER(100),        WRTIN6
     2 EXMAX, SRANGE                                                    WRTIN7
      COMMON /IBLOCK/ IGRID, IPLRES, IPRINT, IQUAD, IUNIT, IWT,         WRTIN8
     1 LINEPG, MIOERR, MQPITR, NEQ, NERFIT, NG, NINTT, NLINF, NORDER,   WRTIN9
     2 ICRIT(2), IPLFIT(2),
     3 IUSER(50), LSIGN(4,4), MOMNMX(2), NENDZ(2),
     4 NFLAT(4,2), NGL, NGLP1, NIN, NINEQ, NNSGN(2), NOUT, NQPROG(2),   WRTIN2
     5 NSGN(4), NY                                                      WRTIN3
      COMMON /LBLOCK/ DOMOM, DOUSIN, DOUSNQ, DOUSOU, LAST, NONNEG,      WRTIN4
     1 ONLY1, PRWT, PRY, SIMULA,                                        WRTIN5
     2 LUSER(30)                                                        WRTIN6
      EQUIVALENCE (IGRID,IEQUIV(1)), (DOMOM,LEQUIV(1))                  WRTIN7
 5999 FORMAT ('1')                                                      WRTIN8
      IF (IPRINT .GE. 3) WRITE(NOUT,5999)                               WRTIN9
 5003 FORMAT (//1X)                                                     WRTIN0
      IF (IPRINT .LT. 3) WRITE(NOUT,5003)                               WRTIN1
 5100 FORMAT (40X,'FINAL VALUES OF CONTROL VARIABLES')                  WRTIN2
      WRITE (NOUT,5100)                                                 WRTIN3
 5110 FORMAT (1X,6A1,' =',1P10E12.5/(9X,10E12.5))                       WRTIN4
      WRITE (NOUT,5110) (LA(K,1),K=1,6),SRMIN                           WRTIN5
      WRITE (NOUT,5110) (LA(K,2),K=1,6),ALPST                           WRTIN6
      WRITE (NOUT,5110) (LA(K,3),K=1,6),GMNMX                           WRTIN7
```

```
      WRITE (NOUT,5110) (LA(K,4),K=1,6),PLEVEL                        WRTIN8
      WRITE (NOUT,5110) (LA(K,5),K=1,6),RSVMNX                        WRTIN9
      WRITE (NOUT,5110) (LA(K,6),K=1,6),RUSER                         WRTIN0
      JJ=6                                                            WRTIN1
 5210 FORMAT (1X,6A1,' =',10I12/(9X,10I12))                           WRTIN2
      DO 210 J=1,15                                                   WRTIN3
        JJ=JJ+1                                                       WRTIN4
        WRITE (NOUT,5210) (LA(K,JJ),K=1,6),IEQUIV(J)                  WRTIN5
  210 CONTINUE                                                        WRTIN6
      WRITE (NOUT,5210) (LA(K,22),K=1,6),ICRIT                        WRTIN7
 5220 FORMAT (1X,6A1,' = ',80A1)                                      WRTIN8
      WRITE (NOUT,5220) (LA(K,23),K=1,6),IFORMT                       WRTIN9
      WRITE (NOUT,5220) (LA(K,24),K=1,6),IFORMW                       WRTIN0
      WRITE (NOUT,5220) (LA(K,25),K=1,6),IFORMY                       WRTIN1
      WRITE (NOUT,5210) (LA(K,26),K=1,6),IPLFIT                       WRTIN2
      WRITE (NOUT,5210) (LA(K,27),K=1,6),IUSER                        WRTIN3
      WRITE (NOUT,5210) (LA(K,28),K=1,6),LSIGN                        WRTIN4
      WRITE (NOUT,5210) (LA(K,29),K=1,6),MOMNMX                       WRTIN5
      WRITE (NOUT,5210) (LA(K,30),K=1,6),NENDZ                        WRTIN6
      WRITE (NOUT,5210) (LA(K,31),K=1,6),NFLAT                        WRTIN7
      WRITE (NOUT,5210) (LA(K,32),K=1,6),NNSGN                        WRTIN8
      WRITE (NOUT,5210) (LA(K,33),K=1,6),NQPROG                       WRTIN9
      WRITE (NOUT,5210) (LA(K,34),K=1,6),NSGN                         WRTIN0
      JJ=34                                                           WRTIN1
 5310 FORMAT (1X,6A1,' =',10L12/(9X,10L12))                           WRTIN2
      DO 310 J=1,10                                                   WRTIN3
        JJ=JJ+1                                                       WRTIN4
        WRITE (NOUT,5310) (LA(K,JJ),K=1,6),LEQUIV(J)                  WRTIN5
  310 CONTINUE                                                        WRTIN6
      WRITE (NOUT,5310) (LA(K,45),K=1,6),LUSER                        WRTIN7
      IF (.NOT.SIMULA .AND. NY.LE.MY)  CALL WRITYT (EXACT, G,IPRINT,IWT,WRTIN8
     1MG,NOUT,NY,PRY,SIMULA,SQRTW,T,Y)                                WRTIN9
 5320 FORMAT (9HOPRECIS =,1PD9.2,10X,8HSRANGE =,E9.2,                 WRTIN2
     1 5X,'RANGE =',D9.2)                                             WRTIN3
      WRITE (NOUT,5320) PRECIS, SRANGE, RANGE                         WRTIN4
      RETURN                                                          WRTIN5
      END                                                             WRTIN6
      SUBROUTINE WRITYT (EXACT,G,IPRINT,IWT,MG,NOUT,NY,PRY,SIMULA,    WRTYT6
     1 SQRTW,T,Y)                                                     WRTYT7
      LOGICAL PRY, SIMULA                                             WRTYT8
      DIMENSION EXACT(NY), SQRTW(NY), T(NY), Y(NY), G(MG)             WRTYT9
      IF (.NOT.PRY)  GO TO 700                                        WRTYT0
 5999 FORMAT ('1')                                                    WRTYT1
      IF (IPRINT .GE. 3)  WRITE (NOUT,5999)                           WRTYT2
 5003 FORMAT (///1X)                                                  WRTYT3
      IF (IPRINT .LT. 3)  WRITE(NOUT,5003)                            WRTYT4
      IF (SIMULA)  GO TO 200                                          WRTYT5
 5110 FORMAT (5(12X,'T',12X,'Y')/(2X,1PE11.3,E13.5,E13.3,E13.5,       WRTYT6
     1 E13.3,E13.5,E13.3,E13.5,E13.3,E13.5))                          WRTYT7
      IF (IWT .NE. 4)  WRITE (NOUT,5110) (T(J),Y(J),J=1,NY)           WRTYT8
 5120 FORMAT (3(17X,'T',12X,'Y',8X,'SQRTW')/(5X,1P3E13.5,5X,3E13.5,   WRTYT9
     1 5X,3E13.5))                                                    WRTYT0
      IF (IWT .EQ. 4)  WRITE (NOUT,5120) (T(J),Y(J),SQRTW(J),J=1,NY)  WRTYT1
      GO TO 700                                                       WRTYT2
 5210 FORMAT (2(17X,'T',12X,'Y',8X,'EXACT',8X,'ERROR'))               WRTYT3
  200 IF (IWT .NE. 4)  WRITE (NOUT,5210)                              WRTYT4
 5211 FORMAT (2(12X,'T',12X,'Y',8X,'EXACT',8X,'ERROR',8X,             WRTYT5
     1 'SQRTW'))                                                      WRTYT6
      IF (IWT .EQ. 4)  WRITE (NOUT,5211)                              WRTYT7
      DO 210 J=2,NY,2                                                 WRTYT8
        DUM=Y(J-1)-EXACT(J-1)                                         WRTYT9
        DDUM=Y(J)-EXACT(J)                                            WRTYT0
 5220   FORMAT (5X,1P4E13.5,5X,4E13.5)                                WRTYT1
        IF (IWT .NE. 4)  WRITE (NOUT,5220) T(J-1),Y(J-1),EXACT(J-1),DUM,WRTYT2
     1 T(J),Y(J),EXACT(J),DDUM                                        WRTYT3
 5221   FORMAT (2X,1PE11.3,4E13.5,E13.3,4E13.5)                       WRTYT4
        IF (IWT .EQ. 4)  WRITE (NOUT,5221) T(J-1),Y(J-1),EXACT(J-1),DUM,WRTYT5
     1 SQRTW(J-1),T(J),Y(J),EXACT(J),DDUM,SQRTW(J)                    WRTYT6
  210 CONTINUE                                                        WRTYT7
      IF (MOD(NY,2) .EQ. 0)  GO TO 700                                WRTYT8
      DUM=Y(NY)-EXACT(NY)                                             WRTYT9
```

```
      IF (IWT .NE. 4)  WRITE (NOUT,5220) T(NY),Y(NY),EXACT(NY),DUM       WRTYT0
      IF (IWT .EQ. 4)  WRITE (NOUT,5221) T(NY),Y(NY),EXACT(NY),DUM,      WRTYT1
     1 SQRTH(NY)                                                         WRTYT2
 700  RETURN                                                             WRTYT3
      END                                                                WRTYT4
      FUNCTION USERLF (JY,JLINF,T,NYDIM)                                 USRLF5
      DOUBLE PRECISION PRECIS, RANGE                                     USRLF6
      LOGICAL DOMOM, DOUSIN, DOUSNQ, DOUSOU, LAST, NONNEG, ONLY1, PRWT,  USRLF7
     1 PRY, SIMULA, LUSER                                                USRLF8
      DIMENSION T(NYDIM)                                                 USRLF9
      CHARACTER IHOLER(6)
      COMMON /SBLOCK/ PRECIS, RANGE, SRMIN,                              USRLF0
     1 ALPST(2), GMNMX(2), PLEVEL(2,2), RSVMNX(2,2), RUSER(100),         USRLF1
     2 EXMAX, SRANGE                                                     USRLF2
      COMMON /IBLOCK/ IGRID, IPLRES, IPRINT, IQUAD, IUNIT, IWT,          USRLF3
     1 LINEPG, MIOERR, MQPITR, NEQ, NERFIT, NG, NINTT, NLINF, NORDER,    USRLF4
     2 ICRIT(2), IPLFIT(2),
     3 IUSER(50), LSIGN(4,4), MOMNMX(2), NENDZ(2),
     4 NFLAT(4,2), NGL, NGLP1, NIN, NINEQ, NNSGN(2), NOUT, NQPROG(2),    USRLF7
     5 NSGN(4), NY                                                       USRLF8
      COMMON /LBLOCK/ DOMOM, DOUSIN, DOUSNQ, DOUSOU, LAST, NONNEG,       USRLF9
     1 ONLY1, PRWT, PRY, SIMULA,                                         USRLF0
     2 LUSER(30)                                                         USRLF1
      DATA IHOLER/'U','S','E','R','L','F'/                               USRLF2
c     function diff(x,y)isp
      double precision function diff(x,y)
      double precision x, y
      diff=x-y
      return
      end IF (JY.GT.NY .OR. JY.LE.0) CALL ERRMES (1,.TRUE.,IHOLER,NOUT)      USRLF3
      IF (JLINF.LT.1 .OR. JLINF.GT.2) CALL ERRMES (2,.TRUE.,IHOLER,      USRLF8
     1 NOUT)                                                             USRLF9
      USERLF=0.                                                          USRLF0
      IF ((JY.LE.IUSER(2) .AND. JLINF.EQ.1) .OR. (JY.GT.IUSER(2)         USRLF1
     1 .AND. JLINF.EQ.2) .OR. IUSER(2).LE.0)  USERLF=1.                  USRLF2
      RETURN                                                             USRLF3
      END                                                                USRLF4
```

APPENDIX C

```
c  condense.fm
c
c  This routine takes two 256 channel 1096 data sets and condenses the
c  data to two 60 channel data sets for use in cont2ang.fm
c
   parameter (ntmax=276,nt=256)
   double precision acf(ntmax), acf2(ntmax)
   double precision t(ntmax), t2(ntmax)
   real param(10)
   character*30 label(10)
   character*20 ifile1, ifile2, ofile
   logical last
c
   ifile1=' '
   ofile=ifile1
   ifile2=ifile1
   print *,'Enter input filename for first angle:'
   read(*,470) ifile1
   print *, 'Enter input filename for second angle:'
   read(*,470) ifile2
   print *,'Enter output filename :'
   read(*,470) ofile
470 format(a)
   open(1,file=ifile1,status='old')
   open(2,file=ifile2,status='old')
   open(3,file=ofile,status='new')
c
c  Read in run parameters and labels. Order of these is somewhat
c  random, since the parameters and label are set up in a reasonable
```

```
c   order in the data sets produced by the acf generating program
c   generate.
c
      read(1,400) label(1),samtim,param(4),param(5),
     +(param(j),j=1,3),(label(j),j=2,6)
  400 format(/,a75,//,12x,e8.1,////////,12x,f5.1,/,10x,f6.2,/,17x,f6.2,
     +/,11x,f6.1,/,6x,f6.1,///,5(a75,/),/)
      read(1,410) (acf(j),j=1,nt)
  410 format(4x,5d15.0)
c
c   Generate array of sample times for first acf.
c
      do 10 j=1,nt
        t(j)=samtim*j
   10 continue
c
c   Read in data for second angle.
c
      read(2,400) label(1),samtim,param(4),param(5),
     +(param(j),j=1,3),(label(j),j=2,6)
      read(2,410) (acf2(j),j=1,nt)
      do 20 j=1,nt
        t2(j)=samtim*j
   20 continue
c
c   Condense data.
c
      call cond(17,17,48,2,acf)
      call cond(17,17,48,2,t)
      call cond(17,17,48,2,acf2)
      call cond(17,17,48,2,t2)
c
      call cond(33,49,128,5,acf)
      call cond(33,49,128,5,t)
      call cond(33,49,128,5,acf2)
      call cond(33,49,128,5,t2)
c
      call cond(49,129,248,10,acf)
      call cond(49,129,248,10,t)
      call cond(49,129,248,10,acf2)
      call cond(49,129,248,10,t2)
c
c   Write out condensed acfs and time vectors to ofile in cont2ang format.
c
      ncond=60
      write(3,450) (t(j),j=1,ncond)
      write(3,450) (t2(j),j=1,ncond)
      write(3,460) (acf(j),j=1,ncond)
      write(3,460) (acf2(j),j=1,ncond)
  450 format(5e15.6)
  460 format(4e17.11)
      stop
      end c   cond.fs
c
      subroutine cond(newst,oldst,oldend,intval,x)
      integer newst, oldst, oldend, intval
      double precision x(1)
      n=newst
      do 20 j=oldst,oldend,intval
        x(n)=x(j)
        if(intval.gt.1) then
          do 10 i=1,intval-1
            x(n)=x(j+i)+x(n)
   10     continue
          x(n)=x(n)/intval
        endif
        n=n+1
   20 continue
      return
      end
```

APPENDIX D

```
PSL 90NM/170NM=DIA, ANG= 144 & 63.2  1:1.3 inten at 63 11/7/85
NQPROG    1       5.0
NG       25
GMNMX     1  0.300000E+03
GMNMX     2  0.300000E+05
NLINF     2
IWT       1
NINTT    -1
DOUSIN
RUSER    10  0.200000E+02
RUSER    11  0.990000E+00
RUSER    12  1.440000E+02
RUSER    13  0.632800E+04
RUSER    14  0.133000E+01
RUSER    15  3.757100E+07
RUSER    16  5.736900E+08
RUSER    17  0.632000E+02
RUSER    18  .9000000E+00
RUSER    25  1.000000E+00
RUSER    26  1.000000E+00
LUSER    11
LUSER    12
LUSER    13
LUSER    18
LUSER    19
IUSER     2      60.
IUSER    11  0.610000E+02
IUSER    12       2.
END
NY      120
```

APPENDIX E

```
c   n3moments.fm
c
c   Files required by program:
c       1>  Driver file (which gives name of other files and various info.
c       2>  File of the 1096 format for each DLS angle.
c       3>  File containing mass/inten conversions as func. of (angle,size bin)
c       4>  File containing CLS data.
c
c   Uses of double precision arrays:
c       a    - kernel (DLS and CLS data and h matrix); c=size bins, r=constraints
c       adup - retains the original (pre-nnls) contents of a)
c       acf  - autocorrelation function (not kept after moment calculations)
c       ata  - a transpose x a (to lessen nnls computation time)
c       b    - the measurement vector (DLS moments, CLS data, zeros for smoothing)
c       bar  - intensity weighted diameter moments
c       bins - center of size histogram bins
c       cls  - classical light scattering measurements as function of angle
c       conver - mass to intensity conversions as function of (angle,bin size)
c       cum  - at 1st contains cums, then inten. weighted inv. diameter moments
c       param - various input parameters defined below
c       scist - holds preliminary scaling factors so they can be later removed
c       scale - magnitudes of rows of a & b for use in error weightings
c       size - edges of histogram size bins
c       time - delay times for acf (not kept after moment calculations)
c       w    - dual vector for nnls
c       x    - mass weighted particle size distribution
c       zz   - working space for nnls
c
c   Uses of real arrays:
c       xsp    - single precision version of x (mass weighted particle dist)
c       binssp - single precision version of bins (central histogram bin sizes)
c       cquad  - quadrature used to calculate moments from x and bins
c
c   Uses of integer arrays:
c       iparam - miscellaneous parameters
c       index  - real/dual index used by nnls
c       iang   - contains the numbers of the angles used (i.e. 1-7)
c
c   Assignments of miscellaneous parameter arrays:
c       iparam(1)=number of time points in acfs
c       iparam(2)=number of dls angles to be used
```

```
c
c       param(1)=temperature
c       param(2)=refractive index of sample suspending medium
c       param(3)=refractive index of particles
c       param(4)=max. particle diameter (bin edge) (nm)
c       param(5)=minimum particle diameter (bin edge) (nm)
c       param(6)=laser wavelength (nm)
c       param(7)=scattering angle
c       param(8)=viscosity of suspending medium (poise)
c       param(9)=(scat vec)^2*(reduced diff coeff)
c
c   Subroutines and functions called:
c       cumul - calculates cumulants of acf (also extrapolates acf to t=0)
c       convcm - converts cumulants to size moments using Stokes-Einstein
c       dsply2 - prints crude histogram of mass dist.
c       getdat - gets data from 1096 (or other) file for one angle
c       moment - calculates the intensity weighted regular moments of diam (nm)
c       nnls - nonnegative least squares algorithm from Lawson and Hanson
c       peaks - subroutine 'moment' from CONTIN - calculates peak moments von x
c       setcon - removes CLS and/or 2nd and later DLS data from fit
c       setdls - enters dls data into kernel array a
c       weight - sets the relative weights for the data points
c
        parameter (maxdat=50,maxbin=25,maxang=7,maxtim=272,maxpar=100)
        parameter (maxrow=250,maxdls=3)
        implicit double precision (a-h,o-z)
        double precision acf(maxtim,maxdls), time(maxtim,maxdls),
       +bins(maxbin), ata(maxbin,maxbin),
       +param(maxpar,maxdls), cum(4,maxang), bar(4,maxang), cls(maxang),
       +a(maxrow,maxbin), size(maxbin), b(maxrow), w(maxbin), zz(maxrow),
       +conver(maxang,maxbin), x(maxbin), adup(maxrow,maxbin),
       +scale(maxrow), bdup(maxrow), scist(maxang)
        double precision rnorm, range, alpha, sum
        real xsp(maxbin), binssp(maxbin), cquad(maxbin)
        integer iparam(maxpar), index(maxbin), iang(maxang)
        character*40 infile, oufile, dfile
        character*1 dumch
        logical tfcls, tfdls
c
c   Set global parameters.
c
        ichan=5
        iochan=9
        nmomen=4
        range=1.d60
        alpha=1.d-40
        infile='n5.in'
        idegmn=-1
        idegmx=2
        do 5 j=1,maxrow
            scale(j)=1.d0
    5   continue
        tfcls=.true.
        tfdls=.true.
        print *,'Use CLS data? (y or n):'
        read(*,*) dumch
        if(dumch.eq.'n') tfcls=.false.
        print *,'Use all DLS data? (y or n):'
        read(*,*) dumch
        if(dumch.eq.'n') tfdls=.false.
c
c   Get names of input 1096 data files.
c
        open(1,file=infile,status='old')
        read(1,*) nangs
        iparam(2)=nangs
        do 10 j=1,nangs
            read(1,*) dfile
            read(1,*) iang(j)
            open(2,file=dfile,status='old')
            call getdat(acf(1,j),time(1,j),param(1,j),iparam,2)
            call cumul(acf(1,j),time(1,j),iparam(1),cum(1,j))
            call convcm(param(1,j),cum(1,j))
            call moment(param(1,j),acf(1,j),time(1,j),iparam(1),bar(1,j),
       +        cum(1,j),j)
```

```
          close(2)
  10 continue
      ntime=iparam(1)
c
c   Get classical light scattering data.
c
      read(1,*) dfile
      open(2,file=dfile,status='old')
      read(2,*) ncls
      do 20 j=1,ncls
         read(2,*) cls(j)
  20 continue
      close(2)
c
c   Read in mass to scattered intensity conversions for all angles.
c
      read(1,*) dfile
      read(1,*) nbins
      iparam(3)=nbins
      open(2,file=dfile,status='old')
      nconv=maxang*nbins
      do 50 j=1,nconv
         read(2,*) m,n,conver(m,n)
  50 continue
c
c   Calculate the kernel elements using the mass/intensity conversions.
c
      diamax=param(4)
      diamin=param(5)
      diafac=exp(alog(diamax/diamin)/nbins)
      size(1)=diamin
      do 52 j=1,nbins
         size(j+1)=size(j)*diafac
  52 continue
      bins(1)=diamin*sqrt(diafac)
      do 53 j=2,nbins
         bins(j)=bins(j-1)*diafac
  53 continue
      open(3,file='dump',status='new')
c
c   Enter DLS constraints into kernel
c
      call setdls(a,conver,bins,param,acf,time,iparam,iang)
c
c   Enter CLS constraints into kernel
c
      ndls=ntime*nangs
      do 56 j=1,ncls
         do 55 i=1,nbins
            a(ndls+j,i)=0.d0
c
c           if(j.eq.1) a(ndls+j,i)=conver(j,i)
            a(ndls+j,i)=conver(j,i)
  55    continue
  56 continue
c
c   Append second order difference part of kernel (h matrix).
c
      nrows=ndls+ncls
      iparam(4)=nrows
      nrtot=nrows+nbins
      do 70 j=1,nbins
         do 60 i=1,nbins
            nrowsi=nrows+i
            a(nrowsi,j)=0.d0
            if(i.eq.j) a(nrowsi,j)=-2.d0*alpha
            if(i+1.eq.j .or. i.eq.j+1) a(nrowsi,j)=1.d0*alpha
  60    continue
  70 continue
c
c   Set up b (measurement vector).
c
      do 80 j=1,ndls
         b(j)=0.d0
```

```
   80 continue
      ndls1=ndls+1
      do 90 j=ndls1,nrows
         b(j)=cls(j-ndls)
   90 continue
      nrows1=nrows+1
      do 100 j=nrows1,nrtot
         b(j)=0.d0
  100 continue
c
c   Scale the rows of the kernel and measurement vector according to
c   variance in each measurement.
c
      call weight(acf,cls,a,b,scale,iang,iparam,maxtim,maxrow,maxang)
      call setcon(a,maxrow,iparam,b,scale,iang,tfcls,tfdls)
c
c   Copy a into adup for later use in computing fit-measurement vector.
c
      do 110 i=1,nrtot
      bdup(i)=b(i)
      do 110 j=1,nbins
         adup(i,j)=a(i,j)
  110 continue
      write(3,455)
  455 format('kernel matrix')
      do 1100 j=1,nbins
      write(3,1201) j
 1201 format('Col = 'i5)
      write(3,1200) (a(i,j),i=1,ntime)
 1100 continue
 1200 format(7e11.3)
      write(3,456)
  456 format('measurement vector')
      write(3,450) (b(i),i=1,nrtot)
  450 format(5f15.7)
c
c   Perform the inversion to get the size distribution.
c
      call ataul(a,maxrow,maxbin,1,a,maxrow,maxbin,0,ata,maxbin,maxbin,
     +nbins,nrows,nbins)
      call ataul(a,maxrow,maxbin,1,bdup,maxrow,1,0,b,maxrow,1,
     +nbins,nrows,1)
      call nnls(ata,maxbin,nbins,nbins,b,x,rnorm,w,zz,index,mode,range)
      call nnls(a,maxrow,nrows,nbins,b,x,rnorm,w,zz,index,mode,range)
c
c   Assign sources of errors.
c
      call ataul(adup,maxrow,maxbin,0,x,maxbin,1,0,b,maxrow,1,
     +nrtot,nbins,1)
      write(3,456)
      write(3,450) (b(i),i=1,nrtot)
      sumdum=0.
      do 141 i=1,nrtot
         bdup(i)=(b(i)-bdup(i))**2
         sumdum=sumdum+bdup(i)
  141 continue
      write(3,490) rnorm,sumdum
  490 format(' nnls euclidean norm:',e15.7,'  n5 euclidean norm:',e15.7)
      do 142 i=1,nrtot
         bdup(i)=bdup(i)/sumdum
  142 continue
      write(3,491) (bdup(i),i=1,nrtot)
  491 format(5f15.7)
c
c   End of error assignment.
c
      write(3,548)
  548 format('scales')
      do 146 j=1,nrows
         write(3,546) j,scale(j)
```

```
 546    format(i4,e15.7)
 146 continue
c
c    Graph results; analyze peaks.
c
     call dsply2(x,nbins,iochan)
     do 145 j=1,nbins
        xsp(j)=x(j)
        binssp(j)=bins(j)
        cquad(j)=1.
 145 continue
     call peaks(binssp,xsp,cquad,nbins,idegmn,idegmx,iochan)
c
c    Calculate moments.
c
     do 150 j=1,nangs
        u1=0.d0
        u2=0.d0
        u3=0.d0
        sum=0.d0
        do 130 i=1,nbins
           amount=x(i)*conver(iang(j),i)
           u1=u1+amount*1.d0/bins(i)
           u2=u2+amount*1.d0/bins(i)**2
           u3=u3+amount*bins(i)
           sum=sum+amount
 130    continue
        u1=u1/sum
        u2=u2/sum-u1*u1
        u1=1.d0/u1
        u3=u3/sum
        write(3,457) j
 457    format('Angle :',i3)
        write(3,458) u1,u3,u2
 458    format('Cumulant mean:',f10.2,'    Mean:',f10.2,'    Mu2:',e14.5)
        u1=1.d0/cum(2,j)
        write(3,458) u1,bar(1,j),cum(3,j)
        write(3,459) sum
 459    format('Normalization: ',e15.7)
 150 continue
     write(3,461)
 461 format('Size histogram')
     write(3,450) (x(j),j=1,nbins)
     write(3,462)
 462 format('Center bin sizes')
     write(3,450) (bins(j),j=1,nbins)
     stop
     end c   convcm.fs
c
c   This subroutine converts the first two cumulants to an intensity
c   weighted inverse diameter (nm) and variance thereof (nm^2),
c   respectively.
c
c   The inputs to the program are:
c      param - contains various parameters defined below
c      cum - on input contains the 1st 3 cumulants, on output contains
c            the zeroth cumulant and the 1st 2 inverse moments (nm, nm^2)
c
c   Contents of array param:
c      param(1)=temperature
c      param(2)=refractive index of sample suspending medium
c      param(3)=refractive index of particles
c      param(4)=max. particle diameter (bin edge) (nm)
c      param(5)=minimum particle diameter (bin edge) (nm)
c      param(6)=laser wavelength (nm)
c      param(7)=scattering angle
c      param(8)=viscosity of suspending medium
c      param(9)=(scat vec)^2*(reduced diff coeff) (calculated by this routine)
c
     subroutine convcm(param,cum)
```

```
      implicit double precision (a-h,o-z)
      double precision param(1), cum(1)
c
c     Set up constants.
c
      pi=3.1415927d0
      sinth2=dsin(param(7)*8.7266464d-3)
      scatt=4.d0*pi*param(2)*sinth2/param(6)
      diffr=1.380622d-9*(273.16d0+param(1))/(3.d0*pi)
      dum=param(8)
      diffr=diffr/dum
      q2diff=scatt*scatt*diffr*1.d14
      print *,'scatt vec=',scatt
      param(9)=q2diff
c
c     Perform conversion.
c
      print *,'diffr=',diffr,'param(8)=',dum,'d2diff=',q2diff,cum(2)
      cum(2)=cum(2)/(q2diff)
      cum(3)=cum(3)/(q2diff*q2diff)
      return
      end c     moment.fs
c
c     This subroutine calculates the intensity weighted mean diameter (nm)
c     and two quantities related to the intensity weighted second moment
c     of the diameter distribution.  The first of these quantities is the
c     delay time at which the normalized (to amp=1) acf crosses the computed
c     normalized acf corresponding to the intensity weighted mean diameter.
c     The second quantity is the area between the two acfs just described,
c     between t=0 and crossing delay time.
c     The arguments are:-
c        param - miscellaneous parameters; only param(9) used =(k^2 * Dred)
c        acf - measured autocorrelation function
c        time - central delay times corresponding to acf points
c        ntime - number of time points at which acf is measured
c        bar - output array containing moments; (moment#,angle)
c        cum - contains the 1st 2 inten weighted inverse mean diam moments
c        jang - number of angle (i.e. 1-7)
c
      subroutine moment(param,acf,time,ntime,bar,cum,jang)
      implicit double precision (a-h,o-z)
      double precision acf(1), time(1), bar(1), param(1),
     +cum(1)
c
c     Compute intensity weighted mean diameter (nm).
c
      anorm=1./acf(1)
      do 10 j=1,ntime
         acf(j)=anorm*acf(j)
   10 continue
      sum=0.d0
      ntime1=ntime-1
      do 20 j=2,ntime1
         sum=sum+.5d0*acf(j)*(time(j+1)-time(j-1))
   20 continue
      sum=sum+acf(1)*(time(2)-time(1))
      sum=sum+acf(ntime)*(time(ntime)-time(ntime-1))
      bar(1)=sum*param(9)
c
c     Compute crossing point (from intersection of logs of acfs).
c
      tcross=0.d0
      cumbar=1.d0/bar(1)
      print *,'cumbar=',cumbar,' cum2=',cum(2),' cum3=',cum(3)
      if(cum(3).gt.0.d0 .and. cum(2).gt.cumbar)
     +    tcross=2.d0*(cum(2)-cumbar)/cum(3)
      bar(2)=tcross
c
c     Compute area between the two normalized acfs.
c
```

```
      gambar=param(2)*cumbar
      sum=0.d0
      do 30 j=2,ntime
         if(time(j).gt.tcross) go to 40
         sum=sum+.5d0*(dexp(-gambar*time(j))-acf(j))*
     +      (time(j+1)-time(j-1))
   30 continue
   40 continue
      bar(3)=sum/d2diff
      return
      end
```

```
c   setmom.fs
c
c   This routine sets up the DLS moment part of the kernel. To do this,
c   it uses the mass to intensity conversion matrix conver(angle,size),
c   the central size bin array and the equations for the moments to
c   compute the kernel elements.
c
c   The arguments are:
c     a - to contain the kernel (constraint#,size)
c     conver - the mass to intensity conversion (angle,size)
c     bins - the size of the geometric centers of the size bins
c     cum - the array containing the inverse moments (moment#,angle)
c     bar - array containing the regular moments (moment#,angle)
c     iang - integer array containing the DLS angles used
c     param - misc. parameters (only param(9)=(sc vec)^2 * Dred is used)
c     maxrow - number of rows in a
c     maxang - maximum number of angles
c     nbins - number of size bins
c     nangs - number of angles
c     nmomen - number of moments/angle
c
      subroutine setmom(a,conver,bins,cum,bar,iang,param,
     +maxrow,maxang,nbins,nangs,nmomen)
      implicit double precision (a-h,o-z)
      double precision a(maxrow,25), conver(maxang,1), bins(1),
     +cum(4,1), bar(4,1), param(1)
      integer iang(maxang)
c
c   Compute moments.
c
      do 20 j=1,nangs
         dectim=dexp(-param(9)/bar(3,j)/bar(1,j))
         jj=(j-1)*nmomen
         do 10 i=1,nbins
            cumdif=(1.d0/bins(i)-cum(2,j))
c   First inverse moment.
            a(jj+1,i)=conver(iang(j),i)*cumdif
c   Second inverse moment.
            a(jj+2,i)=conver(iang(j),i)*(cumdif**2-cum(3,j))
c   First regular moment.
            a(jj+3,i)=conver(iang(j),i)*(bins(i)-bar(1,j))
c   Crossing point in time.
            a(jj+4,i)=conver(iang(j),i)*
     +         (dexp(-param(9)*bar(3,j)/bins(i))-dectim)
            a(jj+1,i)=1.d0
            a(jj+2,i)=1.d0
            a(jj+3,i)=1.d0
            a(jj+4,i)=1.d0
   10    continue
   20 continue
      return
      end
```

```
c  dsply.pr
c
c   this subroutine prints out a crude histogram of the function contained
c   in the array func. func should have no more than 60 components.
c   the arguments of the subroutine are:
c     x - the double precision numbers to be graphed.
```

```
c        nbins - the number of numbers to be graphed
c        ichan - the channel to which the output should be sent
c
      subroutine dsply2(x,nbins,ichan)
      parameter (nrmax=20,nbmax=60)
      integer*2 idisp(nrmax,nbmax), ifunc(nbmax)
      double precision func(nbmax), x(1)
c
c     Double or triple up function if fewer than nb/2 or nb/2 bins needed.
c
      if(nbmax/nbins.eq.2) then
         do 1 j=1,nbins
            func(2*(j-1)+1)=x(j)
            func(2*(j-1)+2)=x(j)
  1      continue
         nb=2*nbins
      endif
      if(nbmax/nbins.eq.3) then
         do 2 j=1,nbins
            func(3*(j-1)+1)=x(j)
            func(3*(j-1)+2)=x(j)
            func(3*(j-1)+3)=x(j)
  2      continue
         nb=nbins*3
      endif
c
c     scale the function to an amplitude of nr
c
      nr=nrmax
      big=0.
      do 10 j=1,nb
      if(func(j).gt.big) big=func(j)
 10   continue
      anorm=nr/big
      do 20 j=1,nb
      ifunc(j)=anorm*func(j)
 20   continue
c
c     fill up each bin of the display array with asterixes to the depth ifunc
c
      do 40 j=1,nb
      do 30 i=1,ifunc(j)
      idisp(i,j)=42
 30   continue
      if(ifunc(j).lt.nr) then
         nblank=ifunc(j)+1
         do 35 i=nblank,nr
         idisp(i,j)=32
 35      continue
      endif
 40   continue
      do 45 j=1,nb
      idisp(1,j)=42
 45   continue
c
c     write out result to channel ichan.
c
      do 50 ii=1,nr
      i=nr+1-ii
      write(ichan,400) (idisp(i,j),j=1,nb)
 400  format(1x,60a2)
 50   continue
      write(ichan,420) (i,i=10,nb,10)
 420  format(1x,8i10)
      return
      end c     getdat.fs
c
c     This subroutine reads in the experimental parameters, acf
c     and time vector for a DLS measurement at one angle. The
c     acf is converted from homodyne to heterodyne format.
```

```
c     The arguments are:
c        acf - the acf (read in as homodyne, returned as heterodyne)
c        time - the time vector corresponding to the acf points (sec)
c        param - an array of experimental parameters defined below
c        iparam - an integer array of misc. parameters
c        ichan - channel from which data should be read
c
c     Contents of param and iparam:
c        iparam(1)=number of time points in acfs
c
c        param(1)=temperature
c        param(2)=refractive index of sample suspending medium
c        param(3)=refractive index of particles
c        param(4)=max. particle diameter (bin edge) (nm)
c        param(5)=minimum particle diameter (bin edge) (nm)
c        param(6)=laser wavelength (nm)
c        param(7)=scattering angle
c        param(8)=viscosity of suspending medium
c        param(9)=(scat vec)^2*(reduced diff coeff)
c
      subroutine getdat(acf,time,param,iparam,ichan)
      double precision acf(1), time(1), param(1)
      integer iparam(1)
c
c     Read in data.
c
      do 10 j=1,8
         read(ichan,*) param(j)
   10 continue
      read(ichan,*) nt
      read(ichan,*) (time(j),j=1,nt)
      read(ichan,*) (acf(j),j=1,nt)
c
c     Convert acf from homodyne to heterodyne format.
c
      do 20 j=1,nt
         if(acf(j).ge.0.d0) acf(j)=dsqrt(acf(j))
         if(acf(j).lt.0.d0) acf(j)=-dsqrt(dabs(acf(j)))
   20 continue
      iparam(1)=nt
      return
      end c     cumul.fs
c
c     This version of cumul is for use with the n5 program using moment
c     constraints. It takes the baseline subtracted heterodyne form
c     acf. The zeroth, first and second cumulants are returned in an array cum.
c     In order to circumvent afterpulsing, any acf points corresponding to
c     delay times less than thresh are ignored in the fit. These points are
c     reconstructed (and entered into acf) by extrapolating from the cumulant
c     fit data.
c
c     The acf that is returned is normalized to an amplitude of 1.
c
c     requires the function 'determ.pr'.
c
c     the arguments of the subroutine are:
c       input -
c
c         ac=the measured auto correlation function
c         time=array with the time delay points at which ac fn is measured
c         nchan= number of channels in the a.c. function. (the first channel
c                in the a.c. function is ignored in the analysis.)
c       output -
c         cum(0)= 0th cumulant
c         cum(1)= 1st cumulant
c         cum(2)= 2nd cumulant
c
      subroutine cumul(ac,time,nc,cum)
      double precision ac(1), time(1), cum(1), percen, x, sumnum,
     +sumden, anorm
c
      real acr(100), timer(100), cumr(10)
```

```
c
c     Global constants.
c
      ncum=3
      percen=5.d-1
c
c     Find the acf point corresponding to percen% of the decay.
c
      percen=(ac(1)-ac(nc))*percen
      j=1
   10 j=j+1
      if(ac(j).gt.percen) go to 10
      nc12=j
c
c     Call polfit to calculate p.s. expansion coeffs.
c
      call polfit(time,ac,sigmay,nc12,ncum,-1,cum,chisqr)
      cum(1)=cum(1)
      cum(2)=-cum(2)
      cum(3)=cum(3)*2.d0
c
c     Use cumulants to fill in any acf points for delay times less than thresh.
c
      do 70 j=1,nc
         if(time(j).gt.thresh) go to 80
         ac(j)=dexp(cum(1)-cum(2)*time(j)+cum(2)*time(j)*time(j)/2.d0)
   70 continue
   80 continue
      anorm=1.d0/dexp(cum(1))
      do 90 j=1,nc
         ac(j)=ac(j)*anorm
   90 continue
      return
      end c     polfit.f
c
c     Taken from Bevington - pp. 140-142.
c
c     Purpose: Least squares fit to data with a polynomial curve.
c
c     Arguements:
c        x    - array of data points ofr independent variable
c        y    - array of data points for dependent variable
c        sigmay - arrys of standard deviations for y data points
c        npts - number of pairs of data-points
c        nterms - number of coefficients (degree of polynomial + 1)
c        mode - determines method of weighting least squares fit.
c               +1 (instrumental) weight(i) = 1./sigmay(i)**2
c                0 (no weighting) weight(i)=1.
c               -1 (heterodyne cumulant) weight=y(i)**4 (change from Bev.)
c               -1 (statistical)  weight(i)=1./y(i) (old Bev.)
c
c     Requires function 'determ'.
c
      subroutine polfit(x,y,sigmay,npts,nterms,mode,a,chisqr)
      implicit double precision (a-h,o-z)
      double precision sumx, sumy, xterm, yterm, array, chisq
      dimension x(1), y(1), sigmay(1), a(1)
      dimension sumx(19), sumy(10), array(10,10)
c     The following statement is added to original Bev. for cum. fitting.
      thresh=4.e-6
c
c     Accumulate weighted sums.
c
   11 nmax=2*nterms-1
      do 13 n=1,nmax
   13 sumx(n)=0.
      do 15 j=1,nterms
   15 sumy(j)=0.
      chisq=0.
   21 do 50 i=1,npts
c     The next three lines are additions to the orignial Bevington.
```

```
      if(x(i).lt.thresh .or. y(i).le.0.) go to 50
      if(y(i).ne.1) yi=alog(y(i))
      if(y(i).eq.1) yi=0.
      xi=x(i)
c     yi=y(i)
31 if(mode) 32, 37, 39
c The following statement replaces the original Bec. for het. cum. weighting.
32 if(yi) 33, 37, 33
c  32 if(yi) 35, 37, 33
c The following statement replaces the original Bev. for het. cum. weighting.
33 weight=y(i)**4
c  33 weight = 1./yi
   go to 41
35 weight=1./(-yi)
   go to 41
37 weight=1.
   go to 41
39 weight=1./sigmay(i)*sigmay(i)
41 xterm=weight
   do 44 n=1,nmax
   sumx(n)=sumx(n)+xterm
44 xterm=xterm*xi
45 yterm=weight*yi
   do 48 n=1,nterms
   sumy(n)=sumy(n)+yterm
48 yterm=yterm*xi
49 chisq=chisq+weight*yi*yi
50 continue
c
c  Construct matrices and calculate coefficients.
c
51 do 54 j=1,nterms
   do 54 k=1,nterms
   n=j+k-1
54 array(j,k)=sumx(n)
   delta=determ(array,nterms)
   if(delta) 61,57,61
57 chisqr=0.
   do 59 j=1,nterms
59 a(j)=0.
   go to 80
61 do 70 l=1,nterms
62 do 66 j=1,nterms
   do 65 k=1,nterms
   n=j+k-1
65 array(j,k)=sumx(n)
66 array(j,l)=sumy(j)
70 a(l)=determ(array,nterms)/delta
c
c  Calculate chi square.
c
71 do 75 j=1,nterms
   chisq=chisq-2.*a(j)*sumy(j)
   do 75 k=1,nterms
   n=j+k-1
75 chisqr=chisq+a(j)*a(k)*sumx(n)
76 free=npts-nterms
77 chisq=chisq/free
80 return
   end
``` c   determ.fs
c
c   Taken from Bevington - p. 294.
c
c   Purpose: To calculate the determinant of a square matrix.
c
c   Arguements:
c      array - matrix wose determinant is required
c      norder - order of determinant (degree of matrix)
c
c   Comments:
c      This function destroys the input matrix array
c      Dimension statement valid for norder up to 10

```
      double precision function detera(array,norder)
      implicit double precision (a-h,o-z)
      double precision array, save
      dimension array(10,10)
   10 detera=1.
   11 do 50 k=1,norder
c
c   Interchange columns if diagonal element is zero.
c
      if (array(k,k)) 41,21,41
   21 do 23 j=k,norder
      if (array(k,j)) 31,23,31
   23 continue
      detera=0.
      go to 60

31 do 34 i=k,norder
      save=array(i,j)
      array(i,j)=array(i,k)
   34 array(i,k)=save
      detera=-detera
c
c   Subtract row k from lower rows to get diagonal matrix.
c
   41 detera=detera*array(k,k)
      if(k-norder) 43,50,50
   43 k1=k+1
      do 46 i=k1,norder
      do 46 j=k1,norder
   46 array(i,j)=array(i,j)-array(i,k)*array(k,j)/array(k,k)
   50 continue
   60 return
      end c   mmul.for
c
c   This subroutine is used to multiply two matrices. The matrices
c   should be dimension in the calling routine as a(nar,nac), etc.
c   The two matrices to be multiplied are a and b, the answer is in c.
c   If the transpose of a or b is to be taken, itra or itrb is set to 1.
c   m, n and l respectively give: the row dimension of a, the row
c   dimension of b and the column dimension of c.
c
      subroutine mmul(a,nar,nac,itra,b,nbr,nbc,itrb,c,nrr,ncc,m,n,l)
      implicit double precision (a-h,o-z)
      dimension a(nar,nac),b(nbr,nbc),c(nrr,ncc)
      zero=0d0
      if(itra.eq.0 .and. itrb.eq.0) go to 50
      if(itra.eq.1 .and. itrb.eq.0) go to 15
      if(itrb.eq.0 .and. itrb.eq.1) go to 30
      do 10 i=1,m
      do 10 j=1,l
      c(i,j)=zero
      do 10 k=1,n
      c(i,j)=c(i,j)+a(k,i)*b(j,k)
   10 continue
      return
   15 do 20 i=1,m
      do 20 j=1,l
      c(i,j)=zero
      do 20 k=1,n
      c(i,j)=c(i,j)+a(k,i)*b(k,j)
   20 continue
      return
   30 do 40 i=1,m
      do 40 j=1,l
      c(i,j)=zero
      do 40 k=1,n
      c(i,j)=c(i,j)+a(i,k)*b(j,k)
   40 continue
      return
   50 do 60 i=1,m
```

```
            do 60 j=1,l
            c(i,j)=zero
            do 60 k=1,n
            c(i,j)=c(i,j)+a(i,k)*b(k,j)
    60      continue
            return
            end
c   setcon.fs
c
c   This routine scales the magnitude of the rows of the kernel and
c   the measurement vector according to the vector 'scale', in order
c   that the weight of each measurement in the fit is in proportion
c   to the error in the measurement.
c
            subroutine setcon(a,maxrow,iparam,b,scale,iang,tfcls,tfdls)
            double precision a(maxrow,1), b(1), scale(1), big, anorm
            integer iparam(1), iang(1)
            logical tfcls, tfdls
c
            ntime=iparam(1)
            nangs=iparam(2)
            nbins=iparam(3)
            nrows=iparam(4)
c
c   tfcls is true if cls data is to be used; tfdls is true if 2nd dls angle
c   dat is to be used.
c
            if(tfcls .and. tfdls) return
c
c   Remove all but 1st dls angle.
c
            if(.not.tfdls) then
                do 30 j=ntime+1,nangs*ntime
                    do 20 i=1,nbins
                        a(j,i)=0.d0
    20              continue
    30          continue
            endif
c
c   Remove all but first CLS angle.
c
            if(.not.tfcls) then
                do 50 j=nangs*ntime+1,nrows
                    if(j-nangs*ntime.ne.iang(1)) then
                        b(j)=0.d0
                        do 40 i=1,nbins
                            a(j,i)=0.d0
    40                  continue
                    else
                        b(j)=1d1*b(j)
                        do 45 i=1,nbins
                            a(j,i)=1d1*a(j,i)
    45                  continue
                    endif
    50          continue
            endif
            return
            end SUBROUTINE peaks (X,Y,CQUAD,N,IDEGMN,IDEGMX,NOUT)              MOENT4
      DIMENSION X(N), Y(N), CQUAD(N)                                 MOENT5
      DIMENSION AMOM(4,5), PKEND(4)                                  MOENT6
      DATA RMIN/1.E-3/                                               MOENT7
      NM=MINO(5,IDEGMX-IDEGMN+1)                                     MOENT8
      IF (NM .LT. 1) RETURN                                          MOENT9
 5110 FORMAT (/9X,'TOTAL CURVE',8X,3(19X,'PEAK',I2,9X)/               MOENT0
     1 '   J',3X,'MOMENT(J)',3X,'M(J)/M(J-1)',                       MOENT1
     2 3(11X,'MOMENT(J)',3X,'M(J)/M(J-1)'))                          MOENT2
      WRITE (NOUT,5110) (J,J=1,3)                                    MOENT3
      THRESH=ABS(Y(1))                                               MOENT4
      DO 110 J=2,N                                                   MOENT5
          THRESH=AMAX1(THRESH,ABS(Y(J)))                             MOENT6
  110 CONTINUE                                                       MOENT7
      THRESH=RMIN*THRESH                                             MOENT8
```

```
      IPEAK=2                                                            MOENT9
      DO 120 JPEAK=1,4                                                   MOENT0
        DO 120 JDEG=1,NM                                                 MOENT1
          AMOM(JPEAK,JDEG)=0.                                            MOENT2
  120 CONTINUE                                                           MOENT3
      DLAST=Y(2)-Y(1)                                                    MOENT4
      DO 150 J=1,N                                                       MOENT5
        PKEND(IPEAK)=X(J)                                                MOENT6
        IF (J.EQ.1 .OR. J.EQ.N) GO TO 160                                MOENT7
        DNEXT=Y(J+1)-Y(J)                                                MOENT8
        IF (DLAST.LT.-THRESH .AND. DNEXT.GT.THRESH)IPEAK=MIN0(IPEAK+1,4) MOENT9
        IF (ABS(DNEXT) .GT. THRESH) DLAST=DNEXT                          MOENT0
  160   IF (IDEGMN.LT.0 .AND. ABS(X(J)).LE.0.) RETURN                    MOENT1
        TERM=Y(J)*CQUAD(J)                                               MOENT2
        IF(IDEGMN .NE. 0)  TERM=TERM*X(J)**IDEGMN                        MOENT3
        DO 170 JDEG=1,NM                                                 MOENT4
          AMOM(IPEAK,JDEG)=AMOM(IPEAK,JDEG)+TERM                         MOENT5
          IF (JDEG .LT. NM) TERM=TERM*X(J)                               MOENT6
  170   CONTINUE                                                         MOENT7
  150 CONTINUE                                                           MOENT8
      DO 180 JDEG=1,NM                                                   MOENT9
        DO 180 JPEAK=2,IPEAK                                             MOENT0
          AMOM(1,JDEG)=AMOM(1,JDEG)+AMOM(JPEAK,JDEG)                     MOENT1
  180 CONTINUE                                                           MOENT2
 5180 FORMAT (1X,I2,1PE12.4,3E34.4)                                      MOENT3
      WRITE (NOUT,5180) IDEGMN,(AMOM(J,1),J=1,IPEAK)                     MOENT4
      IF (NM .EQ. 1) GO TO 300                                           MOENT5
      J=IDEGMN                                                           MOENT6
      DO 210 JDEG=2,NM                                                   MOENT7
        J=J+1                                                            MOENT8
        DO 220 JPEAK=1,IPEAK                                             MOENT9
          IF (ABS(AMOM(JPEAK,JDEG-1)) .GT. 0.)  AMOM(JPEAK,JDEG-1)=      MOENT0
     1    AMOM(JPEAK,JDEG)/AMOM(JPEAK,JDEG-1)                            MOENT1
  220   CONTINUE                                                         MOENT2
 5220   FORMAT (1X,I2,1PE12.4,E14.4,3(E20.4,E14.4))                      MOENT3
        WRITE (NOUT,5220) J,(AMOM(JPEAK,JDEG),AMOM(JPEAK,JDEG-1),        MOENT4
     1  JPEAK=1,IPEAK)                                                   MOENT5
  210 CONTINUE                                                           MOENT6
 5230 FORMAT (' CURRENT PEAK ENDS AND NEXT PEAK BEGINS AT',              MOENT7
     1 1PE11.3,10X,2(16X,E11.3,7X))                                      MOENT8
  300 IF (IPEAK .GT. 2) WRITE (NOUT,5230)(PKEND(J),J=2,IPEAK)            MOENT9
      RETURN                                                             MOENT0
      END                                                                MOENT1 c     setdls.fs
c
c     This routine sets up the kernel for the dls part of the measurement.
c
      subroutine setdls(a,conver,bins,param,acf,time,iparam,iang)
      parameter (maxtim=272,maxdls=3,maxrow=250,maxbin=25,maxang=7)
      parameter (maxpar=100)
      implicit double precision (a-h,o-z)
      dimension a(maxrow,maxbin), conver(maxang,maxbin),
     +param(maxpar,maxdls), iparam(maxpar), bins(1),
     +acf(maxtim,maxdls), time(maxtim,maxdls), iang(1),
     +dum(maxrow,maxbin)
c
      ntime=iparam(1)
      nangs=iparam(2)
      nbins=iparam(3)
c
c  k is index over dls angles, j is index over time, i is index over size bins
c
      do 100 k=1,nangs
        do 50 j=1,ntime
          gamred=param(9,k)*time(j,k)
          do 40 i=1,nbins
            gammat=gamred/bins(i)
            acffit=0.d0
c           if(gammat.lt.5d1) acffit=dexp(-gammat)
            if(gammat.lt.5d1) acffit=exp(-sngl(gammat))
            dum((k-1)*ntime+j,i)=acffit
            a((k-1)*ntime+j,i)=conver(iang(k),i)*(acffit-acf(j,k))
```

```
      40        continue
      50      continue
     100 continue
c        write(3,430)
c     430 format('q2dt')
c        write(3,*) param(9,2)
c        write(3,460)
c     460 format('acf')
c        write(3,410) (acf(i,2),i=1,100)
c        write(3,440)
c     440 format('Time')
c        write(3,410) (time(i,2),i=1,100)
c        write(3,450)
c     450 format('conversion')
c        write(3,410) (conver(iang(2),i),i=1,maxbin)
c        write(3,400)
c     400 format('Fit - meas acf')
c        do 110 j=101,200
c        write(3,420) j
c        write(3,410) (dum(j,i),i=1,25)
c     110 continue
c     410 format(7e11.3)
c     420 format('Row :',i5)
         return
         end c    weight.fs
c
c    This routine sets the weights of the data points.
c
         subroutine weight(acf,cls,a,b,scale,iang,iparam,maxtim,maxrow,
        +maxang)
         parameter (errmin=.01)
         implicit double precision (a-h,o-z)
         double precision acf(maxtim,1), cls(maxang),
        +a(maxrow,1), b(1), scale(1)
         integer iparam(1), iang(1)
c
         varinv(y)=(dmax1(y,errmin))**2/(1d0+y*y)
         nangs=iparam(2)
         nbins=iparam(3)
         ntime=iparam(1)
         nrows=iparam(4)
c
         do 50 k=1,nangs
            do 40 j=1,ntime
               scale((k-1)*ntime+j)=varinv(acf(j,k))
c       +                                    /dmax1(acf(j,k),errmin)
      40    continue
      50 continue
c
         do 60 j=ntime*nangs+1,nrows
            scale(j)=1.d0/(dmax1(errmin,b(j)))
      60 continue
c
         do 80 j=1,nrows
            b(j)=scale(j)*b(j)
            do 70 i=1,nbins
               a(j,i)=scale(j)*a(j,i)
      70    continue
      80 continue
         return
         end
```

APPENDIX F

```
c  n5.fm
c
c  Change made to include .04*supplement of angle scattering.  (Change is
c  one statement before call setdls and an if loop in setdls.)
c
```

```
c    Files required by program:
c       1> Driver file (which gives name of other files and various info.
c       2> File of the 1096 format for each DLS angle.
c       3> File containing mass/inten conversions as func. of (angle,size bin)
c       4> File containing CLS data.
c       5> File containing CLS part of kernel ('clskernel').
c
c    Uses of double precision arrays:
c       a - kernel (DLS and CLS data and h matrix); c=size bins, r=constraints
c       acls - temp storage for the cls part of the kernel (read from disk)
c       adup - retains the original (pre-nnls) contents of a)
c       acf - autocorrelation function (not kept after moment calculations)
c       ata - a transpose x a (to lessen nnls computation time)
c       b - the measurement vector (DLS moments, CLS data,-zeros for smoothing)
c       bar - intensity weighted diameter moments
c       bins - center of size histogram bins
c       cls - classical light scattering measurements as function of angle
c       conver - mass to intensity conversions as function of (angle,bin size)
c       cum - at 1st contains cums, then inten. weighted inv. diameter moments
c       param - various input parameters defined below
c       scist - holds preliminary scaling factors so they can be later removed
c       scale - magnitudes of rows of a & b for use in error weightings
c       time - delay times for acf (not kept after moment calculations)
c       w - dual vector for nnls
c       x - mass weighted particle size distribution
c       zz - working space for nnls
c
c    Uses of real arrays:
c       xsp - single precision version of x (mass weighted particle dist)
c       binssp - single precision version of bins (central histogram bin sizes)
c       cquad - quadrature used to calculate moments from x and bins
c
c    Uses of integer arrays:
c       blines - start and end positions of each baseline
c       iparam - miscellaneous parameters
c       index - real/dual index used by nnls
c       dlsang - contains the numbers of the angles used (i.e. 1-7)
c
c    Assignments of miscellaneous parameter arrays:
c       iparam(1)=number of time points in acfs
c       iparam(2)=number of dls angles to be used
c       iparam(3)=number of size bins
c       iparam(4)=number of dls+cls constraints (nangsused*ntime+ncls)
c       iparam(5)=number of acf channels to use to calc sd of baseline
c       iparam(6)=nangsused*ntime (in other words ndls)
c       iparam(7)=nbins+nangsused+nbase
c       iparam(8)=nangsused
c       iparam(9)=nbase
c       iparam(10)=ncls
c
c       param(1)=temperature
c       param(2)=refractive index of sample suspending medium
c       param(3)=refractive index of particles
c       param(4)=max. particle diameter (bin edge) (nm)
c       param(5)=minimum particle diameter (bin edge) (nm)
c       param(6)=laser wavelength (nm)
c       param(7)=scattering angle
c       param(8)=viscosity of suspending medium (poise)
c       param(9)=(scat vec)^2*(reduced diff coeff)
c
c    Definitions of variables which contain numbers of various items.
c       nbins: number of size bins (does not include baselines)
c       nbase: number of baselines for cls data
c       ntime: number of time points in each acf (must all be the same)
c       nclspp: number of cls points per polarization
c       npolar: number of cls polarizations (1 or 2)
c       ncls:  total number of cls constraints (including both polarizations)
c       nangs: number of dls angles (currently 1-3; not all need be used,
c              but all must be read in)
c       nangsused: number of the dls angles to be included in the analysis
c       ndls: nangsused * ntime (total number of dls constraints)
c       nrows: ncls + ndls (total number of cls and dls constraints)
c       nrtot: nrows+nbins (total number of cls, dls and smoothing constraints)
c       nvar: total number of variables in fit: nbins+nangsused+nbase if(tfcls)
c
c    Subroutines and functions called:
c       basel - adjusts the kernel to allow for acf floating baselines
c       calcmo - calculates weighted 1st and 2nd moments of an array of data
c       cumul - calculates cumulants of acf (also extrapolates acf to t=0)
c       convcm - converts cumulants to size moments using Stokes-Einstein
```

```
c       dlsint - calculates the kernel for single angle intensity calc (sinang)
c       dsply2 - prints crude histogram of mass dist.
c       getdat - gets data from 1096 (or other) file for one angle
c       moment - calculates the intensity weighted regular moments of dism (nm)
c       nnls   - nonnegative-least squares algorithm from Lawson and Hanson
c       peaks  - subroutine 'moment' from CONTIN - calculates peak moments von x
c       pkpos  - calculates peak positions and areas for a histogram
c       setcon - removes CLS and or 2nd and later DLS data from fit
c       setdls - enters dls data into kernel array a
c       sinang - calculates intensity histogram for a single angle (for norm.)
c       sinwei - calculates point weightings for sinang
c       weight - sets the relative weights for the data points
c
c     Assignments of channel numbers to file names:
c       1: n5.in      ! driver file                    !infile
c       2:            ! dls data file                  !dlsdata
c       3: dump       ! output data file               !oufile
c       4:            ! cls data file                  !clsdata
c       6:convert     !int/wt of size conversion file  !sizint
c       7:output      !output of results               !output
c
      parameter (maxdat=50,maxbin=40,maxang=3,maxtim=85,maxpar=100)
      parameter (maxrow=400,maxdls=3,maxcls=100)
      implicit double precision (a-h,o-z)
      double precision acf(maxtim,maxdls), time(maxtim,maxdls),
     +bins(maxbin), sts(maxbin,maxbin),
     +param(maxpar,maxdls), cum(4,maxang), bar(4,maxang), cls(maxcls),
     +a(maxrow,maxbin), b(maxrow), w(maxbin), zz(maxrow),
     +conver(maxang,maxbin), x(maxbin), adup(maxrow,maxbin),
     +scale(maxrow), bdup(maxrow), sclst(maxang), x2(maxbin),
     +where(maxbin), percen(maxbin), geom(maxbin), acls(maxcls,maxbin)
      double precision rnorm, range, alpha, sum, relwt(maxang), relcls
      real xsp(maxbin), binsmp(maxbin), cquad(maxbin)
      integer iparam(maxpar), index(maxbin), dlsang(maxang),
     +blines(10,2)
      character*40 infile, oufile, output
      character*40 dlsconv, clsconv, dlsdata, clsdata, binfile
      character*1 dumch
      logical tfcls, tfdls(maxang)
c
c     xxxxxxxxxxxxxxxxxxxxxxxxxxxxInitializexxxxxxxxxxxxxxxxxxxxxxxxxxxxxxxx
c
c     Set global parameters.
c
      ichan=5
      iochan=9
      nmomen=4
      range=1.d60
      alpha=1.d-40
      write(*,*)'Enter alpha:'
      read(*,*) alpha
      oufile='dump'
      infile='n5.in'
      output='output'
      idegmn=-1
      idegmx=2
c
c     End of global parameters.
c
      do 5 j=1,maxrow
         scale(j)=1.d0
    5 continue
c
c     Get names of input 1096 data files; open files.
c
c                Read driver file.
c
      open(7,file=output,status='new')
      open(1,file=infile,status='old')
      open(3,file=oufile,status='new')
      read(1,*) dlsconv
      read(1,*) clsconv
      read(1,*) dlsdata
      read(1,*) clsdata
      read(1,*) binfile
      read(1,*) nangs
      iparam(2)=nangs
      do 4 j=1,maxang
         dlsang(j)=j
    4 continue
      do 6 j=1,nangs
```

```
            read(1,x) dlsang(j)
    6 continue
      read(1,x) ntime
      read(1,x) nclspp
      read(1,x) npolar
      ncls=nclspp*npolar
      iparam(10)=ncls
      read(1,x) nbase
      iparam(9)=nbase
      do 11 j=1,nbase
         read(1,x) (blines(j,i),i=1,2)
   11 continue
      close(1)
c
c
c                   Read in bin sizes.
c
      open(1,file=binfile,status='old')
      read(1,x) nedges
      do 12 j=1,nedges
         read(1,x) bins(j)
         bins(j)=bins(j)*1d3
   12 continue
      nbins=nedges-1
      do 13 j=1,nbins
         bins(j)=dsqrt(bins(j)*bins(j+1))
   13 continue
      param(4,1)=bins(nedges)
      param(5,1)=bins(1)
      close(1)
      iparam(1)=ntime
      iparam(3)=nbins
c
c             Select which data to use.
c
      nvar=nbins
      tfcls=.false.
      tfdls(1)=.false.
      tfdls(2)=.false.
      tfdls(3)=.false.
      write(x,x)'Use CLS data? (y or n)?'
      read(x,x) duach
      if(duach.eq.'y') then
         tfcls=.true.
         nvar=nvar+nbase
      else
         ncls=0
         iparam(6)=ncls
      endif
      nangsused=0
      do 14 j=1,nangs
         write(x,498) j
  498    format('Use DLS data set ',i3,'? (y or n)?')
         read(x,x) duach
         if(duach.eq.'y') then
            tfdls(j)=.true.
            nangsused=nangsused+1
         endif
   14 continue
      nvar=nvar+nangsused
      iparam(7)=nvar
      iparam(8)=nangsused
      ndls=nangsused*ntime
      iparam(6)=ndls
      write(x,x)'Enter number of complete data sets:'
      read(x,x) ndsets
c
c          Read in relative dls intensities for weightings.
c
      open(2,file=dlsdata,status='old')
      open(4,file=clsdata,status='old')
      do 15 j=1,nangsused-1
         write(x,430) j+1
  430    format('Relative weighting acf',i2,':acf 1?')
         read(x,x) relwt(j)
   15 continue
      if(tfcls) then
         write(x,x)'Enter relative weight of cls data:acf 1?'
         read(x,x) relcls
      endif
      write(x,x) 'Solve for intensity at which DLS angle (1-3) ?'
      read(x,x) intgeom
```

```
c
c          Read in DLS, CLS intensity/weight conversion files.
c
      if(tfcls) then
         open(1,file=clsconv,status='old')
         do 7 i=1,maxcls
         do 7 j=1,maxbin
            acls(i,j)=0d0
 7       continue
         do 9 k=1,npolar
            do 8 j=1,nbins
               read(1,*) (idum,acls((k-1)*nclspp+i,j),i=1,nclspp)
 8          continue
 9       continue
         close(1)
      endif
      open(6,file=dlsconv,status='old')
      nconv=maxang*nbins
      do 50 j=1,nconv
         read(6,*) m,n,conver(m,n)
 50   continue
      close(6)
c
c  Change solution vector to mean relative intensity at dls angle intgeom.
c
      open(16,file='amp1',status='new')
      open(17,file='amp2',status='new')
      write(16,*) nvar
      write(17,*) nvar
      do 49 i=1,nbins
c        prod=1d0
c        do 48 k=1,nangs
c           prod=prod*conver(dlsang(k),i)
c 48     continue
         geom(i)=conver(intgeom,i)
         write(16,*) i,conver(dlsang(1),i)/geom(i)
         write(17,*) i,conver(dlsang(2),i)/geom(i)
 49   continue
      close(16)
      close(17)
      if(tfcls .and. ndls.gt.0) then
         do 59 j=1,ncls
            do 58 i=1,nbins
               acls(j,i)=acls(j,i)/geom(i)
 58         continue
 59      continue
      endif
c
cxxxxxxxxxEnd of Initialization: Begin main loop over data sets.xxxxxxxxxxxxx
c
c          ----------------Set up kernel------------------
c
c  Get DLS data from file dlsdata.
c
      do 999 idset=1,ndsets
      kk=0
      do 10 j=1,nangs
         if(tfdls(j)) then
            call getdat(acf(1,j),time(1,j),scale(ntime*kk+1),
     +           param(1,j),iparam,2)
            call cumul(acf(1,j),time(1,j),iparam(1),cum(1,j))
            u2g=cum(3,j)/cum(2,j)**2
            call convcm(param(1,j),cum(1,j))
            write(*,435) 1d0/cum(2,j), u2g
 435        format('Cum diameter (nm) =',f8.1,'  Mu2/Gamma^2 =',f10.4)
            call moment(param(1,j),acf(1,j),time(1,j),iparam(1),
     +           bar(1,j),cum(1,j),j)
            kk=kk+1
         endif
 10   continue
      iparam(5)=5
c
c  Get classical light scattering data from file clsdata.
c
      if(tfcls) then
         if(clsdata(1:3).ne.'col') then
            call readpd(4,idset,cls,ncls)
         else
            do 20 j=1,ncls
               read(4,*) idum,cls(j)
 20         continue
```

```
            endif
        endif
c
c   Calculate single angle intensity histograms.
c
        do 52 k=1,nangs
            if(tfdls(k)) then
                call sinang(acf(1,k),time(1,k),param(1,k),iparam,adup,
     +              x,bins,scale,param(20,1),sum)
                anorm=1d0/sum
                do 51 j=1,ntime
                    acf(j,k)=acf(j,k)*anorm
51              continue
            endif
52      continue
c
c   Enter DLS constraints into kernel
c
        call setdls(a,conver,geom,bins,param,acf,time,iparam,dlsang,
     +      tfdls)
c       write(*,710) (iii, a(iii,28),iii=1,240)
710     format(i5,d20.10)
        call basel(a,tfdls,tfcls,blines,iparam)
c
c   Enter CLS constraints into kernel
c
        if(tfcls) then
            do 56 j=1,ncls
                do 55 i=1,nbins
                    a(ndls+j,i)=acls(j,i)
55              continue
56          continue
        endif
c
c   Append second order difference part of kernel (h matrix).
c
        nrows=ndls+ncls
        iparam(4)=nrows
        nrtot=nrows+nbins
        do 70 j=1,nbins
            do 60 i=1,nbins
                nrowsi=nrows+i
                a(nrowsi,j)=0.d0
                if(i.eq.j) a(nrowsi,j)=-2.d0*alpha
                if(i+1.eq.j .or. i.eq.j+1) a(nrowsi,j)=1.d0*alpha
60          continue
70      continue
        do 75 j=nbins+1,nvar
            do 73 i=nrows+1,nrows+nbins
                a(i,j)=0d0
73          continue
75      continue
c
c   Set up b (measurement vector).
c
        do 80 j=1,ndls
            b(j)=0.d0
80      continue
        ndls1=ndls+1
        if(tfcls) then
            bigcls=0d0
            do 85 j=1,ncls
                if(cls(j).gt.bigcls) bigcls=cls(j)
85          continue
        endif
        do 90 j=ndls1,nrows
            cls(j-ndls)=cls(j-ndls)/bigcls
            b(j)=cls(j-ndls)
90      continue
        nrowsi=nrows+1
        do 100 j=nrowsi,nrtot
            b(j)=0.d0
100     continue
c
c   Add one cls constraint if only dls data is being analyzed (to
c   force non-trivial solution.
c
        if(.not.tfcls) then
            nrtot=nrtot+1
            do 102 j=1,nbins
                a(nrtot,j)=1d0
```

```
102     continue
        b(nrtot)=1d0
        do 103 j=nbins+1,nvar
          a(nrtot,j)=0d0
103     continue
        endif
c
c   Copy a into adup for later use in computing fit measurement vector.
c
        do 110 i=1,nrtot
        bdup(i)=b(i)
        do 110 j=1,nvar
          adup(i,j)=a(i,j)
110     continue
c
c   Scale the rows of the kernel and measurement vector according to
c   variance in each measurement. Then use magnitude of 1st acf to
c   weight the cls data.
c
        call weight(acf,a,b,scale,dlsang,iparam,relwt,relcls,
       +tfdls,tfcls,blines)
        call setcon(a,maxrow,iparam,b,scale,dlsang,tfcls,tfdls)
c
c   ---------------Kernel is set up. Invert to solve.----------------
c
c       call atmul(a,maxrow,maxbin,1,a,maxrow,maxbin,0,ata,maxbin,maxbin,
c      +nbins,nrows,nbins)
c       call atmul(a,maxrow,maxbin,1,bdup,maxrow,1,0,b,maxrow,1,
c      +nbins,nrows,1)
c       call nnls(ata,maxbin,nbins,nbins,b,x,rnorm,w,zz,index,mode,range)
c       open(20,file='kern',status='new')
c       write(20,502) ((a(i,j),i=1,nrtot),j=1,nvar)
c 502   format(4d18.9)
c       close(20)
        call nnls(a,maxrow,nrtot,nvar,b,x,rnorm,w,zz,index,mode,range)
c
c   ------------Problem solved. Interpret and write out results.---------
c
c   Assign sources of errors.
c
        call atmul(adup,maxrow,maxbin,0,x,maxbin,1,0,b,maxrow,1,
       +nrtot,nvar,1)
c       write(3,456)
c       write(3,450) (b(i),i=1,nrtot)
        sumdum=0.
        do 141 i=1,ntime
          bdup(i)=(b(i)-bdup(i))**2
          sumdum=sumdum+bdup(i)
141     continue
        write(3,490) rnorm,sumdum
490     format(' nnls euclidean norm',e15.7,'  n5 euclidean norm',e15.7)
        do 142 i=1,ntime
          bdup(i)=bdup(i)/sumdum
142     continue
        write(3,496)
496     format('Relative portion of total error.')
        write(3,491) (bdup(i),i=1,ntime)
491     format(5f15.7)
c
c   End of error assignment.
c
        write(3,548)
548     format('scales')
c       do 146 j=1,nrows
c         write(3,546) j,scale(j)
546     format(i4,e15.7)
c 146   continue
c
c   Graph results; analyze peaks.
c
c   First convert x back to represent relative weights.
c
        do 148 j=1,nbins
          x(j)=x(j)/geom(j)
148     continue
        call dsply2(x,nbins,iochan)
        call dsply2(x,nbins,7)
        do 145 j=1,nbins
          xsp(j)=x(j)
          binssp(j)=bins(j)
          equad(j)=1.
```

```
    145 continue
        call peaks(binssp,xsp,cquad,nbins,idegan,idegax,iochan)
        call peaks(binssp,xsp,cquad,nbins,idegan,idegax,7)
c
c   Calculate moments.
c
        do 150 j=1,nangs
            call calcmo(bins,x,dum,nbins,1,u1,u2,u3)
            write(3,457) j
    457     format('Angle :',i3)
            write(3,458) u1,u3,u2
    458     format('Cumulant mean:',f10.2,'   Mean:',f10.2,'   Mu2:',e14.5)
            u1=1.d0/cum(2,j)
            write(3,458) u1,bar(1,j),cum(3,j)
            write(3,459) sum
    459     format('Normalization: ',e15.7)
    150 continue
c
c   Write out tabular histogram and peak data.
c
        write(3,461)
    461 format('Size histogram')
        write(3,472) (bins(j), x(j), j=1,nvar)
    472 format(f10.2,f15.7)
        sum=0d0
        do 190 j=1,nbins
            sum=sum+x(j)
    190 continue
        write(3,468) sum
    468 format('Sum of intensities = ',e15.7)
c
        call pkpos(x,bins,nbins,where,percen,npeaks)
        write(3,510)
    510 format('Peaks        Percentages')
        write(3,520) (where(j),1d2*percen(j),j=1,npeaks)
    520 format(f10.4,f14.10)
c
c   Write out measured and fit acfs for both angles; first measured.
c
        call fit(adup,x,conver,geom,acf,cls,tfdls,tfcls,iparam,dlsang,
       +scale)
    999 continue
c
cXXXXXXXXXXXXXXXXXXXXXXXEnd of main loop over data sets.XXXXXXXXXXXXXXXXXXXX
c
    455 format('kernel matrix')
    1201 format('Col = ',i5)
    1200 format(7e11.3)
    456 format('measurement vector')
    450 format(5f15.7)
        stop
        end c   convcm.fs
c
c   This subroutine converts the first two cumulants to an intensity
c   weighted inverse diameter (nm) and variance thereof (nm^2),
c   respectively.
c
c   The inputs to the program are:
c       param - contains various parameters defined below
c       cum - on input contains the 1st 3 cumulants, on output contains
c           the zeroth cumulant and the 1st 2 inverse moments (nm, nm^2)
c
c   Contents of array param:
c       param(1)=temperature
c       param(2)=refractive index of sample suspending medium
c       param(3)=refractive index of particles
c       param(4)=max. particle diameter (bin edge) (nm)
c       param(5)=minimum particle diameter (bin edge) (nm)
c       param(6)=laser wavelength (nm)
c       param(7)=scattering angle
c       param(8)=viscosity of suspending medium
c       param(9)=(scat vec)^2*(reduced diff coeff) (calculated by this routine)
c
        subroutine convcm(param,cum)
        implicit double precision (a-h,o-z)
        double precision param(1), cum(1)
c
c   Set up constants.
c
```

```
      pi=3.1415927d0
      sinth2=dsin(param(7)*8.7266464d-3)
      scatt=4.d0*pi*param(2)*sinth2/param(6)
      diffr=1.380622d-9*(273.16d0+param(1))/(3.d0*pi)
      dum=param(8)
      diffr=diffr/dum
      q2diff=scatt*scatt*diffr*1.d14
      param(9)=q2diff
c
c     Perform conversion.
c
      cum(2)=cum(2)/(q2diff)
      cum(3)=cum(3)/(q2diff*q2diff)
      return
      end c     moment.fs
c
c     This subroutine calculates the intensity weighted mean diameter (nm)
c     and two quantities related to the intensity weighted second moment
c     of the diameter distribution. The first of these quantities is the
c     delay time at which the normalized (to amp=1) acf crosses the computed
c     normalized acf corresponding to the intensity weighted mean diameter.
c     The second quantity is the area between the two acfs just described,
c     between t=0 and crossing delay time.
c     The arguments are:
c       param - miscellaneous parameters; only param(9) used =(k^2 * Dred)
c       acf   - measured autocorrelation function
c       time  - central delay times corresponding to acf points
c       ntime - number of time points at which acf is measured
c       bar   - output array containing moments: (moment#,angle)
c       cum   - contains the 1st 2 inten weighted inverse mean diam moments
c       jang  - number of angle (i.e. 1-7)
c
      subroutine moment(param,acf,time,ntime,bar,cum,jang)
      implicit double precision (a-h,o-z)
      double precision acf(1), time(1), bar(1), param(1),
     +cum(1)
c
c     Compute intensity weighted mean diameter (nm).
c
      anorm=1./acf(1)
c     do 10 j=1,ntime
c       acf(j)=anorm*acf(j)
c 10  continue
      sum=0.d0
      ntime1=ntime-1
      do 20 j=2,ntime1
        sum=sum+.5d0*acf(j)*(time(j+1)-time(j-1))
 20   continue
      sum=sum+acf(1)*(time(2)-time(1))
      sum=sum+acf(ntime)*(time(ntime)-time(ntime-1))
      bar(1)=sum*param(9)
c
c     Compute crossing point (from intersection of logs of acfs).
c
      tcross=0.d0
      cumbar=1.d0/bar(1)
      write(*,*)cum(3)
      if(cum(3).gt.0.d0 .and. cum(2).gt.cumbar)
     +  tcross=2.d0*(cum(2)-cumbar)/cum(3)
      bar(2)=tcross
c
c     Compute area between the two normalized acfs.
c
      gambar=param(9)*cumbar
      sum=0.d0
      do 30 j=2,ntime
        if(time(j).gt.tcross) go to 40
        sum=sum+.5d0*(dexp(-gambar*time(j))-acf(j))*
     +    (time(j+1)-time(j-1))
 30   continue
 40   continue
      bar(3)=sum/q2diff
      return
      end
```

```
c   setmom.fs
c
c   This routine sets up the DLS moment part of the kernel. To do this,
c   it uses the mass to intensity conversion matrix conver(angle,size),
c   the central size bin array and the equations for the moments to
c   compute the kernel elements.

c   The argumments are:
c       a - to contain the kernel (constraint#,size)
c       conver - the mass to intensity conversion (angle,size)
c       bins - the size of the geometric centers of the size bins
c       cum - the array containing the inverse moments (moment#,angle)
c       bar - array containing the regular moments (moment#,angle)
c       dlsang - integer array containing the DLS angles used
c       param - misc. parameters (only param(9)=(sc vec)^2 x Dred is used)
c       maxrow - number of rows in a
c       maxang - maximum number of angles
c       nbins - number of size bins
c       nangs - number of angles
c       nmomen - number of moments/angle
c
        subroutine setmom(a,conver,bins,cum,bar,dlsang,param,
       +maxrow,maxang,nbins,nangs,nmomen)
        implicit double precision (a-h,o-z)
        double precision a(maxrow,25), conver(maxang,1), bins(1),
       +cum(4,1), bar(4,1), param(1)
        integer dlsang(maxang)
c
c   Compute moments.
c
        do 20 j=1,nangs
           dectim=dexp(-param(9)/bar(3,j)/bar(1,j))
           jj=(j-1)*nmomen
           do 10 i=1,nbins
              cumdif=(1.d0/bins(i)-cum(2,j))
c   First inverse moment.
              a(jj+1,i)=conver(dlsang(j),i)*cumdif
c   Second inverse moment.
              a(jj+2,i)=conver(dlsang(j),i)*(cumdif**2-cum(3,j))
c   First regular moment.
              a(jj+3,i)=conver(dlsang(j),i)*(bins(i)-bar(1,j))
c   Crossing point in time.
              a(jj+4,i)=conver(dlsang(j),i)*
       +          (dexp(-param(9)*bar(3,j)/bins(i))-dectim)
              a(jj+1,i)=1.d0
              a(jj+2,i)=1.d0
              a(jj+3,i)=1.d0
              a(jj+4,i)=1.d0
 10        continue
 20     continue
        return
        end c   dsply.pr
c
c   this subroutine prints-out a crude histogram of the function contained
c   in the array func. func should have no more than 60 components.
c   the arguments of the subroutine are:
c       x - the double precision numbers to be graphed.
c       nbins - the number of numbers to be graphed
c       ichan - the channel to which the output should be sent
c
        subroutine dsply2(x,nbins,ichan)
        parameter (nrmax=20,nbmax=60)
        integer*2 idisp(nrmax,nbmax), ifunc(nbmax)
        double precision func(nbmax), x(1)
c
c   Double or triple up function if fewer than nb/2 or nb/2 bins needed.
c
        if(nbmax/nbins.eq.2) then
           do 1 j=1,nbins
              func(2*(j-1)+1)=x(j)
              func(2*(j-1)+2)=x(j)
 1         continue
           nb=2*nbins
        endif
        if(nbmax/nbins.eq.3) then
           do 2 j=1,nbins
              func(3*(j-1)+1)=x(j)
              func(3*(j-1)+2)=x(j)
              func(3*(j-1)+3)=x(j)
```

```
      2   continue
          nb=nbins=3
          endif
c
c     scale the function to an amplitude of nr
c
          nr=nrmax
          big=0.
          do 10 j=1,nb
          if(func(j).gt.big) big=func(j)
   10     continue
          anorm=nr/big
          do 20 j=1,nb
          ifunc(j)=anorm*func(j)
   20     continue
c
c     fill up each bin of the display array with asterixes to the depth ifunc
c
          do 40 j=1,nb
          do 30 i=1,ifunc(j)
          idisp(i,j)=42
   30     continue
          if(ifunc(j).lt.nr) then
             nblank=ifunc(j)+1
             do 35 i=nblank,nr
             idisp(i,j)=32
   35        continue
          endif
   40     continue
          do 45 j=1,nb
          idisp(1,j)=42
   45     continue
c
c     write out result to channel ichan.
c
          do 50 ii=1,nr
          i=nr+1-ii
          write(ichan,400) (idisp(i,j),j=1,nb)
  400     format(1x,60a2)
   50     continue
          write(ichan,420) (i,i=10,nb,10)
  420     format(1x,8i10)
          return
          end c     getdataccu.fs
c
c     Modified version for use in reading accucomp data sets - has extra
c     passed array (scale) as among arguments.
c
c     This subroutine reads in the experimental parameters, acf
c     and time vector for a DLS measurement at one angle. The
c     acf is converted from homodyne to heterodyne format.
c     The arguments are:
c        acf - the acf (read in as homodyne, returned as heterodyne)
c        time - the time vector corresponding to the acf points (sec)
c        param - an array of experimental parameters defined below
c        iparam - an integer array of misc. parameters
c        ichan - channel from which data should be read
c
c     Contents of param and iparam:
c        iparam(1)=number of time points in acfs
c
c        param(1)=temperature
c        param(2)=refractive index of sample suspending medium
c        param(3)=refractive index of particles
c        param(4)=max. particle diameter (bin edge) (nm)
c        param(5)=minimum particle diameter (bin edge) (nm)
c        param(6)=laser wavelength (nm)
c        param(7)=scattering angle
c        param(8)=viscosity of suspending medium
c        param(9)=(scat vec)^2*(reduced diff coeff)
c
          subroutine getdat(acf,time,scale,param,iparam,ichan)
          implicit double precision (a-h,o-z)
          double precision acf(1), time(1), param(1), scale(1)
          integer iparam(1)
          character*78 line
          character*80 strin, strout
c
c     Set constants.
```

```
      nbase=4
      nt=iparam(1)
      nchans=nt+5
      param(3)=1.6
      param(6)=632.8
c
c     Read in data.
c
   1  if(line(1:3).ne.'RUN') then
         read(ichan,x) line
         go to 1
      else
         go to 2
      endif
   2  continue
      open(21,file='scratch',status='new')
      read(ichan,440)
 440  format(//)
c
      read(ichan,400) strin
 400  format(a79)
      call parse(strin,strout,4,nchar,ierr)
      write(21,405) strout(71:80)
 405  format(a10)
c
      read(ichan,410)
 410  format(/)
      read(ichan,400) strin
      call parse(strin,strout,3,nchar,ierr)
      write(21,405) strout(71:80)
c
      read(ichan,400) strin
      call parse(strin,strout,2,nchar,ierr)
      write(21,405) strout(71:80)
c
      read(ichan,400) strin
      call parse(strin,strout,3,nchar,ierr)
      write(21,405) strout(71:80)
c
      read(ichan,400) strin
      call parse(strin,strout,4,nchar,ierr)
      write(21,405) strout(71:80)
c
      rewind 21
      read(21,x) samtim,param(7),param(1),param(8),param(2)
      close(21)
      if(param(7).eq. 29.8d0) param(7)=30.
      if(param(7).eq. 63.2d0) param(7)=150.
c
   3  if(line(1:11).ne.'CORRELATION') then
         read(ichan,x) line
         go to 3
      else
         go to 4
      endif
   4  continue
      read(ichan,450)
 450  format(//)
      do 10 j=1,nchans,5
         read(ichan,x) idum,(acf(i),i=j,j+4)
  10  continue
c
c     Compute time array.
c
      timeinc=samtim*1d-6
      do 401 j=1,16
         time(j)=timeinc*j
 401  continue
      k=17
      do 501 j=1,6
         timeinc=timeinc*2.d0
         do 501 i=1,8
            time(k)=time(k-1)+timeinc
            k=k+1
 501  continue
      timeinc=2.0*timeinc
      do 601 j=k,k+16
         time(j)=time(j-1)+timeinc
 601  continue
```

```
c
c     Convert acf from homodyne to heterodyne format.
c
      base=0d0
      do 15 j=nt-nbase+1,nt
         base=base+acf(j)
   15 continue
      base=base/nbase
      deltab=dabs(base-acf(nchans))
c     base=acf(nchans)
      width=(time(2)-time(1))/time(1)
      do 20 j=1,nt
         if(j.gt.1) width=(time(j)-time(j-1))/time(1)
         acf(j)=acf(j)-base
         x=(deltab/acf(j))**2
c        if(x.gt.1d1) x=1d1
         scale(j)=0d0
         if(x.lt.10d0) scale(j)=dexp(-3.d0*x)*dsqrt(width)
c        scale(j)=dexp(-3.d0*x)
         if(acf(j).ge.0.d0) acf(j)=dsqrt(acf(j))
         if(acf(j).lt.0.d0) acf(j)=-dsqrt(dabs(acf(j)))
   20 continue
      return
      end c
c     cumul.fs
c
c     This version of cumul is for use with the m5 program using moment
c     constraints. It takes the baseline subtracted heterodyne form -
c     acf. The zeroth, first and second cumulants are returned in an array cum.
c     In order to circumvent afterpulsing, any acf points corresponding to
c     delay times less than thresh are ignored in the fit. These points are
c     reconstructed (and entered into acf) by extrapolating from the cumulant
c     fit data.
c
c     The acf that is returned is normalized to an amplitude of 1.
c
c     requires the function 'determ.pr'.
c
c     the arguments of the subroutine are:
c        input -
c
c           ac=the measured auto correlation function
c           time=array with the time delay points at which ac fn is measured
c           nchan= number of channels in the a.c. function. (the first channel
c                  in the a.c. function is ignored in the analysis.)
c        output -
c           cum(0)= 0th cumulant
c           cum(1)= 1st cumulant
c           cum(2)= 2nd cumulant
c
      subroutine cumul(ac,time,nc,cum)
      double precision ac(1), time(1), cum(1), percen, x, sumnum,
     +sumden, anorm, anorm1, thresh
c     real acr(100), timer(100), cumr(10)
c
c     Global constants.
c
      ncum=3
      percen=5.d-1
      thresh=2d-6
c
c     Find the acf point corresponding to percen% of the decay.
c
      percen=(ac(1)-ac(nc))*percen
      j=1
   10 j=j+1
      if(ac(j).gt.percen) go to 10
      nc12=j
c
c     Call polfit to calculate p.s. expansion coeffs.
c
      call polfit(time,ac,sigmay,nc12,ncum,-1,cum,chisqr)
      cum(1)=cum(1)
      cum(2)=-cum(2)
      cum(3)=cum(3)*2.d0
c
c     Use cumulants to fill in any acf points for delay times less than thresh.
c
      do 70 j=1,nc
         if(time(j).gt.thresh) go to 80
```

```
            ac(j)=dexp(cum(1)-cum(2)*time(j)+cum(2)*time(j)*time(j)/2.d0)
   70 continue
   80 continue
         anorm=1.d0/dexp(cum(1))
c        write(x,x)'Enter normalization for acf (0d0 for self norm)!'
c        read(x,x) anorm
c        if(anorm.ne.0d0) anorm=1.d0/anorm
c        do 90 j=1,nc
c            ac(j)=ac(j)*anorm
c   90 continue
         return
         end c  *polfit.fs
c  -------
c  --Taken from Bevington - pp. 140-142.
c
c  -;Purpose: Least squares fit to data with a polynomial curve.
c
c     Arguements:
c        x - array of data points ofr independent variable
c  -     y - array of data points for dependent variable
c        sigmay - arrya of standard deviations for y data points
c        npts - number of pairs of data points
c        nterms - number of coefficients (degree of polynomial + 1)
c        mode - determines method of weighting least squares fit
c              +1  (instrumental) weight(i) = 1./sigmay(i)**2
c               0  (no weighting) weight(i)=1.
c              -1  (heterodyne cumulant) weight=y(i)**4 (change from Bev.)
c              -1  (statistical) weight(i)=1./y(i) (old Bev.)
c
c     Requires function 'determ'.
c
         subroutine polfit(x,y,sigmay,npts,nterms,mode,a,chisqr)
         implicit double precision (a-h,o-z)
         double precision sumx, sumy, xterm, yterm, array, chisq
         dimension x(1), y(1), sigmay(1), a(1)
         dimension sumx(19), sumy(10), array(10,10)
c  The following statement is added to original Bev. for cum. fitting.
         thresh=4.e-6
c
c  Accumulate weighted sums.
c
   11 nmax=2*nterms-1
      do 13 n=1,nmax
   13 sumx(n)=0.
      do 15 j=1,nterms
   15 sumy(j)=0.
      chisq=0.
   21 do 50 i=1,npts
c  The next three lines are additions to the orignial Bevington.
      if(x(i).lt.thresh .or. y(i).le.0.) go to 50
      if(y(i).ne.1) yi=dlog(y(i))
      if(y(i).eq.1) yi=0.
      xi=x(i)
c     yi=y(i)
   31 if(mode) 32, 37, 39
c  The following statement replaces the original Bec. for het. cum. weighting.
   32 if(yi) 33, 37, 33
c  32 if(yi) 35, 37, 33
c  The following statement replaces the original Bev. for het. cum. weighting.
   33 weight=y(i)**2
c  33 weight = 1./yi
      go to 41
   35 weight=1./(-yi)
      go to 41
   37 weight=1.
      go to 41
   39 weight=1./sigmay(i)*sigmay(i)
   41 xterm=weight
      do 44 n=1,nmax
      sumx(n)=sumx(n)+xterm
   44 xterm=xterm*xi
   45 yterm=weight*yi
      do 48 n=1,nterms
      sumy(n)=sumy(n)+yterm
   48 yterm=yterm*xi
   49 chisq=chisq+weight*yi*yi
   50 continue
```

```
c
c     Construct matrices and calculate coefficients.
c
   51 do 54 j=1,nterms
      do 54 k=1,nterms
      n=j+k-1
   54 array(j,k)=sumx(n)
      delta=determ(array,nterms)
      if(delta) 61,57,61
   57 chisqr=0.
      do 59 j=1,nterms
   59 a(j)=0.
      go to 80
   61 do 70 l=1,nterms
   62 do 66 j=1,nterms
      do 65 k=1,nterms
      n=j+k-1
   65 array(j,k)=sumx(n)
   66 array(j,l)=sumy(j)
   70 a(l)=determ(array,nterms)/delta
c
c     Calculate chi square.
c
   71 do 75 j=1,nterms
      chisq=chisq-2.*a(j)*sumy(j)
      do 75 k=1,nterms
      n=j+k-1
   75 chisqr=chisq+a(j)*a(k)*sumx(n)
   76 free=npts-nterms
   77 chisq=chisq/free
   80 return
      end c    determ.fs
c
c    Taken from Bevington - p. 294.
c
c    Purpose:  To calculate the determinant of a square matrix.
c
c    Arguements:
c       array - matrix wose determinant is required
c       norder - order of determinant (degree of matrix)
c
c    Comments:
c       This function destroys the input matrix array
c       Dimension statement valid for norder up to 10
c
      double precision function determ(array,norder)
      implicit double precision (a-h,o-z)
      double precision array,save
      dimension array(10,10)
   10 determ=1.
   11 do 50 k=1,norder
c
c    Interchange columns if diagonal element is zero.
c
      if (array(k,k)) 41,21,41
   21 do 23 j=k,norder
      if (array(k,j)) 31,23,31
   23 continue
      determ=0.
      go to 60
   31 do 34 i=k,norder
      save=array(i,j)
      array(i,j)=array(i,k)
   34 array(i,k)=save
      determ=-determ
c
c    Subtract row k from lower rows to get diagonal matrix.
c
   41 determ=determ*array(k,k)
      if(k-norder) 43,50,50
   43 k1=k+1
      do 46 i=k1,norder
      do 46 j=k1,norder
   46 array(i,j)=array(i,j)-array(i,k)*array(k,j)/array(k,k)
   50 continue
   60 return
      end c    atsul.for
```

```
c
c   This subroutine is used to multiply two matrices. The matrices
c   should be dimension in the calling routine as a(nar,nac), etc.
c   The two matrices to be multiplied are a and b, the answer is in c.
c   If the transpose of a or b is to be taken, itra or itrb is set to 1.
c   m, n and l respectively give the row dimension of a, the row
c   dimension of b and the column dimension of c.
c
        subroutine amul(a,nar,nac,itra,b,nbr,nbc,itrb,c,nrr,ncc,m,n,l)
        implicit double precision (a-h,o-z)
        dimension a(nar,nac),b(nbr,nbc),c(nrr,ncc)
        zero=0d0
        if(itra.eq.0 .and. itrb.eq.0) go to 50
        if(itra.eq.1 .and. itrb.eq.0) go to 15
        if(itra.eq.0 .and. itrb.eq.1) go to 30
        do 10 i=1,m
        do 10 j=1,l
        c(i,j)=zero
        do 10 k=1,n
        c(i,j)=c(i,j)+a(k,i)*b(j,k)
 10     continue
        return
 15     do 20 i=1,m
        do 20 j=1,l
        c(i,j)=zero
        do 20 k=1,n
        c(i,j)=c(i,j)+a(k,i)*b(k,j)
 20     continue
        return
 30     do 40 i=1,m
        do 40 j=1,l
        c(i,j)=zero
        do 40 k=1,n
        c(i,j)=c(i,j)+a(i,k)*b(j,k)
 40     continue
        return
 50     do 60 i=1,m
        do 60 j=1,l
        c(i,j)=zero
        do 60 k=1,n
        c(i,j)=c(i,j)+a(i,k)*b(k,j)
 60     continue
        return
        end
```

```
      SUBROUTINE peaks (X,Y,CQUAD,N,IDEGMN,IDEGMX,NOUT)              MOENT4
      DIMENSION X(N), Y(N), CQUAD(N)                                 MOENT5
      DIMENSION AMOM(4,5), PKEND(4)                                  MOENT6
      DATA RMIN/1.E-2/                                               MOENT7
      NM=MINO(5,IDEGMX-IDEGMN+1)                                     MOENT8
      IF (NM .LT. 1)  RETURN                                         MOENT9
5110  FORMAT (/9X,'TOTAL CURVE',8X,3(19X,'PEAK',I2,9X)/              MOENT0
     1  '  J',3X,'MOMENT(J)',3X,'M(J)/M(J-1)',                       MOENT1
     2  3(11X,'MOMENT(J)',3X,'M(J)/M(J-1)'))                         MOENT2
      WRITE (NOUT,5110) (J,J=1,3)                                    MOENT3
      THRESH=ABS(Y(1))                                               MOENT4
      DO 110 J=2,N                                                   MOENT5
      THRESH=AMAX1(THRESH,ABS(Y(J)))                                 MOENT6
110   CONTINUE                                                       MOENT7
      THRESH=RMIN*THRESH                                             MOENT8
      IPEAK=2                                                        MOENT9
      DO 120 JPEAK=1,4                                               MOENT0
      DO 120 JDEG=1,NM                                               MOENT1
      AMOM(JPEAK,JDEG)=0.                                            MOENT2
120   CONTINUE                                                       MOENT3
      DLAST=Y(2)-Y(1)                                                MOENT4
      DO 150 J=1,N                                                   MOENT5
      PKEND(IPEAK)=X(J)                                              MOENT6
      IF (J.EQ.1 .OR. J.EQ.N)  GO TO 160                             MOENT7
      DNEXT=Y(J+1)-Y(J)                                              MOENT8
      IF (DLAST.LT.-THRESH .AND. DNEXT.GT.THRESH)IPEAK=MINO(IPEAK+1,4)MOENT9
      IF (ABS(DNEXT) .GT. THRESH)  DLAST=DNEXT                       MOENT0
160   IF (IDEGMN.LT.0 .AND. ABS(X(J)).LE.0.)  RETURN                 MOENT1
      TERM=Y(J)*CQUAD(J)                                             MOENT2
      IF(IDEGMN .NE. 0)  TERM=TERM*X(J)**IDEGMN                      MOENT3
      DO 170 JDEG=1,NM                                               MOENT4
      AMOM(IPEAK,JDEG)=AMOM(IPEAK,JDEG)+TERM                         MOENT5
      IF (JDEG .LT. NM)  TERM=TERM*X(J)                              MOENT6
170   CONTINUE                                                       MOENT7
150   CONTINUE                                                       MOENT8
      DO 180 JDEG=1,NM                                               MOENT9
```

```
      DO 180 JPEAK=2,IPEAK
         AMOM(1,JDEG)=AMOM(1,JDEG)+AMOM(JPEAK,JDEG)
 180  CONTINUE
5180  FORMAT (1X,I2,1PE12.4,3E14.4)
      WRITE (NOUT,5180) IDEGMN,(AMOM(J,1),J=1,IPEAK)
      IF (NM .EQ. 1) GO TO 300
      J=IDEGMN
      DO 210 JDEG=2,NM
         J=J+1
         DO 220 JPEAK=1,IPEAK
            IF (ABS(AMOM(JPEAK,JDEG-1)) .GT. 0.) AMOM(JPEAK,JDEG-1)=
     1         AMOM(JPEAK,JDEG)/AMOM(JPEAK,JDEG-1)
 220     CONTINUE
5220     FORMAT (1X,I2,1PE12.4,E14.4,3(E20.4,E14.4))
         WRITE (NOUT,5220) J,(AMOM(JPEAK,JDEG),AMOM(JPEAK,JDEG-1),
     1      JPEAK=1,IPEAK)
 210  CONTINUE
5230  FORMAT (' CURRENT PEAK ENDS AND NEXT PEAK BEGINS AT',
     1   1PE11.3,10X,2(16X,E11.3,7X))
 300  IF (IPEAK .GT. 2) WRITE (NOUT,5230)(PKEND(J),J=2,IPEAK)
      RETURN
      END c     setdls.fs
c
c     This routine sets up the kernel for the dls part of the measurement.
c
      subroutine setdls(a,conver,geom,bins,param,acf,time,iparm,
     +dlsang,tfdls)
      parameter (maxtim=85,maxdls=3,maxrow=400,maxbin=40,maxang=3)
      parameter (maxpar=100)
      implicit double precision (a-h,o-z)
      dimension a(maxrow,maxbin), conver(maxang,maxbin),
     +param(maxpar,maxdls), iparm(maxpar), bins(1),
     +acf(maxtim,maxdls), time(maxtim,maxdls),
     +dum(maxrow,maxbin), geom(maxbin)
      integer dlsang(1)
      logical tfdls(1)
c
      ntime=iparm(1)
      nangs=iparm(2)
      nbins=iparm(3)
c
c     k is index over dls angles, j is index over time, i is index over size bins
c     kk is index over dls angles which are actually being used
c
      kk=0
      do 100 k=1,nangs
         if(tfdls(k)) then
            kk=kk+1
            do 50 j=1,ntime
               gamred=param(9,k)*time(j,k)
               do 40 i=1,nbins
                  gammat=gamred/bins(i)
                  acffit=0.d0
                  if(gammat.lt.1d2) acffit=dexp(-gammat)
                  dum((kk-1)*ntime+j,i)=acffit
                  a((kk-1)*ntime+j,i)=conver(dlsang(k),i)*
     +                (acffit-acf(j,k))/geom(i)
                  a((kk-1)*ntime+j,i)=a((kk-1)*ntime+j,i)/bins(i)**(0)
 40            continue
 50         continue
         endif
 100  continue
c     write(3,430)
c 430 format('q2dt')
c     write(3,*) param(9,2)
c     write(3,460)
c 460 format('acf')
c     write(3,410) (acf(i,2),i=1,100)
c     write(3,440)
c 440 format('Time')
c     write(3,410) (time(i,2),i=1,100)
c     write(3,450)
c 450 format('conversion')
c     write(3,410) (conver(dlsang(2),i),i=1,maxbin)
c     write(3,400)
c 400 format('Fit - meas acf')
c     do 110 j=101,200
c        write(3,420) j
c        write(3,410) (dum(j,i),i=1,25)
c 110 continue
```

```
c    410 format(7e11.3)
c    420 format('Row :',i5)
        return
        end c    weight.fs
c
c    This routine sets the weights of the data points.
c
        subroutine weight(acf,a,b,scale,dlsang,iparam,relwt,relcls,
       +tfdls,tfcls,blines)
        parameter (maxdat=50,maxbin=40,maxang=7,maxtim=85,maxpar=100)
        parameter (maxrow=400,maxdls=3)
        implicit double precision (a-h,o-z)
        double precision acf(maxtim,maxdls),
       +a(maxrow,maxbin), b(maxrow), scale(maxrow), errmin(maxang),
       +varinv, relwt(1), relcls
        integer iparam(maxpar), dlsang(maxang), blines(10,2)
        logical tfdls(1), tfcls c
        varinv(y,err)=(dmax1(y,err))**2/(3d0+y*y)
        augmen=1d0
c       write(3,415) (scale(i),i=1,160)
    415 format(5e15.7)
        nangs=iparam(2)
        nvar=iparam(7)
        ntime=iparam(1)
        nt=ntime
        nrows=iparam(4)
        nsd=iparam(5)
        nangsused=iparam(8)
        ncls=iparam(10)
        ndls=nangsused*ntime
        nbase=iparam(9)
        errcls=1d-2
        write(*,*)ntime
        write(*,*)nt
c
c    Calculate s.d. of last nsd channels to use in weighting.
c
        do 18 k=1,nangs
           sum=0.d0
           do 16 j=nt-nsd+1,nt
              sum=sum+acf(j,k)/acf(1,k)
     16    continue
           sum=sum/nsd
           var=0d0
           do 17 j=nt-nsd+1,nt
              var=var+(acf(j,k)/acf(1,k)-sum)**2
     17    continue
           if(nsd.gt.1) var=var/(nsd-1)
           errmin(k)=dsqrt(var)
     18 continue
c
c    Set DLS point scales weightings based on errors calculated above.
c
        kk=0
        do 50 k=1,nangs
           if(tfdls(k)) then
              err=errmin(k)
              do 40 j=1,ntime
                 acfdum=acf(j,k)/acf(1,k)
                 scale(kk*ntime+j)=scale(kk*ntime+j)*
       +                                          varinv(acfdum,err)
     40       continue
              kk=kk+1
           endif
     50 continue
c
        do 109 i=1,nangsused-1
           do 108 j=1,ntime
              scale(j+i*ntime)=scale(j+i*ntime)*relwt(i)
    108    continue
    109 continue
c
c    Set cls data scale according to scale of 1st acf, then adjust with
c    relcls; weight side angles more heavily.
c
        if(tfcls) then
           compar=scale(1)
           do 100 j=ndls+1,ndls+ncls
              scale(j)=relcls*compar
```

```
100     continue
        do 110 j=2,nbase,2
            do 105 i=ndls+blines(i,1),ndls+blines(i,2)
                scale(i)=scale(i)*augmen
105         continue
110     continue
    endif
c
c   Set up kernel with the new scaling factors.
c
    do 80 j=1,nrows
        b(j)=scale(j)*b(j)
        do 70 i=1,nvar
            a(j,i)=scale(j)*a(j,i)
70      continue
80  continue
    return
    end c   basel.fs
c
c   This routine adjusts the kernel to allow the columns for separate
c   baselines for each dls angle plus baselines for the cls data.
c
    subroutine basel(a,tfdls,tfcls,blines,iparam)
    parameter (maxdat=50,maxbin=40,maxang=7,maxtim=85,maxpar=100)
    parameter (maxrow=400,maxdls=3)
    double precision a(maxrow,maxbin)
    integer blines(10,2), iparam(maxpar)
    logical tfdls(1), tfcls
c
c   Extract parameters from iparam.
c
    nbins=iparam(3)
    nangs=iparam(2)
    nangsused=iparam(8)
    ntime=iparam(1)
    nbase=iparam(9)
    nvar=iparam(7)
c
c   First the dls angles:
c   k is index over dls angles; j is index over dls columns;
c   i is index over time points; kk is index over angles actually used.
c
    kk=0
    do 100 k=1,nangs
        if(tfdls(k)) then
            kk=kk+1
            ifirst=(kk-1)*ntime+1
            ilast=ifirst+ntime-1
            do 50 j=nbins+1,nvar
                if(j-nbins.ne.kk) then
                    do 30 i=ifirst,ilast
                        a(i,j)=0d0
30                  continue
                else
                    do 35 i=ifirst,ilast
                        a(i,j)=1d0
35                  continue
                endif
50          continue
        endif
100 continue
c
c   Now the cls angles.
c
    if(tfcls) then
        do 140 k=1,nbase
            kk=kk+1
            ifirst=nangsused*ntime+blines(k,1)
            ilast=nangsused*ntime+blines(k,2)
            do 130 j=nbins+1,nvar
                if(j-nbins.ne.kk) then
                    do 120 i=ifirst,ilast
                        a(i,j)=0d0
120                 continue
                else
                    do 125 i=ifirst,ilast
                        a(i,j)=1d0
125                 continue
                endif
```

```
130     continue
140   continue
      endif
      return
      end c - pkpos.fs
c
c   This routine computes the peak positions and integrated areas
c   for a histogram.
c
      subroutine pkpos(x,bins,nbins,where,percen,npeaks)
      implicit double precision (a-h,o-z)
      double precision x(1), bins(1), where(1), percen(1)
      integer ichang(25)
c
      ichang(1)=1
      i=2
      do 20 j=2,nbins-1
         if(x(j-1).gt.x(j) .and. x(j).le.x(j+1)) then
            ichang(i)=j
            i=i+1
         endif
20    continue
      ichang(i)=nbins
c
c  Compute peak positions and pecentages.
c
      total=0d0
      do 25 j=1,nbins
         total=total+x(j)
25    continue
      npeaks=i-1
      do 100 k=1,npeaks
         sum=0d0
         pos=0d0
         do 30 j=ichang(k),ichang(k+1)
            sum=sum+x(j)
            pos=pos+x(j)*bins(j)
30       continue
         where(k)=pos/sum
         percen(k)=sum/total
100   continue
      return
      end c   hstbin.fs
c
c   This routine sets up exponentially spaced histogram size bins
c   given the maximum and minimum sizes, and number of bins.
c
      subroutine hstbin(sizmax,sizmin,nbins,x)
      implicit double precision (a-h,o-z)
      dimension x(1)

sizfac=exp(dlog(sizmax/sizmin)/(nbins-1))
      x(1)=sizmin
      do 10 j=2,nbins
         x(j)=x(j-1)*sizfac
10    continue
      return
      end c   calcmo.fs
c
c   This routine calulates the 1st and 2nd inverse moments and the
c   first moment of a set of data weighted by the vector 'weight'.
c   The data and abscissa are in the n-vectors x and bins respectively.
c   The 1st and 2nd inverse moments
c   and the first moment are returned as u1, u2 and u3 respectively.
c   In the special case of unity weights, the input parameter isu should
c   be set to 1.
c
      subroutine calcmo(bins,x,weight,n,isu,u1,u2,u3)
      implicit double precision (a-h,o-z)
      dimension x(1), weight(1), bins(1)
      u1=0.d0
      u2=0.d0
      u3=0.d0
      sum=0.d0
      do 130 i=1,n
```

```
          if(isw.eq.1) then
              amount=x(i)
          else
              amount=x(i)*weight(i)
          endif
          u1=u1+amount*1.d0/bins(i)
          u2=u2+amount*1.d0/bins(i)**2
          u3=u3+amount*bins(i)
          sum=sum+amount
130   continue
      u1=u1/sum
      u2=u2/sum-u1*u1
      u1=1.d0/u1
      u3=u3/sum
      return
      end
```

```
c   dlsint.fs
c
c   This routine sets up the kernel for the dls individual angle
c   intensity calculation.
c
      subroutine dlsint(a,bins,param,time,iparam,sup)
      parameter (maxtim=85,maxdls=3,maxrow=400,maxbin=40,maxang=7)
      parameter (maxpar=100)
      implicit double precision (a-h,o-z)
      dimension a(maxrow,maxbin),
     +param(maxpar), iparam(maxpar), bins(1),
     +acf(maxtim), time(maxtim)
c
      ntime=iparam(1)
      nangs=iparam(2)
      nbins=iparam(3)
c
c   k is index over dls angles, j is index over time, i is index over size bins
c
      do 50 j=1,ntime
         gamred=param(9)*time(j)
         do 40 i=1,nbins
            gammat=gamred/bins(i)
            acffit=0.d0
            if(gammat.lt.1d2) acffit=dexp(-gammat)
            a(j,i)=acffit
40       continue
         a(j,nbins+1)=1d0
50    continue
      return
      end
```

```
c   sinang.fs
c
c   This subroutine calculates the intensity histogram from the
c   measured acf at a single angle.
c
      subroutine sinang(acf,time,param,iparam,a,x,bins,scale,sup,sum)
      parameter (maxdat=50,maxbin=40,maxang=7,maxtim=85,maxpar=100)
      parameter (maxrow=400,maxdls=3)
      implicit double precision (a-h,o-z)
      dimension acf(1), time(1), param(1), iparam(1), x(1), bins(1),
     +b(maxrow), u(maxrow), zz(maxrow), where(10), percen(10),
     +a(maxrow,maxbin), index(maxbin), scale(1)
c
      range=1d60
      ntime=iparam(1)
      nangs=iparam(2)
      nbins=iparam(3)+1
c   Extra bin for baseline channel.
c
c   Set up kernel and measurement vector.
c
      call dlsint(a,bins,param,time,iparam,sup)
      do 10 j=1,ntime
         b(j)=acf(j)
         a(j,nbins)=1d0
10    continue
c
c   Weight the kernel and measurement vector.
c
      call sinwei(acf,a,b,scale,iparam)
c
c   Find solution; return sum of xi to asin for normaization.
c
```

```
c         open(20,file='kern2',status='new')
c         write(20,502) ((a(i,j),i=1,ntime),j=1,nbins)
c 502 format(4e18.9)
c         close(20)
      call nnls(a,maxrow,ntime,nbins,b,x,rnorm,w,zz,index,mode,range)
      sum=0d0
      do 30 j=1,nbins
         sum=sum+x(j)
  30  continue
c
c  Find and print out peaks.
c
      call pkpos(x,bins,nbins-1,where,percen,npeaks)
      write(3,400)
 400  format('Single angle intensity peaks.')
      do 50 j=1,npeaks
         write(3,410) j,where(j),percen(j)
         write(x,410) j,where(j),percen(j)
 410     format(i4,2f10.2)
  50  continue
      return
      end c  sinwei.fs
c
c  This routine sets the weights of the data points.
c
      subroutine sinwei(acf,a,b,scale,iparam)
      parameter (maxdat=50,maxbin=40,maxang=7,maxtim=85,maxpar=100)
      parameter (maxrow=400,maxdls=3)
      implicit double precision (a-h,o-z)
      double precision acf(maxtim),
     +a(maxrow,maxbin), b(maxrow), scale(maxrow),
     +varinv
      integer iparam(maxpar)

varinv(y,err)=(dmax1(y,err))**2/(1d0+y*y)
c     write(3,415) (scale(i),i=1,140)
 415  format(5e15.7)
      nbins=iparam(3)+1
      ntime=iparam(1)
      nt=ntime
      nrows=iparam(4)
      nsd=iparam(5)
      errcls=1d-2
c     write(x,x)ntime
c     write(x,x)nt
c
c  Calculate s.d. of last nsd channels to use in weighting.
c
      sum=0.d0
      do 16 j=nt-nsd+1,nt
         sum=sum+acf(j)/acf(1)
  16  continue
      sum=sum/nsd
      var=0d0
      do 17 j=nt-nsd+1,nt
         var=var+(acf(j)/acf(1)-sum)**2
  17  continue
      if(nsd.gt.1) var=var/(nsd-1)
      err=dsqrt(var)
c
      do 80 j=1,ntime
         acfdum=acf(j)/acf(1)
         scalej=scale(j)*varinv(acfdum,err)
         b(j)=scalej*b(j)
         do 70 i=1,nbins
            a(j,i)=scalej*a(j,i)
  70     continue
  80  continue
      return
      end c  fit.fs
c
c  This routine calculates the fit acf and fit cls data for use in
c  visualizing how good the fit to the measured data is.
c
      subroutine fit(a,x,conver,geom,acf,cls,tfdls,tfcls,iparam,dlsang,
     +scale)
      parameter (maxdat=50,maxbin=40,maxang=3,maxtim=85,maxpar=100)
      parameter (maxrow=400,maxdls=3,maxcls=100)
```

```
      implicit double precision (a-h,o-z)
      double precision a(maxrow,maxbin), x(maxbin),
     +conver(maxang,maxbin), geom(maxbin), acf(maxtim,maxang),
     +xhat(maxtim,maxang), anorm(maxang), cls(maxcls), scale(1)
      logical tfdls(1), tfcls
      integer iparam(maxpar), dlsang(maxang)
c
c     Globals: unload iparam.
c
      ichan1=16
      ichan2=17
      ntime=iparam(1)
      nbins=iparam(3)
      nangs=iparam(2)
      nangsused=iparam(8)
      ncls=iparam(10)
      nrows=iparam(4)
      nvar=iparam(7)
      ndls=iparam(6)
c
c     Convert x to intensity distributions at each dls angle.
c
      open(ichan1,file='fit',status='new')
      open(ichan2,file='measured',status='new')
      write(ichan1,*) nrows
      write(ichan2,*) nrows
      do 20 k=1,nangs
         anorm(k)=0d0
         do 10 i=1,nbins
            xhat(i,k)=x(i)*conver(dlsang(k),i)/geom(i)
            anorm(k)=anorm(k)+xhat(i,k)
10       continue
20    continue
c
c     Calculate the fit acfs.
c
      irow=1
      kk=0
      do 40 k=1,nangs
         if(tfdls(k)) then
            resid=0d0
            wresid=0d0
            do 30 j=1,ntime
               sum=0d0
               do 25 i=1,nbins
                  if(xhat(i,k).gt.0d0) then
                     sum=sum+xhat(i,k)*(acf(j,k)+a(kk*ntime+j,i)*
     +                   geom(i)/conver(dlsang(k),i))
                  endif
25             continue
               do 27 i=nbins+1,nvar
                  if(x(i).gt.0d0) sum=sum+x(i)*a(j,i)
27             continue
               sum=sum/anorm(k)
               write(ichan1,*) irow, sum
               write(ichan2,*) irow, acf(j,k)
               irow=irow+1
               resid=resid+(sum-acf(j,k))**2
               wresid=wresid+(sum-acf(j,k))**2*scale(kk*ntime+j)
30          continue
            kk=kk+1
            print *,'Sum of squared residuals= ',resid,wresid
            resid=dsqrt(resid/ntime)
            wresid=dsqrt(wresid/ntime)
            print *,'Root mean squared residual= ',resid,wresid
         endif
40    continue
c
c     Now the cls fit data.
c
      if(tfcls) then
         resid=0d0
         wresid=0d0
         do 100 j=ndls+1,nrows
            sum=0d0
            do 80 i=1,nbins
               if(x(i).gt.0d0) sum=sum+x(i)*a(j,i)
80          continue
            do 90 i=nbins+1,nvar
               if(x(i).gt.0d0) sum=sum+x(i)*a(j,i)
90          continue
            write(ichan1,*) irow, sum
```

```
                 clsmeas=cls(j-ndls)
                 write(ichan2,*) irow, clsmeas
                 resid=resid+(sum-clsmeas)**2
                 uresid=uresid+(sum-clsmeas)**2*scale(j)
                 irow=irow+1
 100       continue
           print *,'Sum of squared residuals= ',resid,uresid
           resid=dsqrt(resid/ncls)
           uresid=dsqrt(uresid/ncls)
           print *,'Root mean squared residual= ',resid,uresid
       endif
       close(ichan1)
       close(ichan2)
       return
       end c   readpd.fs
c
c   This subroutine reads data sets in the format output by the program
c   TIGELS/LPA (pddata data sets).
c
c       chan: channel number assigned to file
c       nds:  data set number within file
c       x:    photodetetor number
c       y:    photodetector reading
c
        subroutine readpd(chan, nds, y, ndect)
        double precision y(1)
        integer chan, nds
        character*70 line
        character*5 match
        data match /'100 A'/
c
c   Globals.
c
        nummat=5
c
c   Position read pointer at correct place in file.
c
        do 10 ids=1,nds
 5          read(chan,410) line
 410        format(a70)
            if(index(line,match).eq.0) go to 5
 10     continue
c
c   Read data.
c
        do 20 j=1,ndect
            read(chan,*) idect, y(j)
 20     continue
        return
        end c   parse.fs
c
c   This subroutine searches a string for the nth field and returns that
c   (ASCII) string right justified in an output string.
c   If fewer than nthfield fields are found, ierr=-1, otherwise ierr=1.
c
        subroutine parse(stringin, stringout, nthfield, nchar, ierr)
        parameter (strlen=80)
        character*80 stringin, stringout
        integer last(strlen), first(strlen)
c
        ierr=1
        kfirst=0
        klast=0
        if(stringin(1:1).ne.' ') then
            kfirst=kfirst+1
            first(kfirst)=1
        endif
        do 10 j=2,strlen-1
            if(stringin(j:j).eq.' '.and. stringin(j+1:j+1).ne.' ') then
                kfirst=kfirst+1
                first(kfirst)=j+1
            endif
            if(stringin(j:j).ne.' '.and. stringin(j+1:j+1).eq.' ') then
                klast=klast+1
                last(klast)=j
            endif
```

```
   10 continue
      if(nthfield.gt.klast .or. nthfield.gt.kfirst) then
         ierr=-1
         return
      endif
      nchar=last(nthfield)-first(nthfield)+1
      do 20 j=1,80
         stringout(j:j)=' '
   20 continue
      k=1
      do 30 j=first(nthfield),last(nthfield)
         jj=strlen-nchar+k
         stringout(jj:jj)=stringin(j:j)
         k=k+1
   30 continue
      return
      end c+++++++++++++++ double precision version 2dp (aug 1982) ++++++++++++++
c     subroutine nnls  (a,ada,m,n,b,x,rnorm,w,zz,index,mode,range)
c     based on c.l.lawson and r.j.hanson,
c     'solving least squares problems', prentice-hall, 1974
c
c     xxxxxxxxx    nonnegative least squares    xxxxxxxxx
c
c     given an m by n matrix, a, and an m-vector, b, compute an
c     n-vector, x, which solves the least squares problem
c
c              a * x = b  subject to x .ge. 0
c
c     a(),ada,m,n    ada is the first dimensioning parameter for the
c                    array, a().  on entry a() contains the m by n
c                    matrix, a.     on exit a() contains
c                    the product matrix, q*a , where q is an
c                    m by m orthogonal matrix generated implicitly by
c                    this subroutine.
c     b()            on entry b() contains the m-vector, b.  on exit b() con-
c                    tains q*b.
c     x()            on entry x() need not be initialized.  on exit x() will
c                    contain the solution vector.
c     rnorm          on exit rnorm contains the euclidean norm of the
c                    residual vector.
c     w()            an n-array of working space.  on exit w() will contain
c                    the dual solution vector.  w will satisfy w(i) = 0.
c                    for all i in set p  and w(i) .le. 0. for all i in set z
c     zz()           an m-array of working space.
c     index()        an integer working array of length at least n.
c                    on exit the contents of this array define the sets
c                    p and z as follows..
c
c                    index(1)   thru index(nsetp) = set p.
c                    index(iz1) thru index(iz2)   = set z.
c                    iz1 = nsetp + 1 = npp1
c                    iz2 = n
c     mode           this is a success-failure flag with the following
c                    meanings.
c               1    the solution has been computed successfully.
c               2    the dimensions of the problem are bad.
c                    either m .le. 0 or n .le. 0.
c               3    iteration count exceeded.  more than 3*n iterations.
c
c     range is 2 or 3 orders of magnitude smaller than big, where big is
c         the largest number that does not overflow and 1/big does not
c         underflow. for the double precision version, big and range
c         are in double precision. for the single precision version,
c         they are in single precision (and therefore range=srange).
c-----------------------------------------------------------------------
c     calls subprograms - diff, h12, g1, g2
c-----------------------------------------------------------------------
      subroutine nnls (a,ada,m,n,b,x,rnorm,w,zz,index,mode,range)
      double precision a, alpha, asave, b, cc, diff, dummy,
     1 factor, range, rnorm, sm, ss, t, two, unorm, up, w,
      double precision wmax, x, zero, ztest, zz, quant, quant2
      double precision dv
      dimension a(ada,n), b(m), x(n), w(n), zz(m)
      integer index(n)
x     print *,' Entering nnls.'
      zero=0.d0
      two=2.d0
      factor=1.d-4
      szero = 0.
```

```
      mode=1
      if (m.gt.0.and.n.gt.0) go to 10
      mode=2
      return
   10 iter=0
      itmax=3*n
c
c                 initialize the arrays index() and x().
c
      do 20 i=1,n
      x(i)=zero
   20 index(i)=i
c
      iz2=n
      iz1=1
      nsetp=0
      npp1=1
c                     xxxxxx  main loop begins here   xxxxxx
   30 continue
x     print x,' start of main loop inside nnls, iter= ',iter
x     do 1 inoc=1,nsetp
x     print x,index(inoc), x(index(inoc))
x   1 continue
c                 quit if all coefficients are already in the solution,
c                 or if m cols of a have been triangularized.
c
      if (iz1.gt.iz2.or.nsetp.ge.m) go to 350
c
c     compute components of the dual (negative gradient) vector w().
c
      do 50 iz=iz1,iz2
      j=index(iz)
      sm=zero
         do 40 l=npp1,m
   40    sm=sm+a(l,j)*b(l)
   50 w(j)=sm
c                                 find largest positive w(j).
   60 wmax=zero c++++++++++++++++++ double precision version 2dp (aug 1982) ++++++++++++++++
c.    subroutine nnls  (a,mda,m,n,b,x,rnorm,w,zz,index,mode,range)
c     based on c.l.lawson and r.j.hanson,
c     'solving least squares problems', prentice-hall, 1974
c
c     xxxxxxxxxx   nonnegative least squares   xxxxxxxxxx
c
c     given an m by n matrix, a, and an m-vector, b, compute an
c     n-vector, x, which solves the least squares problem
c
c                   a * x = b  subject to x .ge. 0
c
c     a(),mda,m,n   mda is the first dimensioning parameter for the
c                   array, a().  on entry a() contains the m by n
c                   matrix, a.           on exit a() contains
c                   the product matrix, q*a , where q is an
c                   m by m orthogonal matrix generated implicitly by
c                   this subroutine.
c     b()       on entry b() contains the m-vector, b.  on exit b() con-
c               tains q*b.
c     x()       on entry x() need not be initialized.  on exit x() will
c               contain the solution vector.
c     rnorm     on exit rnorm contains the euclidean norm of the
c               residual vector.
c     w()       an n-array of working space.  on exit w() will contain
c               the dual solution vector.  w will satisfy w(i) = 0.
c               for all i in set p  and w(i) .le. 0. for all i in set z
c     zz()      an m-array of working space.
c     index()   an integer working array of length at least n.
c               on exit the contents of this array define the sets
c               p and z as follows..
c
c               index(1)   thru index(nsetp) = set p.
c               index(iz1) thru index(iz2)   = set z.
c               iz1 = nsetp + 1 = npp1
c               iz2 = n
c     mode      this is a success-failure flag with the following
c               meanings.
c               1     the solution has been computed successfully.
c               2     the dimensions of the problem are bad.
c                     either m .le. 0 or n .le. 0.
c               3     iteration count exceeded.  more than 3*n iterations.
```

```
c    range is 2 or 3 orders of magnitude smaller than big, where big is
c       the largest number that does not overflow and 1/big does not
c       underflow.  for the double precision version, big and range
c       are in double precision.  for the single precision version,
c       they are in single precision (and therefore range=srange).
c-------------------------------------------------------------------
c    calls subprograms - diff, h12, g1, g2
c-------------------------------------------------------------------
      subroutine nnls (a,ada,m,n,b,x,rnorm,w,zz,index,mode,range)
      double precision a, alpha, asave, b, cc, diff, dummy,
     1 factor, range, rnorm, sm, ss, t, two, unorm, up, w
      double precision wmax, x, zero, ztest, zz, quant, quant2
      double precision dv
      dimension a(ada,n), b(m), x(n), w(n), zz(m)
      integer index(n)
x     print *,' Entering nnls.'
      zero=0.d0
      two=2.d0
      factor=1.d-4
      szero = 0.
c
      mode=1
      if (m.gt.0.and.n.gt.0) go to 10
      mode=2
      return
   10 iter=0
      itmax=3*n
c
c                    initialize the arrays index() and x().
c
      do 20 i=1,n
      x(i)=zero
   20 index(i)=i
c
      iz2=n
      iz1=1
      nsetp=0
      npp1=1
c                           xxxxxx main loop begins here  xxxxxx
   30 continue
x     print *,' start of main loop inside nnls, iter= ',iter
x     do 1 inoc=1,nsetp
x     print *,index(inoc), x(index(inoc))
x  1  continue
c                  quit if all coefficients are already in the solution.
c                    or if m cols of a have been triangularized.
c
      if (iz1.gt.iz2.or.nsetp.ge.m) go to 350
c
c          compute components of the dual (negative gradient) vector w().
c
      do 50 iz=iz1,iz2
      j=index(iz)
      sm=zero
         do 40 l=npp1,m
   40    sm=sm+a(l,j)*b(l)
   50 w(j)=sm
c                               find largest positive w(j).
   60 wmax=zero
      do 70 iz=iz1,iz2
      j=index(iz)
      if (w(j).le.wmax) go to 70
      wmax=w(j)
      izmax=iz
   70 continue
c
c          if wmax .le. 0. go to termination.
c          this indicates satisfaction of the kuhn-tucker conditions.
c
c5080 format(1x,'wmax ',d12.2)
      if (wmax.le.zero) go to 350
   80 iz=izmax
      j=index(iz)
c
c    the sign of w(j) is ok for j to be moved to set p.
c    begin the transformation and check new diagonal element to avoid
c    near linear dependence.
c
      asave=a(npp1,j)
      npp2=npp1+1
```

```
      call h12 (1,npp1,npp2,a,a(1,j),1,up,dummy,1,1,0,range)
      unorm=zero
      if (nsetp.eq.0) go to 100
         do 90 l=1,nsetp
 90      unorm=unorm+a(l,j)**2
      unorm=dsqrt(unorm)

c100  if (diff(unorm+abs(a(npp1,j))*factor,unorm)) 130,130,110
 100  quant  = unorm+dabs(a(npp1,j))*factor
      quant2 = quant - unorm
      if (quant2.le.zero) go to 130
cc    if (diff(quant,unorm).le.zero) go to 130
c
c     col j is sufficiently independent.  copy b into zz, update zz and
c     solve for ztest ( = proposed new value for x(j) ).
c
 110     do 120 l=1,m
 120     zz(l)=b(l)
      npp2=npp1+1
      call h12 (2,npp1,npp2,a,a(1,j),1,up,zz,1,1,1,range)
cxx   if (a(npp1,j) .eq. zero) go to 500
      ztest=zz(npp1)/a(npp1,j)
c
c                                      see if ztest is positive
c     reject j as a candidate to be moved from set z to set p,
c     restore a(npp1,j), set w(j)=0., and loop back to test dual
c
cx    if (ztest) 130,130,140
      if (ztest.gt.zero) go to 140
c
c     coeffs again.
c
 130  a(npp1,j)=asave
      w(j)=zero
      go to 60
c
c     the index  j=index(iz)  has been selected to be moved from
c     set z to set p.   update b, update indices, apply householder
c     transformations to cols in new set z,  zero subdiagonal elts in
c     col j, set w(j)=0.
c
 140     do 150 l=1,m
 150     b(l)=zz(l)

index(iz)=index(iz1)
      index(iz1)=j
      iz1=iz1+1
      nsetp=npp1
      npp1=npp1+1 if (iz1.gt.iz2) go to 170
         do 160 jz=iz1,iz2
         jj=index(jz)
 160     call h12 (2,nsetp,npp1,a,a(1,j),1,up,a(1,jj),1,mda,1,range)
 170  continue if (nsetp.eq.m) go to 190
         do 180 l=npp1,m
 180     a(l,j)=zero
 190  continue w(j)=zero
c                              solve the triangular system.
c                              store the solution temporarily in zz().
c
c     the following block of code is used as an internal subroutine
c     to solve the triangular system, putting the solution in zz().
c
 400     do 430 l=1,nsetp
         ip=nsetp+1-l
         if (l.eq.1) go to 420
            do 410 ii=1,ip
 410        zz(ii)=zz(ii)-a(ii,jj)*zz(ip+1)
 420     jj=index(ip)
cxx      if (a(ip,jj) .eq. zero) go to 500
 430     zz(ip)=zz(ip)/a(ip,jj)
c
c                    xxxxxx  secondary loop begins here  xxxxxx
c
c                         iteration counter.
```

```
  210 iter=iter+1
c*       write(6,5010) (zz(ip),ip=1,nsetp)
c5010    format(1x,5d12.2/5d12.2/5d12.2/5d12.2)
      if (iter.le.itmax) go to 220
      mode=3
      go to 350
  220 continue
c
c                      see if all new constrained coeffs are feasible.
c                            if not compute alpha.
c
      alpha=two
          do 240 ip=1,nsetp
          l=index(ip)
          if (zz(ip) .gt. zero) go to 240
c
  230     t=-x(l)/(zz(ip)-x(l))
          if (alpha.le.t) go to 240
          alpha=t
          jj=ip
  240     continue
c
c         if all new constrained coeffs are feasible then alpha will
c         still = 2.   if so exit from secondary loop to main loop.
c
      if (alpha.eq.two) go to 330
c
c         otherwise use alpha which will be between 0. and 1. to
c         interpolate between the old x and the new zz.
c
          do 250 ip=1,nsetp
          l=index(ip)
          x(l)=x(l)+alpha*(zz(ip)-x(l))
  250     continue
c
c         modify a and b and the index arrays to move coefficient i
c         from set p to set z.
c
      i=index(jj)
  260 x(i)=zero
c
      if (jj.eq.nsetp) go to 290
      jj=jj+1
          do 280 j=jj,nsetp
          k=j-1
          ii=index(j)
          index(k)=ii
          call g1 (a(k,ii),a(j,ii),cc,ss,a(k,ii))
          a(j,ii)=zero
              do 270 l=1,n
              if (l.ne.ii) call g2 (cc,ss,a(k,l),a(j,l))
  270         continue
  280     call g2 (cc,ss,b(k),b(j))
  290 npp1=nsetp
      nsetp=nsetp-1
      iz1=iz1-1
      index(iz1)=i
c
c         see if the remaining coeffs in set p are feasible.  they should
c         be because of the way alpha was determined.
c         if any are infeasible it is due to round-off error.  any
c         that are nonpositive will be set to zero
c         and moved from set p to set z.
c
          do 300 jj=1,nsetp
          i=index(jj)
          if (x(i) .le. zero) go to 260
  300     continue
c
c         copy b( ) into zz( ).  then solve again and loop back.
c
          do 310 i=1,m
  310     zz(i)=b(i)
      go to 400
c                         ****** end of secondary loop ******
c
  330     do 340 ip=1,nsetp
          i=index(ip)
  340     x(i)=zz(ip)
c         all new coeffs are positive.  loop back to beginning.
      go to 30
```

```
c
c                    xxxxx  end of main loop  xxxxx
c
c                    come to here for termination.
c                    compute the norm of the final residual vector.
c
  350 sm=zero
      if (npp1.gt.m) go to 370
          do 360 i=npp1,m
  360     sm=sm+b(i)**2
      go to 390
  370     do 380 j=1,n
  380     w(j)=zero
  390 rnorm=dsqrt(sm)
      return
cxx500  mode = 5
cxx     return
      end
c+++++++++++++++++ double precision version 2dp (aug 1982) ++++++++++++++++
c     subroutine h12 (mode,lpivot,l1,m,u,iue,up,c,ice,icv,ncv,range)
c     based on c.l.lawson and r.j.hanson,
c     'solving least squares problems', prentice-hall, 1974
c
c     construction and/or application of a single
c     householder transformation..    q = i + u*(u**t)/b
c
c     mode    = 1 or 2   to select algorithm  h1  or  h2 .
c     lpivot is the index of the pivot element.
c     l1,m   if l1 .le. m   the transformation will be constructed to
c            zero elements indexed from l1 through m.   if l1 gt. m
c            the subroutine does an identity transformation.
c     u(),iue,up    on entry to h1 u() contains the pivot vector.
c                   iue is the storage increment between elements.
c                                       on exit from h1 u() and up
c                   contain quantities defining the vector u of the
c                   householder transformation.   on entry to h2 u()
c                   and up should contain quantities previously computed
c                   by h1.  these will not be modified by h2.
c     c()    on entry to h1 or h2 c() contains a matrix which will be
c            regarded as a set of vectors to which the householder
c            transformation is to be applied.  on exit c() contains the
c            set of transformed vectors.
c     ice    storage increment between elements of vectors in c().
c     icv    storage increment between vectors in c().
c     ncv    number of vectors in c() to be transformed. if ncv .le. 0
c            no operations will be done on c().
c     range is 2 or 3 orders of magnitude smaller than big, where big is
c            the largest number that does not overflow and 1/big does not
c            underflow.  for the double precision version, big and range
c            are in double precision.  for the single precision version,
c            they are in single precision (and therefore range=srange).
c
      subroutine h12 (mode,lpivot,l1,m,u,iue,up,c,ice,icv,ncv,orange)
c
      dimension u(iue,1), c(m)
      double precision sm,b,range,precis,ulp,term,zero
      double precision c, cl, clinv, one, orange, rangin, sm1, u, up
      rangin=1.d-200
      one=1.d0
      zero = 0.d0
c
      if (0.ge.lpivot.or.lpivot.ge.l1.or.l1.gt.m) return
      ulp = u(1,lpivot)
      cl=dabs(ulp)
      if (mode.eq.2) go to 60
c                               xxxxx construct the transformation. xxxxx
          do 10 j=l1,m
      absu=dabs(u(1,j))
   10 if (cl .lt. absu) cl=absu
      if (cl .le. rangin) go to 130
      clinv=one/cl
cx    sm=(u(1,lpivot)*clinv)**2
      sm=ulp*clinv
      sm=sm*sm
          do 30 j=l1,m
          term=u(1,j)*clinv
cx 30     sm=sm+(u(1,j)*clinv)**2
   30     sm=sm+term*term
c                             convert double prec. sm to sngl. prec. sm1
cx    sm1=sm
cx    cl=-sign(cl*sqrt(sm1),u(1,lpivot))
cx
```

```
            cl=cl*dsqrt(sa)
            if (ulp.gt.rangin) cl=-cl
c
            up=ulp-cl
            u(1,lpivot)=cl
            ulp=cl
            go to 70
c                 ***** apply the transformation i+u*(u**t)/b to c. *****
c
   60 if (cl .le. rangin) go to 130
   70 if (ncv.le.0) return
            b=up*ulp
c                          b must be nonpositive here. if b = 0., return.
c
            if (b .ge. -rangin) go to 130
            b=one/b
            i2=1-icv+ice*(lpivot-1)
            incr=ice*(l1-lpivot)
                 do 120 j=1,ncv
                 i2=i2+icv
                 i3=i2+incr
                 i4=i3
                 sm=c(i2)*up
                      do 90 i=l1,m
                      sm=sm+c(i3)*u(1,i)
   90                 i3=i3+ice
                 if (sm.eq.zero) go to 120
  100            sm=sm*b
                 c(i2)=c(i2)+sm*up
                      do 110 i=l1,m
                      c(i4)=c(i4)+sm*u(1,i)
  110                 i4=i4+ice
  120            continue
  130 return
      end
c++++++++++++++++ double precision version 2dp (aug 1982) ++++++++++++++++
c     subroutine g1.
      subroutine g1 (a,b,cos,sin,sig)
c     based on c.l.lawson and r.j.hanson,
c     'solving least squares problems', prentice-hall, 1974
c
c
c     compute orthogonal rotation matrix..
c     compute.. matrix  (c, s) so that (c, s)(a) = (sqrt(a**2+b**2))
c                       (-s,c)        (-s,c)(b)   (     0          )
c     compute sig = sqrt(a**2+b**2)
c          sig is computed last to allow for the possibility that
c          sig may be in the same location as a or b .
c
      double precision a, abs, b, cos, one, sig, sign, sin, sqrt,
     1 xr, yr, zero
      abs(a)=dabs(a)
      sqrt(a)=dsqrt(a)
      sign(a,b)=dsign(a,b)
c     zero=0.e0!sp
      zero=0.d0
c     one=1.e0!sp
      one=1.d0
      if (abs(a).le.abs(b)) go to 10
      xr=b/a
      yr=sqrt(one+xr*xr)
      cos=sign(one/yr,a)
      sin=cos*xr
      sig=abs(a)*yr
      return
   10 if (b) 20,30,20
   20 xr=a/b
      yr=sqrt(one+xr*xr)
      sin=sign(one/yr,b)
      cos=sin*xr
      sig=abs(b)*yr
      return
   30 sig=zero
      cos=zero
      sin=one
      return
      end
c++++++++++++++++ double precision version 2dp (aug 1982) ++++++++++++++++
c     subroutine g2.
      subroutine g2     (cos,sin,x,y)
c     based on c.l.lawson and r.j.hanson,
c     'solving least squares problems', prentice-hall, 1974
```

```
c          apply the rotation computed by g1 to (x,y).
           double precision cos, sin, x, xr, y
           xr=cos*x+sin*y
           y=-sin*x+cos*y
           x=xr
           return
           end
c++++++++++++++++++ double precision version 2dp (aug 1982) ++++++++++++++
c     function diff.
c          based on c.l.lawson and r.j.hanson,
c          'solving least squares problems', prentice-hall, 1974
```

What is claimed is:

1. A system for measuring the size distribution $v(r)$ of particles dispersed in a fluid sample, where r is representative of particle size, comprising:
   A. illumination means for illuminating said sample with a light beam directed along an input axis,
   B. detector means for detecting the intensity of light scattered from said light beam by said sample for m measurements made under an associated one of a set of m measurement conditions, and for n measurements made under an associated one of a set of n measurement conditions, where m is an integer equal to or greater than one, and n is an integer equal to or greater than zero, and the sum of m and n is equal to or greater than two, and at least two of said m+n measurement conditions are different, said detector means further including:
      i. means for generating m intensity signals, each of said intensity signals being representative of the detected intensity of said scattered light as a function of time under a corresponding one of the measurement conditions of said set of m measurement conditions,
      ii. means for generating n average signals, each of said n average signals being representative of the average intensity of said scattered light detected under a corresponding one of the measurement conditions of said set of n measurement conditions,
   C. autocorrelation means for generating m correlation signals, each of said correlation signals being representative of the autocorrelation function of a corresponding one of said intensity signals and being equal to an associated transformation of said distribution $v(r)$,
   D. size processing means responsive to said correlation signals and said average signals, including:
      i. preprocessor means responsive to said m correlation signals for generating a composite correlation signal,
      ii. means for generating a composite scattered light signal from said composite correlation signal and said n average signals
      iii. means for determining a composite transformation operator $J^{-1}$ related to said associated transformations and said n average signals,
      iv. means for transforming said composite scattered light signal in accordance with said determined composite transformation operator $J^{-1}$ to generate a size distribution signal representative of said distribution $v(r)$, and
   E. means for controlling said m+n measurement conditions whereby said intensity signals are mutually independent and said average signals are mutually independent.

2. A system according to claim 1 wherein said preprocessor means includes:
   i. means responsive to said m correlation signals for generating m moment signals, said m moment signals being representative of at least one of the moments of each of said m correlation signals other than the zero$^{th}$ moments of said m correlation signals,
   ii. means for generating a weighted direct sum signal, said weighted sum signal being representative of the direct sum of said m moment signals and corresponding to said composite correlation signal.

3. A system according to claim 2 wherein said means for generating said composite scattered light signal includes means for generating the direct sum of said composite correlation signal and said n average signals, said direct sum corresponding to said composite scattered light signal.

4. A system according to claim 1 wherein said preprocessor means includes:
   i. means responsive to said m correlation signals for generating m unity normalized correlation signals, each of said unity normalized correlation signals being representative of the unity normalized form of the corresponding one of said m correlation signals,
   ii. means for generating a direct sum signal, said sum signal being representative of the direct sum of said unity normalized correlation signals, and corresponding to said composite correlation signal.

5. A system according to claim 4 wherein said means for generating said composite scattered light signal includes means for generating the direct sum of said composite correlation signal and said n average signals, said direct sum corresponding to said composite scattered light signal.

6. A system according to claim 1 wherein said preprocessor includes:
   i. means for generating a direct sum signal, said sum signal being representative of the direct sum of said m correlation signals and corresponding to said composite correlation signal.

7. A system according to claim 6 wherein said means for generating said composite scattered light signal includes means for generating the direct sum of said composite correlation signal and said n average signals, said direct sum corresponding to said composite scattered light signal.

8. A system according to claim 1 wherein said illumination means includes means for directly illuminating said m points with a portion of said light beam.

9. A system according to claim 1 wherein said illumination means includes means for preventing any of said beam from directly illuminating any of said m points.

10. A system according to claim 1 wherein said autocorrelation means includes an autocorrelator means for generating said m correlation signals as time domain autocorrelation signals $g_i(t)$ where t is time and $i=1, \ldots, m$, each of said m autocorrelation signals corresponding to the autocorrelation of a corresponding one of said m intensity signals.

11. A system according to claim 1 wherein said autocorrelation means includes a power spectrum means for generating said m correlation signal as frequency domain power spectrum signals $G_i(f)$ where f is frequency and $i=1,\ldots,m$, each of said m power spectrum signals corresponding to the power spectrum of a corresponding one of said m intensity signals.

12. A system according to claim 1 wherein said associated transformations are linear transformations and wherein said composite transformation operator $J^{-1}$ is the generalized inverse of the operator corresponding to the direct sum of the operators for said associated transformations.

13. A system according to claim 12 wherein said inverse transformation operator $J^{-1}$ corresponds to the inverse of the matrix corresponding to the direct sum of the matrices of said associated transformations.

14. A system according to claim 12 wherein said inverse tranformation operator $J^{-1}$ corresponds to $[J^tJ+\alpha H]^{-1}J^t$ where J is the matrix corresponding to the direct sum of the matrices corresponding to said associated transformations, $J^t$ is the transpose of the matrix J, H is a conditioning matrix, and alpha ($\alpha$) is a smoothing parameter.

15. A system according to claim 12 wherein said inverse transformation operator $J^{-1}$ corresponds to $[J^tJ+\alpha H]^{-1}J^t$ where J is the matrix corresponding the direct sum of the matrices corresponding to said associated tranformations, $J^t$ is the transpose of the matrix J, H is a conditioning matrix, and alpha ($\alpha$) is a smoothing parameter and where all components of the vector representative of said distribution function v(r) are constrained to be greater than or equal to zero.

16. A system according to claim 1 wherein said associated transformations are non-linear and wherein said size distribution is characterized by v(r,p), where p is a characterization parameter vector having K components, and wherein said composite transformation operator $J^{-1}$ is the p solution algorithm for $$\frac{\partial}{\partial p_l} \sum_{i=1}^{m} \sum_{j=1}^{q} J_{ij}[v(r,p)] - g_i(t_j))^2 = 0, l = 1, \ldots, k$$

where i is an integer $1,\ldots,m$, j is an integer $1,\ldots,q$, l is an integer $1,\ldots,k$, $p_l$ is the $l^{th}$ component of p and where $g_i(t_j)$ is the autocorrelation function of the intensity signal for the $i^{th}$ of said angle at the $j^{th}$ time interval and $J_{ij}$ is an operator related to the associated transformations.

17. A system according to claim 1 wherein $m \geq 1$ and $n \geq 1$.

18. A system according to claim 1 wherein $m \geq 2$ and $n \geq 0$.

19. A system according to claim 2 wherein $m \geq 1$ and $n \geq 1$.

20. A system according to claim 2 wherein $m \geq 2$ and $n = 0$.

21. A system according to claim 4 wherein $m \geq 1$ and $n \geq 1$.

22. A system according to claim 4 wherein $m \geq 2$ and $n = 0$.

23. A system according to claim 6 wherein $m \geq 1$ and $n \geq 1$.

24. A system according to claim 6 wherein $m \geq 2$ and $n = 0$.

25. A system according to claim 1 wherein said measurement condition controlling means comprises means for establishing the position of said detector means whereby one or more of said m intensity signals is representative of the intensity of light from said light beam at points angularly displaced from said input axis, and one or more of said n average signals is representative of the average intensity of said scattered light at points angularly displaced from said input axis different from said points for which said intensity signals are generated.

26. A system according to claim 1 wherein said measurement condition controlling means comprises means operative during at least one of said m+n measurements for selectively controlling the polarization of light from said beam incident on said sample to have a first predetermined polarization, and for selectively controlling the polarization of light scattered from said sample incident on said detector to have a said first polarization.

27. A system according to claim 1 wherein said measurement condition controlling means comprises means operative during at least one of said m+n measurements for selectively controlling the polarization of light from said beam incident on said sample to have a second predetermined polarization, and for selectively controlling the polarization of light scattered from said sample incident on said detector to have said second polarization, and wherein said second predetermined polarization is orthogonal to said first predetermined polarization.

28. A system according to claim 26 wherein said first predetermined polarization is circular.

29. A system according to claim 27 wherein said first and second predetermined polarizations are circular.

30. A system according to claim 26 wherein first predetermined polarization is linear.

31. A system according to claim 27 wherein first and second predetermined polarizations are linear.

32. A system according to claim 1 wherein said measurement condition controlling means comprises means operative during at least one of said m+n measurement for selectively controlling the temperature of said sample to m at a first predetermined temperature and operative during at least one other of said m+n measurements for selectively controlling the temperature of said sample to be at a second predetermined temperature.

33. A system according to claim 25 wherein said detector means includes a first sensor means for generating said m intensity signals and a second sensor means for generating said n average signals.

34. A system according to claim 33 wherein said second sensor means includes a first curvilinear array of spaced apart photosensors and a second curvilinear array of spaced apart photosensors, said first array extending along an arc disposed about said sample, wherein the photosensors in said first array are offset from said sample by relatively small angles measured from said input axis, and said second array extending along an arc disposed about said sample wherein the photosensors in said second array are offset from said sample by ninety degrees plus relatively small angles measured from said input axis.

35. A system according to claim 34 wherein said first and second arrays lie in orthogonal planes.

36. A system according to claim 34 including means for supporting a container for said sample, said container having opposed parallel planar lateral surfaces, said container having a rectangular cross-section bounded by said lateral surfaces, and wherein said supporting means includes means for maintaining one pair of lateral surfaces perpendicular to said input axis, and the other pair of lateral surfaces parallel to said input axis.

37. A system according to claim 35 including means for supporting a container for said sample, said container having opposed parallel planar lateral surfaces, said container having a rectangular cross-section bounded by said lateral surfaces, and wherein said supporting means includes means for maintaining one pair of lateral surfaces perpendicular to said input axis, and the other pair of lateral surfaces parallel to said input axis.

38. A method for measuring the size distribution v(r) of particles dispersed in a fluid sample, where r is representative of particle size, comprising the steps of:

A. illuminating said sample with a light beam directed along an input axis,

B. detecting the intensity of light scattered from said light beam by said sample for m measurements made under an associated one of a set of m measurement conditions, and for n measurements made under an associated one of a set of n measurement conditions, where m is an integer equal to or greater than one, and n is an integer equal to or greater than zero, and the sum of m and n is equal to or greater than two, and at least two of said m+n measurement conditions are different, including the substeps of:

i. generating m intensity signals, each of said intensity signals being representative of the detected intensity of said scattered light as a function of time under a corresponding one of the measurement conditions of said set of m measurement conditions, ii. generating n average signals, each of said n average signals being representative of the average intensity of said scattered light detected under a corresponding one of the measurement conditions of said set of n measurement conditions, C. generating m correlation signals, each of said correlation signals being representative of the autocorrelation function of a corresponding one of said intensity signals and being equal to an associated transformation of said distribution v(r), D. in response to said correlation signals and said average signals, including the substeps of:

i. preprocessing said m correlation signals for generating a composite correlation signal, ii. generating a composite scattered light signal from said composite correlation signal and said n average signals iii. determining a composite transformation operator $J^{-1}$ related to said associated transformations and said n average signals, iv. transforming said composite scattered light signal in accordance with said determined composite transformation operator $J^{-1}$ to generate a size distribution signal representative of said distribution v(r), and E. controlling said m+n measurement conditions whereby said intensity signals are mutually independent and said average signals are mutually independent.

39. A method according to claim 38 wherein said preprocessng step includes the substeps of:

i. in response to said m correlation signals, generating m moment signals, said m moment signals being representative of at least one of the moments of each of said m correlation signals other than the zero$^{th}$ moments of said m correlation signals, ii. generating a weighted direct sum signal, said weighted sum signal being representative of the direct sum of said m moment signals and corresponding to said composite correlation signal.

40. A method according to claim 39 wherein said step of generating said composite scattered light signal includes the step of generating the direct sum of said composite correlation signal and said n average signals, said direct sum corresponding to said composite scattered light signal.

41. A method according to claim 38 wherein said preprocessing steps includes the substeps of:

i. in response to said m correlation signals, generating m unity normalized correlation signals, each of said unity normalized correlation signals being representative of the unity normalized form of the corresponding one of said m correlation signals, ii. generating a direct sum signal, said sum signal being representative of the direct sum of said unity normalized correlation signals, and corresponding to said composite correlation signal.

42. A method according to claim 41 wherein said step of generating said composite scattered light signal includes the step of generating the direct sum of said composite correlation signal and said n average signals, said direct sum corresponding to said composite scattered light signal.

43. A method according to claim 38 wherein said preprocessing step includes the step of:

i. generating a direct sum signal, said sum signal being representative of the direct sum of said m correlation signals and corresponding to said composite correlation signal.

44. A method according to claim 43 wherein said step of generating said composite scattered light signal includes the step of generating the direct sum of said composite correlation signal and said n average signals, said direct sum corresponding to said composite scattered light signal.

* * * * *